US009474755B2

(12) United States Patent
Boehm et al.

(10) Patent No.: US 9,474,755 B2
(45) Date of Patent: Oct. 25, 2016

(54) GLP-1 RECEPTOR MODULATORS

(71) Applicant: Receptos, Inc., San Diego, CA (US)

(72) Inventors: Marcus F. Boehm, San Diego, CA (US); Esther Martinborough, San Diego, CA (US); Manisha Moorjani, San Diego, CA (US); Junko Tamiya, Carlsbad, CA (US); Liming Huang, San Diego, CA (US); Adam R. Yeager, La Mesa, CA (US); Enugurthi Brahmachary, San Diego, CA (US); Thomas Fowler, Melton Mowbray (GB); Andrew Novak, Long Eaton (GB); Premji Meghani, Loughborough (GB); Michael Knaggs, Burton-on-Trent (GB)

(73) Assignee: Celgene International II SARL, Couvet (CH)

( * ) Notice: Subject to any disclaimer, the term of this patent is extended or adjusted under 35 U.S.C. 154(b) by 0 days.

(21) Appl. No.: 14/809,020

(22) Filed: Jul. 24, 2015

(65) Prior Publication Data

US 2016/0038487 A1 Feb. 11, 2016

Related U.S. Application Data

(60) Provisional application No. 62/161,650, filed on May 14, 2015, provisional application No. 62/090,040, filed on Dec. 10, 2014, provisional application No. 62/028,962, filed on Jul. 25, 2014.

(51) Int. Cl.

| | |
|---|---|
| ***C07D 401/10*** | (2006.01) |
| ***C07D 403/10*** | (2006.01) |
| ***A61K 31/506*** | (2006.01) |
| ***C07D 403/06*** | (2006.01) |
| ***C07D 403/14*** | (2006.01) |
| ***C07D 409/12*** | (2006.01) |
| ***C07D 409/14*** | (2006.01) |
| ***A61K 38/05*** | (2006.01) |
| ***C07D 401/14*** | (2006.01) |
| ***C07D 471/08*** | (2006.01) |
| ***C07K 5/078*** | (2006.01) |

(52) U.S. Cl.

CPC ............. *A61K 31/506* (2013.01); *A61K 38/05* (2013.01); *C07D 401/14* (2013.01); *C07D 403/06* (2013.01); *C07D 403/10* (2013.01); *C07D 403/14* (2013.01); *C07D 409/12* (2013.01); *C07D 409/14* (2013.01); *C07D 471/08* (2013.01); *C07K 5/06139* (2013.01)

(58) Field of Classification Search

CPC C07D 401/10; C07D 401/14; C07D 403/10; C07D 403/14; C07D 409/10; C07D 409/14; A61K 31/506

USPC .......................................... 544/333; 514/256

See application file for complete search history.

(56) References Cited

U.S. PATENT DOCUMENTS

| | | | |
|---|---|---|---|
| 4,004,008 | A | 1/1977 | Makovec et al. |
| 4,067,726 | A | 1/1978 | Sasse et al. |
| 5,424,286 | A | 6/1995 | Eng |
| 6,174,905 | B1 | 1/2001 | Suzuki et al. |
| 6,191,171 | B1 | 2/2001 | DeLaszlo et al. |
| 6,583,139 | B1 | 6/2003 | Thorsett et al. |
| 6,902,744 | B1 | 6/2005 | Kolterman et al. |
| 7,297,761 | B2 | 11/2007 | Beeley et al. |
| 7,368,427 | B1 | 5/2008 | Dong et al. |
| 7,825,139 | B2 | 11/2010 | Campbell et al. |

(Continued)

FOREIGN PATENT DOCUMENTS

| | | |
|---|---|---|
| EP | 1 477 482 A1 | 11/2004 |
| EP | 1 700 850 A1 | 9/2006 |

(Continued)

OTHER PUBLICATIONS

Banker et al., (eds.), *Modern Pharmaceutics 3rd Edition*, New York, Marcel Dekker Inc., 1996, pp. 451 and 596, 3 pages.

(Continued)

*Primary Examiner* — Deepak Rao

(74) *Attorney, Agent, or Firm* — Seed IP Law Group PLLC

(57) ABSTRACT

Compounds are provided that modulate the glucagon-like peptide 1 (GLP-1) receptor, as well as methods of their synthesis, and methods of their therapeutic and/or prophylactic use. Such compounds can act as modulators or potentiators of GLP-1 receptor on their own, or with incretin peptides such as GLP-1(7-36), GLP-1(9-36), and oxyntomodulin, or with peptide-based therapies, such as exenatide and liraglutide, and have the following general structure (where "⌇" represents either or both the R and S form of the compound):

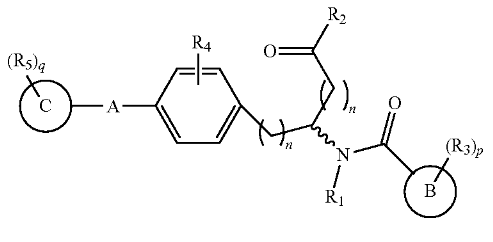

where A, B, C, $R_1$, $R_2$, $R_3$, $R_4$, $R_5$, n, p and q are as defined herein.

80 Claims, No Drawings

(56) References Cited

U.S. PATENT DOCUMENTS

| | | | |
|---|---|---|---|
| 8,501,982 B2 | 8/2013 | Boehm et al. | |
| 8,778,923 B2 | 7/2014 | Boehm et al. | |
| 8,816,121 B2 | 8/2014 | Boehm et al. | |
| 9,260,427 B2 * | 2/2016 | Boehm | C07D 417/04 |
| 2001/0031772 A1 | 10/2001 | Schoenafinger et al. | |
| 2005/0222141 A1 | 10/2005 | Sagi et al. | |
| 2008/0300193 A1 | 12/2008 | Ahn et al. | |
| 2010/0292143 A1 | 11/2010 | Bhuniya et al. | |
| 2011/0306542 A1 | 12/2011 | Boehm et al. | |
| 2013/0178420 A1 | 7/2013 | Boehm et al. | |
| 2014/0031290 A1 | 1/2014 | Boehm et al. | |
| 2014/0336185 A1 | 11/2014 | Boehm et al. | |
| 2015/0011527 A1 | 1/2015 | Boehm et al. | |
| 2015/0038416 A1 | 2/2015 | Boehm et al. | |

FOREIGN PATENT DOCUMENTS

| | | |
|---|---|---|
| WO | 99/06437 A1 | 2/1999 |
| WO | 99/10312 A1 | 3/1999 |
| WO | 03/048158 A1 | 6/2003 |
| WO | 2005/077915 A1 | 8/2005 |
| WO | 2011/094890 A1 | 8/2011 |
| WO | 2011-097300 A1 | 8/2011 |
| WO | 2011/156655 A2 | 12/2011 |
| WO | 2012/166951 A9 | 12/2012 |
| WO | 2013/090454 A2 | 6/2013 |

OTHER PUBLICATIONS

Bungaard (ed.), "Chapter 1: Design of prodrugs: Bioreversible derivatives for various functional groups and chemical entities," in *Design of Prodrugs*, Amsterdam, The Netherlands, Elsevier Science Publishers B.V., 1985, 3 pages.

International Search Report and Written Opinion, mailed Dec. 1, 2011, for International Application No. PCT/US2011/039873, 9 pages.

Knudsen et al., "Small-molecule agonists for the glucagon-like peptide 1 receptor," *PNAS 104*(3):937-942, Jan. 16, 2007.

PubChem Compound, Compound Summary for CID 2980472, "N-benzyl-4-[(2-phenylacetyl)amino]benzamide," retrieved from https://pubchem.ncbi.nih.gov/summary/summary cgi?cid=29804 . . . , on Sep. 10, 2014, 6 pages.

PubChem Compound, Compound Summary for CID 4884981, "SMR000154147," retrieved from https://pubchem.ncbi.nih.gov/summary/summary cgi?cid=48849 . . . , on Sep. 10, 2014, 6 pages.

Reid, "Practical Use of Glucagon-Like Peptide-1 Receptor Agonist Therapy in Primary Care," *Clinical Diabetes 31*(4):148-157, 2013.

Silverman, "Chapter 8: Prodrugs and Drug Delivery Systems," in *The Organic Chemistry of Drug Design and Drug Action*, London, United Kingdom, Academic Press Inc., 1992, pp. 352-400.

Thorsett et al., "Preparation of N-sulfonylated dipeptide derivatives as inhibitors of leukocyte adhesion mediated by VLA-4," Chem. Abstracts Service Database accession No. 2003:485719, abstract, retrieved on Jul. 18, 2003, 3 pages.

Thorsett et al., "Preparation of N-sulfonylproline dipeptide derivatives and analogs as inhibitors of leukocyte adhesion mediated by VLA-4," Chem. Abstracts Service Database accession No. 1999:113712, retrieved on Jul. 18, 2013, 3 pages.

Underwood et al., "Crystal Structure of Glucagon-like Peptide-1 in Complex with the Extracellular Domain of the Glucagon-like Peptide-1 Receptor," *Journal of Biological Chemistry 285*(1):723-730, Jan. 1, 2010.

West, "Chapter 7: Phase Diagrams and their Interpretation," in *Solid State Chemistry and Its Applications 2nd Edition*, New York, John Wiley & Sons, 1988, pp. 358 and 365, 3 pages.

Wolff, (ed.), "vol. 1: Principles and Practice," in *Burger's Medicinal Chemistry and Drug Discovery 5th Edition*, New York, John Wiley & Sons, 1995, pp. 975-977, 4 pages.

Wolff, (ed.), "Part 1: The Basis of medicinal Chemistry," in *Burger's Medicinal Chemistry 4th Edition*, New York, John Wiley & Sons, 1979, pp. 336-337, 4 pages.

* cited by examiner

GLP-1 RECEPTOR MODULATORS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 800059_411_SEQUENCE_LISTING.txt. The text file is 1.7 KB, was created on May 6, 2016, and is being submitted electronically via EFS-Web.

FIELD OF THE INVENTION

The invention relates to compounds that bind the glucagon-like peptide 1 (GLP-1) receptor, methods of their synthesis, and methods of their therapeutic and/or prophylactic use. The present invention is directed to compounds adapted to act as modulators of the GLP-1 receptor, and potentiators of incretin peptides, such as GLP-1(7-36), GLP-1(9-36), and oxyntomodulin, as well as peptide-based therapies such as exenatide and liraglutide.

BACKGROUND

Glucagon-like peptide 1 receptor (GLP-1R) belongs to Family B1 of the seven-transmembrane G protein-coupled receptors, and its natural agonist ligand is the peptide hormone glucagon-like peptide-1 (GLP-1). GLP-1 is a peptide hormone arising by its alternative enzymatic cleavage from proglucagon, the prohormone precursor for GLP-1, which is highly expressed in enteroendocrine cells of the intestine, the alpha cells of the endocrine pancreas (islets of Langerhans), and the brain (Kieffer T. J. and Habener, J. F. Endocrin. Rev. 20:876-913 (1999); Drucker, D. J., Endocrinology 142:521-7 (2001); Holst, J. J., Diabetes Metab. Res. Rev. 18:430-41 (2002)). The initial actions of GLP-1 observed were on the insulin-producing cells of the islets, where it stimulates glucose-dependent insulin secretion. Subsequently, multiple additional antidiabetogenic actions of GLP-1 were discovered including the stimulation of the growth and inhibition of the apoptosis of pancreatic beta cells (Drucker, D. J., Endocrinology 144:5145-8 (2003); Holz, G. G. and Chepurny O. G., Curr. Med. Chem. 10:2471-83 (2003); List, J. F. and Habener, J. F., Am. J. Physiol. Endocrinol. Metab. 286:E875-81 (2004)).

Like GLP-1, Oxyntomodulin is also generated from L-cell derived proglucagon by alternative proteolysis. Oxyntomodulin is identical to glucagon plus an additional 8 amino acid carboxyterminal extension (Bataille D., et al, Peptides 2 Suppl s:41-4 (1981)). Oxyntomodulin is a dual agonist of both GLP-1 receptor and glucagon receptor. Oxyntomodulin induces glucose dependent insulin secretion from pancreatic β cells (Maida, A., et al, Endocrinology 149:5670-8 (2008), and in vivo, oxyntomodulin modulates food intake (Dakin, C. L. et al, Endocrinology 142:4244-50 (2001)) and is significantly anorectic (Baggio, L. L. et al, Gastroenterology 127:46-58 (2004)).

On activation, GLP-1 receptors couple to the α-subunit of G protein, with subsequent activation of adenylate cyclase and increase of cAMP levels, thereby potentiating glucose-stimulated insulin secretion. Therefore, GLP-1 is an attractive therapeutic target to lower blood glucose and preserve the β-cells of the pancreas of diabetic patients. Glucagon has been used for decades in medical practice within diabetes and several glucagon-like peptides are being developed for various therapeutic indications. GLP-1 analogs and derivatives are being developed for the treatment for patients suffering from diabetes.

SUMMARY OF THE INVENTION

The present invention is directed to compounds adapted to act as potentiators or modulators of GLP-1 receptor; methods of their preparation and methods of their use, such as in treatment of a malcondition mediated by GLP-1 receptor activation, or when modulation or potentiation of GLP-1 receptor is medically indicated.

Certain embodiments of the present invention comprise a compound having the structure of Formula I-R or I-S or a pharmaceutically acceptable isomer, enantiomer, racemate, salt, isotope, prodrug, hydrate or solvate thereof:

I-R

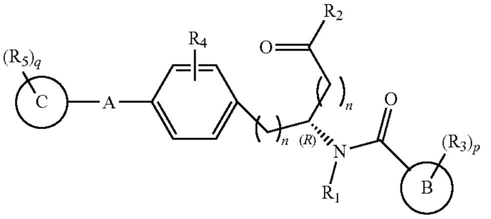

I-S

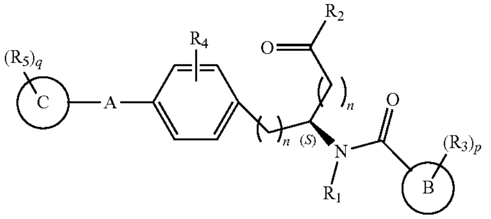

wherein

A is pyrimidinyl, pyridinyl, pyridazinyl or pyrazinyl, each of which may be optionally substituted with one or more of $R_4$;

B is phenyl or heterocycle;

C is a nonaromatic carbocyclyl or nonaromatic carbocyclylalkyl;

each $R_1$ is independently H or $C_{1-4}$ alkyl;

$R_2$ is —OH, —O—$R_8$, —N($R_1$)—$SO_2$—$R_7$, —$NR_{41}R_{42}$, —N($R_1$)—$(CR_aR_b)_m$—$COOR_8$, —N($R_1$)—$(CR_aR_b)_m$—CO—N($R_1$)($R_{40}$), —N($R_1$)—$(CR_aR_b)_m$—N($R_1$)C(O)O($R_8$), —N($R_1$)—$(CR_aR_b)_m$—N($R_1$)($R_{40}$), —N($R_1$)—$(CR_aR_b)_m$—CO—N($R_1$)-heterocyclyl, or —N($R_1$)—$(CR_aR_b)_m$-heterocyclyl, which heterocyclyl may be optionally (singly or multiply) substituted with $R_7$;

each $R_3$ and $R_4$ is independently H, halo, alkyl, alkyl substituted (singly or multiply) with $R_{31}$, alkoxy, haloalkyl, perhaloalkyl, haloalkoxy, perhaloalkoxy, aryl, heterocyclyl, —OH, —$OR_7$, —CN, —$NO_2$, —$NR_1R_7$, —C(O)$R_7$, —(O)$NR_1R_7$, —$NR_1$C(O)$R_7$, —$SR_7$, —S(O)$R_7$, —$S(O)_2R_7$, —$OS(O)_2R_7$, —$S(O)_2NR_1R_7$, —$NR_1S(O)_2R_7$, —$(CR_aR_b)_mNR_1R_7$, —$(CR_aR_b)_mO(CR_aR_b)_mR_7$, —$(CR_aR_b)_mNR_1(CR_aR_b)_mR_7$ or —$(CR_aR_b)_mNR_1(CR_aR_b)_mCOOR_8$; or any two $R_3$ or $R_4$ groups on the same carbon atom taken together form oxo;

$R_5$ is $R_7$, —$(CR_aR_b)_m$—$(CR_aR_b)_m$—$R_7$, or —(-$L_3$-$(CR_aR_b)_r$-$L_3$-$R_7$, wherein the carbon atoms of any two adjacent —$(CR_aR_b)_m$ or $(CR_aR_b)_r$ groups may be taken together to form a double bond (—C($R_a$)═(C($R_a$)—) or triple bond (—C≡C—);

$R_6$ is H, alkyl, aryl, heteroaryl, heterocyclyl, heterocycloalkyl, any of which may be optionally substituted (singly or multiply) with $R_7$ or $—(CR_aR_b)_m$-$L_2$-$(CR_aR_b)_m—R_7$;

each $R_7$ is independently $R_{10}$; a ring moiety selected from cycloalkyl, aryl, aralkyl, heterocyclyl or heterocyclylalkyl, where such ring moiety is optionally (singly or multiply) substituted with $R_{10}$; or when a carbon atom bears two $R_7$ groups such two $R_7$ groups are taken together to form oxo or thioxo, or are taken together (when attached to the same carbon atom or different carbon atoms) to form a ring moiety selected from cycloalkyl, aryl, heterocyclyl or heterocyclylalkyl, wherein such ring moiety is optionally singly or multiply substituted with $R_{10}$;

each $R_8$ is independently H, alkyl, haloalkyl, aryl, $—(CR_aR_b)_m$-$L_2$-$(CR_aR_b)_m—R_1$ or $—(-L_3-(CR_aR_b)_r-)_s-L_3-R_1$;

each $R_{10}$ is independently H, halo, alkyl, haloalkyl, haloalkoxy, perhaloalkyl, perhaloalkoxy, $—(CR_aR_b)_mOH$, $—(CR_aR_b)_mOR_8$, $—(CR_aR_b)_mCN$, $—(CR_aR_b)_mNH(C{=}NH)NH_2$, $—(CR_aR_b)_mNR_1R_8$, $—(CR_aR_b)_mO(CR_aR_b)_mR_8$, $—(CR_aR_b)_mNR_1(CR_aR_b)_mR_8$, $—(CR_aR_b)_mC(O)R_8$, $—(CR_aR_b)_mC(O)OR_8$, $—(CR_aR_b)_mC(O)NR_1R_8$, $—(CR_aR_b)_mNR_1(CR_aR_b)_mC(O)OR_8$, $—(CR_aR_b)_mNR_1C(O)R_8$, $—(CR_aR_b)_mC(O)NR_1S(O)_2R_8$, $—(CR_aR_b)_mSR_8$, $—(CR_aR_b)_mS(O)R_8$, $—(CR_aR_b)_mS(O)_2R_8$, $—(CR_aR_b)_mS(O)_2NR_1R_8$ or $—(CR_aR_b)_mNR_1S(O)_2R_8$;

each $R_{31}$ is independently H, halo, hydroxyl, $—NR_{41}R_{42}$, or alkoxy;

each $R_{40}$ is independently H, $R_7$, alkyl which may be optionally (singly or multiply) substituted with $R_7$, or $R_{40}$ and $R_1$ taken together with the N atom to which they are attached form a 3- to 7-membered heterocyclyl which may be optionally (singly or multiply) substituted with $R_7$;

each $R_{41}$ and $R_{42}$ is independently $R_{40}$, $—(CHR_{40})_n—C(O)O—R_{40}$, $—(CHR_{40})_n—C(O)—R_{40}$, $—(CH_2)_n—N(R_1)(R_7)$, aryl or heteroaryl any of which aryl or heteroaryl may be optionally (singly or multiply) substituted with $R_7$; or any two $R_{41}$ and $R_{42}$ taken together with the N atom to which they are attached form a 3- to 7-membered heterocyclyl which may be optionally (singly or multiply) substituted with $R_7$;

each $R_a$ and $R_b$ is independently H, halo, alkyl, alkoxy, aryl, aralkyl, heterocyclyl, heterocyclylalkyl (any of which alkyl, alkoxy, aryl, aralkyl, heterocyclyl or heterocyclylalkyl may be optionally (singly or multiply) substituted with $R_7$), $—(CHR_{40})_mC(O)OR_{40}$, $—(CHR_{40})_mOR_{40}$, $—(CHR_{40})_mSR_{40}$, $—(CHR_{40})_mNR_{41}R_{42}$, $—(CHR_{40})_mC(O)NR_{41}R_{42}$, $—(CHR_{40})_mC(O)N(R_1)(CHR_{40})_mNR_{41}R_{42}$, $—(CHR_{40})_mC(O)N(R_1)(CHR_{40})_mC(O)NR_{41}R_{42}$, $—(CHR_{40})_mC(O)N(R_1)—(CHR_{40})_mC(O)OR_{40}$, or $—(CHR_{40})_m—S—S—R_{40}$; or any two $R_a$ and $R_b$ taken together with the carbon atom(s) to which they are attached form a cycloalkyl or heterocyclyl optionally substituted (singly or multiply) with $R_7$; or $R_1$ and any one of $R_a$ or $R_b$ taken together with the atoms to which they are attached form heterocyclyl optionally substituted (singly or multiply) with $R_7$;

$L_2$ is independently, from the proximal to distal end of the structure of Formula I-R or I-S, null, —O—, —OC(O)—, $—NR_1—$, $—C(O)NR_1—$, $—N(R_1)—C(O)—$, $—S(O_2)—$, —S(O)—, —S—, —C(O)— or $—S(O_2)—N(R_1)—$;

each $L_3$ is independently null, —O—, or $—N(R_1)—$ each m is independently 0, 1, 2, 3, 4, 5 or 6;

each n is independently 0 or 1 or 2;

p is 0, 1, 2 or 3;

q is 0, 1, 2 or 3;

each r is independently 2, 3, or 4; and each s is independently 1, 2, 3, or 4.

In certain embodiments, a pharmaceutical composition comprising a compound of the invention together with at least one pharmaceutically acceptable carrier, diluent or excipient is provided.

In certain embodiments, a method of use of a compound of the invention comprising preparation of a medicament is provided.

In certain embodiments, the invention provides a pharmaceutical combination comprising a compound of the invention and a second medicament. In various such embodiments, the second medicament is an agonist or modulator for glucagon receptor, GIP receptor, GLP-2 receptor, or PTH receptor, or glucagon-like peptide 1 (GLP-1) receptor. In various such embodiments, the second medicament is exenatide, liraglutide, taspoglutide, albiglutide, or lixisenatide or other insulin regulating peptide. In various embodiments, the second medicament is medically indicated for the treatment of type II diabetes. In various embodiments, the second medicament is a biguanide, a sulfonylurea, a meglitinide, a thiazolidinedione, an α-glucosidase inhibitor, a bile acid sequestrant, an SGLT inhibitor, and/or a dopamine-2 agonist, and in more specific embodiments is metformin (a biguanide), sitagliptin (a DPPIV inhibitor), or canagliflozin, dapagliflozin or empagliflozin (an SGLT inhibitor).

In certain embodiments, a method of activation, potentiation or agonism of a GLP-1 receptor is provided comprising contacting the receptor with a compound, pharmaceutical composition or pharmaceutical combination of the invention.

In certain embodiments, a method is provided for treatment of a malcondition in a subject for which activation, potentiation or agonism of a GLP-1 receptor is medically indicated where such method comprises administering to such subject a compound, pharmaceutical composition or pharmaceutical combination of the invention. In various such embodiments, selective activation, potentiation or agonism of a GLP-1 receptor, is medically indicated. In various such embodiments, the malcondition comprises type I diabetes, type II diabetes, gestational diabetes, obesity, excessive appetite, insufficient satiety, or metabolic disorder.

In certain embodiments, the invention provides methods for synthesis of certain compounds including compounds of the invention. In certain other embodiments, the invention provides certain intermediate compounds associated with such methods of synthesis.

DETAILED DESCRIPTION OF THE INVENTION

Certain embodiments comprise a compound having the chiral structure of Formula I-R or I-S (with the chirality as indicated) or a pharmaceutically acceptable isomer, enantiomer, racemate, salt, isotope, prodrug, hydrate or solvate thereof:

Certain embodiments of the present invention comprise a compound having the structure of Formula I-R or I-S or a pharmaceutically acceptable isomer, enantiomer, racemate, salt, isotope, prodrug, hydrate or solvate thereof:

I-R

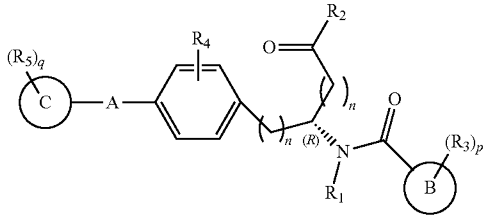

I-S

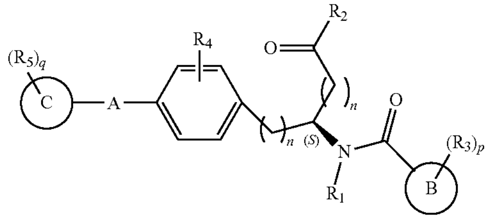

where A, B, C, $R_1$, $R_2$, $R_3$, $R_4$, $R_5$, n, p and q are as defined above.

In certain embodiments, the invention provides a compound of Formula I-R and/or Formula I-S where B is phenyl.

In certain embodiments, the invention provides a compound of Formula I-R and/or Formula I-S where B is heterocyle.

In certain embodiments, the invention provides a compound of Formula I-R and/or Formula I-S where B is thiophenyl.

In certain embodiments, the invention provides a compound of Formula I-R and/or Formula I-S where B is pyrimidinyl.

In certain embodiments, the invention provides a compound of Formula I-R and/or Formula I-S where B is pyrazolyl.

In certain embodiments, the invention provides a compound of Formula I-R and/or Formula I-S where B is pyridinyl.

In certain embodiments, the invention provides a compound of Formula I-R and/or Formula I-S where B is indolyl.

Certain embodiments of the present invention comprise a compound having the structure of Formula I-R or I-S or a pharmaceutically acceptable isomer, enantiomer, racemate, salt, isotope, prodrug, hydrate or solvate thereof:

I-R

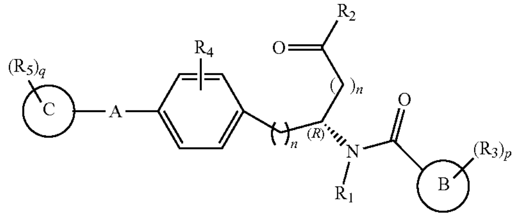

-continued

I-S

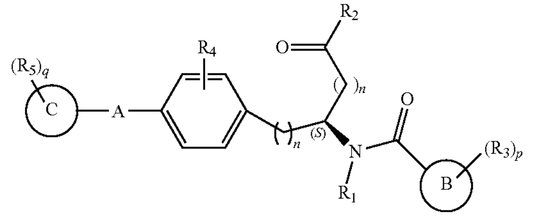

wherein

A is pyrimidinyl, pyridinyl, pyridazinyl or pyrazinyl, each of which may be optionally substituted with one or more of $R_4$;

B is phenyl or thiophenyl;

C is a nonaromatic carbocyclyl or nonaromatic carbocyclylalkyl;

each $R_1$ is independently H or $C_1$-4 alkyl;

$R_2$ is —OH, —O—$R_8$, —$N(R_1)$—$SO_2$—$R_7$, —$NR_{41}R_{42}$, —$N(R_1)$—$(CR_aR_b)_m$—$COOR_8$, —$N(R_1)$—$(CR_aR_b)_m$—CO—$N(R_1)(R_{40})$, —$N(R_1)$—$(CR_aR_b)_m$—$N(R_1)C(O)O(R_8)$, —$N(R_1)$—$(CR_aR_b)_m$—$N(R_1)(R_{40})$, —$N(R_1)$—$(CR_aR_b)_m$—CO—$N(R_1)$-heterocyclyl, or —$N(R_1)$—$(CR_aR_b)_m$-heterocyclyl, which heterocyclyl may be optionally (singly or multiply) substituted with $R_7$;

each $R_3$ and $R_4$ is independently H, halo, alkyl, alkyl substituted (singly or multiply) with $R_{31}$, alkoxy, haloalkyl, perhaloalkyl, haloalkoxy, perhaloalkoxy, aryl, heterocyclyl, —OH, —$OR_7$, —CN, —$NO_2$, —$NR_1R_7$, —$C(O)R_7$, —$(O)NR_1R_7$, —$NR_1C(O)R_7$, —$SR_7$, —$S(O)R_7$, —$S(O)_2R_7$, —$OS(O)_2R_7$, —$S(O)_2NR_1R_7$, —$NR_1S(O)_2R_7$, —$(CR_aR_b)_mNR_1R_7$, —$(CR_aR_b)_mO(CR_aR_b)_mR_7$, —$(CR_aR_b)_mNR_1(CR_aR_b)_mR_7$ or —$(CR_aR_b)_mNR_1(CR_aR_b)_mCOOR_8$; or any two $R_3$ or $R_4$ groups on the same carbon atom taken together form oxo;

$R_5$ is $R_7$, —$(CR_aR_b)_m$—$(CR_aR_b)_m$—$R_7$, or —$(-L_3-(CR_aR_b)_r-L_3-R_7$, wherein the carbon atoms of any two adjacent —$(CR_aR_b)_m$ or $(CR_aR_b)_r$ groups may be taken together to form a double bond (—$C(R_a)$═$C(R_a)$—) or triple bond (—C≡C—);

$R_6$ is H, alkyl, aryl, heteroaryl, heterocyclyl, heterocycloalkyl, any of which may be optionally substituted (singly or multiply) with $R_7$ or —$(CR_aR_b)_m$-$L_2$-$(CR_aR_b)_m$—$R_7$;

each $R_7$ is independently $R_{10}$; a ring moiety selected from cycloalkyl, aryl, aralkyl, heterocyclyl or heterocyclylalkyl, where such ring moiety is optionally (singly or multiply) substituted with $R_{10}$; or when a carbon atom bears two $R_7$ groups such two $R_7$ groups are taken together to form oxo or thioxo, or are taken together to form a ring moiety selected from cycloalkyl, aryl, heterocyclyl or heterocyclylalkyl, wherein such ring moiety is optionally singly or multiply substituted with $R_{10}$;

each $R_8$ is independently H, alkyl, haloalkyl, aryl, —$(CR_aR_b)_m$-$L_2$-$(CR_aR_b)_m$—$R_1$ or —$(-L_3-(CR_aR_b)_r-)_s-L_3-R_1$;

each $R_{10}$ is independently H, halo, alkyl, haloalkyl, haloalkoxy, perhaloalkyl, perhaloalkoxy, —$(CR_aR_b)_mOH$, —$(CR_aR_b)_mOR_8$, —$(CR_aR_b)_mCN$, —$(CR_aR_b)_mNH(C{=}NH)NH_2$, —$(CR_aR_b)_mNR_1R_8$, —$(CR_aR_b)_mO(CR_aR_b)_mR_8$, —$(CR_aR_b)_mNR_1(CR_aR_b)_mR_8$, —$(CR_aR_b)_mC(O)R_8$, —$(CR_aR_b)_mC(O)OR_8$, —$(CR_aR_b)_mC(O)NR_1R_8$, —$(CR_aR_b)_mNR_1(CR_aR_b)_mC(O)OR_8$, —$(CR_aR_b)_mNR_1C(O)R_8$, —$(CR_aR_b)_mC(O)NR_1S(O)_2R_8$, —$(CR_aR_b)_mSR_8$, —$(CR_aR_b)_mS(O)R_8$, —$(CR_aR_b)_mS(O)_2R_8$, —$(CR_aR_b)_mS(O)_2NR_1R_8$ or —$(CR_aR_b)_mNR_1S(O)_2R_8$;

each $R_{31}$ is independently H, halo, hydroxyl, —$NR_{41}R_{42}$, or alkoxy;

each $R_{40}$ is independently H, $R_7$, alkyl which may be optionally (singly or multiply) substituted with $R_7$, or $R_{40}$ and $R_1$ taken together with the N atom to which they are attached form a 3- to 7-membered heterocyclyl which may be optionally (singly or multiply) substituted with $R_7$;

each $R_{41}$ and $R_{42}$ is independently $R_{40}$, —$(CHR_{40})_n$—C(O)O—$R_{40}$, —$(CHR_{40})_n$—C(O)—$R_{40}$, —$(CH_2)_n$—$N(R_1)(R_7)$, aryl or heteroaryl any of which aryl or heteroaryl may be optionally (singly or multiply) substituted with $R_7$; or any two $R_{41}$ and $R_{42}$ taken together with the N atom to which they are attached form a 3- to 7-membered heterocyclyl which may be optionally (singly or multiply) substituted with $R_7$;

each $R_a$ and $R_b$ is independently H, halo, alkyl, alkoxy, aryl, aralkyl, heterocyclyl, heterocyclylalkyl (any of which alkyl, alkoxy, aryl, aralkyl, heterocyclyl or heterocyclylalkyl may be optionally (singly or multiply) substituted with $R_7$), —$(CHR_{40})_mC(O)OR_{40}$, —$(CHR_{40})_mOR_{40}$, —$(CHR_{40})_mSR_{40}$, —$(CHR_{40})_mNR_{41}R_{42}$, —$(CHR_{40})_mC(O)NR_{41}R_{42}$, —$(CHR_{40})_mC(O)N(R_1)(CHR_{40})_mNR_{41}R_{42}$, —$(CHR_{40})_mC(O)N(R_1)(CHR_{40})_mC(O)NR_{41}R_{42}$, —$(CHR_{40})_mC(O)N(R_1)$—$(CHR_{40})_mC(O)OR_{40}$, or —$(CHR_{40})_m$—S—S—$R_{40}$; or any two $R_a$ and $R_b$ taken together with the carbon atom(s) to which they are attached form a cycloalkyl or heterocyclyl optionally substituted (singly or multiply) with $R_7$; or $R_1$ and any one of $R_a$ or $R_b$ taken together with the atoms to which they are attached form heterocyclyl optionally substituted (singly or multiply) with $R_7$;

$L_2$ is independently, from the proximal to distal end of the structure of Formula I-R or I-S, null, —O—, —OC(O)—, —$NR_1$—, —C(O)$NR_1$—, —$N(R_1)$—C(O)—, —$S(O_2)$—, —S(O)—, —S—, —C(O)— or —$S(O_2)$—$N(R_1)$—;

each $L_3$ is independently null, —O—, or —$N(R_1)$— each m is independently 0, 1, 2, 3, 4, 5 or 6;

each n is independently 0 or 1 or 2;

p is 0, 1, 2 or 3;

q is 0, 1, 2 or 3;

each r is independently 2, 3, or 4; and each s is independently 1, 2, 3, or 4.

In certain embodiments, the compounds have the structure of Formula I-R or a pharmaceutically acceptable isomer, enantiomer, salt, isotope, prodrug, hydrate or solvate thereof. In other embodiments, the compounds have the structure of Formula I-S or a pharmaceutically acceptable isomer, enantiomer, salt, isotope, prodrug, hydrate or solvate thereof.

In certain embodiments, the compounds can be substantially enantiomerically pure.

In certain embodiments, the invention provides a compound of Formula I-R and/or Formula I-S where A is pyrimidinyl optionally substituted with one or more of $R_4$. Representative compounds of this embodiment include compounds of the following structures (wherein "∿" represents either or both the R and S form of the compound):

I-R/S (1)

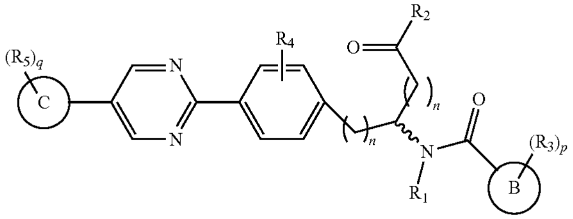

In certain embodiments, the invention provides a compound of Formula I-R and/or Formula I-S where A is pyridinyl optionally substituted with one or more of $R_4$. Representative compounds of this embodiment include compounds of the following structures (wherein "∿" represents either or both the R and S form of the compound):

I-R/S (2)

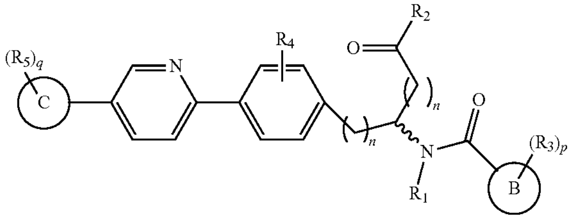

I-R/S (3)

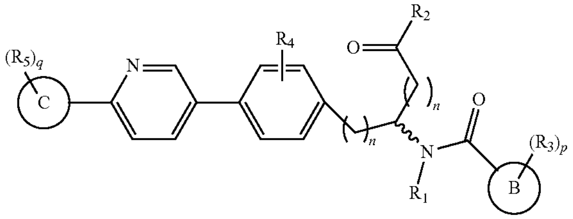

In certain embodiments, the invention provides a compound of Formula I-R and/or Formula I-S where A is pyridazinyl optionally substituted with one or more of $R_4$. Representative compounds of this embodiment include compounds of the following structures (wherein "∿" represents either or both the R and S form of the compound):

I-R/S (4)

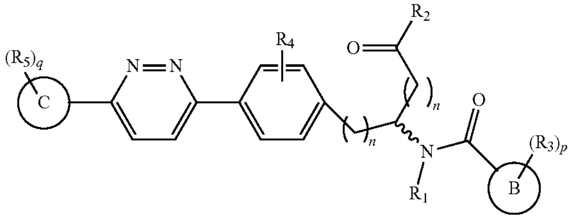

In certain embodiments, the invention provides a compound of Formula I-R and/or Formula I-S where A is pyrazinyl optionally substituted with one or more of $R_4$. Representative compounds of this embodiment include compounds of the following structures (wherein "∿" represents either or both the R and S form of the compound):

I-R/S (5)

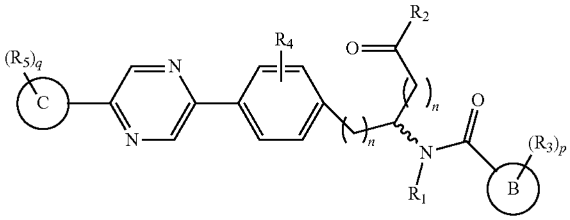

In certain embodiments, the invention provides compounds of each of structures I-R/S (1)-(5) where B is pyrimidinyl, pyrazolyl, pyridinyl or indolyl, and in further embodiments the invention provides compounds of each of structures I-R/S (1)-(5) where the B group is:

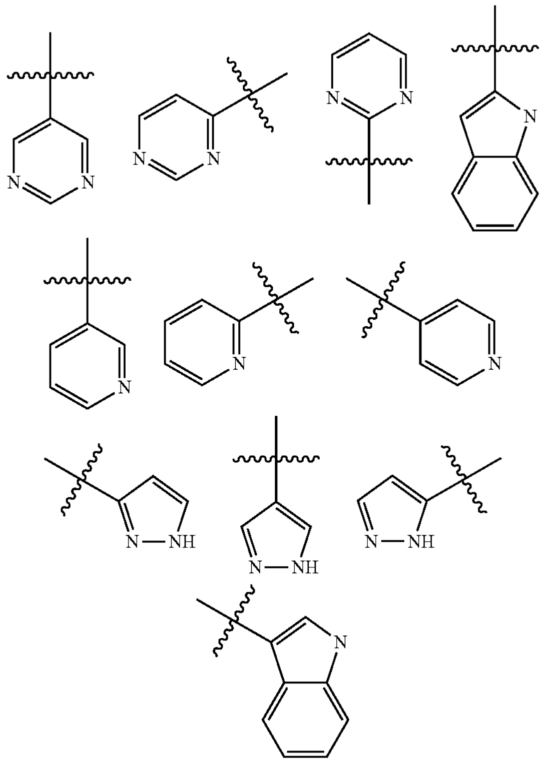

In certain embodiments, the invention provides compounds of each of structures I-R/S (1)-(5) where the B group is phenyl. Representative compounds of this embodiment include compounds of the following structures (wherein “~” represents either or both the R and S form of the compound):

I-R/S (7)

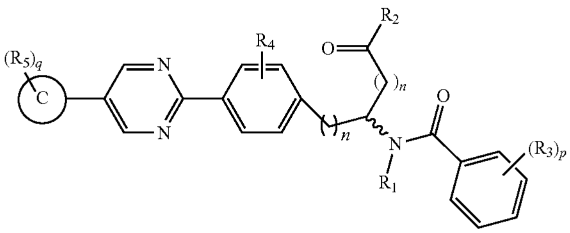

-continued

I-R/S (8)

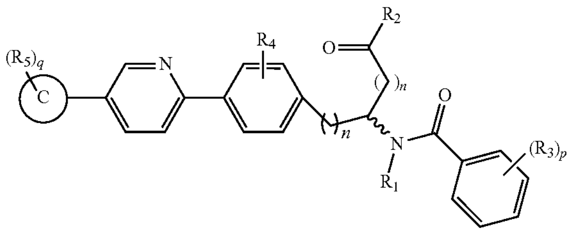

I-R/S (9)

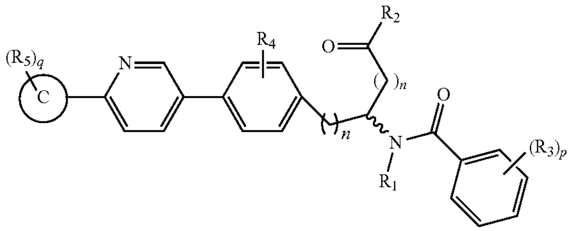

In certain embodiments, the invention provides compounds of each of structures I-R/S (7)-(9) where n is 0 or 1. Representative compounds of this embodiment include compounds of the following structures (wherein “~” represents either or both the R and S form of the compound):

I-R/S (10)

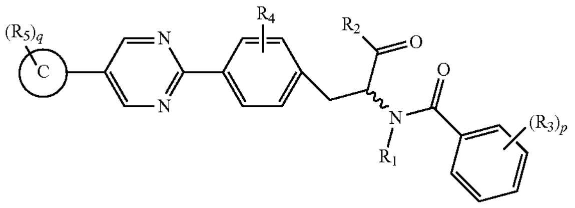

I-R/S (11)

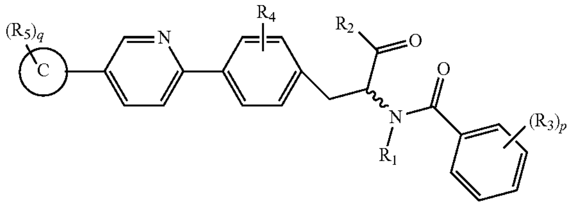

I-R/S (12)

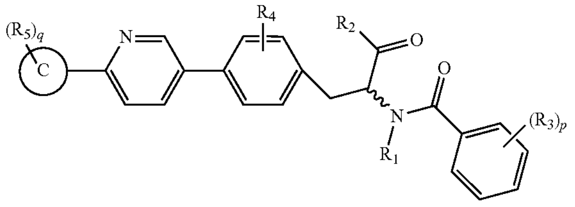

In certain embodiments, the invention provides compounds of each of structures I-R/S (1)-(3) where the B group is thiophenyl. Representative compounds of this embodiment include compounds of the following structures (wherein “~” represents either or both the R and S form of the compound):

I-R/S (13)

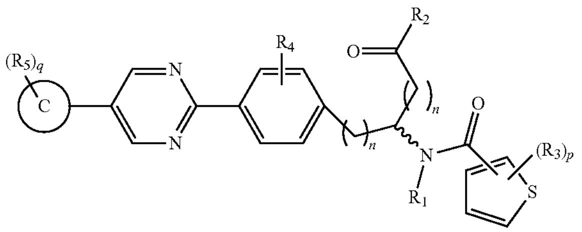

I-R/S (14)

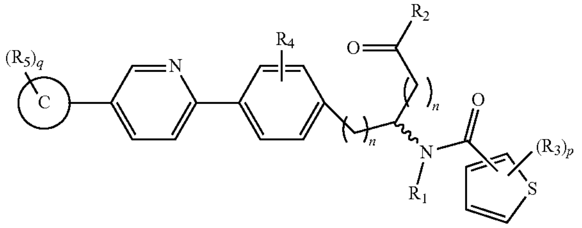

I-R/S (15)

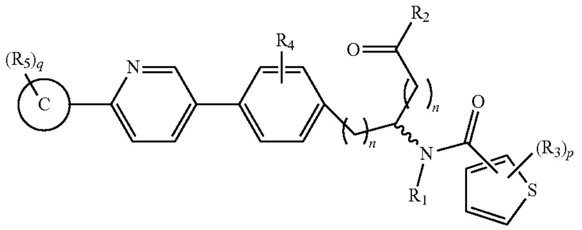

In certain embodiments, the invention provides compounds of each of structures I-R/S (13)-(15) where the B group is thiophen-2-yl. Representative compounds of this embodiment include compounds of the following structures (wherein "~" represents either or both the R and S form of the compound):

I-R/S (16)

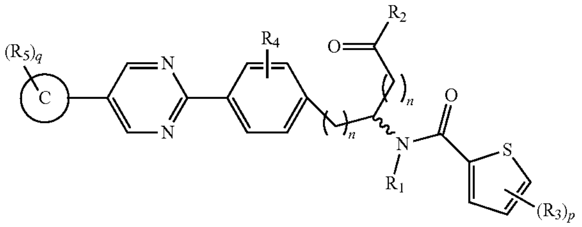

I-R/S (17)

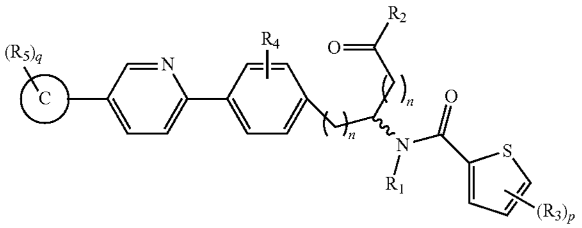

-continued

I-R/S (18)

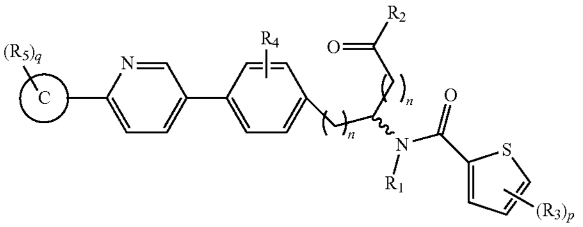

In certain embodiments, the invention provides compounds of each of structures I-R/S (16)-(18) where n is 0 or 1. Representative compounds of this embodiment include compounds of the following structures (wherein "~" represents either or both the R and S form of the compound):

I-R/S (19)

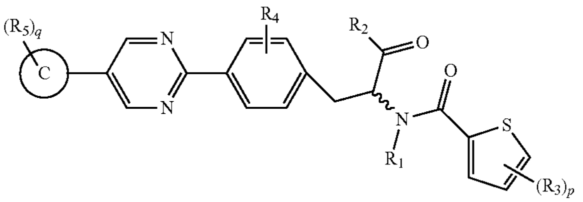

I-R/S (20)

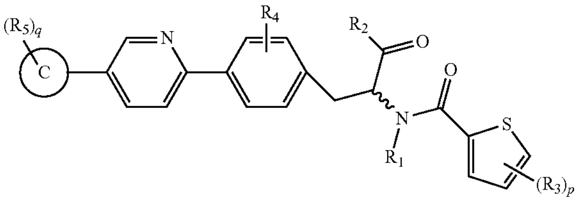

I-R/S (21)

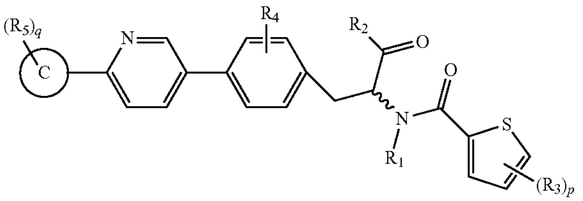

In certain embodiments, the invention provides compounds of each of structures I-R/S (1)-(21) where the C group is nonaromatic carbocyclyl.

In certain embodiments, the invention provides compounds of each of structures I-R/S (1)-(21) where the C group is cycloalkyl.

In certain embodiments, the invention provides compounds of each of structures I-R/S (1)-(21) where the C group is cycloalkenyl.

In certain embodiments, the invention provides compounds of each of structures I-R/S (1)-(21) where the C group is nonaromatic carbocyclylalkyl.

In certain embodiments, the invention provides compounds of each of structures I-R/S (1)-(21) where the C group is cycloalkylalkyl.

In certain embodiments, the invention provides compounds of each of structures I-R/S (1)-(21) where the C group is cycloalkenylalkyl.

In certain embodiments, the invention provides compounds of each of structures I-R/S (1)-(21) where the C group is:

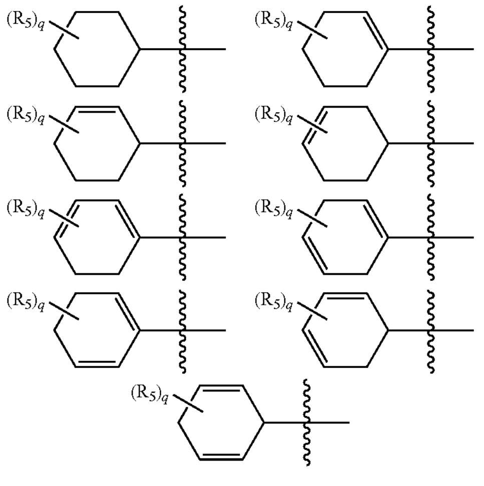

In certain embodiments, the invention provides compounds of structures I-R/S (22)-(23):

I-R/S (22)

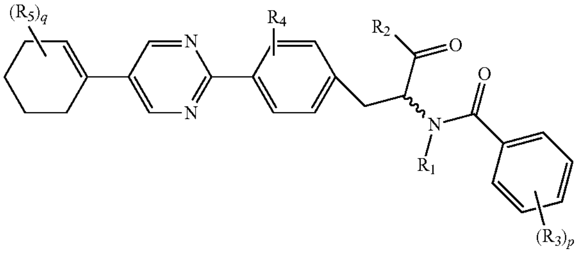

I-R/S (23)

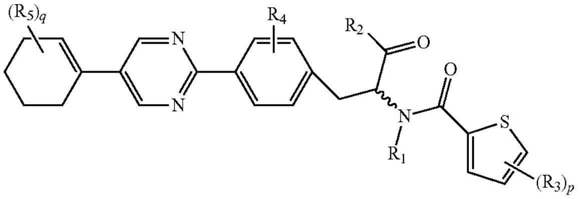

In certain embodiments, the invention provides compounds of each of structures I-R/S (1)-(23) where $R_1$ is H.

In certain embodiments, the invention provides compounds of each of structures I-R/S (1)-(23) where $R_4$ is H.

In certain embodiments, the invention provides compounds of each of structures I-R/S (1)-(23) where q is zero.

In certain embodiments, the invention provides compounds of each of structures I-R/S (1)-(23) where q is one, two or three.

In certain embodiments, the invention provides compounds of each of structures I-R/S (1)-(23) where q is one.

In certain embodiments, the invention provides compounds of structure I-R/S(1)-(23) where q is one and $R_5$ is $-(CR_aR_b)_m$-$L_2$-$(CR_aR_b)_m$—$R_7$ or —(-$L_3$-$(CR_aR_b)_r$-$)_s$-$L_3$-$R_7$.

In certain embodiments, the invention provides compounds of structure I-R/S(1)-(23) where q is one and $R_5$ is $R_7$.

In certain embodiments, the invention provides compounds of structure I-R/S(1)-(23) where q is one and $R_5$ is $R_7$ and $R_7$ is halo, alkyl, haloalkyl, perhaloalkyl, alkoxy, $-(CR_aR_b)_mOH$, $-(CR_aR_b)_mOR_8$, $-(CR_aR_b)_mCN$, $-(CR_aR_b)_mNH(C{=}NH)NH_2$, $-(CR_aR_b)_mNR_1R_8$, $-(CR_aR_b)_mO(CR_aR_b)_mR_8$, $-(CR_aR_b)_mNR_1(CR_aR_b)_mR_8$, $-(CR_aR_b)_mC(O)R_8$, $-(CR_aR_b)_mC(O)OR_8$, $-(CR_aR_b)_mC(O)NR_1R_8$, $-(CR_aR_b)_mNR_1(CR_aR_b)_mC(O)OR_8$, $-(CR_aR_b)_mNR_1C(O)R_8$, $-(CR_aR_b)_mC(O)NR_1R_8$, $-(CR_aR_b)_mSR_8$, $-(CR_aR_b)_mS(O)R_8$, $-(CR_aR_b)_mS(O)_2R_8$, $-(CR_aR_b)_mS(O)_2NR_1R_8$, $-(CR_aR_b)_mNR_1S(O)_2R_8$.

In certain embodiments, the invention provides compounds of structure I-R/S(1)-(23) where q is one and $R_5$ is $R_7$ and $R_7$ is a ring moiety selected from cycloalkyl, aryl, aralkyl, heterocyclyl or heterocyclylalkyl, where such ring moiety is optionally (singly or multiply) substituted with halo, —OH, —CN, alkyl, alkoxy, haloalkyl or perhaloalkyl.

In certain embodiments, the invention provides compounds of structure I-R/S(1)-(23) where q is one and $R_5$ is $R_7$ and $R_7$ is a ring moiety selected from cycloalkyl singly substituted with alkyl.

In certain embodiments, the invention provides compounds of structure I-R/S(1)-(23) where q is one and $R_5$ is $R_7$ and $R_7$ is a ring moiety selected from cycloalkyl singly substituted with a linear $C_{3-6}$alkyl.

In certain embodiments, the invention provides compounds of structure I-R/S(1)-(23) where p is one and $R_3$ is halo, alkyl, alkyl substituted with $R_{31}$, alkoxy, haloalkyl, perhaloalkyl, haloalkoxy, perhaloalkoxy, aryl, heterocyclyl, —OH, $-OR_7$, —CN, $-NO_2$, $-NR_1R_7$, $-C(O)R_7$, $-C(O)NR_1R_7$, $-NR_1C(O)R_7$, $-SR_7$, $-S(O)R_7$, $-S(O)_2R_7$, $-OS(O)_2R_7$, $-S(O)_2NR_1R_7$, $-NR_1S(O)_2R_7$, $-(CR_aR_b)_mNR_1R_7$, $-(CR_aR_b)_mO(CR_aR_b)_mR_7$, $-(CR_aR_b)_mNR_1(CR_aR_b)_mR_7$ or $-(CR_aR_b)_mNR_1(CR_aR_b)_mCOOR_8$.

In certain embodiments, the invention provides compounds of structure I-R/S(1)-(23) where p is one and $R_3$ is alkyl.

In certain embodiments, the invention provides compounds of structure I-R/S(1)-(23) where p is one and $R_3$ is t-butyl.

In certain embodiments, the invention provides compounds of structures I-R/S (24)-(25):

I-R/S (24)

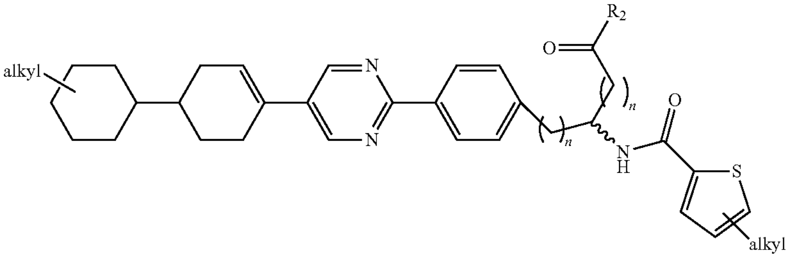

-continued

I-R/S (25)

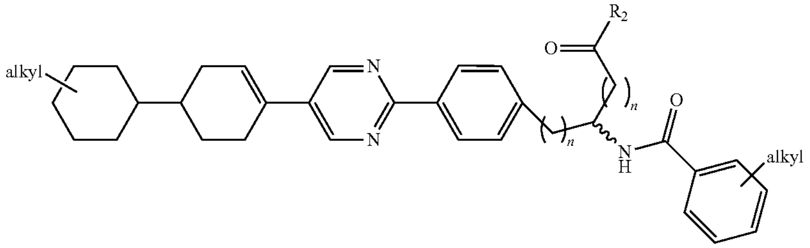

In certain embodiments, the invention provides compounds of structures I-R/S (26)-(27):

I-R/S (26)

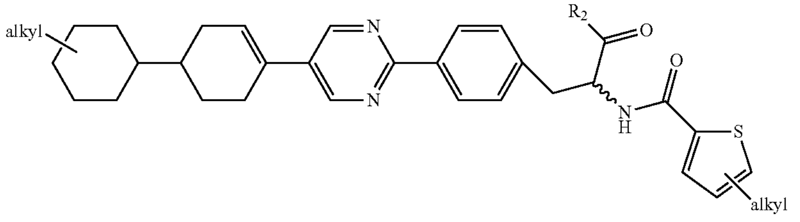

I-R/S (27)

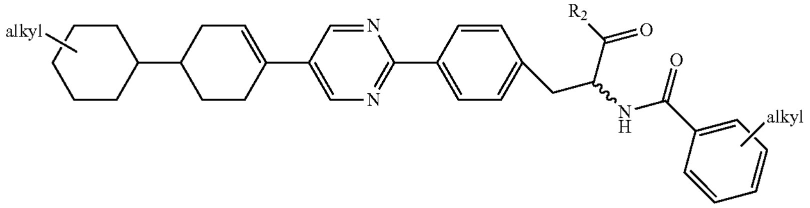

In certain embodiments, the invention provides compounds of structure I-R/S(24)-(27) where each depicted alkyl is a straight chain or branched alkyl, and in some embodiments is a $C_1$-$C_8$ straight chain or branched alkyl, such as methyl, ethyl, n-propyl, n-butyl, n-pentyl, n-hexyl, isopropyl, iso-butyl, sec-butyl or t-butyl.

In certain embodiments, the invention provides compounds of structure I-R/S(1)-(27) where $R_2$ is —OH.

In certain embodiments, the invention provides compounds of structure I-R/S(1)-(27) where $R_2$ is —N($R_1$)($CR_aR_b$)$_m$COO$R_8$.

In certain embodiments, the invention provides compounds of structure I-R/S(1)-(27) where $R_2$ is —N($R_1$)$SO_2R_7$.

In certain embodiments, the invention provides compounds of structure I-R/S(1)-(27) where $R_2$ is —NH$CH_2$COOH.

In certain embodiments, the invention provides compounds of structure I-R/S(1)-(27) where $R_2$ is —NH(CH$R_b$)COOH where $R_b$ is alkyl optionally substituted with $R_7$, —(CH$R_{40}$)$_m$O$R_{40}$, —(CH$R_{40}$)$_m$S$R_{40}$, —(CH$R_{40}$)$_m$N$R_{41}R_{42}$, —(CH$R_{40}$)$_m$C(O)N$R_{41}R_{42}$, —(CH$R_{40}$)$_m$C(O)N($R_1$)(CH$R_{40}$)$_m$N$R_{41}R_{42}$, —(CH$R_{40}$)$_m$C(O)N($R_1$)(CH$R_{40}$)$_m$C(O)N$R_{41}R_{42}$, —(CH$R_{40}$)$_m$C(O)N($R_1$)(CH$R_{40}$)$_m$C(O)O$R_{40}$ or —(CH$R_{40}$)$_m$—S—S—$R_{40}$.

In certain embodiments, the invention provides compounds of structure I-R/S(1)-(27) where $R_2$ is —NH($CR_aR_b$)$_m$COOH where $R_a$ and $R_b$ are independently H, alkyl optionally substituted with $R_7$, —(CH$R_{40}$)$_m$O$R_{40}$, —(CH$R_{40}$)$_m$S$R_{40}$, —(CH$R_{40}$)$_m$N$R_{41}R_{42}$, —(CH$R_{40}$)$_m$C(O)N$R_{41}R_{42}$, —(CH$R_{40}$)$_m$C(O)N($R_1$)(CH$R_{40}$)$_m$—N$R_{41}R_{42}$, —(CH$R_{40}$)$_m$C(O)N($R_1$)—(CH$R_{40}$)$_m$C(O)N$R_{41}R_{42}$, —(CH$R_{40}$)$_m$C(O)N($R_1$)(CH$R_{40}$)$_m$C(O)O$R_{40}$ or —(CH$R_{40}$)$_m$—S—S—$R_{40}$.

In certain embodiments, the invention provides compounds of structure I-R/S(1)-(27) where $R_2$ is —N$R_1$(CH$R_b$)$_m$COOH where $R_1$ and $R_b$ taken together form heterocyclyl.

In certain embodiments, the invention provides compounds of structure I-R/S(1)-(27) where $R_2$ is —N$R_1$($CR_aR_b$)$_m$COOH where $R_1$ and one of $R_b$ taken together form heterocyclyl.

In certain embodiments, the invention provides compounds of structure I-R/S(1)-(27) where $R_2$ is —N$R_1$($CR_aR_b$)$_m$COOH where any two $R_a$ and $R_b$ taken together with the carbon to which they are attached form a cycloalkyl.

In certain embodiments, the invention provides compounds of structure I-R/S(1)-(27) where $R_2$ is —NH($CR_aR_b$)$_m$COOH where one of $R_a$ and $R_b$ is H and the other $R_a$ and $R_b$ is aryl substituted with $R_7$.

In certain embodiments, the invention provides compounds of structure I-R/S(1)-(27) where $R_2$ is —N$R_1$ $(CR_aR_b)_mCOOH$, m is 2, $R_1$ is hydrogen, each occurrence of $R_a$ and $R_b$ are hydrogen, and $R_8$ is hydrogen:

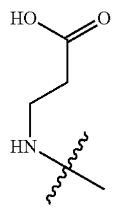
($R_2$-a)

In certain embodiments, the invention provides compounds of structure I-R/S(1)-(27) where $R_2$ is —$NR(CR_aR_b)_mCOOH$, m is 1 and $R_1$, $R_b$ and $R_8$ are hydrogen:

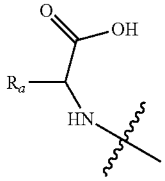
($R_2$-b)

In certain embodiments, the invention provides compounds of structure I-R/S(1)-(27) where $R_2$ is —$NR_1(CR_aR_b)_mCOOH$, m is 2, a single $R_a$ (i.e., one of the two) is hydrogen, each occurrence of $R_b$ is hydrogen, and $R_8$ is hydrogen:

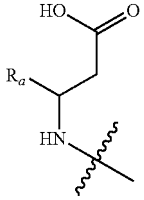
($R_2$-c)

In certain embodiments, the invention provides compounds of structure I-R/S(1)-(27) where $R_2$ is ($R_2$-b) or ($R_2$-c) where $R_a$ is alkyl optionally substituted with $R_7$, wherein alkyl includes straight and branched alkyl groups such as methyl, ethyl, n-propyl, iso-propyl, n-butyl, iso-butyl, sec-butyl and tert-butyl, as well as cycloalkyl groups such as cyclopropyl, cyclobutyl, cyclopentyl and cyclohexyl.

In certain embodiments, the invention provides compounds of structure I-R/S(1)-(27) where $R_2$ is ($R_2$-b) or ($R_2$-c) where $R_a$ is methyl, ethyl, n-propyl, iso-propyl, n-butyl, iso-butyl, sec-butyl or tert-butyl.

In certain embodiments, the invention provides compounds of structure I-R/S(1)-(27) where $R_2$ is ($R_2$-b) or ($R_2$-c) where $R_a$ is methyl.

In certain embodiments, the invention provides compounds of structure I-R/S(1)-(27) where $R_2$ is ($R_2$-b) or ($R_2$-c) where $R_a$ is cyclopropyl, cyclobutyl, cyclopentyl or cyclohexyl.

In certain embodiments, the invention provides compounds of structure I-R/S(1)-(27) where $R_2$ is ($R_2$-b) or ($R_2$-c) where $R_a$ is heterocycle or heterocyclylalkyl, either which may be optionally substituted with $R_7$.

In certain embodiments, the invention provides compounds of structure I-R/S(1)-(27) where $R_2$ is ($R_2$-b) or ($R_2$-c) where $R_a$ is heterocycle, such as pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, furanyl, tetrahydrofuranyl, tetrahydro-2H-pyranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl, any of which may be optionally substituted with $R_7$.

In certain embodiments, the invention provides compounds of structure I-R/S(1)-(27) where $R_2$ is ($R_2$-b) or ($R_2$-c) where $R_a$ is aryl or aralkyl, either of which may be optionally substituted with $R_7$.

In certain embodiments, the invention provides compounds of structure I-R/S(1)-(27) where $R_2$ is ($R_2$-b) or ($R_2$-c) where $R_a$ is aryl or aralkyl, such as phenyl or benzyl.

In certain embodiments, the invention provides compounds of structure I-R/S(1)-(27) where $R_2$ is ($R_2$-b) or ($R_2$-c) where $R_a$ is aryl or heteroaryl substituted with $R_7$.

In certain embodiments, the invention provides compounds of structure I-R/S(1)-(27) where $R_2$ is ($R_2$-b) or ($R_2$-c) where $R_a$ is phenyl or benzyl substituted with hydroxyl.

In certain embodiments, the invention provides compounds of structure I-R/S(1)-(27) where $R_2$ is ($R_2$-b) or ($R_2$-c) where $R_a$ is —$CH(OH)C_6H_5$.

In certain embodiments, the invention provides compounds of structure I-R/S(1)-(27) where $R_2$ is ($R_2$-b) or ($R_2$-c) where $R_a$ is —$(CHR_{40})_mC(O)OR_{40}$.

In certain embodiments, the invention provides compounds of structure I-R/S(1)-(27) where $R_2$ is ($R_2$-b) or ($R_2$-c) where $R_a$ is —$(CH_2)_mC(O)OH$.

In certain embodiments, the invention provides compounds of structure I-R/S(1)-(27) where $R_2$ is ($R_2$-b) or ($R_2$-c) where $R_a$ is —$(CHR_{40})_mOR_{40}$.

In certain embodiments, the invention provides compounds of structure I-R/S(1)-(27) where $R_2$ is ($R_2$-b) or ($R_2$-c) where $R_a$ is —$(CH_2)_mOH$.

In certain embodiments, the invention provides compounds of structure I-R/S(1)-(27) where $R_2$ is ($R_2$-b) or ($R_2$-c) where $R_a$ is —$CH_2OH$.

In certain embodiments, the invention provides compounds of structure I-R/S(1)-(27) where $R_2$ is ($R_2$-b) or ($R_2$-c) where $R_a$ is —$(CHR_{40})_mSR_{40}$.

In certain embodiments, the invention provides compounds of structure I-R/S(1)-(27) where $R_2$ is ($R_2$-b) or ($R_2$-c) where $R_a$ is —$(CH_2)_mSR_{40}$, where $R_{40}$ is H or alkyl.

In certain embodiments, the invention provides compounds of structure I-R/S(1)-(27) where $R_2$ is ($R_2$-b) or ($R_2$-c) where $R_a$ is —$(CHR_{40})_mNR_{41}R_{42}$.

In certain embodiments, the invention provides compounds of structure I-R/S(1)-(27) where $R_2$ is ($R_2$-b) or ($R_2$-c) where $R_a$ is —$(CH_2)_mNR_{41}R_{42}$.

In certain embodiments, the invention provides compounds of structure I-R/S(1)-(27) where $R_2$ is ($R_2$-b) or ($R_2$-c) where $R_a$ is —$(CHR_{40})_mC(O)NR_{41}R_{42}$.

In certain embodiments, the invention provides compounds of structure I-R/S(1)-(27) where $R_2$ is ($R_2$-b) or ($R_2$-c) where $R_a$ is $-(CH_2)_mC(O)NR_{41}R_{42}$.

In certain embodiments, the invention provides compounds of structure I-R/S(1)-(27) where $R_2$ is ($R_2$-b) or ($R_2$-c) where $R_a$ is $-CH_2C(O)NH_2$ or $-CH_2CH_2C(O)NH_2$ In certain embodiments, the invention provides compounds of structure I-R/S(1)-(27) where $R_2$ is ($R_2$-b) or ($R_2$-c) where $R_a$ is $-(CHR_{40})_mC(O)N(R_1)(CHR_{40})_mNR_{41}R_{42}$.

In certain embodiments, the invention provides compounds of structure I-R/S(1)-(27) where $R_2$ is ($R_2$-b) or ($R_2$-c) where $R_a$ is $-(CH_2)_mC(O)N(R_1)(CH_2)_mNR_{41}R_{42}$.

In certain embodiments, the invention provides compounds of structure I-R/S(1)-(27) where $R_2$ is ($R_2$-b) or ($R_2$-c) where $R_a$ is $-(CHR_{40})_mC(O)N(R_1)(CHR_{40})_mC(O)NR_{41}R_{42}$.

In certain embodiments, the invention provides compounds of structure I-R/S(1)-(27) where $R_2$ is ($R_2$-b) or ($R_2$-c) where $R_a$ is $-(CH_2)_mC(O)N(R_1)(CH_2)_mC(O)NR_{41}R_{42}$.

In certain embodiments, the invention provides compounds of structure I-R/S(1)-(27) where $R_2$ is ($R_2$-b) or ($R_2$-c) where $R_a$ is $-(CHR_{40})_mC(O)N(R_1)(CHR_{40})_mC(O)OR_{40}$.

In certain embodiments, the invention provides compounds of structure I-R/S(1)-(27) where $R_2$ is ($R_2$-b) or ($R_2$-c) where $R_a$ is $-(CH_2)_mC(O)N(R_1)(CH_2)_mC(O)OR_{40}$.

In certain embodiments, the invention provides compounds of structure I-R/S(1)-(27) where $R_2$ is ($R_2$-b) or ($R_2$-c) where $R_a$ is $-(CHR_{40})_m-S-S-R_{40}$.

In certain embodiments, the invention provides compounds of structure I-R/S(1)-(27) where $R_2$ is ($R_2$-b) or ($R_2$-c) where, within the $R_a$ group, $R_1$, $R_{40}$, $R_{41}$ and $R_{42}$ are hydrogen.

In certain embodiments, the invention provides compounds of structure I-R/S(1)-(27) where $R_2$ is ($R_2$-b) or ($R_2$-c) where, within the $R_a$ group, m is 1.

In certain embodiments, the invention provides compounds of structure I-R/S(1)-(27) where $R_2$ is ($R_2$-b) or ($R_2$-c) where, within the $R_a$ group, m is 2.

In certain embodiments, the invention provides compounds of structure I-R/S(1)-(27) where $R_2$ is $-N(R_1)(CR_aR_b)_mCOOR_8$ where m is 1, $R_8$ is hydrogen, $R_b$ is hydrogen and $R_1$ and $R_a$ taken together with the atoms to which they are attached form a heterocyclyl optionally substituted (singly or multiply) with $R_7$:

($R_2$-d)

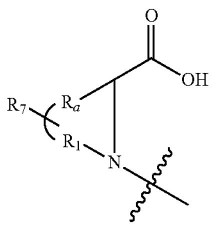

In certain embodiments, the invention provides compounds of structure I-R/S(1)-(27) where $R_2$ is $-N(R_1)(CR_aR_b)_mCOOR_8$ where m is 2, $R_8$ is hydrogen, $R_b$ of the second ($CR_aR_b$) group is hydrogen and $R_1$ and $R_a$ of the second ($CR_aR_b$) group taken together with the atoms to which they are attached form a heterocyclyl optionally substituted (singly or multiply) with $R_7$:

($R_2$-e)

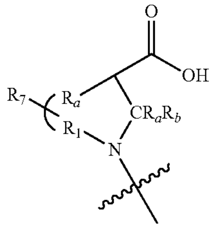

In certain embodiments, the invention provides compounds of structure I-R/S(1)-(27) where $R_2$ is ($R_2$-d) or ($R_2$-e) where $R_1$ and $R_a$ taken together with the atoms to which they are attached form azetidinyl, pyrrolindinyl or piperidinyl, each of which is optionally substituted (singly or multiply) with $R_7$. Representative compounds of this embodiment include compounds of structure I-R/S(1)-(27) where $R_2$ is:

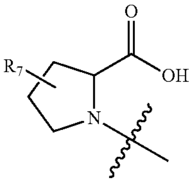

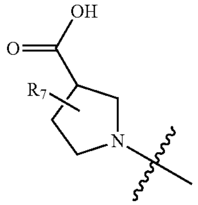

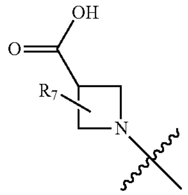

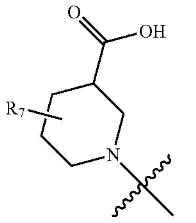

In certain embodiments, the invention provides compounds of structure I-R/S(1)-(27) where $R_2$ is $N(R_1)(R_{42})$:

(R2-f)

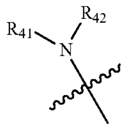

In certain embodiments, the invention provides compounds of structure I-R/S(1)-(27) where $R_2$ is ($R_2$-f) where $R_{41}$ and $R_{42}$ are independently $R_{40}$, $-(CHR_{40})_n-C(O)OR_{40}$, $-(CHR_{40})_n-C(O)R_{40}$, $-(CH_2)_nN(R_1)(R_7)$, aryl or heteroaryl, which aryl or heteroaryl is optionally substituted (singly or multiply) with $R_7$.

In certain embodiments, the invention provides compounds of structure I-R/S(1)-(27) where $R_2$ is ($R_2$-f) where $R_{41}$ is hydrogen and $R_{42}$ is alkyl optionally substituted (singly or multiply) with $R_7$.

In certain embodiments, the invention provides compounds of structure I-R/S(1)-(27) where $R_2$ is ($R_2$-f) where $R_{41}$ is hydrogen and $R_{42}$ is $-(CHR_{40})_nC(O)OR_{40}$.

In certain embodiments, the invention provides compounds of structure I-R/S(1)-(27) where $R_2$ is ($R_2$-f) where $R_{41}$ is hydrogen and $R_{42}$ is $-(CHR_{40})_nC(O)R_{40}$ In certain embodiments, the invention provides compounds of structure I-R/S(1)-(27) where $R_2$ is ($R_2$-f) where $R_{41}$ is hydrogen and $R_{42}$ is $-(CH_2)_nN(R_1)(R_7)$.

In certain embodiments, the invention provides compounds of structure I-R/S(1)-(27) where $R_2$ is ($R_2$-f) where $R_{41}$ is hydrogen and $R_{42}$ is aryl optionally substituted (singly or multiply) with $R_7$.

In certain embodiments, the invention provides compounds of structure I-R/S(1)-(27) where $R_2$ is ($R_2$-f) where $R_{41}$ is hydrogen and $R_{42}$ is heteroaryl optionally substituted (singly or multiply) with $R_7$.

In certain embodiments, the invention provides compounds of structure I-R/S(1)-(27) where $R_2$ is ($R_2$-f) where $R_{41}$ and $R_{42}$ taken together with the N atom to which they are attached form a 3- to 7-membered heterocyclyl optionally substituted (singly or multiply) with $R_7$.

In certain embodiments, the invention provides compounds of structure I-R/S(1)-(27) where $R_2$ is ($R_2$-f) where $R_{41}$ and $R_{42}$ taken together with the N atom to which they are attached form pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, piperidinyl, piperazinyl, morpholinyl, pyrrolyl, pyrazolyl, triazolyl, tetrazolyl, oxazolyl, isoxazolyl, thiazolyl or pyridinyl, any of which may be optionally substituted (singly or multiply) with $R_7$.

In certain embodiments, the invention provides compounds of structure I-R/S(1)-(27) where $R_2$ is $-N(R_1)(CR_aR_b)_mCON(R_1)(R_{40})$.

In certain embodiments, the invention provides compounds of structure I-R/S(1)-(27) where $R_2$ is $R_2$ is $-N(R_1)(CR_aR_b)_mCON(R_1)(R_{40})$ where m is 1, $R_b$ is hydrogen and $R_1$ and $R_a$ taken together with the atoms to which they are attached form a heterocyclyl optionally substituted (singly or multiply) with $R_7$:

($R_2$-g)

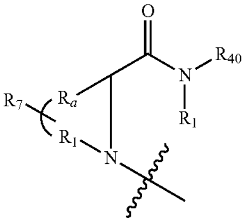

In certain embodiments, the invention provides compounds of structure I-R/S(1)-(27) where $R_2$ is $R_2$ is $-N(R_1)(CR_aR_b)_mCON(R_1)(R_{40})$ where m is 2, $R_b$ of the second $(CR_aR_b)$ group is hydrogen and $R_1$ and $R_a$ of the second $(CR_aR_b)$ group taken together with the atoms to which they are attached form a heterocyclyl optionally substituted (singly or multiply) with $R_7$:

($R_2$-h)

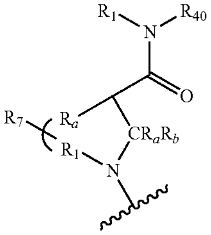

In certain embodiments, the invention provides compounds of structure I-R/S(1)-(27) where $R_2$ is ($R_2$-h) where $R_1$ and $R_a$ taken together with the atoms to which they are attached form azetidinyl, pyrrolindinyl, piperidinyl optionally substituted (singly or multiply) with $R_7$. Representative compounds of this embodiment include compounds of structure I-R/S(1)-(27) where $R_2$ is:

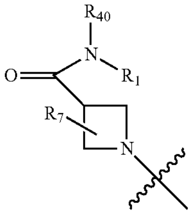

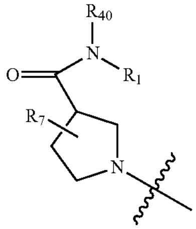

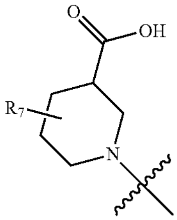

In certain embodiments, the invention provides compounds of structure I-R/S(1)-(27) where $R_2$ is $-N(R_1)(CR_aR_b)_mN(R_1)C(O)O(R_8)$.

In certain embodiments, the invention provides compounds of structure I-R/S(1)-(27) where $R_2$ is $-N(R_1)(CR_aR_b)_mN(R_1)(R_7)$.

In certain embodiments, the invention provides compounds of structure I-R/S(1)-(27) where $R_2$ is $-N(R_1)(CR_aR_b)_mCON(R_1)$heterocyclyl.

In certain embodiments, the invention provides compounds of structure I-R/S(1)-(27) where $R_2$ is $-N(R_1)(CR_aR_b)_m$-heterocyclyl, which heterocyclyl may be optionally substituted with $R_7$.

In certain embodiments, the invention provides a pharmaceutical composition comprising a compound of the invention together with at least one pharmaceutically acceptable carrier, diluent or excipient.

In certain embodiments, the invention provides a pharmaceutical composition comprising a compound of the invention and a second medicament. In certain of such embodiments, the second medicament is a GLP-1 agonist or a DPPIV inhibitor.

In certain embodiments, the invention provides a method of use of compounds of the invention for preparation of a medicament.

In certain embodiments, the invention provides a pharmaceutical combination comprising a compound of the invention and a second medicament. In various such embodiments, the second medicament is an agonist or modulator for glucagon receptor, GIP receptor, GLP-2 receptor, or PTH receptor, or glucagon-like peptide 1 (GLP-1) receptor. In various such embodiments, the second medicament is exenatide, liraglutide, taspoglutide, albiglutide, or lixisenatide or other insulin regulating peptide. In various such embodiments, the second medicament is a DPPIV inhibitor, such as sitagliptin. In various such embodiments, the second medicament is medically indicated for the treatment of type II diabetes. In various combinations, the second medicament is a sodium-glucose co-transporter (SGLT) inhibitor, such as a SGLT1 and/or SGLT2 inhibitor, including dapagliflozin, empagliflozin and canagliflozin. In various such embodiments, the second medicament is a biguanide such as metformin, a sulfonylurea such as glibenclamide, glipizide, gliclazide, and glimepiride, a meglitinide such as repaglinide and mateglinide, a thiazolidinedione such as pioglitazone and rosiglitazone, an α-glucosidase inhibitor such as acarbose and miglitol, a bile acid sequestrant such as colesevelam, and/or a dopamine-2 agonist such as bromocriptine.

In certain embodiments, the invention provides a pharmaceutical composition comprising a compound of the invention and a second medicament, wherein the second medicament is metformin.

In certain embodiments, the invention provides a pharmaceutical composition comprising a compound of the invention and a second medicament, wherein the second medicament is sitagliptin.

In certain embodiments, a method is provided for activation, potentiation or agonism of a glucagon-like peptide 1 comprising contacting the receptor with an effective amount of a compound, pharmaceutical composition or pharmaceutical combination of the invention.

In further embodiments, a method is provided for activation or agonism of a GLP-1 receptor by contacting the receptor with an effective amount of an invention compound and GLP-1 peptides GLP-1(9-36) and GLP-1(7-36), pharmaceutical composition or pharmaceutical combination, wherein the GLP-1 receptor is disposed within a living mammal; in certain embodiments wherein such mammal is a human.

In certain embodiments, a method is provided for treatment of a malcondition in a subject for which activation, potentiation or agonism of a GLP-1 receptor is medically indicated, by administering an effective amount of an invention compound to the subject at a frequency and for a duration of time sufficient to provide a beneficial effect to the patient. In yet further embodiments, a method is provided for treatment of a malcondition in a patient for which activation, potentiation, or agonism of a GLP-1 receptor is medically indicated, by administering an effective amount of an invention compound to the patient at a frequency and for a duration of time sufficient to provide a beneficial effect to the patient, wherein the malcondition comprises type I diabetes, type II diabetes, gestational diabetes, obesity, excessive appetite, insufficient satiety, or metabolic disorder. In certain embodiments, the subject is a patient or a human being. In certain embodiments, the human being is afflicted with, or at risk of developing, a disease or condition selected from the group consisting of type I diabetes, type II diabetes, gestational diabetes, obesity, excessive appetite, insufficient satiety, and metabolic disorder. In certain of such embodiments, said disease is type I diabetes or type II diabetes.

In certain embodiments, the invention provides methods for synthesis of certain compounds including compounds of the invention as more fully illustrated herein. In certain other embodiments, the invention provides certain intermediate compounds associated with such methods of synthesis as illustrated herein.

In certain embodiments, methods are provided for use of an invention compound for preparation of a medicament adapted for treatment of a disorder or a malcondition wherein activation or inhibition of a GLP-1 receptor is medically indicated. In certain embodiments, the malcondition comprises type I diabetes, type II diabetes, gestational diabetes, obesity, excessive appetite, insufficient satiety, and metabolic disorder. Preferably said disease is type I diabetes or type II diabetes.

In certain embodiments, the method additionally comprises administering to the subject a second medicament selected from the group of biguanides, peptidic GLP-1 agonists and DPPIV inhibitors, wherein such second medicament is either a component of the pharmaceutical composition or a second pharmaceutical composition. In certain of such embodiments, the second medicament can be metformin, exenatide or sitagliptin.

As used in the specification and the appended claims, the singular forms "a," "an" and "the" include plural referents unless the context clearly dictates otherwise.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

As used herein, "individual" (as in the subject of the treatment) means both mammals and non-mammals. Mammals include, for example, humans; non-human primates, e.g., apes and monkeys; cattle; horses; sheep; and goats. Non-mammals include, for example, fish and birds.

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist." Certain molecules bind to receptors at locations other than the binding sites of their natural ligands and such allosteric binding molecules may potentiate, activate or agonize the receptor and may enhance the effect of a natural ligand or a co-administered ligand.

A "GLP-1 compound" or "GLP-1 agonist" or "GLP-1 activator" or "GLP-1 inhibitor" or "GLP-1 antagonist" or "GLP-1 potentiator" or "GLP-1 modulator" as the terms are used herein refer to compounds that interact in some way with the GLP-1 receptor. They can be agonists, potentiators, or activators, or they can be antagonists or inhibitors. A "GLP-1 compound" of the invention can be selective for action of the GLP-1 receptor family.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Substantially enantiomerically or diasteromerically" pure means a level of enantiomeric or diasteromeric enrichment of one enantiomer with respect to the other enantiomer or diasteromer of at least about 80%, and more preferably in excess of 80%, 85%, 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by GLP-1 refers to the amount of a compound of the invention that is effective to bind to as an agonist or as an antagonist a GLP-1 receptor in the individual's tissues, wherein the GLP-1 is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of GLP-1 activity. A therapeutically effective amount is also one in which any toxic or detrimental effects of compounds of the invention are outweighed by the therapeutically beneficial effects. For example, in the context of treating a malcondition mediated by activation of a GLP-1 receptor, a therapeutically effective amount of a GLP-1 receptor agonist of the invention is an amount sufficient to control the malcondition, to mitigate the progress of the malcondition, or to relieve the symptoms of the malcondition. Examples of malconditions that can be so treated include, but not limited to, type II diabetes.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

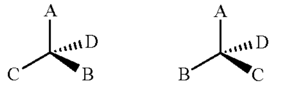

(R) configuration (S) configuration

"Isolated optical isomer" means a compound which has been substantially purified from the corresponding optical isomer(s) of the same formula. Preferably, the isolated isomer is at least about 80%, and preferably at least 80% or even at least 85% pure. In other embodiments, the isolated isomer is at least 90% pure or at least 98% pure, or at least about 99% pure, by weight.

Enantiomers are sometimes called optical isomers because a pure enantiomer rotates plane-polarized light in a particular direction. If the light rotates clockwise, then that enantiomer is labeled "(+)" or "d" for dextrorotatory, its counterpart will rotate the light counterclockwise and is labeled "(−)" or "1" for levorotatory.

The terms "racemate" and "racemic mixture" are frequently used interchangeably. A racemate is an equal mixture of two enantiomers. A racemate is labeled "(±)" because it is not optically active (i.e., will not rotate plane-polarized light in either direction since its constituent enantiomers cancel each other out).

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species, example shown below. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of compounds of the invention which are biologically active in the treatment of type I diabetes, type II diabetes, gestational diabetes, obesity, excessive appetite, insufficient satiety, or metabolic disorder

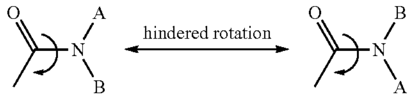

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds. Further, isotopes of the atoms depicted (such as deuterium and tritium in the case of hydrogen) are encompassed within the scope of this invention. For example, it should be understood that depiction herein of compounds having one or more hydrogen atoms is intended to encompass compounds having such hydrogen atoms replaced with deuterium (or tritium) at one or more locations. Such "deuterated compounds", whether partial (i.e., less than all the hydrogen atoms replaced with deuterium) or complete (i.e., all hydrogen atoms replaced with deuterium) are within the scope of the compounds of this invention.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, $CF_3$, $OCF_3$, R', O, S, C(O), S(O), methylenedioxy, ethylenedioxy, N(R')$_2$, SR', SOR', $SO_2$R', $SO_2$N(R')$_2$, $SO_3$R', C(O)R', C(O)C(O)R', C(O)$CH_2$C(O)R', C(S)R', C(O)OR', OC(O)R', C(O)N(R')$_2$, OC(O)N(R')$_2$, C(S)N(R')$_2$, $(CH_2)_{0-2}$NHC(O)R', $(CH_2)_{0-2}$N(R')N(R')$_2$, N(R')N(R')C(O)R', N(R')N(R')C(O)OR', N(R')N(R')CON(R')$_2$, N(R')$SO_2$R', N(R')$SO_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups include substituted aryl, heterocyclyl and heteroaryl groups. Substituted ring groups can be substituted by one or more substituents at any available ring position. In some embodiments, two substituents on a substituted ring group may taken together with the ring to which they are attached to form a ring, such that the two rings are fused together. For example, benzodioxolyl is a fused ring system formed by two substituents taken together on a phenyl group.

Such substituted ring groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S,"or "[variable] is O, S . . . " are used, they are understood to encompass all of the sulfide, sulfoxide and sulfone oxidation states of sulfur.

"Alkyl" groups include straight chain and branched alkyl groups and cycloalkyl groups having from 1 to about 20 carbon atoms, and typically from 1 to 12 carbons ($C_1$-$C_{12}$ alkyl), or, in some embodiments, from 1 to 8 carbon atoms ($C_1$-$C_8$ alkyl), or, in some embodiments, from 1 to 4 carbon atoms ($C_1$-$C_4$ alkyl). In the case of cycloalkyl groups, such groups have from 3-20 carbon atoms. Examples of straight chain alkyl groups include, but are not limited to, methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Alkyl groups as used herein may optionally include one or more further substituent groups. Representative substituted alkyl groups can be substituted one or more times with any of the groups listed above, for example, amino, hydroxy, cyano, carboxy, nitro, thio, alkoxy, and halogen groups.

"Alkenyl" groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH=CH$_2$, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, —CH=CHCH$_2$CH$_3$, —CH=CH(CH$_2$)$_2$CH$_3$, —CH=CH(CH$_2$)$_3$CH$_3$, —CH=CH(CH$_2$)$_4$CH$_3$, vinyl, cyclohexenyl, cyclopentenyl, cyclohexadienyl, butadienyl, pentadienyl, and hexadienyl among others.

"Alkynyl" groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$), among others.

"Cycloalkyl" groups are alkyl groups forming a ring structure, which can be substituted or unsubstituted, wherein the ring is either completely saturated, partially unsaturated, or fully unsaturated, wherein if there is unsaturation, the conjugation of the pi-electrons in the ring do not give rise to aromaticity. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted one or more times with any of the groups listed above, for example, but not limited to, amino, hydroxy, cyano, carboxy, nitro, thio, alkoxy, and halogen groups.

"(Cycloalkyl)alkyl" groups, also referred to as "cycloalkylalkyl", are alkyl groups as defined above in which a hydrogen or carbon bond of the alkyl group is replaced with a bond to a cycloalkyl group as defined above.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups, as well as polycyclic and/or bridging ring systems such as adamantine.

"(Cycloalkenyl)alkyl" groups, also referred to as "cycloalkylalkyl", are alkyl groups as defined above in which a hydrogen or carbon bond of the alkyl group is replaced with a bond to a cycloalkenyl group as defined above.

The terms "carbocyclic" and "carbocyclyl" denote a ring structure wherein the atoms of the ring are carbon. In some embodiments, the carbocyclyl has 3 to 8 ring members, whereas in other embodiments the number of ring carbon atoms is 4, 5, 6, or 7. Carbocyclyl includes, for example, cycloalkyl and cycloalkenyl. Unless specifically indicated to the contrary, the carbocyclic ring can be substituted with as many as N substituents wherein N is the size of the carbocyclic ring with for example, amino, hydroxy, cyano, carboxy, nitro, thio, alkyl, alkoxy, and halogen groups.

"(Carbocyclyl)alkyl" groups, also referred to as "carbocyclylalkyls", are alkyl groups as defined above in which a hydrogen or carbon bond of the alkyl group is replaced with a bond to a carbocyclyl as defined above.

A "nonaromatic carbocyclyl" or a "nonaromatic carbocyclylalkyl" is a group in which the carbocyclic ring of the carbocyclyl or carbocyclylalkyl is a completely saturated, a partially unsaturated, or a fully unsaturated carbocyclyl, wherein if there is unsaturation, the conjugation of the pi-electrons of the carbocyclic ring do not give rise to aromaticity.

"Aryl" groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

"Aralkyl" groups are alkyl, alkenyl or alkynyl groups as defined above in which a hydrogen atom of an alkyl, alkenyl or alkynyl group is replaced with an aryl group as defined above. Representative aralkyl groups include benzyl ($-CH_2$phenyl), phenylethyl ($-CH_2CH_2$phenyl) and phenylethylene ($-CH{=}CH$phenyl) groups and fused (cycloalkylaryl)alkyl groups such as 4-ethyl-indanyl. The aryl moiety or the alkyl, alkenyl or alkynyl moiety or both are optionally substituted with other groups, including but not limited to alkyl, halo, amino, hydroxy, cyano, carboxy, nitro, thio, or alkoxy groups.

"Heterocyclyl" or "heterocyclic" groups include aromatic and non-aromatic ring moieties containing 3 or more ring members, of which one or more is a heteroatom such as, but not limited to, N, O, S, or P. In some embodiments, heterocyclyl groups include 3 to 20 ring members, whereas other such groups have 3 to 15 ring members, including for example single ring systems containing 5, 6 or 7 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-ring with two carbon atoms and three heteroatoms, a 6-ring with two carbon atoms and four heteroatoms, and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms.

The term "heterocyclyl" includes fused ring species including those having fused aromatic and non-aromatic groups. The phrase also includes polycyclic and/or bridging ring systems containing a heteroatom such as, but not limited to, quinuclidyl and 7-azabicyclo[2.2.1]heptane, and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrazinyl, pyrimidinyl, pyridazinyl, thiadiazolyl, oxadiazolyl, imidazolinyl, hexahydropyrimidinyl, diazepanyl, triazinyl, imidazolyl, pyrrolidinyl, furanyl, tetrahydrofuranyl, tetrahydro-2H-pyranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups, and in the case of two substituents on the same carbon atom of the heterocycle include oxo (=O) and thioxo (=S).

"Heteroaryl" groups are aromatic ring moieties containing 5 or more ring members, of which, one or more is a heteroatom such as, but not limited to, N, O, and S. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, pyridinyl, pyridazinyl, pyrimidyl, pyrazyl, pyrazinyl, pyrimidinyl, thiadiazolyl, imidazolyl, oxadiazolyl, thienyl, triazolyl, tetrazolyl, triazinyl, thiazolyl, thiophenyl, oxazolyl, isoxazolyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl(1-anthracenyl, 2-anthracenyl, 3-anthracenyl), thiophenyl(2-thienyl, 3-thienyl), furyl(2-furyl, 3-furyl), indolyl, oxadiazolyl(1,2,4-oxadiazolyl, 1,3,4-oxadiazolyl), thiadiazolyl(1,2,4-thiadiazolyl, 1,3,4-thiadiazolyl), isoxazolyl, quinazolinyl, fluorenyl, xanthenyl, isoindanyl, benzhydryl, acridinyl, thiazolyl, pyrrolyl(2-pyrrolyl), pyrazolyl(3-pyrazolyl), imidazolyl(1-imidazolyl, 2-imidazolyl, 4-imidazolyl, 5-imidazolyl), triazolyl (1,2,3-triazol-1-yl, 1,2,3-triazol-2-yl, 1,2,3-triazol-4-yl, 1,2,4-triazol-3-yl), oxazolyl(2-oxazolyl, 4-oxazolyl, 5-oxazolyl), thiazolyl(2-thiazolyl, 4-thiazolyl, 5-thiazolyl), pyridyl(2-pyridyl, 3-pyridyl, 4-pyridyl, pyrimidinyl(2-pyrimidinyl, 4-pyrimidinyl, 5-pyrimidinyl, 6pyrimidinyl), pyrazinyl, pyridazinyl(3-pyridazinyl, 4-pyridazinyl, 5-pyridazinyl), prazolo[1,5-a]pyridinyl, quinolyl(2-quinolyl, 3-quinolyl, 4-quinolyl, 5-quinolyl, 6-quinolyl, 7-quinolyl, 8-quinolyl), isoquinolyl(1-isoquinolyl, 3-isoquinolyl, 4-isoquinolyl, 5-isoquinolyl, 6-isoquinolyl, 7-isoquinolyl, 8-isoquinolyl), benzo[b]furanyl(2-benzo[b]furanyl, 3-benzo[b]furanyl, 4-benzo[b]furanyl, 5-benzo[b]furanyl, 6-benzo[b]furanyl, 7-benzo[b]furanyl), isobenzofuranyl, 2,3-dihydro-benzo[b]furanyl(2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl(2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl(1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl(1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl(1-benzothiazolyl, 2-benzothiazolyl, 4-benzothiazolyl, 5-benzothiazolyl, 6-benzothiazolyl, 7-benzothiazolyl), benzo[d]isoxazolyl, carbazolyl(1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl, alkenyl or alkynyl groups as defined above in which a hydrogen or carbon bond of an alkyl, alkenyl or alkynyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl(β-picolyl), pyridine-4-yl methyl(γ-picolyl), tetrahydrofuran-2-yl ethyl, and indol-2-yl propyl. Heterocyclylalkyl groups can be substituted on the heterocyclyl moiety, the alkyl, alkenyl or alkynyl moiety, or both.

"Heteroarylalkyl" groups are alkyl, alkenyl or alkynyl groups as defined above in which a hydrogen or carbon bond of an alkyl, alkenyl or alkynyl group is replaced with a bond to a heteroaryl group as defined above. Heteroarylalkyl groups can be substituted on the heteroaryl moiety, the alkyl, alkenyl or alkynyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocyclic, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

When two "R" groups are said to be joined together or taken together to form a ring, it is meant that together with the carbon atom or a non-carbon atom (e.g., nitrogen atom), to which they are bonded, they may form a ring system. In general, they are bonded to one another to form a 3- to 7-membered ring, or a 5- to 7-membered ring. Non-limiting specific examples are the cyclopentyl, cyclohexyl, cycloheptyl, piperidinyl, piperazinyl, pyrolidinyl, pyrrolyl, pyridinyl.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, n-heptyloxy, n-octyloxy n-nonyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each. Accordingly, any compound substituted with an amino group can be viewed as an amine.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)$NR_2$, and —NRC(O)R groups, respectively. Amide groups therefore include but are not limited to carbamoyl groups (—C(O)$NH_2$) and formamide groups (—NHC(O)H). A "carboxamido" group is a group of the formula C(O)$NR_2$, wherein R can be H, alkyl, aryl, etc.

The term "carbonyl," refers to a —C(O)— group.

"Halo," "halogen," and "halide" include fluorine, chlorine, bromine and iodine.

The term "perhaloalkyl" refers to an alkyl group where all of the hydrogen atoms are replaced by halogen atoms. Perhaloalkyl groups include, but are not limited to, —$CF_3$ and —C($CF_3$)$_3$. The term "haloalkyl" refers to an alkyl group where some but not necessarily all of the hydrogen atoms are replaced by halogen atoms. Haloalkyl groups include but are not limited to —$CHF_2$ and —$CH_2F$.

The term "perhaloalkoxy" refers to an alkoxy group where all of the hydrogen atoms are replaced by halogen atoms. Perhaloalkoxy groups include, but are not limited to, —$OCF_3$ and —OC($CF_3$)$_3$. The term "haloalkoxy" refers to an alkoxy group where some but not necessarily all of the hydrogen atoms are replaced by halogen atoms. Haloalkoxy groups include but are not limited to —$OCHF_2$ and —$OCH_2F$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, panthothenic, trifluoromethanesulfonic, 2-hydroxyethanesulfonic, p-toluenesulfonic, sulfanilic, cyclohexylaminosulfonic, stearic, alginic, 3-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula I compounds, for example in their purification by recrystallization. All of these salts may be prepared by conventional means from the corresponding compound according to Formula I by reacting, for example, the appropriate acid or base with the compound according to Formula I. The term "pharmaceutically acceptable salts" refers to nontoxic inorganic or organic acid and/or base addition salts, see, for example, Lit et al., Salt Selection for Basic Drugs (1986), *Int J Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals.

"Isotopes" are well known in the art and refer to atoms with the same number of protons but different number of neutrons. For example, carbon 12, the most common form of carbon, has six protons and six neutrons, whereas carbon 14 has six protons and eight neutrons.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

The GLP-1 compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g., intravenous, oral, topical, suppository, or parenteral).

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another GLP-1agonist or another type of therapeutic agent or second medicament, or both. Non-limiting examples of the GLP-1 receptor agonists include exenatide, liraglutide, taspoglutide, albiglutide, lixisenatide, and mixtures thereof.

In one embodiment, the GLP-1agonist is exenatide (Byetta®) or Byetta LAR®. Exenatide is described, for example, in U.S. Pat. Nos. 5,424,286; 6,902,744; 7,297,761, and others, the contents of each of which is herein incorporated by reference in its entirety.

In one embodiment, the GLP-1agonist is liraglutide (VICTOZA®) (also called NN-2211 and [Arg34, Lys26]-(N-epsilon-(gamma-Glu(N-alpha-hexadecanoyl))-GLP-1 (7-37)), includes the sequence HAEGTFTSDVSSYLEGQAAKEFIAWKVRGRG (SEQ ID NO: 1) and is available from Novo Nordisk (Denmark) or Scios (Fremont, Calif. USA). See, e.g., Elbrond et al., 2002, Diabetes Care. August; 25(8):1398404; Agerso et al., 2002, Diabetologia. February; 45(2): 195-202).

In one embodiment, the GLP-1agonist is taspoglutide (CAS Registry No. 275371-94-3) and is available from Hoffman La-Roche. See, for example, U.S. Pat. No. 7,368, 427, the contents of which are herein incorporated by reference in its entirety.

In one embodiment, the GLP-1 agonist isalbiglutide (SYNCRIA® from GlaxoSmithKline).

In another embodiment, the GLP-1 agonist is lixisenatide (Lyxumia® from Sanofi-Aventis/Zealand Pharma).

Non-limiting examples of the second medicaments are as disclosed above. In various such embodiments, the second medicament is exenatide, liraglutide, taspoglutide, albiglutide, or lixisenatide or other insulin regulating peptide. In various such embodiments, the second medicament is a DPPIV inhibitor. In various such embodiments, the second medicament is medically indicated for the treatment of type II diabetes. In various such embodiments, the second medicament is a biguanide, a sulfonylurea, a meglitinide, a thiazolidinedione, an α-glucosidase inhibitor, a bile acid sequestrant, and/or a dopamine-2 agonist.

In another embodiment, the second medicament is metformin.

In another embodiment, the second medicament is sitagliptin.

As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g., as described in Remington: *The Science and Practice of Pharmacy,* 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician. Dosing regimens include, for example, dose titration to the extent necessary or useful for the indication to be treated, thus allowing the patient's body to adapt to the treatment and/or to minimize or avoid unwanted side effects associated with the treatment. Other dosage forms include delayed or controlled-release forms. Suitable dosage regimens and/or forms include those set out, for example, in the latest edition of the *Physicians' Desk Reference*, incorporated herein by reference.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g., specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other GLP-1 modulators and/or ii) one or more other types of therapeutic agents or second medicaments which can be administered orally in the same dosage form, in a separate oral dosage form (e.g., sequentially or non-sequentially) or by injection together or separately (e.g., sequentially or non-sequentially). Examples of combination therapeutic agents include Metformin, Sitagliptin (MK-0431, Januvia) an oral antihyperglycemic (antidiabetic drug) of the dipeptidyl peptidase-4 (DPP-4) inhibitor class and Exenatide (Byetta) an incretin mimetic. In other embodiments, the second medicament is a biguanide such as metformin, a sulfonylurea such as glibenclamide, glipizide, gliclazide, and glimepiride, a meglitinide such as repaglinide and nateglinide, a thiazolidinedione such as pioglitazone and rosiglitazone, an α-glucosidase inhibitor such as acarbose and miglitol, a bile acid sequestrant such as colesevelam, and/or a dopamine-2 agonist such as bromocriptine.

Combinations of the invention include mixtures of compounds from i) and ii) in a single formulation and compounds from i) and ii) as separate formulations. Some combinations of the invention can be packaged as separate formulations in a kit. In some embodiments, two or more compounds from ii) are formulated together while a compound of the invention is formulated separately.

The dosages and formulations for the other agents to be employed, where applicable, will be as set out in the latest edition of the *Physicians' Desk Reference*, incorporated herein by reference.

In certain embodiments, the present invention encompasses compounds that bind with high affinity and specificity to the GLP-1 receptor in an agonist manner or as an activator or a potentiator. In certain embodiments a compound of the invention acts as a positive allosteric modulator of GLP-1 receptor.

In certain embodiments, the present invention provides a method for activating, potentiating, or agonizing (i.e., to have an agonic effect, to act as an agonist) a GLP-1 receptor, with a compound of the invention. The method involves contacting the receptor with a suitable concentration of an inventive compound to bring about activation of the receptor. The contacting can take place in vitro, for example in carrying out an assay to determine the GLP-1 receptor activation activity of an inventive compound undergoing experimentation related to a submission for regulatory approval.

In certain embodiments, the method for activating a GLP-1 receptor, can also be carried out in vivo, that is, within the living body of a mammal, such as a human patient or a test animal. The inventive compound can be supplied to the living organism via one of the routes as described above, e.g., orally, or can be provided locally within the body tissues. In the presence of the inventive compound, activation of the receptor takes place, and the effect thereof can be studied.

An embodiment of the present invention provides a method of treatment of a malcondition in a patient for which activation of an GLP-1 receptor is medically indicated, wherein the patient is administered the inventive compound in a dosage, at a frequency, and for a duration to produce a beneficial effect on the patient. The inventive compound can be administered by any suitable means, examples of which are described above.

In certain embodiments, the present invention is directed to compounds adapted to act as modulators or potentiators of Class B GPCRs. These compounds may have activity on their own or in the presence of receptor ligands. Receptors include incretin peptides including GLP-1(7-36) and GLP-1(9-36).

Methods of treatments provided by the invention include administration of a compound of the invention, alone or in combination with another pharmacologically active agent or second medicament to a subject or patient having a malcondition for which activation, potentiation or agonism of a glucagon-like peptide 1 receptor is medically indicated such as type I diabetes, type II diabetes, gestational diabetes, obesity, excessive appetite, insufficient satiety, or metabolic disorder.

In another embodiment, methods of treatment provided by the invention include administration of a compound of the invention for the treatment of non-alcoholic fatty liver disease (NAFLD) and/or non-alcoholic steatohepatitis (NASH). NAFLD is believed to be caused by the disruption of hepatic lipid homeostasis and, at least in a portion of patients, can progress to NASH. NAFLD is associated with insulin resistance in type 2 diabetes mellitus, and GLP1 increases insulin sensitivity and aids glucose metabolism. The compounds of this invention are beneficial in this context by serving to increase fatty acid oxidation, decrease lipogenesis, and/or improve hepatic glucose metabolism (see e.g., Lee et. al., Diabetes Metab. J. 36:262-267, 2012; Trevaskis et al. Am. J. Physiol. Gastrointest. Liver Physiol. 302:G762-G772, 2012; Kim et al. Korean J. Physiol. Pharmacol. 18:333-339, 2014; and see: Armstrong et. al., Journal of Hepatology 62:S187-S212, 2015 for results with Liraglutide in Phase II trials).

General Synthetic Methods for Preparing Compounds

Molecular embodiments of the present invention can be synthesized using standard synthetic techniques known to those of skill in the art. Compounds of the present invention can be synthesized using the general synthetic procedures set forth in Schemes 1-9.

Scheme 1:

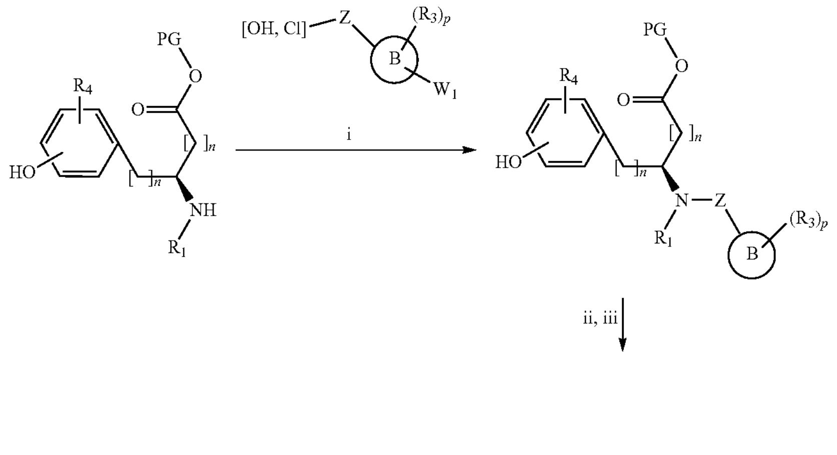

-continued

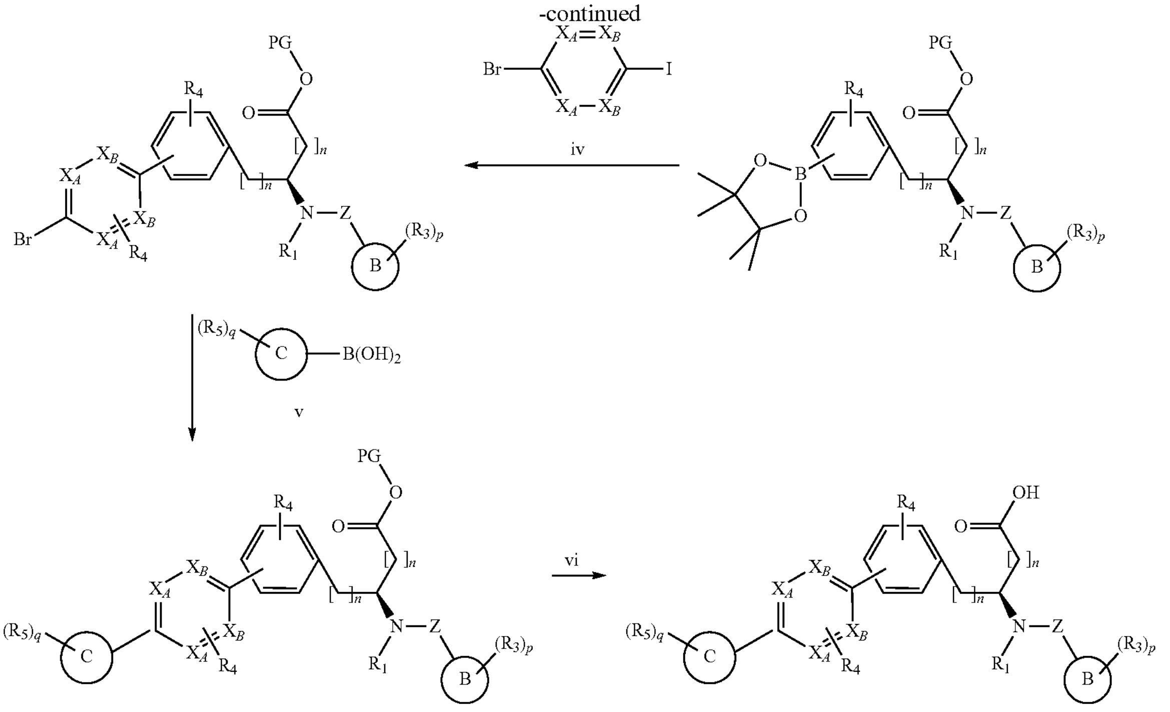

Reagents: PG is a protecting group and $X_A$ and $X_B$ are $CR_4$ or N; (i) For Z═CO, then amide coupling with acid chloride: DIEA, DCM or amide coupling with acid: EDC, HOBt, DMF or HATU, DMF; For Z═$SO_2$, then coupling with sulfonyl chloride: DIEA or $NEt_3$, DCM or DMF (ii) DIEA, 1,1,1-trifluoro-N-phenyl-N-((trifluoromethyl)sulfonyl) methanesulfonamide, DCM; (iii) KOAc, bis-pinacolatoborane, $PdCl_2(dppf)$ or $Pd(dppf)Cl_2$, $Na_2CO_3$, THF, ACN, water; (iv) $Pd(dppf)Cl_2$, $Na_2CO_3$, THF, ACN, water; (v) $Pd(dppf)Cl_2$, $Na_2CO_3$, THF, ACN, water; (vi) Deprotection e.g., methyl ester deprotection: NaOH, MeOH, water.

The other enantiomer and/or diastereomers can be prepared in a similar manner using Scheme 1.

Scheme 2:

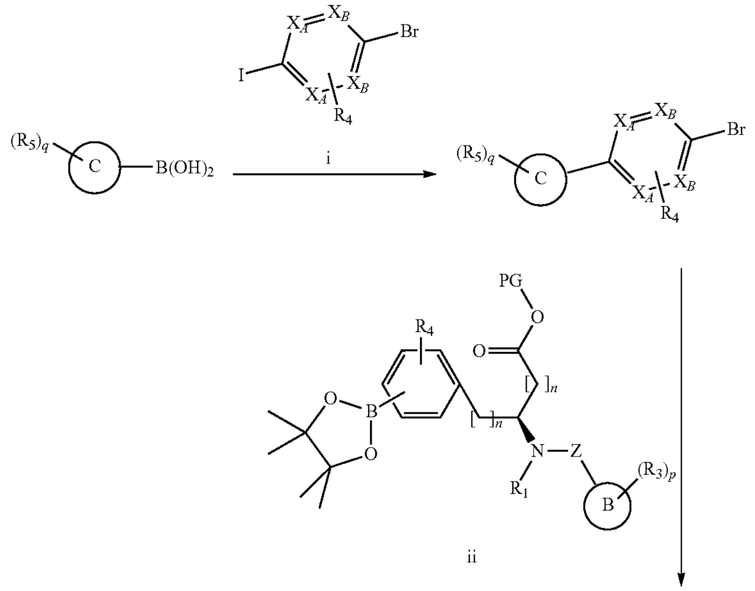

-continued

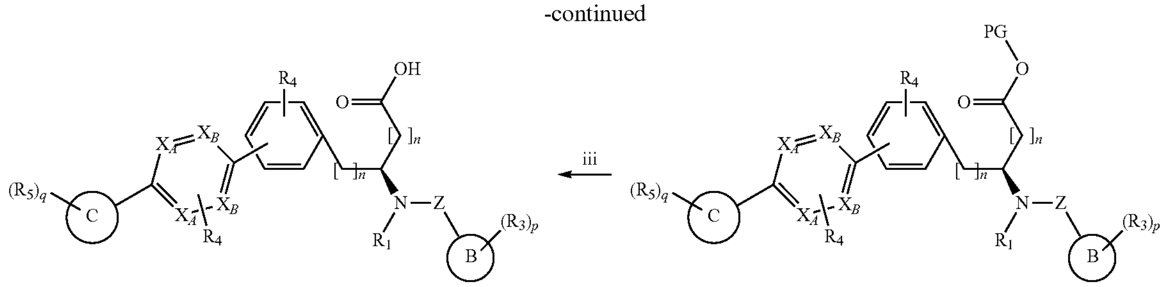

Reagents: PG is a protecting group and $X_A$ and $X_B$ are $CR_4$ or N; (i) Pd(dppf)$Cl_2$, $Na_2CO_3$, THF, ACN, water; (ii) Pd(dppf)$Cl_2$, $Na_2CO_3$, THF, ACN, water; (iii) Deprotection e.g., methyl ester deprotection: NaOH, MeOH, water.

The other enantiomer and/or diastereomers can be prepared in a similar manner using Scheme 2.

Scheme 3:

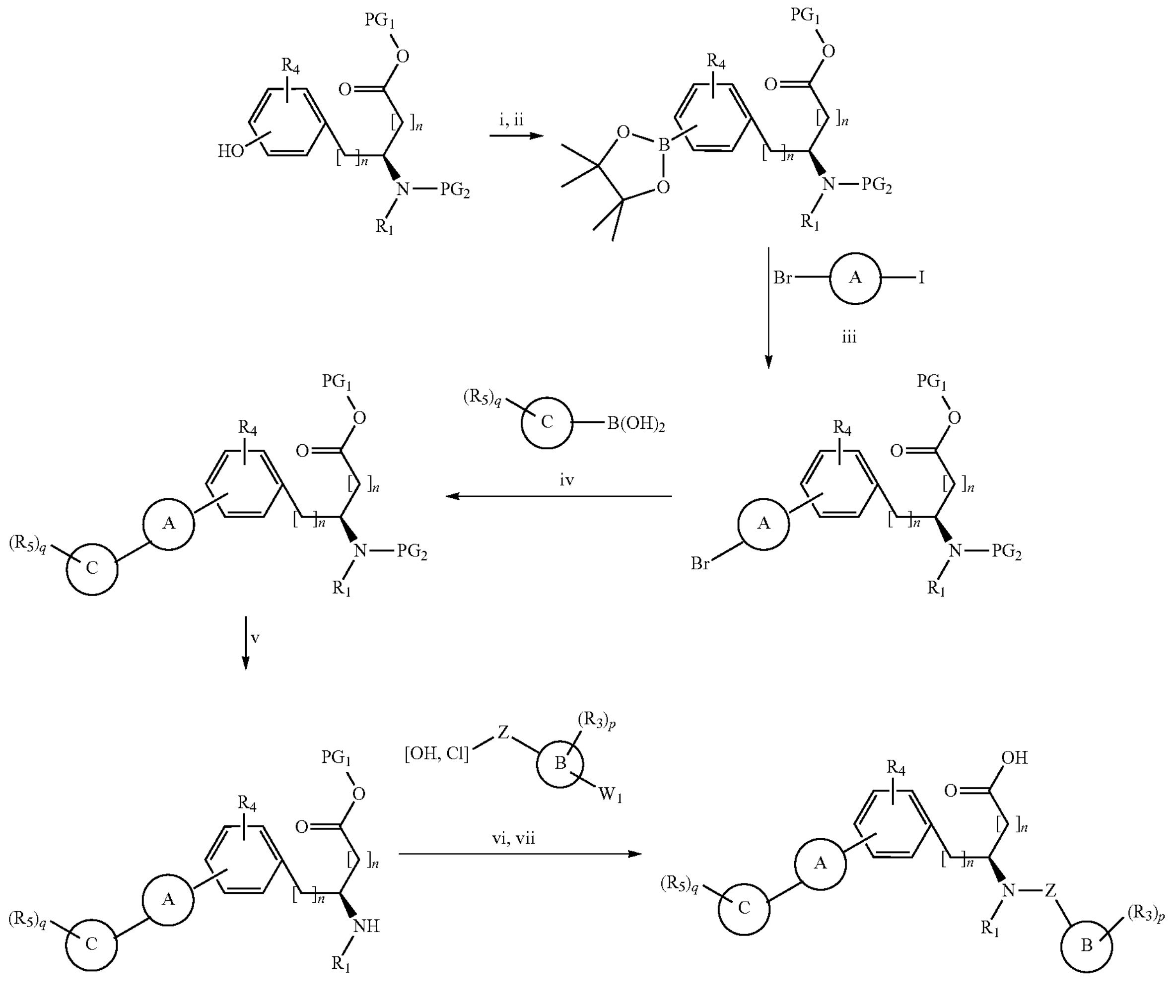

Reagents: $PG_1$ and $PG_2$ are protecting groups; (i) DIEA, 1,1,1-trifluoro-N-phenyl-N-((trifluoromethyl)sulfonyl) methanesulfonamide, DCM; (ii) KOAc, bis-pinacolatoborane, $PdCl_2$(dppf); (iii) Pd(dppf)$Cl_2$, $Na_2CO_3$, THF, ACN, water; (iv) Pd(dppf)$Cl_2$, $Na_2CO_3$, THF, ACN, water; (v) Deprotection of $PG_2$, e.g. CBZ: Pd/C, $H_2$, EA; (vi) If Z=CO then amide coupling with acid chloride: DIEA, DCM or amide coupling with acid: EDC, HOBt, DMF or HATU, DMF; If Z=$SO_2$, then coupling with sulfonyl chloride: DIEA or $NEt_3$, DCM or DMF; (vii) Deprotection of $PG_1$, e.g., tert-butyl ester deprotection: DCM, TFA.

The other enantiomer and/or diastereomers can be prepared in a similar manner using Scheme 3.

Scheme 4:

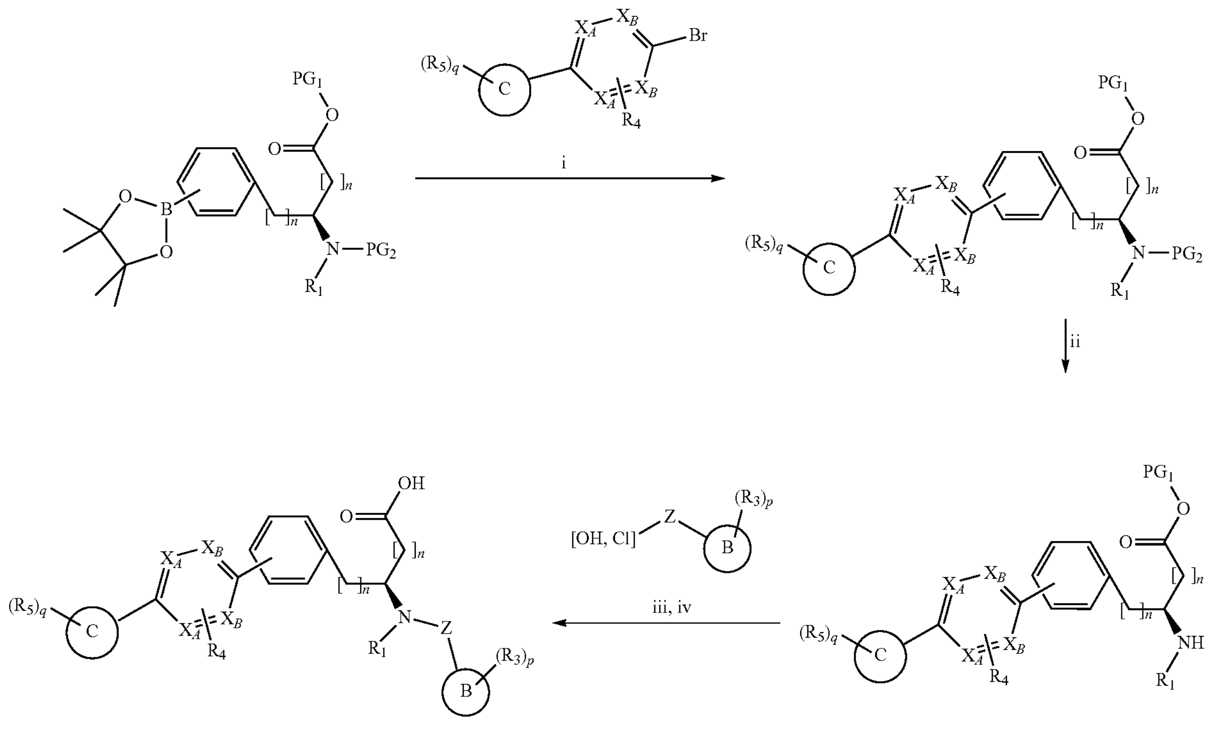

Reagents: $PG_1$ and $PG_2$ are protecting groups and $X_A$ and $X_B$ are $CR_4$ or N; (i) Pd(dppf)$Cl_2$, $Na_2CO_3$, THF, ACN, water; (ii) Deprotection of $PG_2$, e.g. CBZ: Pd/C, $H_2$, EA; (iii) If Z═CO then amide coupling with acid chloride: DIEA, DCM or amide coupling with acid: EDC, HOBt, DMF or HATU, DMF; If Z═$SO_2$, then coupling with sulfonyl chloride: DIEA or $NEt_3$, DCM or DMF; (iv) Deprotection of $PG_1$, e.g., tert-butyl ester deprotection: DCM, TFA.

The other enantiomer and/or diastereomers can be prepared in a similar manner using Scheme 4.

Scheme 5:

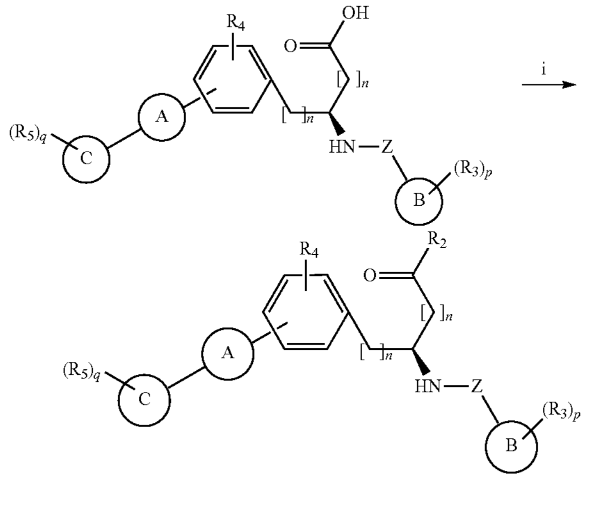

Reagents: PG is a protecting group; (i) (a) where $R_2$ is $NR_1$—$(CR_aR_b)_m$—COOH: $NHR_1$—$(CR_aR_b)_m$—COOPG, HATU, DMF then deprotection e.g., tert-butyl ester deprotection: DCM, TFA; (b) where $R_2$ is NH—$SO_2$—$R_8$: $R_8SO_2NH_2$, DCC, DMAP, DCM (c) where $R_2$ is $NR_{41}R_{42}$: $HNR_{41}R_{42}$, HATU, DMF then deprotection e.g., tert-butyl ester deprotection: DCM, TFA; (d) where $R_2$ is $N(R_1)$—$(CR_aR_b)_m$—CO—$N(R_1)$-heterocyclyl: $HN(R_1)$—$(CR_aR_b)_m$—CO—$N(R_1)$-heterocyclyl, HATU, DMF then deprotection e.g., tert-butyl ester deprotection: DCM, TFA; (e) where $R_2$ is —$N(R_1)$—$(CR_aR_b)_m$—CO—$N(R_1)(R_7)$: $NH_2$—$(CR_aR_b)_m$—COOPG, HATU, DMF then deprotection e.g., tert-butyl ester deprotection: DCM, TFA then $HN(R_1)(R_7)$, HATU, DMAP, DCM (f) where $R_2$ is $N(R_1)$—$(CR_aR_b)_m$-heterocyclyl: $HN(R_1)$—$(CR_aR_b)_m$-heterocyclyl, HATU, DMF then deprotection e.g., tert-butyl ester deprotection: DCM, TFA.

The other enantiomer and/or diastereoisomers can be prepared in a similar manner using Scheme 5.

Scheme 6:

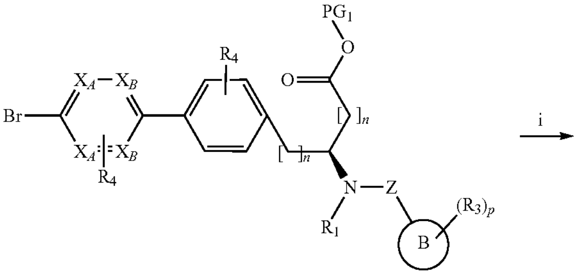

-continued
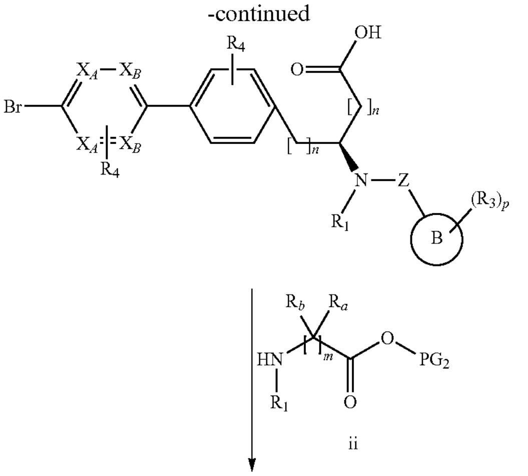
-continued
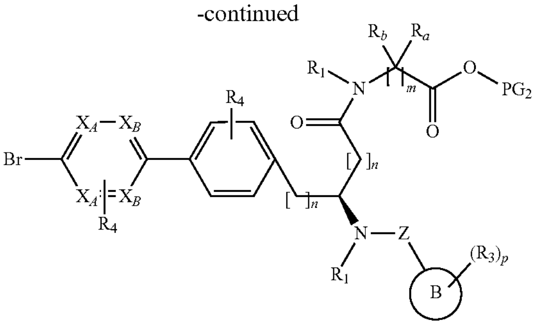
Reagents: $PG_1$ and $PG_2$ are protecting groups and $X_A$ and $X_B$ are $CR_4$ or N; (i) Deprotection of $PG_1$, e.g., tert-butyl ester deprotection: DCM, TFA; (ii) HATU, DIEA, DMF.
The other enantiomer and/or diastereoisomers can be prepared in a similar manner using Scheme 6.
Scheme 7:
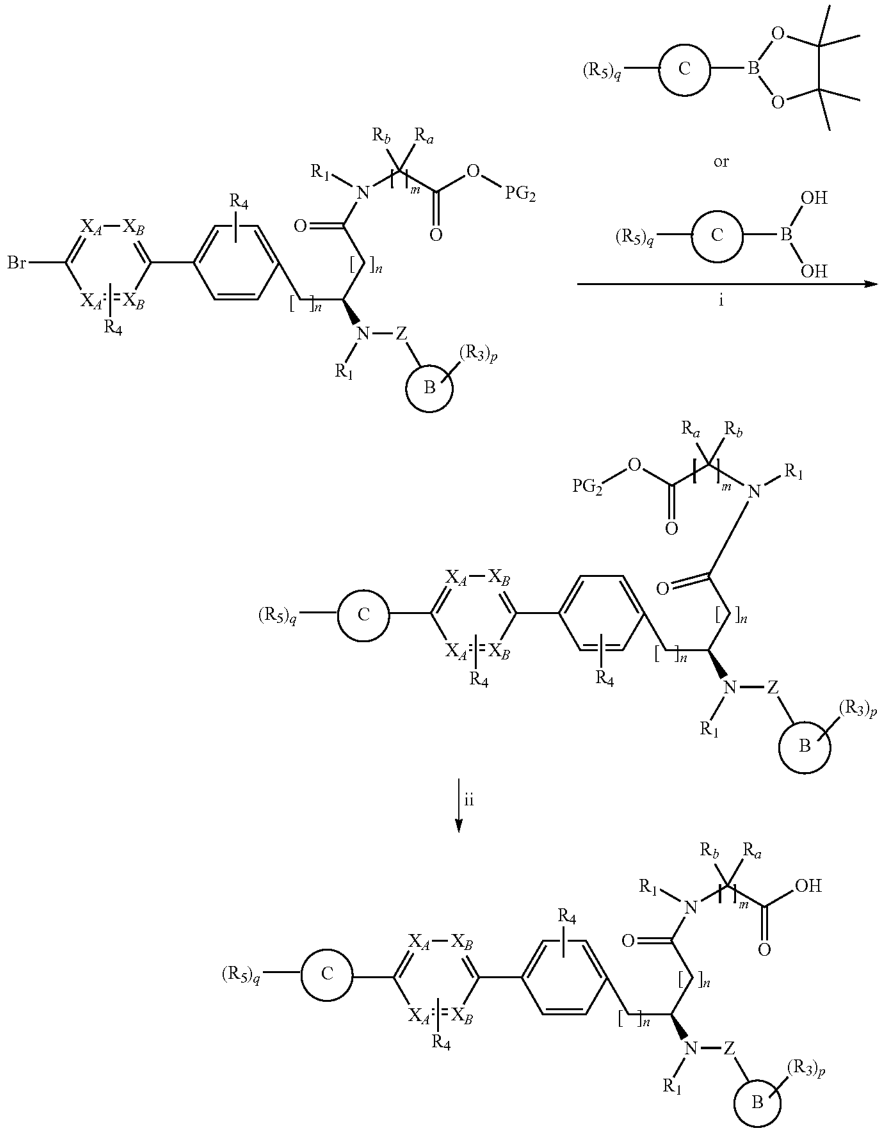

Reagents: $PG_1$ and $PG_2$ are protecting groups and $X_A$ and $X_B$ are $CR_4$ or N; (i) $Pd(dppf)Cl_2$, $Na_2CO_3$, THF, ACN, water; (ii) Deprotection of $PG_2$, e.g., tert-butyl ester deprotection: DCM, TFA.

The other enantiomer and/or diastereoisomers can be prepared in a similar manner using Scheme 7.

Scheme 8:

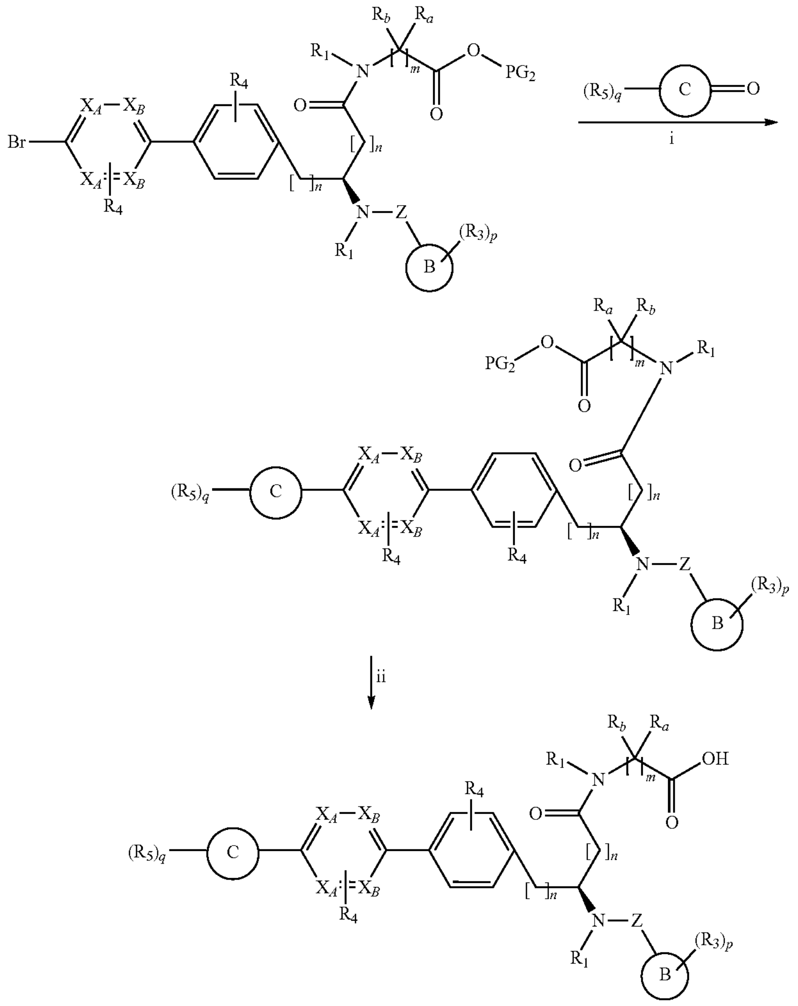

Reagents: $PG_1$ and $PG_2$ are protecting groups and $X_A$ and $X_B$ are $CR_4$ or N; (i) Tosylhydrazine, LiOtBu, XPhos, $Pd_2(dba)_3$, diaoxane, 100° C. (ii) Deprotection of $PG_2$, e.g., tert-butyl ester deprotection: DCM, TFA.

The other enantiomer and/or diastereoisomers can be prepared in a similar manner using Scheme 8.

Scheme 9:

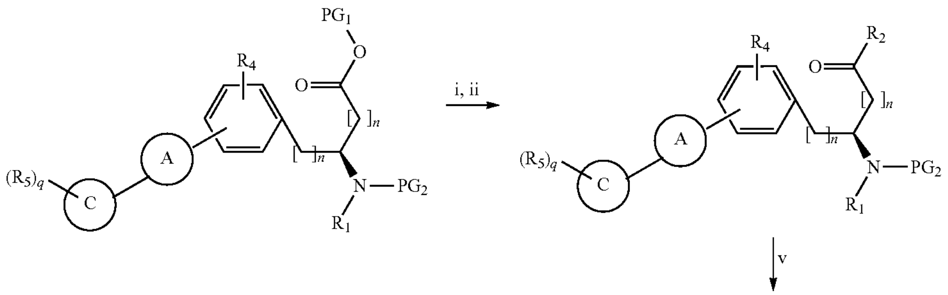

-continued

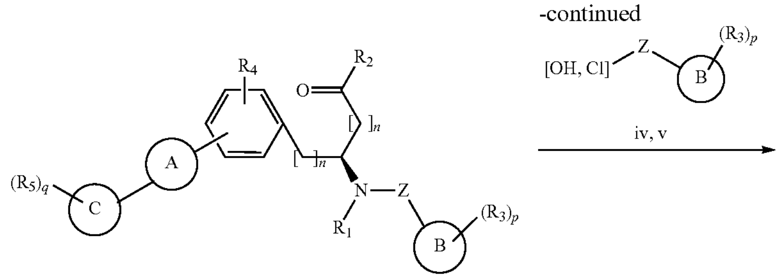

Reagents: $PG_1$, $PG_2$, and $PG_3$ are protecting groups; (i) Deprotection of $PG_1$, e.g., tert-butyl ester deprotection: DCM, TFA; (ii) (a) where $R_2$ is $NR_1—(CR_aR_b)_m—COOH$: $NHR_1—(CR_aR_b)_m—COOPG_3$, HATU, DMF; (b) where $R_2$ is $NH—SO_2—R_8$: $R_8SO_2NH_2$, DCC, DMAP, DCM (c) where $R_2$ is $NR_{41}R_{42}$: $HNR_{41}R_{42}$, HATU, DMF (d) where $R_2$ is $N(R_1)—(CR_aR_b)_m—CO—N(R_1)$-heterocyclyl: $HN(R_1)—(CR_aR_b)_m—CO—N(R_1)$-heterocyclyl, HATU, DMF (e) where $R_2$ is $—N(R_1)—(CR_aR_b)_m—CO—N(R_1)(R_7)$: $NH_2—(CR_aR_b)_m—COOPG_3$, HATU, DMF then deprotection e.g., tert-butyl ester deprotection: DCM, TFA then $HN(R_1)(R_7)$, HATU, DMAP, DCM (f) where $R_2$ is $N(R_1)$-heterocyclyl: $HN(R_1)$-heterocyclyl, HATU, (iii) Deprotection of $PG_2$, e.g. CBZ: Pd/C, $H_2$, EA; (iv) If Z═CO then amide coupling with acid chloride: DIEA, DCM or amide coupling with acid: EDC, HOBt, DMF or HATU, DMF; If $Z═SO_2$, then coupling with sulfonyl chloride: DIEA or $NEt_3$, DCM or DMF; (v) Deprotection of $PG_3$, e.g., tert-butyl ester deprotection: DCM, TFA.

The other enantiomer and/or diastereoisomers can be prepared in a similar manner using Scheme 9.

Scheme 10:

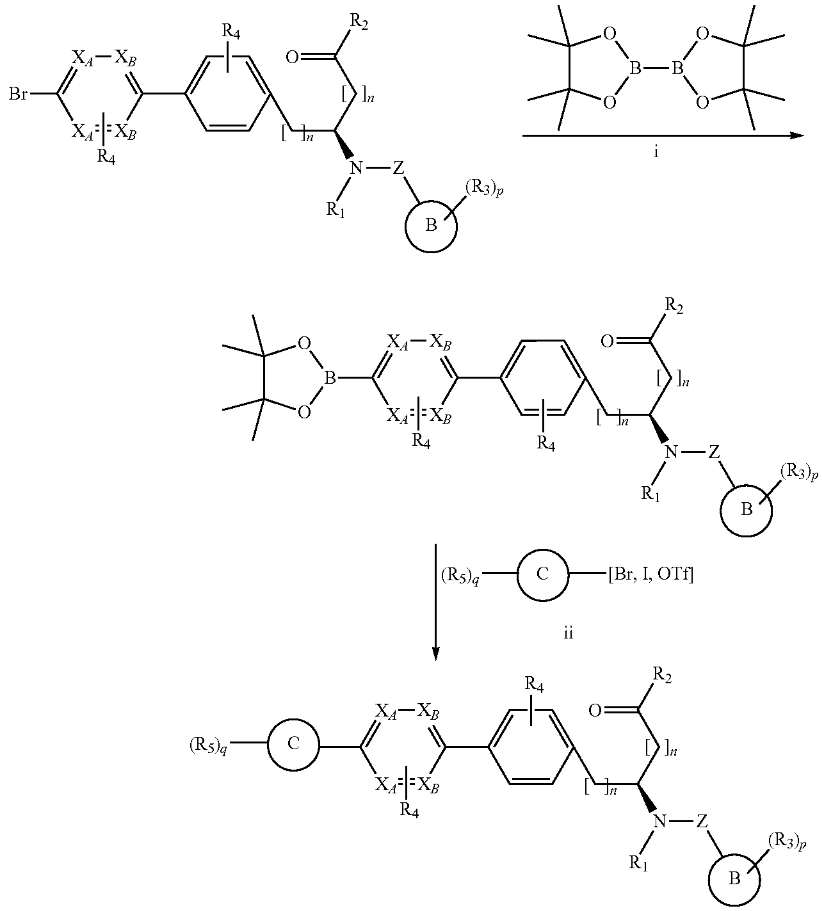

Reagents: $PG_1$ and $PG_2$ are protecting groups and $X_A$ and $X_B$ are $CR_4$ or N; (i) $Pd(dppf)Cl_2$, KOAc, $Na_2CO_3$, THF, ACN, water; (ii) $Pd(dppf)Cl_2$, $Na_2CO_3$, THF, ACN, water.

The other enantiomer and/or diastereoisomers can be prepared in a similar manner using Scheme 10.

Scheme 11:

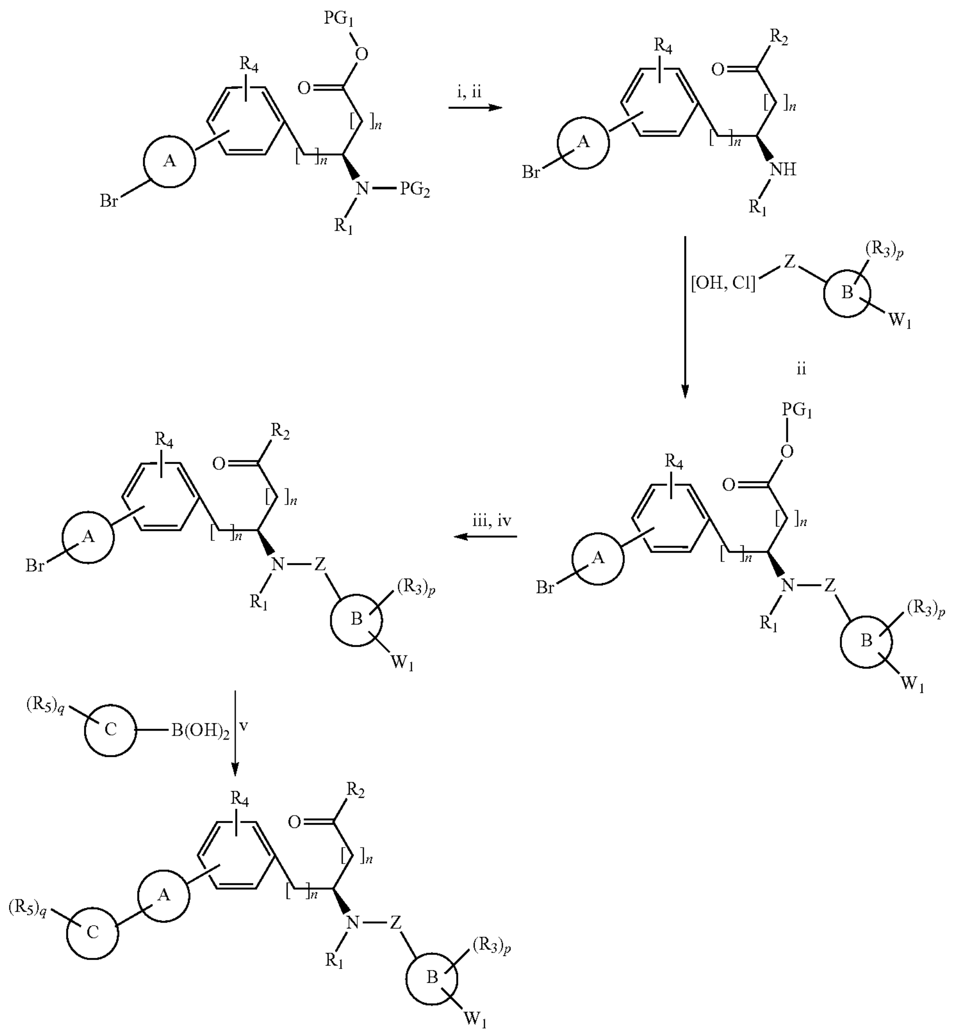

Reagents: $PG_1$, $PG_2$, and $PG_3$ are protecting groups; (i) Deprotection of $PG_2$, e.g., Boc deprotection: 6N HCl in isopropanol, DCM; (ii) If Z═CO then amide coupling with acid chloride: DIEA, DCM or amide coupling with acid: EDC, HOBt, DMF or HATU, DMF; If Z═$SO_2$, then coupling with sulfonyl chloride: DIEA or $NEt_3$, DCM or DMF; (iii) Deprotection of $PG_1$, e.g., tert-butyl ester deprotection: DCM, TFA; (iv) (a) where $R_2$ is NH—$(CR_aR_b)_m$—COOH: $NH_2$—$(CR_aR_b)_m$—$COOPG_3$, HATU, DMF then deprotection e.g., tert-butyl ester deprotection: DCM, TFA; (b) where $R_2$ is NH—$SO_2$—$R_8$: $R_8SO_2NH_2$, DCC, DMAP, DCM (c) where $R_2$ is $NR_{41}R_{42}$: $HNR_{41}R_{42}$, HATU, DMF then deprotection e.g., tert-butyl ester deprotection: DCM, TFA: (d) where $R_2$ is $N(R_1)$—$(CR_aR_b)_m$—CO—$N(R_1)$-heterocyclyl: $HN(R_1)$—$(CR_aR_b)_m$—CO—$N(R_1)$-heterocyclyl, HATU, DMF then deprotection e.g., tert-butyl ester deprotection: DCM, TFA; (e) where $R_2$ is —$N(R_1)$—$(CR_aR_b)_m$—CO—N$(R_1)(R_7)$: $NH_2$—$(CR_aR_b)_m$—$COOPG_3$, HATU, DMF then deprotection e.g., tert-butyl ester deprotection: DCM, TFA then $HN(R_1)(R_7)$, HATU, DMAP, DCM (f) where $R_2$ is $N(R_1)$-heterocyclyl: $HN(R_1)$-heterocyclyl, HATU, DMF then deprotection e.g., tert-butyl ester deprotection: DCM, TFA; (v) $Pd(dppf)Cl_2$, $Na_2CO_3$, THF, ACN, water.

The other enantiomer and/or diastereoisomers can be prepared in a similar manner using Scheme 11.

EXAMPLES

The invention is further illustrated by the following examples. The examples below are non-limiting are merely representative of various aspects of the invention.

Solid and dotted wedges within the structures herein disclosed illustrate relative stereochemistry, with absolute stereochemistry depicted only when specifically stated or delinieated.

General Methods

NMR Spectra $^1H$ NMR (400 MHz) and $^{13}C$ NMR (100 MHz) were obtained in solution of deuteriochloroform ($CDCl_3$) or dimethyl sulfoxide ($d_6$-DMSO). NMR spectra were processed using MestReNova 6.0.3-5604.

LCMS Data

Mass spectra (LCMS) were obtained using one of 6 systems. System 1a: Agilent 1100/6110 HPLC system equipped with a Thompson ODS-A, 100 A, 5μ (50×4.6 mm) column using water with 0.1% formic acid as the mobile phase A, acetonitrile with 0.1% formic acid as the mobile phase B, water with 5 mM ammonium acetate as the mobile phase C, and acetonitrile with 5 mM ammonium acetate as the mobile phase D with a flow rate of 1 mL/min. Method 1: 20-100% mobile phase B (80-0% A) over 2.5 min then held at 100% B for 2.5 min. Method 2: 5% mobile phase B (95% A) for 1 min, 5-95% B over 9 min, then held at 95% B for 5 min. Method 3: 20-100% mobile phase B (80-0% A) over 2.5 min then held at 100% B for 4.5 min. Method 12: 5% D (95% C) for 1 min. then 5-95% D over 9 min. and held at 95% D for 5 min. System 1b: Agilent 1100/6110 HPLC system equipped with a Agilent Poroshell 120 EC-C8, 2.7μ (50×3 mm) column using water with 5 mM ammonium acetate as the mobile phase C, and acetonitrile with 5 mM ammonium acetate as the mobile phase D with a flow rate of 1 mL/min. Method 13: 5% D (95% C) to 95% D over 12 min. then held at 95% D for 2.8 min. and to 5% D over 0.2 min. System 1c: Agilent 1100/6110 HPLC system equipped with a Agilent Poroshell 120 EC-C18, 2.7μ (50×3 mm) column using water with 5 mM ammonium acetate as the mobile phase C, and acetonitrile with 5 mM ammonium acetate as the mobile phase D with a flow rate of 1 mL/min. Method 14: 5% D (95% C) to 95% D over 12 min. then held at 95% D for 2.8 min. and then to 5% D over 0.2 min. Method 15: 20% D (80% C) to 95% D over 3 min. and hold at 95% D 1.8 min then to 20% D over 0.2 min. Method 16: 20% D (80% C) to 95% D over 3.0 min. and hold at 95% D for 3.8 min. then 20% D over 0.2 min. System 1d: Agilent 1100/6110 HPLC system equipped with a Agilent Poroshell 120 EC-C8, 2.7μ (50×3 mm) column using water with 5 mM ammonium acetate as the mobile phase C, and acetonitrile with 5 mM ammonium acetate as the mobile phase D with a flow rate of 1 mL/min. Method 18: 20% D (80% C) to 95% D over 3 min. and hold at 95% D 1.8 min then to 20% D over 0.2 min. Method 19: 20% D (80% C) to 95% D over 3.0 min. and hold at 95% D for 3.8 min. then 20% D over 0.2 min. Method 20: 5% D (95% C) to 95% D over 12 min then held at 95% D for 2.8 min. and then to 5% D over 0.2 min. System 1e: Agilent 1100/6110 HPLC system equipped with a Waters X-Bridge C-8, 3.5μ (50×4.6 mm) column using water with 5 mM ammonium acetate as the mobile phase C, and acetonitrile with 5 mM ammonium acetate as the mobile phase D with a flow rate of 1 mL/min. Method 25: 20% D (80% C) to 95% D over 3 min. then held at 95% D for 3.8 min. and then to 5% D over 0.2 min. Method 26: 20% D (80% C) to 95% D over 3 min. and hold at 95% D 1.8 min then to 20% D over 0.2 min. Method 28: 20% D (80% C) to 95% D over 12.0 min. and hold at 95% D for 2.8 min. then 20% D over 0.2 min. System 2: Agilent 1200 LCMS equipped with an Agilent Zorbax Extend RRHT 1.8 μm (4.6×30 mm) column using water with 0.1% formic acid as mobile phase A and acetonitrile with 0.1% formic acid as mobile phase B. Method 4: 5-95% mobile phase B over 3.0 min with a flow rate of 2.5 mL/min, then held at 95% for 0.5 min with a flow rate of 4.5 mL/min. Method 5: 5-95% mobile phase B over 14 min with a flow rate of 2.5 mL/min, then held at 95% for 0.5 min with a flow rate of 4.5 mL/min. System 3: Waters Fractionlynx LCMS system equipped with an Agilent Zorbax Extend RRHT 1.8 μm, (4.6×30 mm) column using water with 0.1% formic acid as mobile phase A and acetonitrile with 0.1% formic acid as mobile phase B. Method 6: 5-95% mobile phase B over 3.0 min with a flow rate of 2.5 mL/min, then held at 95% for 0.5 min with a flow rate of 4.5 mL/min. Method 7: 5-95% mobile phase B over 14 min with a flow rate of 2.5 mL/min, then held at 95% for 0.5 min with a flow rate of 4.5 mL/min. System 4: Agilent 1260 LCMS equipped with an Agilent Zorbax Extend RRHT 1.8 m (4.6×30 mm) column using water with 0.1% formic acid as mobile phase A and acetonitrile with 0.1% formic acid as mobile phase B. Method 8: 5-95% mobile phase B over 3.0 min with a flow rate of 2.5 mL/min, then held at 95% for 0.5 min with a flow rate of 4.5 mL/min. Method 9: 5-95% mobile phase B over 14 min with a flow rate of 2.5 mL/min, then held at 95% for 0.5 min with a flow rate of 4.5 mL/min. System 5: Agilent 1260 LCMS equipped with a Waters Xselect CSH C18 3.5 μm (4.6×50 mm) column using water with 0.1% formic acid as mobile phase A and acetonitrile with 0.1% formic acid as mobile phase B. Method 10: The gradient was 5-95% mobile phase B over 13.0 min with a flow rate of 2.5 mL/min, then held at 95% for 1.0 min with a flow rate of 4.5 mL/min. Method 11: The gradient was 5-95% mobile phase B over 3.0 min with a flow rate of 2.5 mL/min, then held at 95% for 0.6 min with a flow rate of 4.5 mL/min. System 6: Waters Acquity UPLC system equipped with a Acquity UPLC BEH C18, 1.7 μm (2.1×50 mm) or Phenomenex Kinetex C18, 1.7 μm (2.1×50 mm) column using water with 10 mM ammonium formate as mobile phase A, acetonitrile as mobile phase B with a flow rate of 0.5 mL/min. Method 17: 10% mobile phase B (90% A) for 0.5 min, 10-95% B over 3 min, then held at 95% B for 1.1 min, 95-10% B over 0.1 min then held for 0.3 min and the total run time is 5 min. Method 23: 20% mobile phase B (80% A) for 0.5 min, 20-95% B over 3 min, then held at 95% B for 1.1 min, 95-20% B over 0.1 min, then held for 0.3 min and the total run time is 5 min. Method 24: 30% mobile phase B (70% A) for 0.5 min, 30-95% B over 2.2 min, then held at 95% B for 1.9 min, 95-30% B over 0.1 min, then held for 0.3 min and the total run time is 5 min. Method 27: 40% mobile phase B (60% A) for 0.5 min, 40-95% B over 1.9 min, then held at 95% B for 2.2 min, 95-40% B over 0.1 min, then held for 0.3 min and the total run time is 5 min. Method 21: 20% mobile phase B (80% A) for 0.5 min, 20-95% B over 2.7 min, then held at 95% B for 1.4 min, 95-20% B over 0.1 min, then held for 0.3 min and the total run time is 5 min. Method 22: 40% mobile phase B (60% A) for 0.5 min, 40-95% B over 1.6 min, then held at 95% B for 2.5 min, 95-40% B over 0.1 min, then held for 0.3 min and the total run time is 5 min.

Hydrogenations

Hydrogenation reactions were performed using a Thales Nanotechnology H-Cube reactor equipped with the specified CatCart or using standard laboratory techniques.

Reaction Conditions and Abbreviations

Pyridine, dichloromethane (DCM), tetrahydrofuran (THF), and toluene used in the procedures were from Aldrich Sure-Seal bottles or Acros AcroSeal dry solvent and kept under nitrogen ($N_2$). All reactions were stirred magnetically and temperatures are external reaction temperatures. The following abbreviations are used: ethyl acetate (EA), 1-methy-2-pyrrolidinone (NMP), triethylamine (TEA), N-hydroxybenzotriazole (HOBt), 1-ethyl-3-(3-dimethylaminopropyl) carbodiimide hydrochloride (EDC), N,N-dimethylformamide (DMF), dimethyl acetamide (DMA), Di-tert-butyl dicarbonate ($Boc_2O$), N,N-Diisopropylethylamine (DIEA), acetic acid (AcOH), hydrochloric acid (HCl), O-(7-azabenzotriazol-1-yl)-N,N,N'N'-tetramethyluronium hexafluorophosphate (HATU), 4-dimethylaminopyridine (DMAP), tert-butanol (t-BuOH), sodium hydride (NaH), sodium triacetoxyborohydride ($Na(OAc)_3BH$), ethanol (EtOH), methanol (MeOH), acetonitrile (ACN).

Purifications

Chromatographies were carried out using a Combiflash Rf flash purification system (Teledyne Isco) equipped with Redisep (Teledyne Isco), Telos (Kinesis) or GraceResolv (Grace Davison Discovery Sciences) silica gel ($SiO_2$) columns. Preparative HPLC purifications were performed using one of two systems. System 1: Varian ProStar/PrepStar system equipped with a Waters SunFire Prep C18 OBD, 5 μm (19×150 mm) column using water containing 0.05% trifluoroacetic acid as mobile phase A, and acetonitrile with 0.05% trifluoroacetic acid as mobile phase B. The gradient was 40-95% mobile phase B over 10 min, held at 95% for 5-10 min, and then return to 40% over 2 min with flow rate of 18 mL/min. Fractions were collected using a Varian Prostar fraction collector by UV detection at 254 nm and were evaporated using a Savant SpeedVac Plus vacuum pump or a Genevac EZ-2. System 2: Waters Fractionlynx system equipped with an Agilent Prep-C18, 5 μm (21.2×50 mm) column using water containing 0.1% formic acid as mobile phase A, and acetonitrile with 0.1% formic acid as mobile phase B. The gradient was 45-95% mobile phase B over 7.5 min, held at 95% for 1 min, and then returned to 45% over 1.5 min with a flow rate of 28 mL/min. Fractions were collected by UV detection at 254 nm or by mass and evaporated using a Genevac EZ-2.

Chiral Methods

Chiral Method 1:

This method was used to detect enantiomeric excess of the tyrosine chiral center and not other stereocenters within the exemplified compounds. Enantiomeric excess was determined by integration of peaks that were separated on a Diacel Chiralpak IA, 4.6×250 mm column, 5 m particle size. The solvents used were "Solvent A": 4:1 (hexanes with 0.2% TFA): DCM, and "Solvent B": EtOH. The flow rate was held at 1.0 mL/min with the following gradient: Increase Solvent B from 2-10% over 30 min, hold Solvent B at 10% for 15 min.

Chiral Method 2:

Enantiomeric excess was determined by integration of peaks that were separated on a Daicel Chiralpak IC, 4.6×250 mm column, 5 m particle size running an isocratic mixture of 76% (0.2% TFA in iso-hexanes), 19% DCM and 5% EtOH at a flow rate of 1.5 mL/min.

Chiral Preparative HPLC:

This was carried out using a Gilson preparative HPLC system equipped with a Daicel Chiralpak IC column, 20×250 mm column, 5 μm particle size running an isocratic mixture of mobile phase A (60% (0.2% TFA in iso-hexanes) and 40% DCM) at 15 mL/min and at-column-dilution with mobile phase B (EtOH) at 1.5 mL/min. Fractions were collected by UV detection at 254 nm and evaporated using a Genevac EZ-2.

General Procedures

General Procedure 4: Hydrolysis of Esters to Acids.

To a stirring solution of ester (1 eq) in THF or dioxane and water, was added NaOH or LiOH (1-3 eq). The reaction mixture was stirred at up to 60° C. for up to 18 h. The reaction mixture was neutralized with AcOH or HCl and either diluted with water or concentrated. If the reaction mixture was diluted with water, then HCl was added to acidify the reaction mixture to a pH of approximately 2. The resulting precipitate was isolated by filtration to yield product which can be purified by chromatography, preparative HPLC, or used without purification. If the reaction mixture was concentrated, the crude material was diluted with DCM or EA and washed with brine. The organic layer was concentrated and purified by chromatography or preparative HPLC to give final product. Alternatively, the crude material can be carried forward without purification.

General Procedure 7: Preparation of Amides Via Peptide Coupling.

A solution of amine (1.0 eq) and base (DIEA, TEA or NMM) (0-3.0 eq) in DCM or DMF (0.08-0.10 M) was treated with the appropriate carboxylic acid (1.0-1.5 eq). To this mixture was added the coupling reagent. The coupling reagent could be HATU (1.05-2.5 eq) optionally with DMAP (0.01-1 eq), EDC (1.5 eq) with HOBt (1.5 eq) or DMAP (0.01-1 eq), DCC (1.1 eq) with HOBt (1.1 eq) or DCC (1.5 eq) with DMAP (2.0 eq). The reaction mixture was stirred until the reaction was complete. The reaction was diluted with EA and washed with saturated aqueous $NaHCO_3$. The organic layer was dried over $MgSO_4$ and concentrated. The product was purified by chromatography or alternatively can be carried on to the next step without further purification.

General Procedure 8: Deprotection of Esters to Acids, Deprotection of Boc-Amines, and/or Protodesilylation of Protected Alcohols A solution of the tert-butyl ester or Boc-amine (1.00 eq) in DCM (0.06 M) was treated with TFA (0.16-0.33 M) or 1-4N HCl in ether or dioxane (10.0-20.0 eq). The reaction mixture was stirred at either room temperature or 30° C. until complete. The solvent was removed and the product was purified by chromatography or preparative HPLC. This procedure was also applicable for protodesilylation of tert-butyl, dimethylsilyl protected alcohols. A solution of the methyl ester (1.00 eq) in dioxane (0.04-0.08 M) was treated with 1-6N aqueous HCl (10-100 eq). The reaction mixture was stirred at either room temperature or 30° C. until complete. The solvent was removed and the product was purified by chromatography or preparative HPLC.

General Procedure 9: Formation of Triflate.

A solution of the phenol (1.0 eq) in DCM (0.25 M) was treated with 1,1-trifluoro-N-phenyl-N-((trifluoromethyl)sulfonyl)methanesulfonamide (1.1 eq). The reaction mixture was stirred at room temperature until complete. The reaction was stirred with water and saturated aqueous $NaHCO_3$. The organic layers was dried and concentrated. The material was purified by chromatography or alternatively used without purification.

General Procedure 10: Palladium-Catalyzed Coupling Reactions.

A solution of boronic acid or boronate ester (1.0-1.3 eq), halide (1.0-1.3 eq), sodium bicarbonate or sodium carbonate decahydrate (2.0-2.5 eq), and dichloro[1,1'-bis(di-tert-butylphosphino)ferrocene]palladium(II) or $Pd(dppf)Cl_2$ were combined in THF, acetonitrile, or dioxane (0.1-0.2 M) and water (0.25-0.50 M). The reaction was heated at 80 to 100° C. until complete. The reaction was diluted with EA and washed with saturated aqueous $NaHCO_3$. The organic layer was dried over $MgSO_4$ and concentrated. The product can be purified by chromatography, preparative HPLC, or carried on to the next step without further purification.

General Procedure 13: Sulfonate or Sulfonamide Formation.

To a solution of alcohol or amine in DCM (0.02 M) was added the sulfonyl chloride (2 eq) and triethylamine (3 eq). The reaction was stirred at room temperature until complete. The reaction was diluted with DCM and washed with saturated aqueous $NaHCO_3$. The organic layer was dried over $MgSO_4$ and concentrated. The product can be purified by chromatography, preparative HPLC, or carried on to the next step without further purification.

To a solution of acid in DCM (0.02 M) was added sulfonamide (2 eq), EDC (2 eq) and them DMAP (2 eq) at 0° C. The reaction mixture was stirred allowed to stir at room temperature until completion. Reaction was diluted with DCM and washed with saturated aqueous $NaHCO_3$, water and then brine. The organic layer was dried over MgSO4 and concentrated. The product can be purified by chromatography or preparative HPLC.

General Procedure 18: Deprotection of Cbz to Amine or Deprotection of Benzyl Esters to Acids.

Conventional Hydrogenations: To a stirring solution of Cbz-protected amine or benzyl protected ester (1.0 eq) in EA, THF, EtOH, or MeOH (0.01-0.05 M) was added Pd/C and the reaction was stirred under hydrogen until complete. The catalyst was filtered and the solvent was removed. The product was purified by chromatography or alternatively can be carried onto the next step without further purification.

Hydrogenation using H-cube: A solution of Cbz-protected amine or benzyl protected ester (1.0 eq) in dioxane or THF (0.01-0.03 M) was passed over a 10% Pd/C CatCart in a Thales Nanotechnology H-Cube reactor at 1 mL/min. The solvent was evaporated and the product was carried to the next step without further purification.

General Procedure 37: Ketone Coupling

To a stirring solution of aryl bromide (1 eq) in dioxane (0.06 M) was added ketone (1-2 eq), tosylhydrazine (1-2 eq), lithium tert-butoxide (3-5.5 eq), $Pd_2dba_3$ (2 mol %) and Xphos (8 mol %). The mixture was heated to 100° C. for 16 h then quenched with aqueous acetic acid and extracted with DCM. The combined organic extracts were dried over $MgSO_4$ and solvents evaporated. The product was isolated by column chromatography or preparative HPLC.

Synthesis of Representative Compounds

(S)-tert-butyl 2-(((benzyloxy)carbonyl)amino)-3-(4-(((trifluoromethyl)sulfonyl)oxy)-phenyl)propanoate (INT-5)

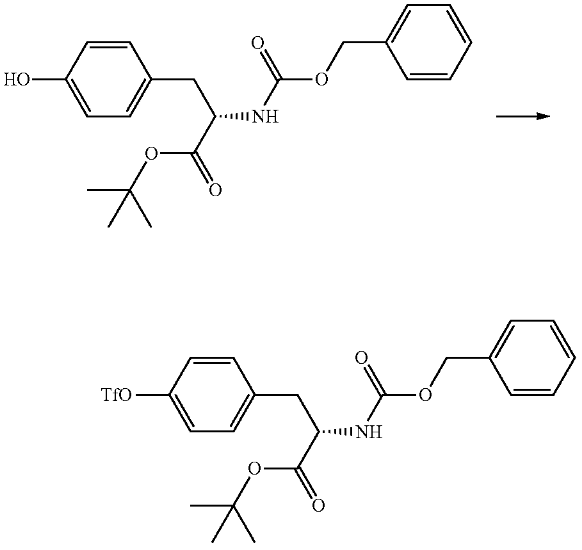

Prepared using General Procedure 9: A stirred solution of (S)-tert-butyl 2-(((benzyloxy)carbonyl)amino)-3-(4-hydroxyphenyl)propanoate hydrate (25 g, 64.2 mmol) in DCM (100 mL) was treated with $MgSO_4$ (4.01 g, 33.7 mmol). After 15 min, the mixture was filtered and washed with DCM (2×20 mL). The organics were treated with N-ethyl-N-isopropylpropan-2-amine (17.41 g, 134.7 mmol) and stirred. This solution was treated with 1,1,1-trifluoro-N-phenyl-N-((trifluoromethyl)sulfonyl)methanesulfonamide (26.44 g, 74.01 mmol) and the mixture was allowed to stir overnight at room temperature. The mixture was treated with water (50 mL) and saturated aqueous $NaHCO_3$ (20 mL) and stirred vigorously for 10 min. The layers were separated and the organic layer was further washed with saturated aqueous $NaHCO_3$ (2×50 mL), water (50 mL), and saturated aqueous $NaHCO_3$ (50 mL) and concentrated. The compound was purified by chromatography (EA/hexanes) to afford 26.85 g (79%) of (S)-tert-butyl 2-(((benzyloxy)carbonyl)amino)-3-(4-(((trifluoromethyl)sulfonyl)oxy)phenyl) propanoate INT-5. LCMS-ESI (m/z) calculated for $C_{22}H_{24}F_3NO_7S$: 503.1. found 526.1 $[M+Na]^+$, $t_R$=4.12 min (Method 3).

(S)-Tert-butyl 2-(((benzyloxy)carbonyl)amino)-3-(4-(4,4,5,5-tetramethyl-1,3,2-dioxaborolan-2-yl)phenyl) propanoate (INT-6)

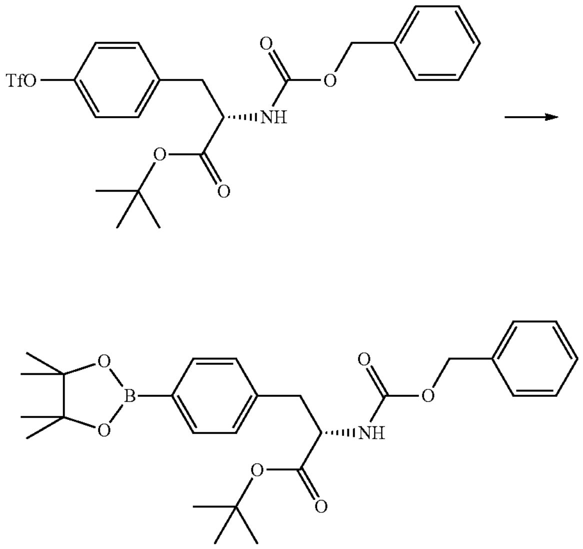

A solution of (S)-tert-butyl 2-(((benzyloxy) carbonyl) amino)-3-(4-(((trifluoromethyl)sulfonyl)oxy)phenyl)propanoate INT-5 (26.85 g, 53.4 mmol), potassium acetate (15.71 g, 160.1 mmol), bis-pinacolatoborane (27.1 g, 106.7 mmol) and DMSO (100 mL) was degassed with a steady flow of nitrogen gas for 5 minutes. To this solution was added $PdCl_2(dppf)$ (1.95 g, 2.67 mmol) and the solution further degassed and kept under an atmosphere of nitrogen. The mixture was heated at 100° C. for 18 h then cooled to room temperature and diluted with EA (50 mL) and washed with saturated aqueous $NaHCO_3$ (20 mL), water (3×30 mL), dried over $MgSO_4$, filtered, and the solvent removed under reduced pressure. The compound was purified by column chromatography to give 11.10 g (41%) of (S)-tert-butyl 2-(((benzyloxy)carbonyl)amino)-3-(4-(4,4,5,5-tetramethyl-1,3,2-dioxaborolan-2-yl)phenyl) propanoate INT-6 as a oil. LCMS-ESI (m/z) calculated for $C_{27}H_{36}BNO_6$: 481.3. found 504.3 $[M+Na]^+$, $t_R$=4.21 min (Method 3). $^1H$ NMR (400 MHz, DMSO) δ 7.72 (d, J=8.3 Hz, 1H), 7.60 (d, J=8.0 Hz, 2H), 7.42-7.11 (m, 6H), 4.98 (s, 2H), 4.22-4.08 (m, 1H), 3.03 (dd, J=13.7, 5.2 Hz, 1H), 2.85 (dd, J=13.6, 10.1 Hz, 1H), 1.36 (s, 6H), 1.30 (s, 9H), 1.22-1.13 (m, 6H).

(S)-Tert-butyl 2-(((benzyloxy)carbonyl)amino)-3-(4-(5-bromopyrimidin-2-yl)phenyl)propanoate (INT-7)

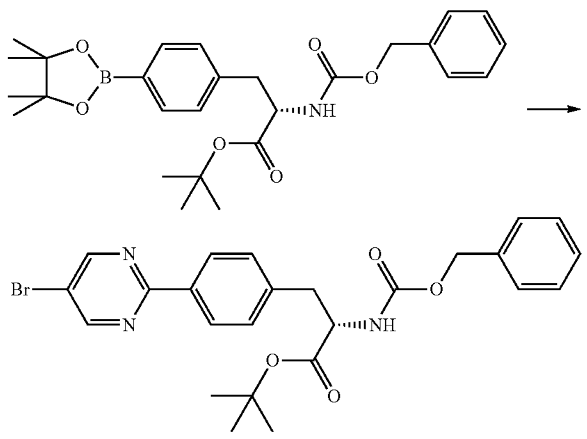

Prepared using General Procedure 10: A stirred mixture of (S)-tert-butyl 2-(((benzyloxy)carbonyl)amino)-3-(4-(4,4,5,5-tetramethyl-1,3,2-dioxaborolan-2-yl)phenyl) propanoate INT-6 (21.7 g, 45.0 mmol) and 5-bromo-2-iodopyrimidine (15.4 g, 54.0 mmol) in dioxane (400 mL) with sodium carbonate decahydrate (25.7 g, 90 mmol) in water (100 mL) was de-gassed. $PdCl_2(dppf)$ (0.99 g, 1.4 mmol) was added and the mixture further de-gassed then heated to reflux for 5 h. The mixture was allowed to cool while stirring overnight. The mixture was poured onto water (1 L) and EA (300 mL) and stirred for 30 min. The mixture was filtered and the layers were separated. The aqueous layer was further extracted with EA (2×200 mL) and the combined organic layers were washed with water (2×100 mL) then brine (50 mL), dried over $MgSO_4$ and concentrated. Column chromatography (EA/hexanes) gave 14.84 g (63%) of (S)-tert-butyl 2-(((benzyloxy)carbonyl)amino)-3-(4-(5-bromopyrimidin-2-yl)phenyl) propanoate INT-7. LCMS-ESI (m/z) calculated for $C_{25}H_{26}BrN_3O_4$: 511.1. found 534.0 $[M+Na]^+$, $t_R$=2.97 min (Method 11).

Tert-butyl (4-(tert-butyl)benzoyl)-L-tyrosinate

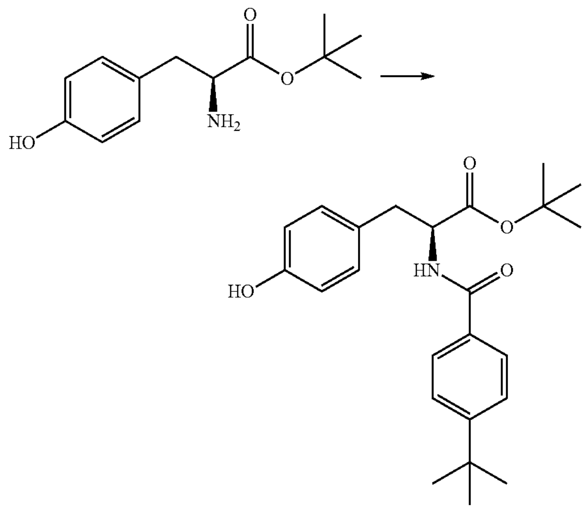

Prepared using General Procedure 7: Into a solution of 4-(tert-butyl)benzoic acid (8.3 g, 46.4 mmol) in DMF (100 mL) were added HATU (19.2 g, 50.6 mmol), TEA (17.6 mL, 126.4 mmol) and (S)-tert-butyl 2-amino-3-(4-hydroxyphenyl) propanoate (10.0 g, 42.1 mmol). After 5 h, the reaction mixture was diluted with EA, washed with saturated aqueous $NaHCO_3$ and brine, then dried ($Na_2SO_4$), concentrated, and purified by chromatography (EA/hexanes) to provide 12.9 g (69%) of tert-butyl (4-(tert-butyl)benzoyl)-L-tyrosinate. LCMS-ESI (m/z) calculated for $C_{24}H_{31}NO_4$: 397.5; no m/z observed, $t_R$=3.59 min (Method 1). $^1H$ NMR (400 MHz, $CDCl_3$) δ7.71-7.65 (m, 2H), 7.47-7.39 (m, 2H), 7.04 (t, J=5.7 Hz, 2H), 6.78-6.70 (m, 2H), 6.59 (d, J=7.5 Hz, 1H), 4.91 (dt, J=7.5, 5.6 Hz, 1H), 3.15 (qd, J=14.0, 5.6 Hz, 2H), 1.45 (s, 9H), 1.33 (s, 9H).

Tert-butyl (S)-2-(4-(tert-butyl)benzamido)-3-(4-(((trifluoromethyl)sulfonyl)oxy)phenylpropanoate (INT-12)

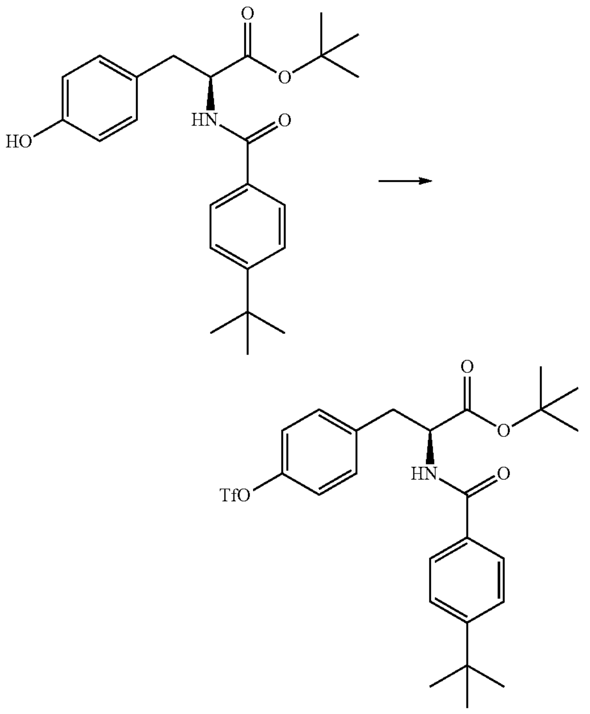

Prepared using General Procedure 9: Into a solution of tert-butyl (4-(tert-butyl)benzoyl)-L-tyrosinate (8.0 g, 17.9 mmol) were added DIEA (3.7 mL, 1.2 mmol) and N-Phenyl bis(trifluoromethanesulfonimide) (7.0 g, 19.7 mmol). After stirring for 36 h, the reaction mixture was diluted with DCM then washed with 10% aqueous citric acid and saturated aqueous $NaHCO_3$. The organic layer was dried over $Na_2SO_4$, and concentrated to provide 9.5 g (100%) tert-butyl (S)-2-(4-(tert-butyl)benzamido)-3-(4-(((trifluoromethyl)sulfonyl)oxy)phenyl) propanoate INT-12, which was used without further purification. LCMS-ESI (m/z) calculated for $C_{25}H_{30}F_3NO_6S$: 529.6; no m/z observed, $t_R$=4.42 min (Method 1). $^1H$ NMR (400 MHz, $CDCl_3$) δ 7.71-7.65 (m, 2H), 7.49-7.43 (m, 2H), 7.32-7.26 (m, 2H), 7.22-7.16 (m, 2H), 6.69 (d, J=7.0 Hz, 1H), 4.94 (dt, J=6.9, 5.9 Hz, 1H), 3.24 (t, J=7.1 Hz, 2H), 1.41 (s, 9H), 1.33 (s, 9H).

Tert-butyl (S)-2-(4-(tert-butyl)benzamido)-3-(4-(4,4,5,5-tetramethyl-1,3,2-dioxaborolan-2-yl)phenyl) propanoate (INT-13)

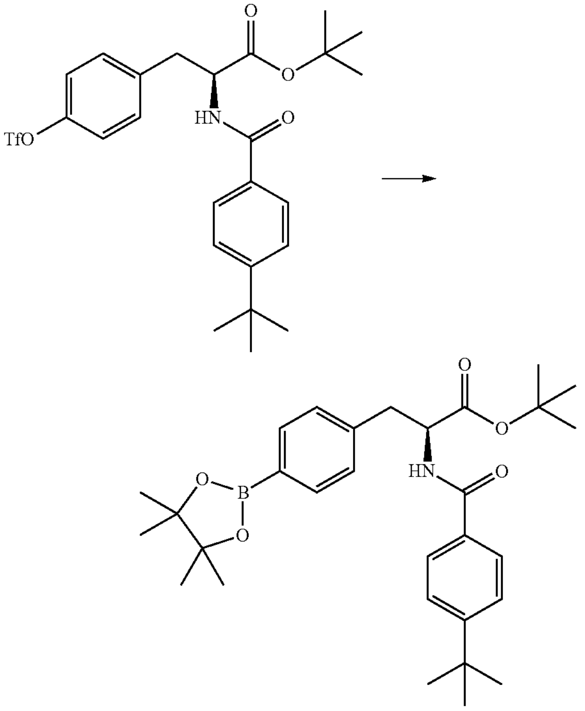

Into a degassed solution of (S)-2-(4-(tert-butyl)benzamido)-3-(4-(((trifluoromethyl)sulfonyl)oxy)phenyl) propanoate INT-12 (9.5 g, 24 mmol), KOAc (7.0 g, 72 mmol), and bis-pinacolatoborane (9.1 g, 36 mmol) in DMSO (20 mL) was added Pd(dppf)$Cl_2$ (0.87 g, 1 mmol). The reaction mixture was heated at 100° C. for 12 h under an atmosphere of $N_2$. The reaction mixture was diluted with EA then washed with saturated aqueous $NaHCO_3$ and $H_2O$. The organic layer was dried over $Na_2SO_4$, concentrated, and purified by chromatography (EA/hexanes) to provide 7.2 g (60%) of tert-butyl (S)-2-(4-(tert-butyl)benzamido)-3-(4-(4,4,5,5-tetramethyl-1,3,2-dioxaborolan-2-yl)phenyl)-propanoate INT-13. LCMS-ESI (m/z) calculated for $C_{30}H_{42}BNO_5$: 507.5; no m/z observed, $t_R$=4.53 min (Method 1). $^1$H NMR (400 MHz, $CDCl_3$) δ 7.74 (d, J=8.0 Hz, 2H), 7.72-7.67 (m, 2H), 7.48-7.43 (m, 2H), 7.21 (d, J=8.0 Hz, 2H), 6.59 (d, J=7.4 Hz, 1H), 5.05-4.92 (m, 1H), 3.27 (qd, J=13.7, 5.4 Hz, 2H), 1.47 (s, 9H), 1.36 (m, 21H).

Tert-butyl (S)-3-(4-(5-bromopyrimidin-2-yl)phenyl)-2-(4-(tert-butyl)benzamido)-propanoate (INT-14)

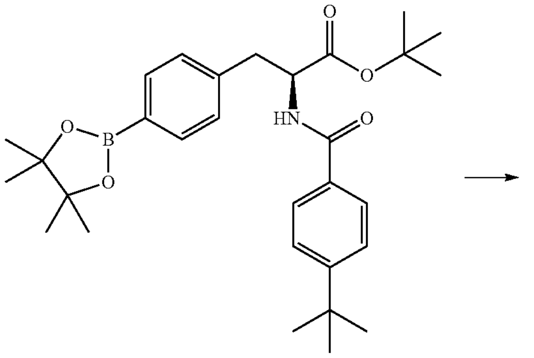

-continued

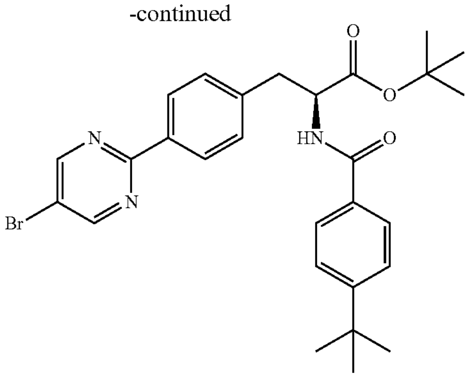

Prepared using General Procedure 10: Into a degassed solution of (S)-2-(4-(tert-butyl)benzamido)-3-(4-(4,4,5,5-tetramethyl-1,3,2-dioxaborolan-2-yl)phenyl)-propanoate INT-13 (1.0 g, 2.0 mmol), $NaHCO_3$ (420 mg, 3.9 mmol), and 5-bromo-2-iodopyrimidine (615 mg, 2.2 mmol) in 2/2/1 ACN/THF/$H_2O$ was added Pd(dppf)$Cl_2$ (140 mg, 0.2 mmol). The reaction mixture was heated at 110° C. for 1 h in a microwave reactor. The reaction mixture was concentrated, dissolved in DCM and washed with $H_2O$. The organic layer was dried over $Na_2SO_4$, concentrated, and purified by chromatography (EA/hexanes) to provide 630 mg (58%) of tert-butyl (S)-3-(4-(5-bromopyrimidin-2-yl)phenyl)-2-(4-(tert-butyl)benzamido)propanoate INT-14. LCMS-ESI (m/z) calculated for $C_{28}H_{32}BrN_4O_3$: 538.5; no m/z observed, $t_R$=4.66 min (Method 1). $^1$H NMR (400 MHz, $CDCl_3$) δ 8.84-8.78 (s, 2H), 8.31 (t, J=7.0 Hz, 2H), 7.75-7.64 (m, 2H), 7.46-7.38 (m, 2H), 7.30 (dd, J=12.9, 7.1 Hz, 2H), 6.65 (d, J=7.2 Hz, 1H), 5.10-4.94 (m, 1H), 3.43-3.20 (m, 2H), 1.45 (s, 9H), 1.32 (s, 9H).

Tert-butyl (5-(tert-butyl)thiophene-2-carbonyl)-L-tyrosinate

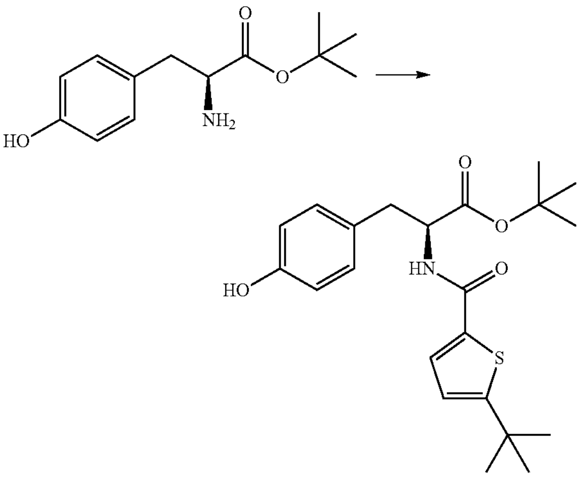

Prepared using General Procedure 7: Into a solution of 5-(tert-butyl)thiophene-2-carboxylic acid (1.93 g, 10.0 mmol) in DMF (20 mL) were added HATU (4.56 g, 12.0 mmol) and TEA (4.18 mL, 30.0 mmol). The mixture was stirred at room temperature for 30 min and (S)-tert-butyl 2-amino-3-(4-hydroxyphenyl) propanoate (2.37 g, 10.0 mmol) was added. After 1 h, the reaction mixture was poured into 400 mL of ice-water and the solid was filtered. The solid was dissolved in DCM and EA, dried over $MgSO_4$, concentrated, and purified by chromatography (EA/hexanes) to provide 3.6 g (89%) of tert-butyl (5-(tert-butyl)thiophene-2-carbonyl)-L-tyrosinate. LCMS-ESI (m/z) calculated for $C_{22}H_{29}NO_4S$: 403.2. found: 426.1 $[M+Na]^+$, $t_R$=9.07 min (Method 2).

Tert-butyl (S)-2-(5-(tert-butyl)thiophene-2-carboxamido)-3-(4-(((trifluoromethyl)sulfonyl)oxy)phenyl) propanoate (INT-15)

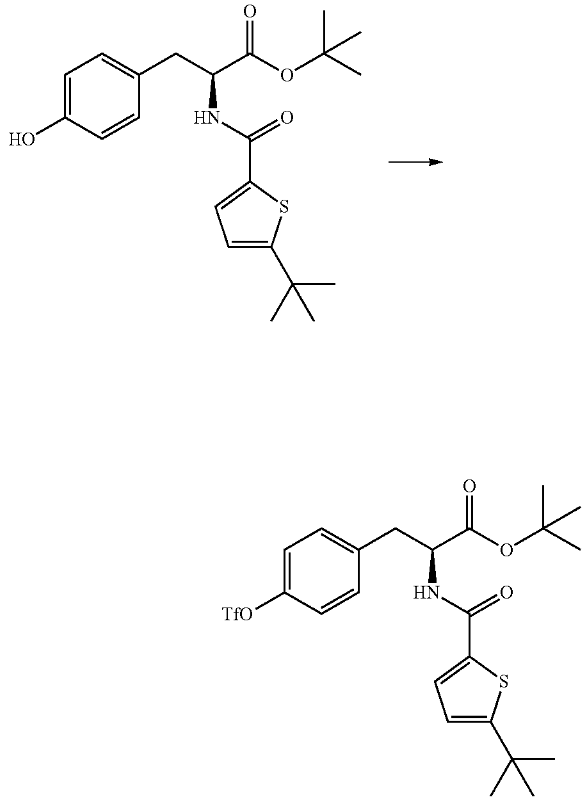

Prepared using General Procedure 9: Into a solution of tert-butyl (5-(tert-butyl)thiophene-2-carbonyl)-L-tyrosinate (3.52 g, 8.72 mmol) were added DIEA (4.56 mL, 26.17 mmol) and N-phenyl bis(trifluoromethanesulfonimide) (3.27 g, 9.16 mmol). After stirring for 18 h, the reaction mixture was diluted with DCM then washed with saturated aqueous $NaHCO_3$. The organic layer was dried over $MgSO_4$ and concentrated. The crude product was purified by chromatography to provide 4.10 g (87.6%) of tert-butyl (S)-2-(5-(tert-butyl)thiophene-2-carboxamido)-3-(4-(((trifluoromethyl)sulfonyl)oxy)phenyl)-propanoate INT-15. LCMS-ESI (m/z) calculated for $C_{23}H_{28}F_3NO_6S_2$: 535.1; no m/z observed, $t_R$=4.22 min (Method 3).

Tert-butyl (S)-2-(5-(tert-butyl)thiophene-2-carboxamido)-3-(4-(4,4,5,5-tetramethyl-1,3,2-dioxaborolan-2-yl)phenyl)propanoate (INT-16)

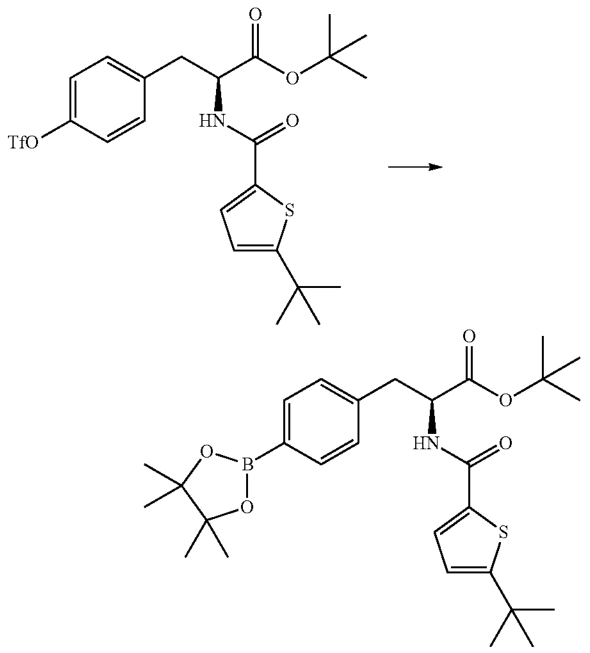

Into a degassed solution of tert-butyl (S)-2-(5-(tert-butyl)thiophene-2-carboxamido)-3-(4-(((trifluoromethyl)sulfonyl)oxy)phenyl)propanoate INT-15 (3.89 g, 7.26 mmol), KOAc (2.14 g, 21.79 mmol), and bis-pinacolatoborane (2.40 g, 9.44 mmol) in DMSO (50 mL) was added Pd(dppf)$Cl_2$ (0.27 g, 0.36 mmol). The reaction mixture was heated at 100° C. for 18 h under an atmosphere of $N_2$. The reaction mixture was poured into 600 mL of ice-water and the solid was filtered. The precipitate was diluted with EA, dried over $MgSO_4$, concentrated, and purified by chromatography (EA/hexanes) to provide 3.68 g (99%) of tert-butyl (S)-2-(5-(tert-butyl)thiophene-2-carboxamido)-3-(4-(4,4,5,5-tetramethyl-1,3,2-dioxaborolan-2-yl)phenyl) propanoate INT-16. LCMS-ESI (m/z) calculated for $C_{28}H_{40}BNO_5S$: 513.3; no m/z observed, $t_R$=4.51 min (Method 3).

Tert-butyl (S)-3-(4-(5-bromopyrimidin-2-yl)phenyl)-2-(5-(tert-butyl)thiophene-2-carboxamido)propanoate (INT-17)

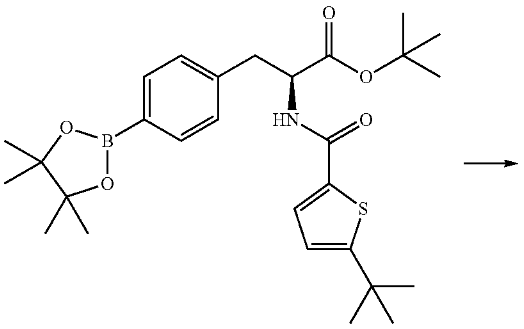

-continued

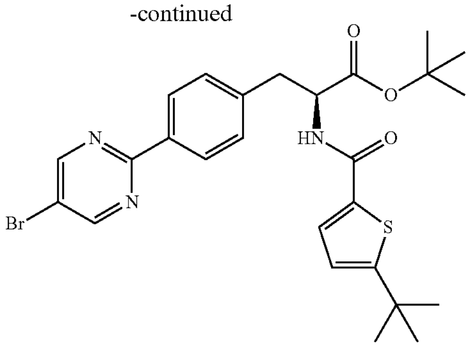

Prepared using General Procedure 10: Into a degassed solution of tert-butyl (S)-2-(5-(tert-butyl)thiophene-2-carboxamido)-3-(4-(4,4,5,5-tetramethyl-1,3,2-dioxaborolan-2-yl)phenyl)propanoate INT-16 (510 mg, 1.0 mmol) and 5-bromo-2-iodopyrimidine (570 mg, 2.0 mmol) in 2/2/1 ACN/THF/saturated aqueous $NaHCO_3$ (10 mL) was added Pd(dppf)$Cl_2$ (30 mg, 0.4 mmol). The reaction mixture was heated at 120° C. for 1 h in a microwave reactor. The reaction mixture was diluted with water (100 mL) and EA (50 mL) and filtered over Celite. The aqueous layer was extracted with EA (3×30 mL) and the combined organic layer was dried over $MgSO_4$, concentrated, and purified by chromatography (EA/hexanes) to provide 342 mg (63%) of tert-butyl (S)-3-(4-(5-bromopyrimidin-2-yl)phenyl)-2-(5-(tert-butyl)thiophene-2-carboxamido)propanoate INT-17. LCMS-ESI (m/z) calculated for $C_{26}H_{30}BrN_3O_3S$: 543.1. found: 488.0 $[M-tBu+H]^+$, $t_R$=10.95 min (Method 2).

(S)-3-(4-(5-bromopyrimidin-2-yl)phenyl)-2-(4-(tert-butyl)benzamido)propanoic acid (INT-27)

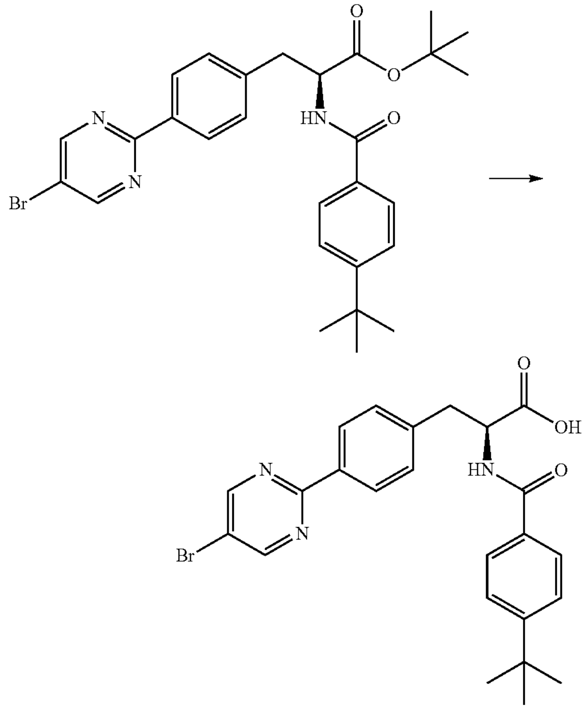

Prepared using General Procedure 8 and INT-14: LCMS-ESI (m/z) calculated for $C_{24}H_{24}BrN_3O_3$: 482.3. found 481.1 $[M-H]^+$, $t_R$=2.6 min (Method 15), and 98.7% e.e. (Chiral Method 1, isocratic with 2% Solvent A, 98% Solvent B). 1H NMR (400 MHz, $CDCl_3$) δ 8.87 (s, 2H), 8.32 (d, J=8.3 Hz, 2H), 7.64 (d, J=8.5 Hz, 2H), 7.45 (d, J=8.5 Hz, 2H), 7.36 (d, J=8.3 Hz, 2H), 6.64 (d, J=6.9 Hz, 1H), 5.16 (dd, J=12.7, 5.7 Hz, 1H), 3.42 (ddd, J=38.8, 14.0, 5.7 Hz, 2H), 1.32 (s, 9H).

Tert-butyl ((S)-3-(4-(5-bromopyrimidin-2-yl)phenyl)-2-(4-(tert-butyl)benzamido)-propanoyl)-D-alaninate (INT-32)

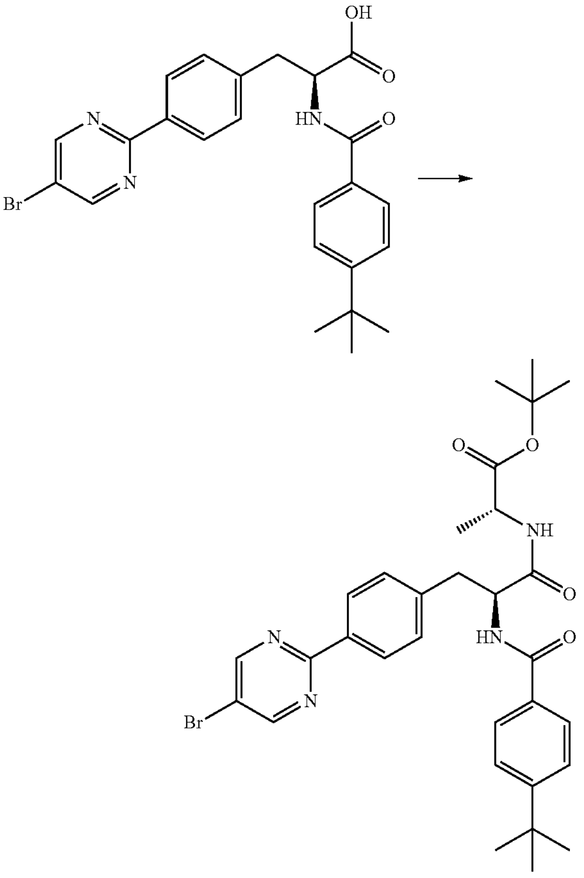

Prepared using General Procedure 7: To a stirring solution of (S)-3-(4-(5-bromopyrimidin-2-yl)phenyl)-2-(4-(tert-butyl)benzamido)propanoic acid INT-27 (1.50 g, 3.10 mmol) in DMF (15 mL) were added tert-butyl D-alaninate (680.0 mg, 3.73 mmol) and $Et_3N$ (802.3 mg, 6.2 mmol). The reaction was stirred for 1 hour at 0° C. and then HATU (877.5 mg, 3.37 mmol) in 2 mL DMF was added. The reaction was stirred for 1 hour at 0° C. and then warmed to room temperature with stirring for 18 hours. The reaction solution was extracted with aqueous $NaHCO_3$ (3×20 mL). The combined organics were dried over $MgSO_4$ and evaporated. The crude product was purified by column chromatography (50% EA in hexanes) to afford 1.44 g (76%) of tert-butyl ((S)-3-(4-(5-bromopyrimidin-2-yl)phenyl)-2-(4-(tert-butyl)benzamido)-propanoyl)-D-alaninate INT-32 as a solid powder. LCMS-ESI (m/z) calculated for $C_{31}H_{37}BrN_4O_4$: 609.6. found 610.2 $[M+H]^+$, $t_R$=4.05 min.

(Method 16). $^1H$ NMR (400 MHz, DMSO) δ 9.03 (s, 2H), 8.49 (d, J=8.7 Hz, 1H), 8.41 (d, J=7.2 Hz, 1H), 8.24 (d, J=8.2 Hz, 2H), 7.73 (t, J=7.4 Hz, 2H), 7.54-7.37 (m, 4H), 4.85 (td, J=10.1, 4.6 Hz, 1H), 4.16 (t, J=7.2 Hz, 1H), 3.24-2.97 (m, 2H), 1.50-1.29 (m, 9H), 1.32-1.17 (m, 12H).

(S)-3-(4-(5-bromopyrimidin-2-yl)phenyl)-2-(5-(tert-butyl)thiophene-2 carboxamido)-propanoic acid

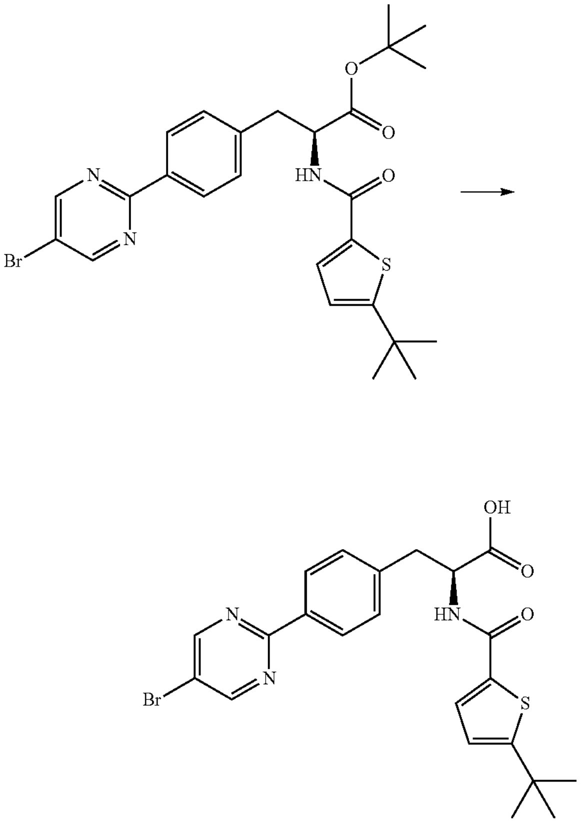

Prepared using General Procedure 8: To a stirring solution of tert-butyl (S)-3-(4-(5-bromopyrimidin-2-yl)phenyl)-2-(5-(tert-butyl)thiophene-2-carboxamido) propanoate INT-17 (15.7 g, 28.8 mmol) in DCM (30 mL) was treated with TFA (30.0 g, 263.1 mmol). The reaction mixture was stirred at room temperature for 18 hours to complete. The solvent was evaporated and then co-evaporated with toluene (3×20 mL) to remove trace TFA. The compound was dried under vacuum overnight to afford 13.7 g (97%) of (S)-3-(4-(5-bromopyrimidin-2-yl)phenyl)-2-(5-(tert-butyl)thiophene-2-carboxamido)propanoic acid as powder. LCMS-ESI (m/z) calculated for $C_{22}H_{22}BrN_3O_3S$: 487.1. found 488.1 $[M+H]^+$, $t_R$=2.55 min. (Method 16). $^1H$ NMR (400 MHz, DMSO) δ 9.05 (d, J=5.0 Hz, 2H), 8.64 (d, J=8.4 Hz, 1H), 8.25 (d, J=8.1 Hz, 2H), 7.62 (d, J=3.8 Hz, 1H), 7.45 (d, J=8.2 Hz, 2H), 6.92 (d, J=3.8 Hz, 2H), 4.64 (td, J=10.5, 4.5 Hz, 1H), 3.26 (dd, J=13.8, 4.4 Hz, 1H), 3.11 (dd, J=13.7, 10.7 Hz, 1H), 1.32 (s, 9H).

Methyl (S)-1-((S)-3-(4-(5-bromopyrimidin-2-yl) phenyl)-2-(5-(tert-butyl)thiophene-2-carboxamido) propanoyl)pyrrolidine-3-carboxylate (INT-35)

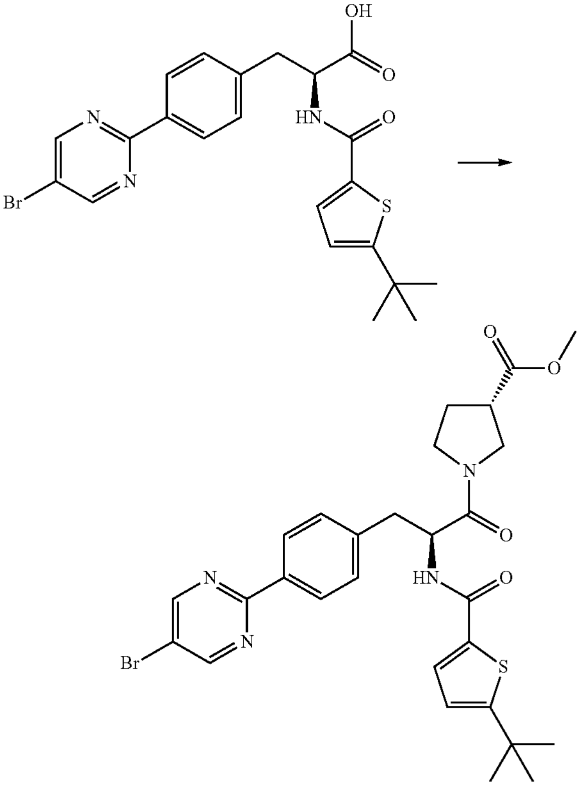

Prepared using General Procedure 7: To a stirring solution of methyl (S)-pyrrolidine-3-carboxylate (357.0 mg, 2.16 mmol) in DMF (10 mL) were added DIEA (465.26 mg, 3.60 mmol) and (S)-3-(4-(5-bromopyrimidin-2-yl)phenyl)-2-(5-(tert-butyl)thiophene-2-carboxamido)propanoic acid (700.0 mg, 1.44 mmol). The solution was cooled to 0° C. at ice bath and then HATU (677.55 mg, 2.88 mmol) in 2 mL DMF solution was slowly added. The reaction was stirred 1 hour at 0° C. and then warmed to RT with stirring for 2 hours. The reaction solution was extracted with DCM (3×20 mL) and aqueous $NaHCO_3$ (3×10 mL). The combined organics were dried over $MgSO_4$ and evaporated. The final compound was purified by column chromatography (40% DCM in hexane) to afford 501.0 mg (58%) of methyl (S)-1-((S)-3-(4-(5-bromopyrimidin-2-yl)phenyl)-2-(5-(tert-butyl)thiophene-2-carboxamido)propanoyl)pyrrolidine-3-carboxylate INT-35 as a powder. LCMS-ESI (m/z) calculated for $C_{28}H_{31}BrN_4O_4S$: 598.1. found 599.3 $[M+H]^+$, $t_R$=3.553 min. (Method 16). $^1H$ NMR (400 MHz, DMSO) δ 9.05 (d, J=1.1 Hz, 2H), 8.77 (dd, J=11.5, 8.3 Hz, 1H), 8.25 (d, J=7.7 Hz, 2H), 7.72 (d, J=3.5 Hz, 1H), 7.46 (d, J=8.3 Hz, 2H), 6.92 (d, J=3.8 Hz, 1H), 4.98-4.73 (m, 1H), 3.88 (dd, J=10.3, 8.0 Hz, 1H), 3.71 (dd, J=15.5, 7.5 Hz, 1H), 3.50 (ddd, J=18.3, 12.2, 5.4 Hz, 2H), 3.38 (dd, J=17.3, 7.6 Hz, 1H), 3.23 (ddd, J=28.0, 15.0, 8.7 Hz, 1H), 3.18-2.85 (m, 3H), 2.17-1.96 (m, 2H), 1.87 (td, J=15.2, 7.4 Hz, 1H), 1.32 (s, 9H).

Tert-butyl (S)-1-(3-(4-(5-bromopyrimidin-2-yl)phenyl)-2-(5-(tert-butyl)thiophene-2-carboxamido)propanoyl)azetidine-3-carboxylate (INT-38)

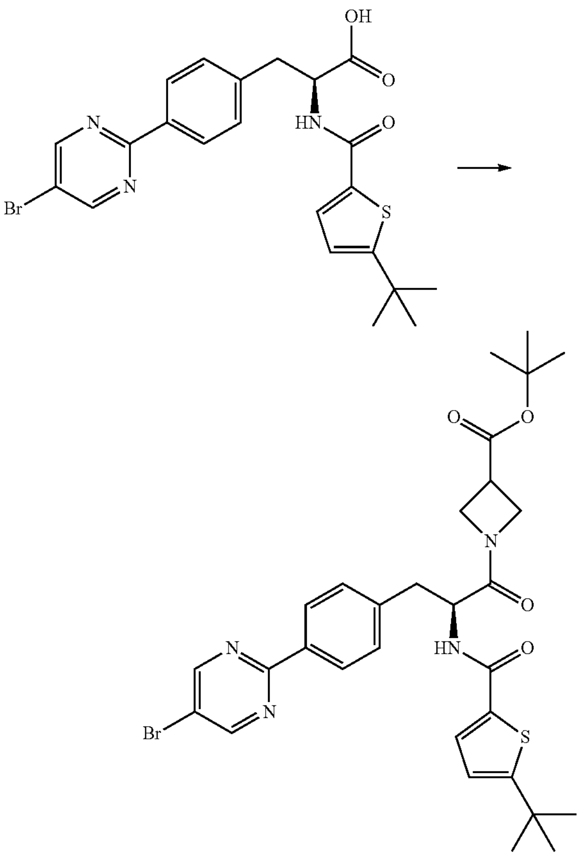

Prepared using General Procedure 7: To a stirring solution of tert-butyl azetidine-3-carboxylate (64.55 mg, 0.41 mmol) in DMF (1 mL) were added DIEA (169.6 mg, 1.31 mmol), and (S)-3-(4-(5-bromopyrimidin-2-yl)phenyl)-2-(5-(tert-butyl)thiophene-2-carboxamido)propanoic acid (100.0 mg, 0.21 mmol). The solution was cooled to 0° C. at ice bath and then HATU (74.11 mg, 1.31 mmol) in 1 mL DMF solution was slowly added. The reaction was stirred 1 hour at 0° C. and then warmed to RT with stirring for 2 hours. The reaction solution was extracted with DCM (3×10 mL) and aqueous $NaHCO_3$ (3×10 mL). The combined organics were dried over $MgSO_4$ and evaporated to afford 117.6 mg (85%) of tert-butyl (S)-1-(3-(4-(5-bromopyrimidin-2-yl)phenyl)-2-(5-(tert-butyl)thiophene-2-carboxamido) propanoyl) azetidine-3-carboxylate INT-38 as a solid powder without further purification for next step. LCMS-ESI (m/z) calculated for $C_{30}H_{35}BrN_4O_4S$: 626.2. found 627.2 [M+H]+, $t_R$=3.884 min. (Method 16). $^1$H NMR (400 MHz, DMSO) δ 9.03 (d, J=1.0 Hz, 2H), 8.66 (dd, J=30.6, 8.1 Hz, 1H), 8.25 (dd, J=8.1, 6.1 Hz, 2H), 7.82-7.60 (m, 1H), 7.44 (dd, J=8.2, 4.5 Hz, 2H), 6.91 (dd, J=3.8, 1.2 Hz, 1H), 4.77-4.49 (m, 1H), 4.36 (t, J=8.9 Hz, 0.5H), 4.31-4.24 (m, 0.5H), 4.20 (t, J=8.8 Hz, 0.5H), 4.06-3.94 (m, 1H), 3.93-3.83 (m, 1H), 3.78 (dd, J=9.6, 6.1 Hz, 0.5H), 3.44-3.30 (m, 1H), 3.06 (tdd, J=13.6, 11.5, 5.4 Hz, 2H), 1.40 (d, J=5.7 Hz, 4H), 1.35-1.27 (m, 14H).

(S)-tert-butyl 1-((S)-3-(4-(5-bromopyrimidin-2-yl)phenyl)-2-(5-(tert-butyl)thiophene-2-carboxamido)propanoyl)pyrrolidine-2-carboxylate (INT-54)

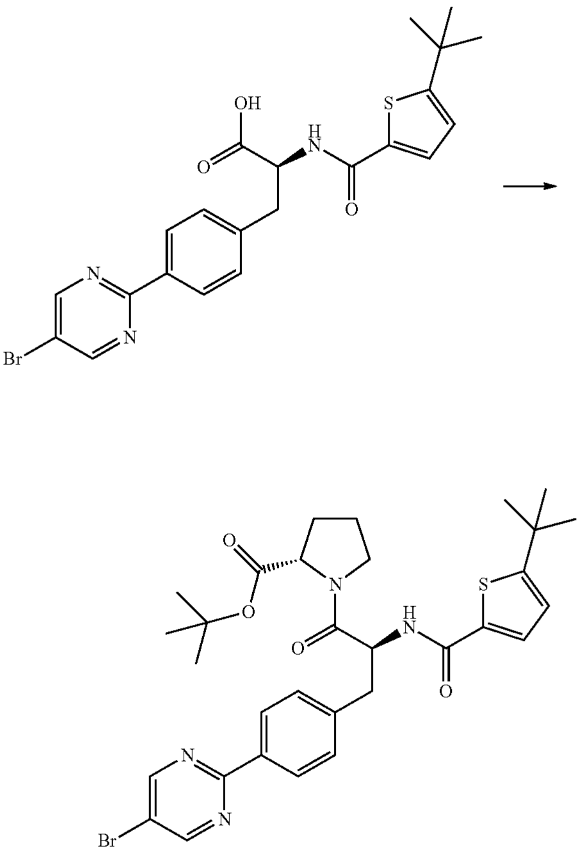

Prepared using General Procedure 7: To a stirred solution of (S)-3-(4-(5-bromopyrimidin-2-yl)phenyl)-2-(5-(tert-butyl)thiophene-2-carboxamido) propanoic acid (1.0 g, 2.05 mmol) in DMF (5 mL) at 0° C. was added DIPEA (2.14 mL, 12.28 mmol) followed by tert-butyl-L-prolinate hydrochloride (0.468 g, 2.25 mmol). To the mixture was added HATU (0.856 g, 2.25 mmol) dissolved in DMF (1.5 mL), portion wise, over 10 minutes. The reaction was allowed to warm to room temperature and stirred overnight. The reaction was diluted with saturated sodium bicarbonate solution and extracted with DCM (3×30 mL). The combined organic layers were dried over $MgSO_4$ and solvents evaporated. The crude product was purified by column chromatography (0-40% EtOAc/Hexanes) to afford 1.06 g (81%) of (S)-tert-butyl 1-((S)-3-(4-(5-bromopyrimidin-2-yl)phenyl)-2-(5-(tert-butyl)thiophene-2-carboxamido) propanoyl)pyrrolidine-2-carboxylate (INT-54). LCMS-ESI (m/z) calculated for $C_{31}H_{37}BrN_4O_4S$: 640.2. found 641.3 [M+H]+, $t_R$=10.63 min (Method 14). $^1$H NMR (400 MHz, DMSO-d6) δ 9.03 (s, 2H), 8.70 (d, J=8.4 Hz, 1H), 8.23 (d, J=9.1 Hz, 2H), 7.68 (d, J=3.9 Hz, 1H), 7.52 (d, J=8.3 Hz, 2H), 6.90 (d, J=3.8 Hz, 1H), 4.97-4.84 (m, 1H), 4.23 (m, 1H), 3.83-3.62 (m, 2H), 3.09 (m, 2H), 2.18 (m, 1H), 1.96 (m, 2H), 1.82 (m, 1H), 1.39-1.28 (m, 18H).

Tert-butyl ((S)-3-(4-(5-bromopyrimidin-2-yl)phenyl)-2-(5-(tert-butyl)thiophene-2-carboxamido)propanoyl)-D-alaninate

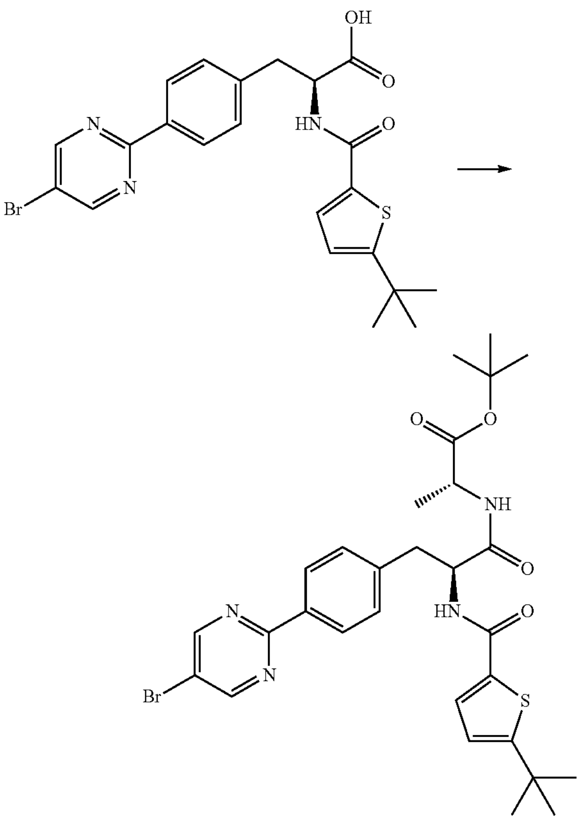

Prepared using General Procedure 7: To a stirring solution of tert-butyl D-alaninate (5.60 g, 30.80 mmol) in DMF (50 mL) were added DIEA (8.29 g, 64.18 mmol) and (S)-3-(4-(5-bromopyrimidin-2-yl)phenyl)-2-(5-(tert-butyl)thiophene-2-carboxamido)-propanoic acid (12.5 g, 25.67 mmol). The solution was cooled to 0° C. at ice bath and then HATU (9.06 g, 38.50 mmol) in 15 mL DMF solution was slowly added. The reaction was stirred 1 hour at 0° C. and then warmed to RT with stirring for 2 hours. The reaction solution was extracted with DCM (3×50 mL) and aqueous $NaHCO_3$ (3×30 mL). The combined organics were dried over $MgSO_4$ and evaporated. The final compound was purified by column chromatography (40% DCM in hexane) to afford 14.7 g (94%) of tert-butyl ((S)-3-(4-(5-bromopyrimidin-2-yl)phenyl)-2-(5-(tert-butyl)thiophene-2-carboxamido)propanoyl)-D-alaninate as solid powder. LCMS-ESI (m/z) calculated for $C_{29}H_{35}BrN_4O_4S$: 614.2. found 615.3 $[M+H]^+$, $t_R$=3.914 min. (Method 16). $^1H$ NMR (400 MHz, $CDCl_3$) δ 8.83 (d, J=3.6 Hz, 2H), 8.36 (d, J=8.2 Hz, 2H), 7.39 (d, J=8.2 Hz, 2H), 7.34 (d, J=3.8 Hz, 1H), 6.81 (d, J=3.8 Hz, 1H), 6.66 (d, J=7.6 Hz, 1H), 6.34 (d, J=7.2 Hz, 1H), 4.88 (d, J=5.9 Hz, 1H), 4.41 (t, J=7.2 Hz, 1H), 3.31 (dd, J=13.6, 5.8 Hz, 1H), 3.20 (dd, J=13.6, 7.8 Hz, 1H), 1.51-1.32 (m, 18H), 1.27 (d, J=7.1 Hz, 3H). $^{13}C$ NMR (101 MHz, DMSO) δ 172.02, 171.31, 162.28, 162.13, 161.42, 158.55, 142.27, 136.34, 134.66, 130.20, 128.82, 127.92, 123.07, 118.63, 80.90, 54.45, 48.86, 39.59, 39.38, 32.39, 28.04, 17.68.

(2R)-tert-butyl 2-((2S)-2-(5-(tert-butyl)thiophene-2-carboxamido)-3-(4-(5-(4'-propyl-[1,1'-bi(cyclohexan)]-3-en-4-yl)pyrimidin-2-yl)phenyl)propanamido)propanoate

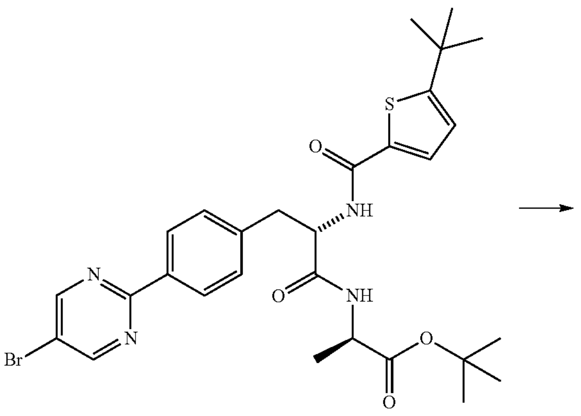

-continued

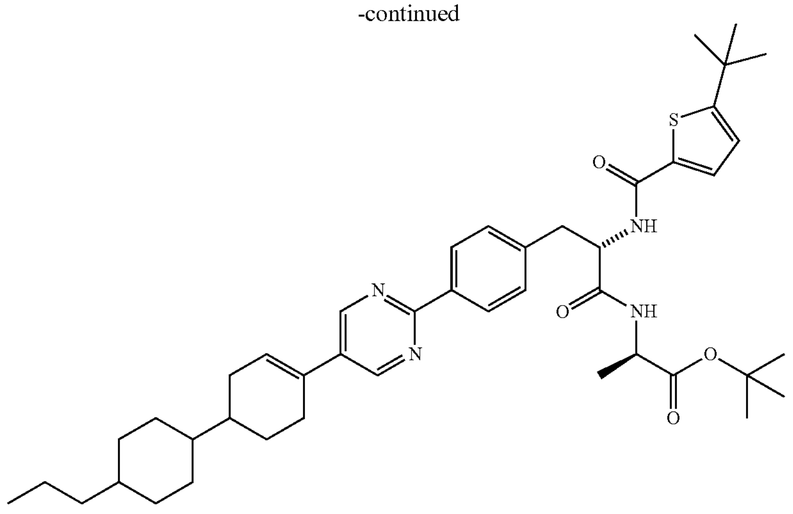

Prepared using General Procedure 10: A stirred solution of (R)-tert-butyl 2-((S)-3-(4-(5-bromopyrimidin-2-yl)phenyl)-2-(5-(tert-butyl)thiophene-2-carboxamido) propanamido)propanoate (0.15 g, 0.244 mmol) and (4'-propyl-[1,1'-bi(cyclohexan)]-3-en-4-yl)boronic acid (0.061 g, 0.244 mmol) in dioxane (12 mL) was treated with sodium hydrogencarbonate (0.54 mL of a 0.9 M aqueous solution, 0.487 mmol), warmed to 40° C. and de-gassed. $PdCl_2$dppf (7.13 mg, 9.75 mol) was charged, the mixture de-gassed, then heated under reflux for 3 h. The reaction was allowed to cool to RT, poured onto water (50 mL) and extracted with EA (3×50 mL). The combined organic extracts were dried over $Na_2SO_4$ and evaporated. Column chromatography (EA/iso-hexanes) gave 142 mg (78%) of a mixture of diastereomers (2R)-tert-butyl 2-((2S)-2-(5-(tert-butyl)thiophene-2-carboxamido)-3-(4-(5-(4'-propyl-[1,1'-bi(cyclohexan)]-3-en-4-yl) pyrimidin-2-yl)phenyl)propanamido)propanoate as an off-white solid. LCMS-ESI (m/z) calculated for $C_{44}H_{60}N_4O_4S$: 741.1; no m/z observed, $t_R$=3.49 min (Method 11).

(S)-2-(((benzyloxy)carbonyl)amino)-3-(4-(5-bromopyrimidin-2-yl)phenyl)propanoic acid

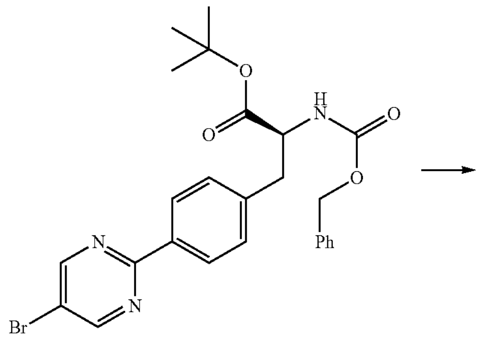

-continued

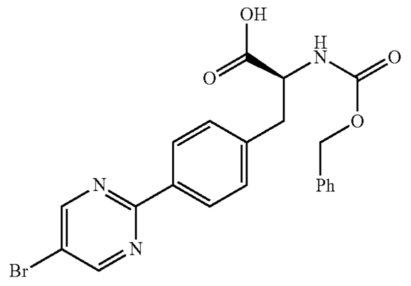

Prepared using General Procedure 8: To a stirring solution of tert-butyl (S)-2-(((benzyloxy)carbonyl)amino)-3-(4-(5-bromopyrimidin-2-yl)phenyl)propanoate INT-7 (3.0 g, 5.8 mmol) in DCM (20 mL) was treated with TFA (10 mL). The reaction mixture was stirred at room temperature for 18 h. The solvent was evaporated and then co-evaporated with toluene (3×20 mL) to remove residual TFA. The compound was dried under vacuum overnight to afford 13.7 g (97%) of (S)-3-(4-(5-bromopyrimidin-2-yl)phenyl)-2-(5-(tert-butyl) thiophene-2-carboxamido)propanoic acid as powder. LCMS-ESI (m/z) calculated for $C_{21}H_{18}BrN_3O_4$: 456.30. found 457.43 $[M+H]^+$, $t_R$=2.21 min (Method 16).

Tert-butyl (S)-1-(2-(((benzyloxy)carbonyl amino)-3-(4-(5-bromopyrimidin-2-yl)phenyl)propanoyl)azetidine-3-carboxylate

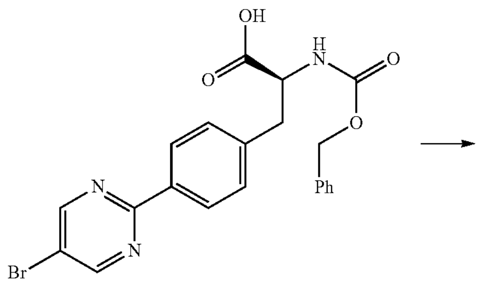

-continued

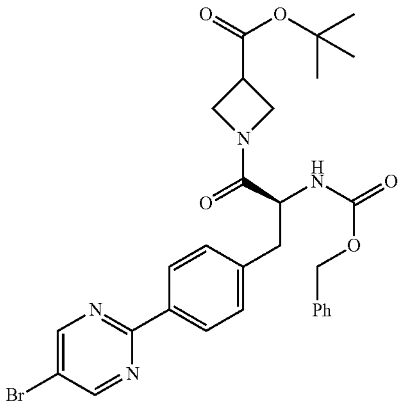

Prepared using General Procedure 7: To a stirred solution of (S)-2-(((benzyloxy)carbonyl)amino)-3-(4-(5-bromopyrimidin-2-yl)phenyl)propanoic acid (6.0 g, 12.2 mmol) in DMF (20 mL) at 0° C. was added DIPEA (15.8 g, 122 mmol) followed by tert-butyl azetidine-3-carboxylate hydrochloride (2.85 g, 14.7 mmol). To the mixture was added HATU (14 g, 36 mmol) slowly in three portions with 30 minute intervals. The reaction was allowed to stir at 0° C. for 2 h and then allowed to warm to RT over 2 h. Then the reaction mixture was diluted with saturated sodium bicarbonate solution (25 mL), water (25 mL) and EA (100 mL). The layers were separated and the aqueous layer was extracted with EA (2×100 mL). The combined organic layers were washed with water, brine and then dried over $MgSO_4$ and concentrated. The crude product was purified by column chromatography (0-40% EA/Hexanes) to afford 4.6 g (60%) of tert-butyl (S)-1-(2-(((benzyloxy)carbonyl)amino)-3-(4-(5-bromopyrimidin-2-yl)phenyl)propanoyl)azetidine-3-carboxylate. LCMS-ESI (m/z) calculated for $C_{29}H_{31}BrN_4O_5$: 595.5. found 596.6 $[M+H]^+$, $t_R$=3.59 min (Method 16).

Tert-butyl 1-((2S)-2-(((benzyloxy)carbonyl)amino)-3-(4-(5-(4'-propyl-[1,1'-bi(cyclohexan)]-3-en-4-yl)pyrimidin-2-yl)phenyl)propanoyl)azetidine-3-carboxylate

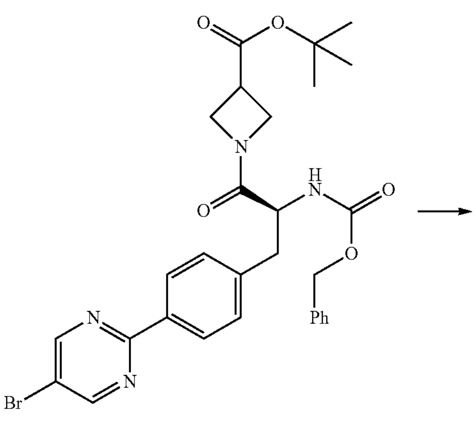

-continued

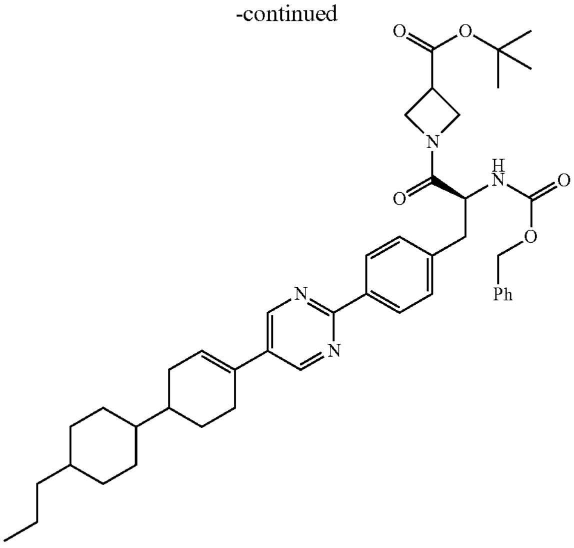

Prepared using General Procedure 10: A stirred solution of tert-butyl (S)-1-(2-(((benzyloxy)carbonyl)amino)-3-(4-(5-bromopyrimidin-2-yl)phenyl) propanoyl) azetidine-3-carboxylate (1.5 g, 2.52 mmol) and (4'-propyl-[1,1'-bi(cyclohexan)]-3-en-4-yl)boronic acid (0.76 g, 3.02 mmol) in 3:1 mixture of dioxane and water (20 mL) was treated with sodium carbonate (0.30 g, 5.0 mmol) and the mixture was de-gassed for 5 min. $PdCl_2dppf$ (0.18 g, 0.25 mmol) was charged, the mixture was de-gassed again for 2 min, then heated at 70° C. for 7 h. The reaction mixture was allowed to cool to RT and then diluted with EA (20 mL) and water (20 mL). The layers were separated and the aqueous layer was extracted with EA (3×50 mL). The combined organic extracts were dried over $MgSO_4$ and solvent evaporated. Column chromatography of crude product (0-60% EA/Hexanes) gave 1.56 g (85%) of a mixture of diastereomers tert-butyl 1-((2S)-2-(((benzyloxy)carbonyl)amino)-3-(4-(5-(4'-propyl-[1,1'-bi(cyclohexan)]-3-en-4-yl)pyrimidin-2-yl)phenyl)propanoyl)azetidine-3-carboxylate as an off-white solid. LCMS-ESI (m/z) calculated for $C_{44}H_{56}N_4O_5$: 720.95. found 721.63 $[M+H]^+$, $t_R$=7.02 min (Method 16).

Tert-butyl 1-((2S)-2-amino-3-(4-(5-(4'-propyl-[1,1'-bi(cyclohexan)]-3-en-4-yl)pyrimidin-2-yl)phenyl)propanoyl)azetidine-3-carboxylate (INT-64)

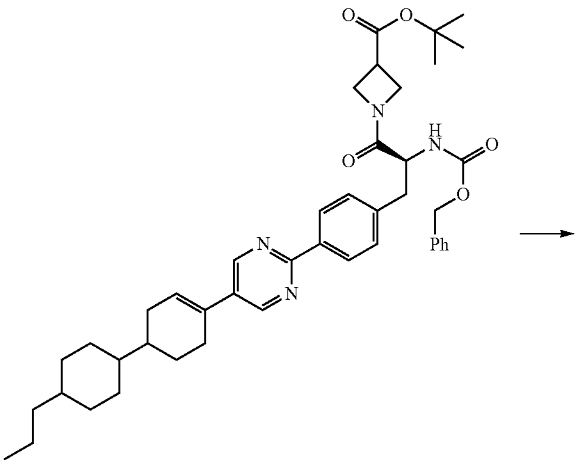

-continued

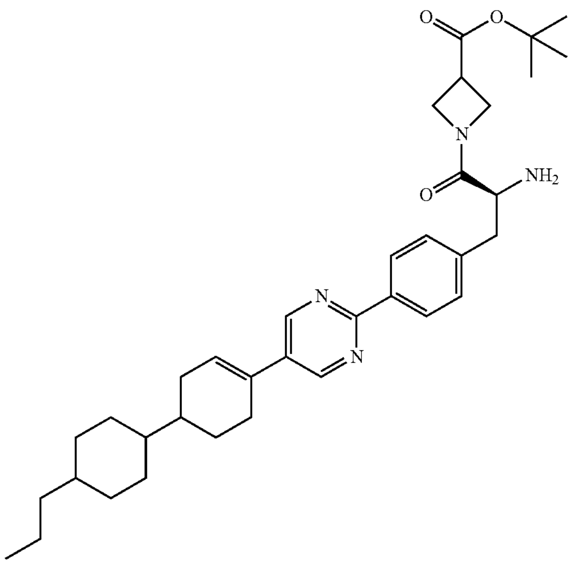

Prepared using General Procedure 18. To a stirring solution of a diastereomeric mixture of tert-butyl 1-((2S)-2-(((benzyloxy)carbonyl)amino)-3-(4-(5-(4'-propyl-[1,1'-bi (cyclohexan)]-3-en-4-yl)pyrimidin-2-yl)phenyl)propanoyl) azetidine-3-carboxylate (1.0 g, 1.38 mmol) in EA (40 mL) was added Pd/C (0.1 g, 0.1 mmol) and the reaction was flushed with hydrogen gas three times. The reaction mixture was stirred under an atmosphere of hydrogen for 36 hours, the mixture was filtered over Celite, and then concentrated to give 0.75 g (92%) of a mixture of diastereomers tert-butyl 1-((2S)-2-amino-3-(4-(5-(4'-propyl-[1,1'-bi(cyclohexan)]-3-en-4-yl)pyrimidin-2-yl)phenyl)propanoyl)azetidine-3-carboxylate (INT-64) as gray solid. The material was used without further purification. LCMS-ESI (m/z) calculated for $C_{36}H_{50}N_4O_3$: 586.8 found 587.4 $[M+H]^+$, $t_R$=5.82 min (Method 16). This material contains ~10% olefin reduced bi-product, tert-butyl (S)-1-(2-amino-3-(4-(5-(4'-propyl-[1, 1'-bi(cyclohexan)]-4-yl)pyrimidin-2-yl)phenyl)propanoyl) azetidine-3-carboxylate and could not be separated by column chromatography. LCMS-ESI (m/z) calculated for $C_{36}H_{52}N_4O_3$: 588.82. found 589.4 $[M+H]^+$, $t_R$=5.58 min (Method 16).

Methyl (S)-1-(3-(4-(5-bromopyrimidin-2-yl)phenyl)-2-(5-(tert-butyl)thiophene-2-carboxamido)propanoyl)azetidine-3-carboxylate

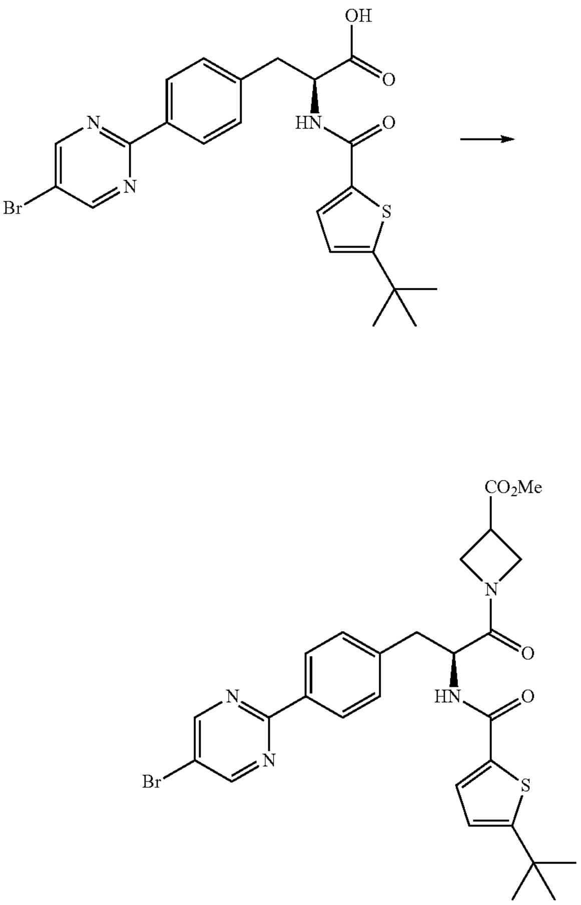

Prepared using General Procedures 7: To a stirred solution of (S)-3-(4-(5-bromopyrimidin-2-yl)phenyl)-2-(5-(tert-butyl)thiophene-2-carboxamido)propanoic acid (3.85 g, 7.90 mmol) in DMF (50 mL), treated with methyl azetidine-3-carboxylate hydrochloride (3.59 g, 23.69 mmol) and cooled to −5° C. whereupon DIEA (8.75 mL, 47.4 mmol) was added. When a clear solution was observed, HATU (7.51 g, 19.74 mmol) was added portionwise, to maintain internal temperature between 0 and −5° C. After 15 min, further HATU (0.75 g, 1.97 mmol) was charged. After a further 30 min the mixture was quenched with water (2 mL) and allowed to warm to room temperature. The mixture was diluted with water (~30 mL) and acidified with AcOH. The precipitate was collected by filtratrion, washing successively with water (3x30 mL) then ACN (2x5 mL) to afford 4.25 g (92%) of methyl (S)-1-(3-(4-(5-bromopyrimidin-2-yl)phenyl)-2-(5-(tert-butyl)thiophene-2-carboxamido) propanoyl) azetidine-3-carboxylate. LCMS-ESI (m/z) calculated for $C_{27}H_{29}BrN_4O_4S$: 584.1. found 585.0 $[M+H]^+$, $t_R$=2.55 min (Method 11).

(S)-1-(3-(4-(5-bromopyrimidin-2-yl)phenyl)-2-(5-(tert-butyl)thiophene-2-carboxamido)propanoyl) azetidine-3-carboxylic acid (INT-71)

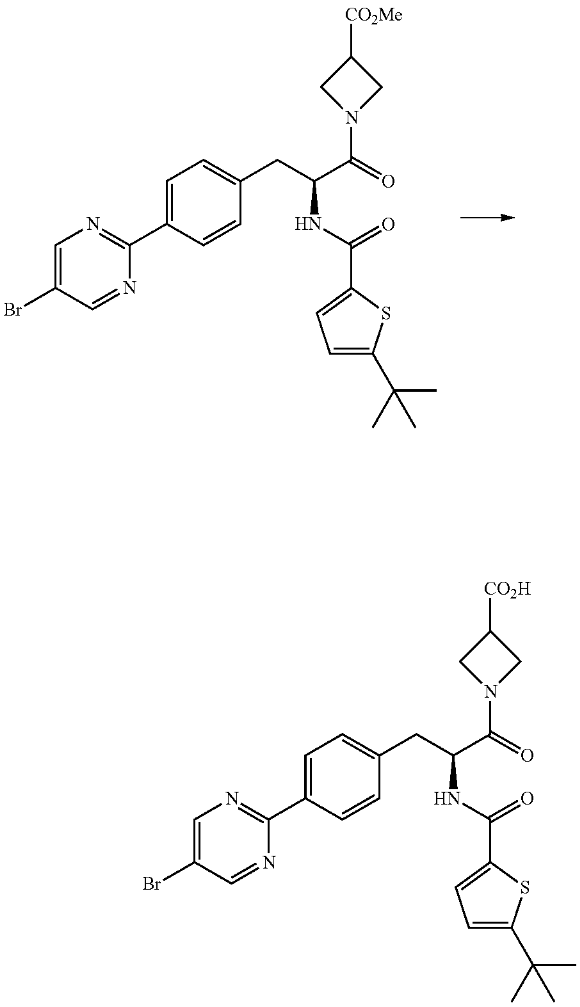

To a stirred mixture of water (140 mL) and AcOH (140 mL) was added sulfuric acid (53.2 mL, 993 mmol) and the mixture allowed to cool to room temperature. This was then added to a stirred solution of (S)-methyl 1-(3-(4-(5-bromopyrimidin-2-yl)phenyl)-2-(5-(tert-butyl)thiophene-2-carboxamido) propanoyl) azetidine-3-carboxylate (19.39 g, 33.1 mmol) in dioxane (225 mL). After 20 h, the mixture was diluted with ice water (500 mL) and extracted with DCM (2×350 mL). The combined organic extracts were washed with water (2×500 mL) dried over $MgSO_4$ and solvents evaporated. Column chromatography (DCM/EA/AcOH) gave 12.96 g (69%) of (S)-1-(3-(4-(5-bromopyrimidin-2-yl)phenyl)-2-(5 (tert-butyl)thiophene-2-carboxamido) propanoyl)azetidine-3-carboxylic acid INT-71. LCMS-ESI (m/z) calculated for $C_{26}H_{27}BrN_4O_4S$: 570.1. found 571.0 $[M+H]^+$, $t_R$=2.36 min (Method 11).

((S)-3-(4-(5-bromopyrimidin-2-yl)phenyl)-2-(5-(tert-butyl)thiophene-2-carboxamido)propanoyl)-D-alanine (INT-72)

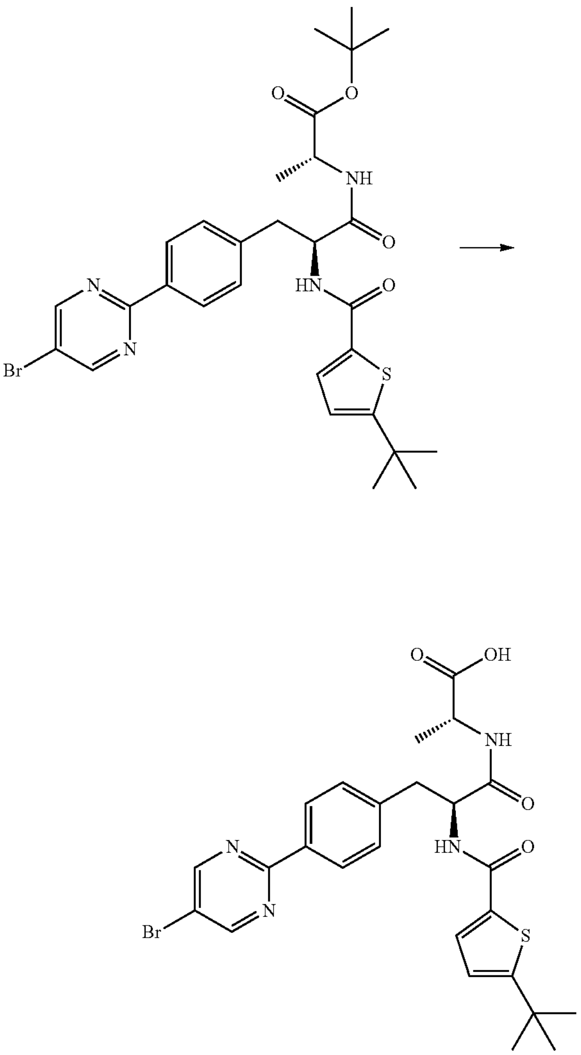

Prepared using General Procedure 8: To a stirred solution of (R)-tert-butyl 2-((S)-3-(4-(5-bromopyrimidin-2-yl)phenyl)-2-(5-(tert-butyl)thiophene-2-carboxamido) propanamido) propanoate (4.8 g, 7.80 mmol) in DCM (150 mL) was added TFA (18 mL). After 16 h, the reaction was diluted with toluene (100 mL) and solvents evaporated to afford 4.36 g (100%) of ((S)-3-(4-(5-bromopyrimidin-2-yl)phenyl)-2-(5-(tert-butyl)thiophene-2-carboxamido)propanoyl)-D-alanine INT-72. LCMS-ESI (m/z) calculated for $C_{25}H_{27}BrN_4O_4S$: 558.1; no m/z observed, $t_R$=2.43 min (Method 11).

((2S)-2-(5-(tert-butyl)thiophene-2-carboxamido)-3-(4-(5-(4'-propyl-[1,1'-bi(cyclohexan)]-3-en-4-yl) pyrimidin-2-yl)phenyl)propanoyl)-D-alanine (Compound 1)

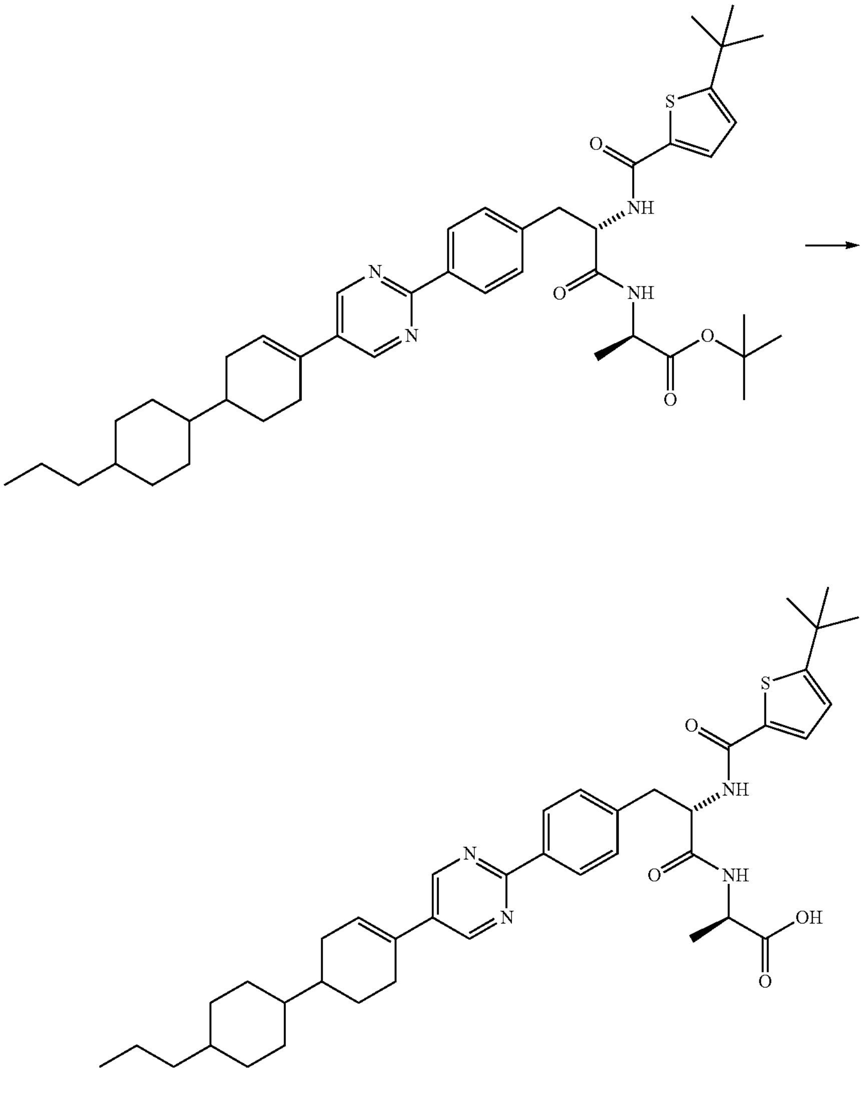

Prepared using General Procedure 8: To a stirring solution of a diastereomeric mixture of (2R)-tert-butyl 2-((2S)-2-(5-(tert-butyl)thiophene-2-carboxamido)-3-(4-(5-(4'-propyl-[1, 1'-bi(cyclohexan)]-3-en-4-yl) pyrimidin-2-yl)phenyl)propanamido)propanoate (136 mg, 0.184 mmol) in DCM (10 mL) was added TFA (1.7 mL, 22 mmol). After 16 h, the reaction was diluted with toluene (10 mL) and solvents evaporated. The mixture was further co-evaporated with toluene (2×10 mL) to give a pale brown glass. Column chromatography (EA/AcOH/DCM/iso-hexanes) gave 94 mg (75%) of a mixture of diastereomers (2R)-2-((2S)-2-(5-(tert-butyl)thiophene-2-carboxamido)-3-(4-(5-(4'-propyl-[1,1'-bi (cyclohexan)]-3-en-4-yl)pyrimidin-2-yl)phenyl)propanamido) propanoic acid (Compound 1) as a cream solid. LCMS-ESI (m/z) calculated for $C_{40}H_{52}N_4O_4S$: 684.4; no m/z observed, $t_R$=12.15 min (Method 10). Chiral analysis showed 92.8% d.e. $t_R$=21.00 min (Chiral Method 1). $^1H$ NMR (400 MHz, DMSO-d6) δ 12.60 (s, 1H), 8.90 (s, 2H), 8.51 (d, J=8.7 Hz, 1H), 8.44 (d, J=7.4 Hz, 1H), 8.31-8.20 (m, 2H), 7.67-7.65 (m, 1H), 7.51-7.44 (m, 2H), 6.91 (dd, J=3.9, 2.0 Hz, 1H), 6.44 (br s, 1H), 4.80 (td, J=9.5, 4.4 Hz, 1H), 4.25 (p, J=7.1 Hz, 1H), 3.17-2.95 (m, 2H), 2.47-2.18 (m, 2H), 1.99-1.92 (m, 2H), 1.83-1.75 (m, 4H), 1.44-0.78 (m, 28H).

Compound 2 was prepared from (R)-tert-butyl 2-((S)-3-(4-(5-bromopyrimidin-2-yl)phenyl)-2-(5-(tert-butyl)thiophene-2-carboxamido)propanamido) propanoate using General Procedures 10 then 8.

Compound 3 was prepared from INT-35 using General Procedures 10 then 4.

1-((2S)-2-(5-(tert-butyl)thiophene-2-carboxamido)-3-(4-(5-(4'-pentyl-[1,1'-bi(cyclohexan)]-3-en-4-yl)pyrimidin-2-yl)phenyl)propanoyl)azetidine-3-carboxylic acid (Compound 4)

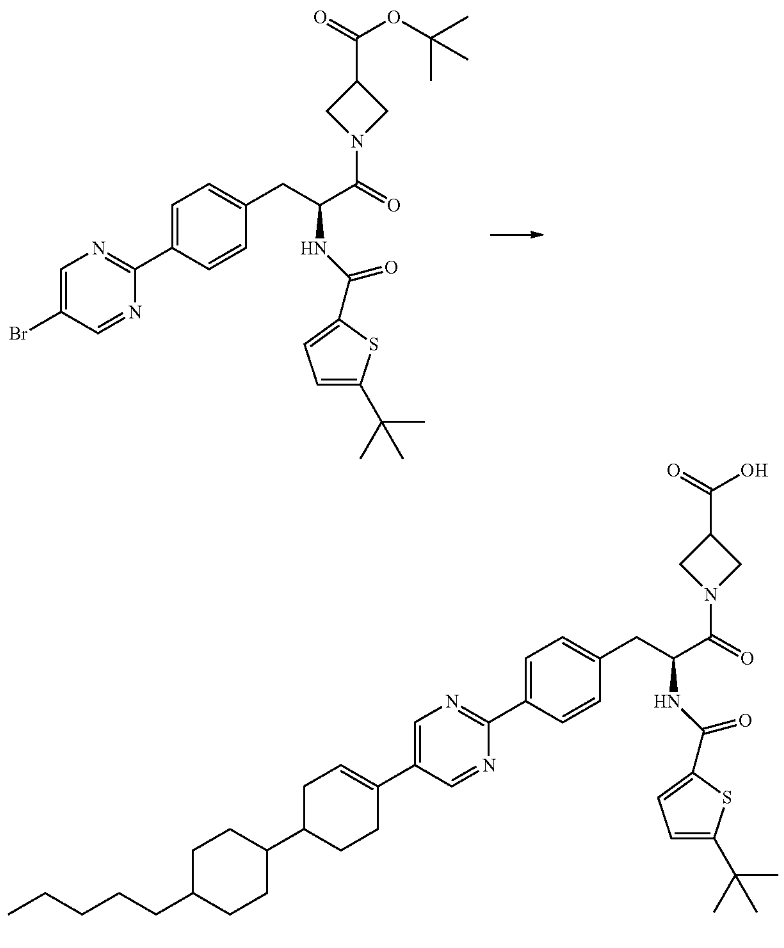

Prepared using General Procedures 10 and 8: A stirring solution of (4'-pentyl-[1,1'-bi(cyclohexan)]-3-en-4-yl)boronic acid (200.3 mg, 0.72 mmol), sodium carbonate decahydrate (57.6 mg, 0.96 mmol), tert-butyl (S)-1-(3-(4-(5-bromopyrimidin-2-yl)phenyl)-2-(5-(tert-butyl)thiophene-2-carboxamido) propanoyl)azetidine-3-carboxylate INT-38 (300.0 mg, 0.48 mmol) and Pd(dppf)$Cl_2$ (35.1 mg, 0.048 mmol) in dioxane (9 mL) and water (3 mL) was degassed by nitrogen and was heated to 60° C. for 2 hours. The reaction solution was evaporated under reduced pressure and then diluted with DCM (20 mL). The crude material was extracted with aqueous $NaHCO_3$ (3x20 mL). The combined organics were dried over $MgSO_4$ and the solvent was evaporated. The crude product was purified by column chromatography (50% EA in hexanes) to afford 302.5 mg (80.8%) of tert-butyl 1-((2S)-2-(5-(tert-butyl)thiophene-2-carboxamido)-3-(4-(5-(4'-pentyl-[1,1'-bi(cyclohexan)]-3-en-4-yl) pyrimidin-2-yl)phenyl)propanoyl)azetidine-3-carboxylate as an intermediate. The intermediate was dissolved in DCM (10 ml) and treated with 5.0 mL of TFA and stirred at room temperature for 18 hours. The product was co-evaporated with $CH_3CN$ (5x10 mL) to afford 268.2 mg (77%) of a mixture of diastereomers 1-((2S)-2-(5-(tert-butyl)thiophene-2-carboxamido)-3-(4-(5-(4'-pentyl-[1,1'-bi(cyclohexan)]-3-en-4-yl)pyrimidin-2-yl)phenyl)propanoyl) azetidine-3-carboxylic acid (Compound 4) as a solid powder. LCMS-ESI (m/z) calculated for $C_{43}H_{56}N_4O_4S$: 724.4. found 725.3 $[M+H]^+$, $t_R$=12.55 min. (Method 14); $^1$H NMR (400 MHz, DMSO) δ 8.90 (d, J=1.0 Hz, 2H), 8.70 (d, J=8.1 Hz, 1H), 8.27 (dd, J=8.1, 4.6 Hz, 2H), 7.69 (d, J=3.9 Hz, 1H), 7.43 (d, J=8.0 Hz, 2H), 6.92 (d, J=3.8 Hz, 1H), 6.42 (s, 1H), 4.76-4.54 (m, 3H), 4.43 (t, J=8.8 Hz, 1H), 4.37-4.23 (m, 1H), 4.17 (dd, J=18.4, 7.7 Hz, 1H), 4.11-3.96 (m, 2H), 3.95-3.77 (m, 1H), 3.38 (d, J=44.3 Hz, 1H), 3.18-2.94 (m, 2H), 2.40 (s, 1H), 2.27 (d, J=18.8 Hz, 1H), 1.97 (d, J=18.0 Hz, 2H), 1.86-1.63 (m, 4H), 1.46-1.19 (m, 16H), 1.15 (s, 4H), 0.98 (dd, J=24.6, 11.9 Hz, 2H), 0.8-0.95 (m, J=7.0 Hz, 4H). $^{13}$C NMR (101 MHz, DMSO) δ 173.44, 170.43, 162.00, 161.32, 160.81, 153.27, 140.57, 135.44, 135.27, 131.62, 130.53, 129.53, 129.49, 128.47, 127.22, 122.66, 52.60, 50.29, 50.17, 41.77, 39.52, 39.31, 39.10, 38.89, 38.02, 37.25, 34.36, 32.94, 31.88, 31.56, 29.54, 29.32, 29.28, 26.30, 25.97, 25.68, 22.04, 13.86.

Compounds 5 and 8 were prepared from INT-54 using General Procedures 10 then 8.

1-((2S)-2-(5-(tert-butyl)thiophene-2-carboxamido)-3-(4-(5-(4'-propyl-[1,1'-bi(cyclohexan)]-3-en-4-yl)pyrimidin-2-yl)phenyl)propanoyl)azetidine-3-carboxylic acid (Compound 6)

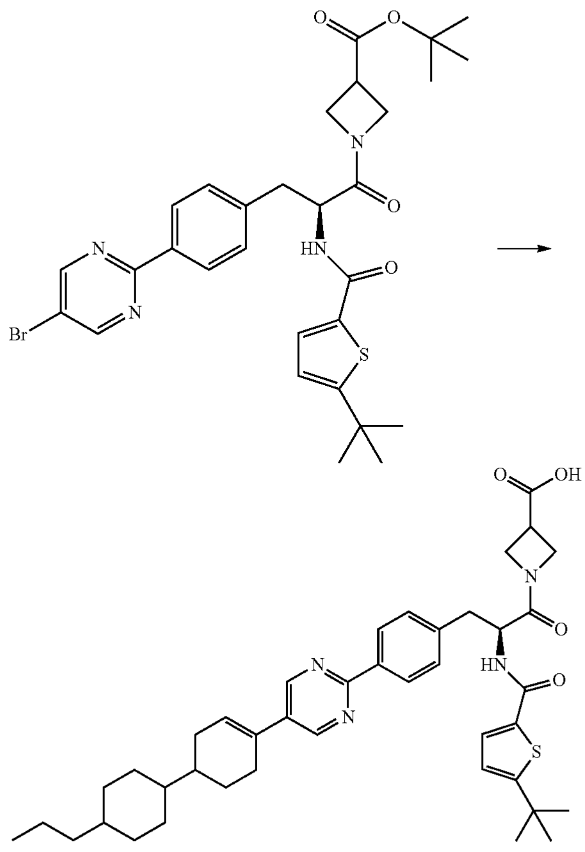

Prepared using General Procedure 10 and 8: To a stirring solution of (4'-propyl-[1,1'-bi(cyclohexan)]-3-en-4-yl)boronic acid (31.9 mg, 0.13 mmol), sodium carbonate decahydrate (7.8 mg, 0.13 mmol), tert-butyl (S)-1-(3-(4-(5-bromopyrimidin-2-yl)phenyl)-2-(5-(tert-butyl)thiophene-2-carboxamido) propanoyl)-azetidine-3-carboxylate INT-38 (40.0 mg, 0.064 mmol) and Pd(dppf)$Cl_2$ (46.8 mg, 0.048 mmol) in dioxane (3 mL) and water (1.0 mL). The reaction solution was degassed by nitrogen and was heated to 60° C. for 2 hours. The reaction solvent was evaporated under reduced pressure and then diluted in DCM (10 mL). The crude material was extracted with aqueous $NaHCO_3$ (2×3 mL). The combined organics were dried over $MgSO_4$ and the solvent was evaporated. To the crude material in 1 ml DCM was added 0.1 mL of TFA and stirred at room temperature for 18 hours. The final product was purified by HPLC to afford 1.14 mg (2.6%) of a mixture of diastereomers 1-((2S)-2-(5-(tert-butyl)thiophene-2-carboxamido)-3-(4-(5-(4'-propyl-[1,1'-bi(cyclohexan)]-3-en-4-yl)pyrimidin-2-yl)phenyl)propanoyl) azetidine-3-carboxylic acid (Compound 6) as a solid. LCMS-ESI (m/z) calculated for $C_{41}H_{52}N_4O_4S$: 696.4. found: 697.4[M+H]$^+$, $t_R$=11.38 min. (Method 14). Chiral analysis showed 97.2% d.e. $t_R$=21.01 min (Chiral Method 1); $^1$H NMR (400 MHz, DMSO) δ 12.59 (s, 1H), 8.90 (d, J=1.5 Hz, 2H), 8.68 (dd, J=8.2, 2.6 Hz, 0.9H), 8.56 (d, J=8.0 Hz, 0.1H), 8.26 (dd, J=8.1, 4.5 Hz, 2H), 7.68 (d, J=3.9 Hz, 0.8H), 7.61 (d, J=3.8 Hz, 0.2H), 7.42 (d, J=7.9 Hz, 2H), 6.91 (d, J=3.8 Hz, 1H), 6.42 (s, 1H), 4.64 (dd, J=11.5, 6.3 Hz, 1H), 4.43-4.2 (m, 0.5H), 4.33-4.22 (m, 0.5H), 4.23-4.09 (m, 1H), 4.09-3.95 (m, 1H), 3.96-3.79 (m, 1H), 3.47-3.37 (m, 1H), 3.07-3.08 (m, 2H), 2.53-2.52 (m, 0.5H), 2.32 (dd, J=45.3, 16.2 Hz, 2.5H), 1.97 (d, J=18.6 Hz, 2H), 1.86-1.65 (m, 4H), 1.43-1.20 (m, 13H), 1.21-1.07 (m, 4H), 0.99 (dt, J=24.4, 12.2 Hz, 2H), 0.92-0.77 (m, 5H). $^{13}$C NMR (101 MHz, DMSO) δ 173.44, 172.90, 170.44, 162.00, 161.31, 160.82, 153.25, 140.56, 135.48, 135.28, 135.25, 131.60, 130.52, 129.53, 129.48, 129.35, 128.47, 127.23, 127.19, 127.14, 122.65, 53.65, 52.61, 50.30, 50.17, 41.78, 38.02, 36.96, 36.31, 36.19, 32.90, 31.88, 31.58, 29.53, 29.31, 29.28, 28.96, 26.31, 25.68, 19.42, 14.20.

1-((2R)-2-(5-(tert-butyl)thiophene-2-carboxamido)-3-(4-(5-(4'-propyl-[1,1'-bi(cyclohexan)]-3-en-4-yl)pyrimidin-2-yl)phenyl)propanoyl) azetidine-3-carboxylic acid (Compound 81) was prepared using similar procedures. Chiral analysis showed 97.3% e.e. at the Tyrosine chiral center. $t_R$=14.84 min (Chiral Method 1).

(3S)-1-((2S)-2-(5-(tert-butyl)thiophene-2-carboxamido)-3-(4-(5-(4'-propyl-[1,1'-bi(cyclohexan)]-3-en-4-yl)pyrimidin-2-yl)phenyl)propanoyl)pyrrolidine-3-carboxylic acid (Compound 7)

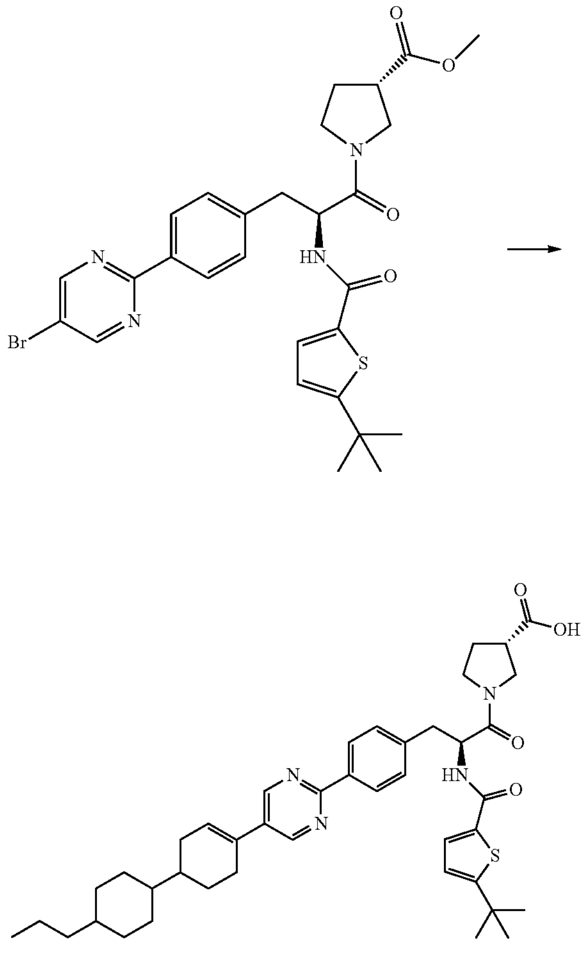

Prepared using General Procedure 10 and 4. To a stirring solution of (4'-propyl-[1,1'-bi(cyclohexan)]-3-en-4-yl)boronic acid (31.9 mg, 0.13 mmol), sodium carbonate decahydrate (7.8 mg, 0.13 mmol), methyl (S)-1-((S)-3-(4-(5-bromopyrimidin-2-yl)phenyl)-2-(5-(tert-butyl)thiophene-2-carboxamido)propanoyl)-pyrrolidine-3-carboxylate INT-35 (38.9 mg, 0.064 mmol) and Pd(dppf)$Cl_2$ (46.8 mg, 0.048 mmol) in dioxane (3 mL) and water (1.0 mL). The reaction solution was degassed by nitrogen and was heated to 60° C. for 2 hours. The reaction solvent was evaporated under reduced pressure and then diluted in DCM (5 mL). The crude material was extracted with aqueous $NaHCO_3$ (2×1 mL). The combined organics were dried over $MgSO_4$ and the solvent was evaporated. The crude material was dissolved in 1 ml MeOH and 0.1 mL of aqueous 1N NaOH and stirred at room temperature for 18 hours. The final product was purified by HPLC to afford 0.52 mg (1.1%) of a mixture of diastereomers (3S)-1-((2S)-2-(5-(tert-butyl)thiophene-2-carboxamido)-3-(4-(5-(4'-propyl-[1,1'-bi(cyclohexan)]-3-en-4-yl)pyrimidin-2-yl)phenyl)-propanoyl)pyrrolidine-3-carboxylic acid (Compound 7) as a solid. LCMS-ESI (m/z) calculated for $C_{42}H_{54}N_4O_4S$: 710.4. found: 711.4 $[M+H]^+$, $t_R$=11.84 min. (Method 14). $^1H$ NMR (400 MHz, DMSO) δ 12.47 (s, 1H), 8.90 (s, 2H), 8.70 (d, J=7.9 Hz, 1H), 8.26 (d, J=7.9 Hz, 2H), 7.71 (s, 1H), 7.56-7.12 (m, 2H), 6.91 (d, J=3.8 Hz, 1H), 6.42 (s, 1H), 5.06-4.68 (m, 1H), 3.69 (d, J=7.6 Hz, 0.5H), 3.63-3.50 (m, 1.5H), 3.43 (dd, J=17.0, 10.2 Hz, 1H), 3.05 (ddd, J=23.8, 16.8, 8.0 Hz, 4H), 2.42-2.17 (m, 2H), 1.97 (dd, J=28.0, 9.5 Hz, 4H), 1.86-1.61 (m, 4H), 1.50-1.21 (m, 13H), 1.21-1.09 (m, 4H), 1.00 (dt, J=24.7, 12.2 Hz, 3H), 0.92-0.78 (m, 5H).

Compound 9 was prepared from INT-17 using General Procedures 10 then 8.

Compound 10 was prepared from INT-17 using General Procedures 10, 7 then 8.

Compound 11 was prepared from INT-38 using General Procedures 10 then 8.

Compounds 13, 15, 17, 19, 21-24, 26, 27, 29, 30, 32, 33, 34 and 35 were prepared from INT-64 using General Procedures 7 then 8.

1-((S)-2-(4-(tert-butyl)benzamido)-3-(4-(5-((1RS,1's,4'RS)-4'-propyl-[1,1'-bi(cyclohexan)]-3-en-4-yl) pyrimidin-2-yl)phenyl)propanoyl)azetidine-3-carboxylic acid (Compound 14)

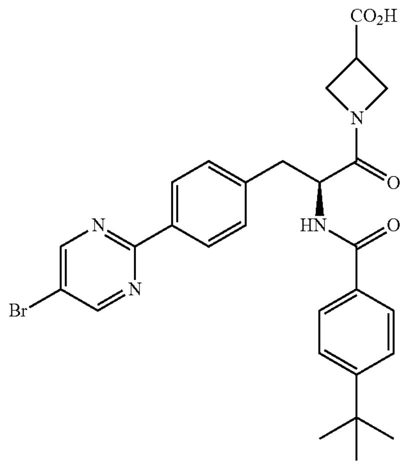

-continued

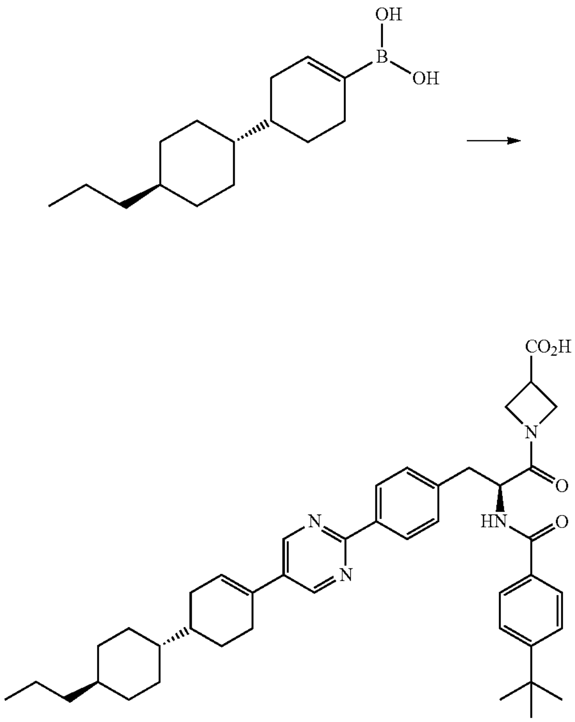

Prepared using General Procedure 10: To stirring solution of (S)-1-(3-(4-(5-bromopyrimidin-2-yl)phenyl)-2-(4-(tert-butyl)benzamido)propanoyl) azetidine-3-carboxylic acid (made from INT-27 using General Procedure 7 followed by General Procedure 4) (21.3 g, 37.7 mmol) and racemic (1RS,1's,4'RS)-4'-propyl-[1,1'-bi(cyclohexan)]-3-en-4-yl) boronic acid (11.66 g, 45.2 mmol) in dioxane (500 mL) was added a solution of sodium hydrogencarbonate (105 mL of a 0.9 M aqueous solution, 94 mmol). The mixture was warmed to 40° C. and degassed. $PdCl_2$dppf (1.230 g, 1.51 mmol) was added and the mixture heated at 95° C. for 1.5 h. The mixture was allowed to cool then diluted with 1 M HCl (400 mL) and extracted with EA (2×500 mL). The combined organic extracts were evaporated. The residue was purified by column chromatography (THF/AcOH/iso-hexanes/DCM) then re-slurry from ACN to afford 16.42 g (63%) of a mixture of diastereomers 1-((S)-2-(4-(tert-butyl) benzamido)-3-(4-(5-((1RS,1's,4'RS)-4'-propyl-[1,1'-bi(cyclohexan)]-3-en-4-yl) pyrimidin-2-yl)phenyl) propanoyl) azetidine-3-carboxylic acid. LCMS-ESI (m/z) calculated for $C_{43}H_{54}N_4O_4$: 690.4; no m/z observed, $t_R$=3.46 min (Method 11). Chiral analysis (Chiral Method 1) showed >95% single peak. $^1H$ NMR (400 MHz, DMSO-$d_6$) δ 12.71 (s, 1H), 8.91 (s, 2H), 8.74-8.68 (m, 1H), 8.30-8.24 (m, 2H), 7.76 (d, J=8.4 Hz, 2H), 7.49-7.41 (m, 4H), 6.43 (s, 1H), 4.74-4.65 (m, 1H), 4.45 (app t, J=8.6 Hz, 0.5H), 4.34-4.27 (m, 0.5H), 4.25-4.13 (m, 1H), 4.10-3.98 (m, 1H), 3.96-3.85 (m, 1H), 3.48-3.40 (m, 1H), 3.17-3.02 (m, 2H), 2.45-2.21 (m, 2H), 2.02-1.87 (m, 2H), 1.85-1.69 (m, 4H), 1.42-0.78 (m, 25H).

1-((S)-2-(5-ethylthiophene-2-carboxamido)-3-(4-(5-((1RS,1's,4'RS)-4'-propyl-[1,1'-bi(cyclohexan)]-3-en-4-yl)pyrimidin-2-yl)phenyl)propanoyl)azetidine-3-carboxylic acid (Compound 31)

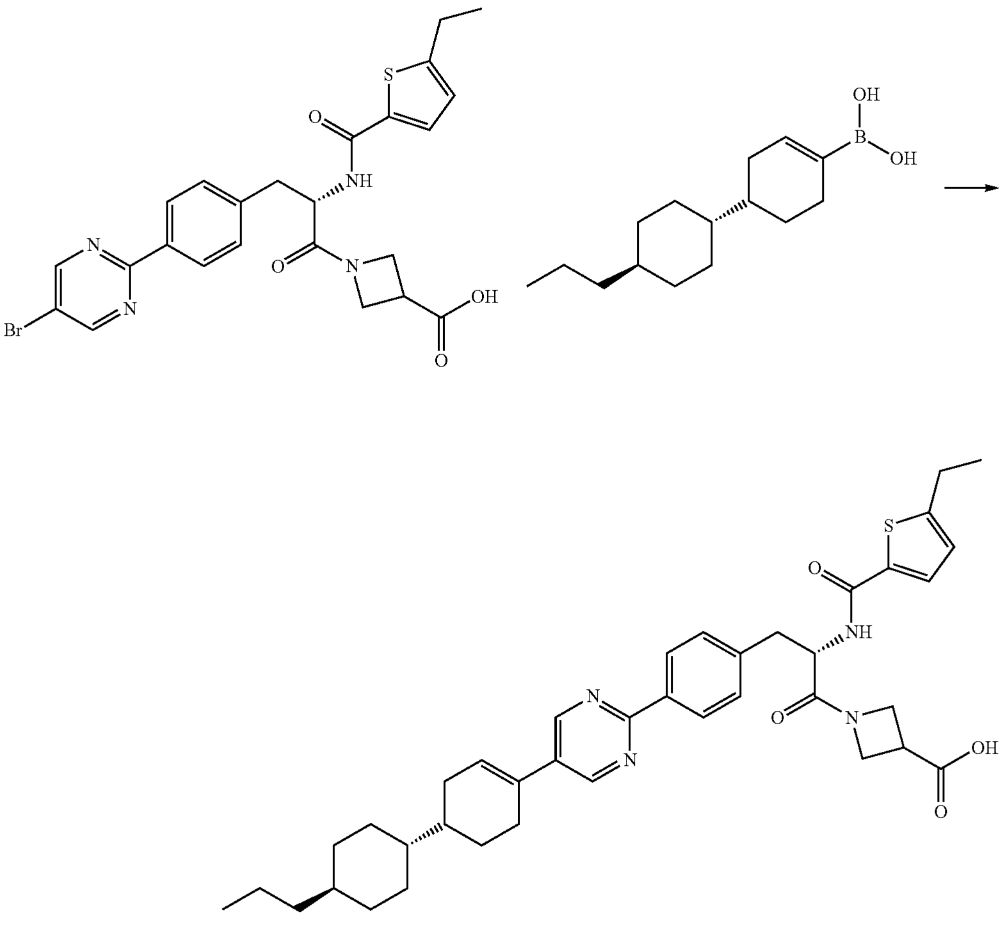

Prepared using General Procedure 10: A stirring mixture of (S)-1-(3-(4-(5-bromopyrimidin-2-yl)phenyl)-2-(5-ethylthiophene-2-carboxamido)propanoyl) azetidine-3-carboxylic acid (4.4 g, 8.10 mmol) (from INT-73 using General Procedure 8) and racemic (1RS,1's,4'RS)-4'-propyl-[1,1'-bi(cyclohexan)]-3-en-4-yl)boronic acid (2.228 g, 8.91 mmol) in dioxane (100 mL) and $NaHCO_3$ (27.0 mL, of a 0.9 M aqueous solution, 24.29 mmol) was warmed to 40° C. and de-gassed. $PdCl_2dppf$ (0.178 g, 0.24 mmol) was charged and the mixture heated under reflux. After 6 h, the mixture was diluted with water (200 mL) and acidified with acetic acid (3.41 mL, 48.6 mmol). After stirring for 1 h, the precipitate was collected by filtration, washed with water (2×30 mL) then MeOH (20 mL). The residue was purified by column chromatography (AcOH/EtOAc/DCM) then re-slurried from MeOH (100 mL) to afford 4.1 g (76%) of a mixture of diastereomers 1-((S)-2-(5-ethylthiophene-2-carboxamido)-3-(4-(5-((1RS,1's,4'RS)-4'-propyl-[1,1'-bi(cyclohexan)]-3-en-4-yl)pyrimidin-2-yl)phenyl)propanoyl)azetidine-3-carboxylic acid. LCMS-ESI (m/z) calculated for $C_{39}H_{48}N_4O_4S$: 688.3; no m/z observed, $t_R$=11.44 min (Method 10). Chiral analysis (Chiral Method 1) showed >95% single peak. $^1H$ NMR (400 MHz, DMSO-$d_6$) δ 12.70 (s, 1H), 8.91 (app d, J=1.7 Hz, 2H), 8.73 (app dd, J=8.3, 2.2 Hz, 1H), 8.40-8.20 (m, 2H), 7.70 (d, J=3.7 Hz, 1H), 7.43 (app dd, J=8.3, 1.4 Hz, 2H), 6.87 (app dd, J=3.7, 1.2 Hz, 1H), 6.54-6.35 (m, 1H), 4.67-4.60 (m, 1H), 4.45 (t, J=8.0 Hz, 0.5H), 4.31-4.27 (m, 0.5H), 4.25-4.10 (m, 1H), 4.08-3.98 (m, 1H), 3.93-3.85 (m, 1H), 3.47-3.39 (m, 0.5H), 3.33-3.27 (m, 0.5H), 3.18-2.95 (m, 2H), 2.79 (q, J=7.5 Hz, 2H), 2.55-2.26 (m, 3H), 2.00-1.92 (m, 2H), 1.83-1.74 (m, 4H), 1.35-1.11 (m, 11H), 1.11-0.95 (m, 2H), 0.91-0.84 (t, J=7.3 Hz, 5H).

Compounds 12, 16, 18, 20, 25, and 28 were prepared from tert-butyl (S)-1-(2-amino-3-(4-(5-(4'-propyl-[1,1'-bi(cyclohexan)]-4-yl)pyrimidin-2-yl)phenyl)propanoyl) azetidine-3-carboxylate using General Procedures 7 then 8.

Compounds 36-40, and 77 were prepared from INT-71 using General Procedure 10.

Compound 41 was prepared from INT-71 using General procedures 10 and 18 sequentially.

Compounds 43, 45-47 and 48 were prepared from INT-71 using General procedure 37.

1-((S)-2-(5-(tert-butyl)thiophene-2-carboxamido)-3-(4-(5-((1RS,1'r,4'RS)-4'-methyl-[1,1'-bi(cyclohexan)]-3-en-4-yl)pyrimidin-2-yl)phenyl)propanoyl) azetidine-3-carboxylic acid (Compound 44)

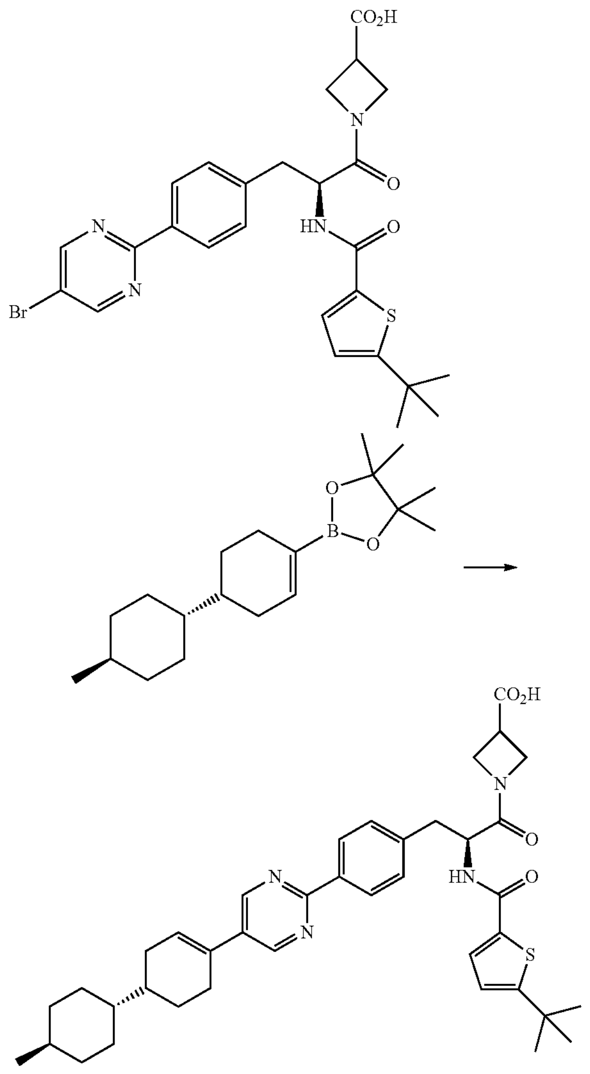

Prepared using General Procedure 10: To a stirring solution of (S)-1-(3-(4-(5-bromopyrimidin-2-yl)phenyl)-2-(5-(tert-butyl)thiophene-2-carboxamido) propanoyl) azetidine-3-carboxylic acid INT-71 (3.14 g, 5.50 mmol) and racemic 4,4,5,5-tetramethyl-2-((1RS,1'r,4'RS)-4'-methyl-[1,1'-bi(cyclohexan)]-3-en-4-yl)-1,3,2-dioxaborolane (1.84 g, 6.05 mmol) in dioxane (110 mL) was added $NaHCO_3$ (18.3 mL of a 0.9 M aqueous solution, 16.49 mmol). The mixture was degassed and treated with $PdCl_2$(dppf) (0.201 g, 0.28 mmol) then heated under reflux for 4 h. The mixture was allowed to cool then diluted with 1 M HCl (100 mL) and extracted with EA (3×150 mL). The combined organic extracts were dried over $MgSO_4$ and solvents evaporated. Column chromatography (AcOH/EA/DCM/iso-hexanes) then re-slurry from ACN then DCM/iso-hexanes gave 2.78 g (76%) of a mixture of diastereomers 1-((S)-2-(5-(tert-butyl)thiophene-2-carboxamido)-3-(4-(5-((1RS,1'r,4'RS)-4'-methyl-[1,1'-bi (cyclohexan)]-3-en-4-yl)pyrimidin-2-yl)phenyl)propanoyl) azetidine-3-carboxylic acid. LCMS-ESI (m/z) calculated for $C_{39}H_{48}N_4O_4S$: 688.3; no m/z observed, $t_R$=11.03 min (Method 10). Chiral analysis (Chiral Method 1) showed >95% single peak. $^1H$ NMR (400 MHz, DMSO-$d_6$) δ 12.74 (s, 1H), 8.91 (d, J=1.9 Hz, 2H), 8.75 (dd, J=8.5, 2.9 Hz, 1H), 8.32-8.18 (m, 2H), 7.69 (d, J=3.9 Hz, 1H), 7.43 (d, J=8.0 Hz, 2H), 6.92 (dd, J=3.9, 1.6 Hz, 1H), 6.51-6.36 (m, 1H), 4.79-4.55 (m, 1H), 4.52-3.77 (m, 4H), 3.49-3.37 (m, 0.5H), 3.34-3.31 (m, 0.5H), 3.17-2.95 (m, 2H), 2.59-2.19 (m, 3H), 2.10-1.85 (m, 2H), 1.86-1.58 (m, 4H), 1.45-1.20 (m, 12H), 1.17-0.71 (m, 8H).

Compounds 49-66 and 69 were prepared from INT-72 using General procedure 10.

Compound 67 was prepared from INT-72 using General procedures 10 and 18 sequentially.

Compound 70 was prepared from INT-72 using General procedure 37.

Compounds 71, 73, 74 and 75 were prepared from Compound 9 using General Procedures 7 then 8.

1-((S)-2-(5-(tert-butyl)thiophene-2-carboxamido)-3-(4-(5-((1RS,1'r,4'RS)-4'-ethyl-[1,1'-bi(cyclohexan)]-3-en-4-yl)pyrimidin-2-yl)phenyl)propanoyl)azetidine-3-carboxylic acid (Compound 76)

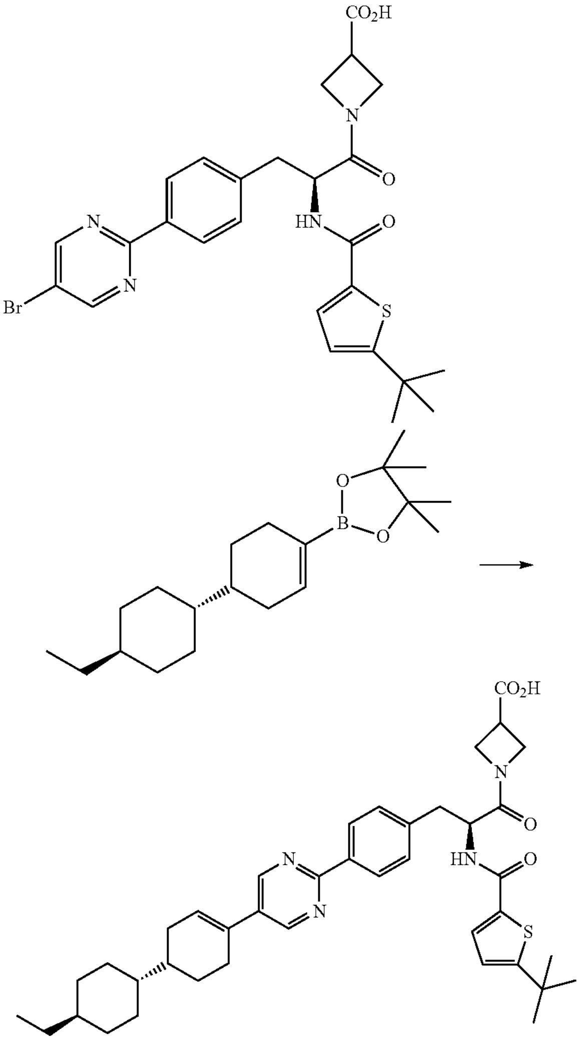

Prepared using General Procedure 10: To a stirring solution of (S)-1-(3-(4-(5-bromopyrimidin-2-yl)phenyl)-2-(5-(tert-butyl)thiophene-2-carboxamido)propanoyl) azetidine-3-carboxylic acid INT-71 (5.5 g, 9.62 mmol) and racemic 2-((1RS,1'r,4'RS)-4'-ethyl-[1,1'-bi(cyclohexan)]-3-en-4-yl)-4,4,5,5-tetramethyl-1,3,2-dioxaborolane (3.37 g, 10.59 mmol) in dioxane (100 mL) was added a solution of $NaHCO_3$ (2.021 g, 24.06 mmol) in water (100 mL) and the mixture de-gassed. $PdCl_2$(dppf) (0.352 g, 0.48 mmol) was added and the mixture heated under reflux for 1 h. The mixture was allowed to cool then diluted with water (200 mL), acidified with AcOH and extracted with EA (2×150 mL). The combined organic extracts were evaporated and the residue purified by column chromatography (AcOH/EA/DCM/iso-hexanes) then re-slurry from ACN to afford 5.7 g (87%) of a mixture of diastereomers 1-((S)-2-(5-(tert-butyl)thiophene-2-carboxamido)-3-(4-(5-((1RS,1'r,4'RS)-4'-ethyl-[1,1'-bi(cyclohexan)]-3-en-4-yl)pyrimidin-2-yl)phenyl)propanoyl)azetidine-3-carboxylic acid. LCMS-ESI (m/z) calculated for $C_{40}H_{50}N_4O_4S$: 682.4. found 683.4 $[M+H]^+$, $t_R$=3.41 min (Method 11). Chiral analysis (Chiral Method 1) showed >95% single peak. $^1H$ NMR (400 MHz, DMSO-$d_6$) δ 12.68 (s, 1H), 8.90 (app d, J=1.8 Hz, 2H), 8.74 (app dd, J=8.3, 2.9 Hz, 1H), 8.32-8.20 (m, 2H), 7.68 (d, J=3.9 Hz, 1H), 7.42 (d, J=8.0 Hz, 2H), 6.91 (app dd, J=3.9, 1.5 Hz, 1H), 6.51-6.30 (m, 1H), 4.64 (tt, J=9.4, 4.5 Hz, 1H), 4.42 (t, J=8.0 Hz, 0.5H), 4.29 (dd, J=8.7, 6.1 Hz, 0.5H), 4.24-4.10 (m, 1H), 4.07-3.98 (m, 1H), 3.94-3.85 (m, 1H), 3.42 (ddd, J=15.2, 9.2, 6.0 Hz, 0.5H), 3.31-3.27 (m, 0.5H), 3.13-2.99 (m, 2H), 2.53-2.24 (m, 3H), 1.98-1.91 (m, 2H), 1.82-1.75 (m, 4H), 1.36-1.29 (m, 10H), 1.23-0.78 (m, 12H).

Compound 72 was prepared from Compound 9 using General Procedures 7, 4 then 8.

Compound 78 and 80 were prepared from Compound 9 using General Procedures 7 then 4.

Compound 79 was prepared from Compound 9 using General Procedure 13.

Compound 82 was prepared from (S)-tert-butyl 3-(4-(5-bromopyrimidin-2-yl)phenyl)-2-(5-(tert-butyl)thiophene-2-carboxamido)propanoate INT-17 using General Procedures 8, 10, 7 and 8 sequentially.

(1s,4s)-4-(1,4-dioxaspiro[4.5]decan-8-yl)cyclohexan-1-ol

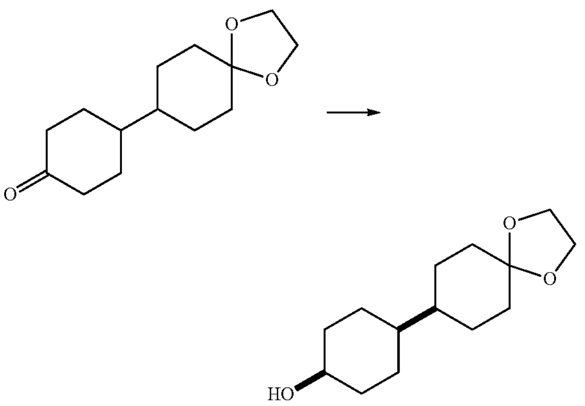

To a stirring solution of L-selectide (7.24 mL of a 1.0 M solution in THF, 7.24 mmol) was added a solution of 4-(1,4-dioxaspiro[4.5]decan-8-yl)cyclohexanone (1.15 g, 4.83 mmol) in THF (10 mL). The resulting reaction mixture was stirred for 3 h. The reaction mixture was quenched with water (1 mL) and EtOH (4 mL). After 5 min stirring, 2 M NaOH (9 mL) was added followed by slow addition of 30% aqueous $H_2O_2$ (4 mL). After min, saturated aqueous $Na_2CO_3$ (10 mL) was added. The mixture was extracted with $Et_2O$ (3×10 mL), dried over $MgSO_4$, filtered and solvents evaporated. The residue was purified by column chromatography (EA/iso-hexane) to afford 748 mg (65%) of (1s,4s)-4-(1,4-dioxaspiro[4.5]decan-8-yl)cyclohexan-1-ol as a white solid.

8-((1s,4s)-4-ethoxycyclohexyl)-1,4-dioxaspiro[4.5]decane

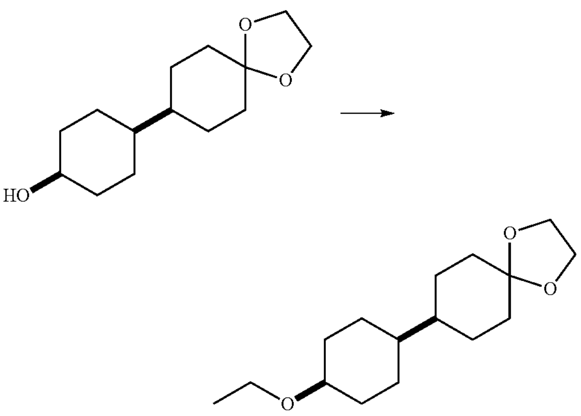

To a stirring solution of (1s,4s)-4-(1,4-dioxaspiro[4.5]decan-8-yl)cyclohexanol (748 mg, 3.11 mmol) in THF (6 mL) at 0° C. was added sodium hydride (149 mg of a 60% dispersion in mineral oil, 3.73 mmol). The resulting reaction mixture was stirred at 0° C. for 10 min. Iodoethane (747 μL, 9.34 mmol) was then added and the mixture was stirred at room temperature overnight. Further sodium hydride (75 mg, 1.89 mmol) and iodethane (375 μL, 4.69 mmol) were added and the mixture stirred at room temperature overnight. EA (20 mL), water (5 mL) and saturated $NH_4Cl$ solution (10 mL) were added and the layers were separated. The aqueous was extracted with EA (2×30 mL). The combined organic layers were washed with 1 M HCl (10 mL), dried over $MgSO_4$ and solvents evaporated. The residue was purified by column chromatography (EA/iso-hexane) to afford 345 mg (39%) of 8-((1s,4s)-4-ethoxycyclohexyl)-1,4-dioxaspiro[4.5]decane as a colourless oil.

(1's,4's)-4'-ethoxy-[1,1'-bi(cyclohexan)]-4-one

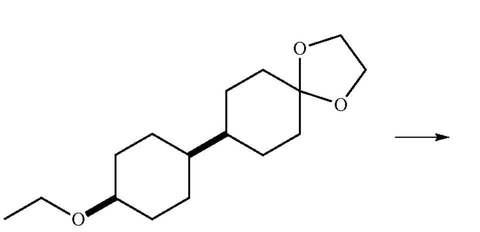

-continued

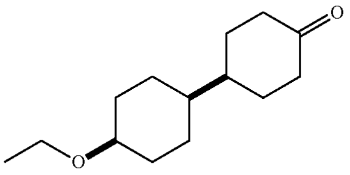

To a stirring solution of 8-((1s,4s)-4-ethoxycyclohexyl)-1,4-dioxaspiro[4.5]decane (345 mg, 1.29 mmol) in a mixture of acetone (3 mL) and water (1.5 mL) was added TFA (2.4 mL, 31.2 mmol). The resulting reaction mixture was stirred at room temperature for 72 h. Solvents were evaporated and chased off with toluene. The residue was purified by column chromatography (EA/iso-hexane) to afford 219 mg (74%) of (1's,4's)-4'-ethoxy-[1,1'-bi(cyclohexan)]-4-one as a pale yellow oil. Molecular formula: $C_{14}H_{24}O_2$. $^1$H NMR (400 MHz, Chloroform-d) δ 3.56-3.49 (m, 1H), 3.44 (q, J=7.0 Hz, 2H), 2.43-2.24 (m, 4H), 2.10-2.02 (m, 2H), 1.92-1.85 (m, 2H), 1.64-1.54 (m, 1H), 1.51-1.36 (m, 8H), 1.29-1.22 (m, 1H), 1.19 (t, J=7.0 Hz, 3H).

Compound 83 was prepared from (S)-1-(3-(4-(5-bromopyrimidin-2-yl)phenyl)-2-(5-(tert-butyl)thiophene-2-carboxamido)propanoyl)azetidine-3-carboxylic acid INT-71 and (1's,4's)-4'-ethoxy-[1,1'-bi(cyclohexan)]-4-one using General Procedure 37.

(1r,4r)-4-(1,4-dioxaspiro[4.5]decan-8-yl)cyclohexan-1-ol

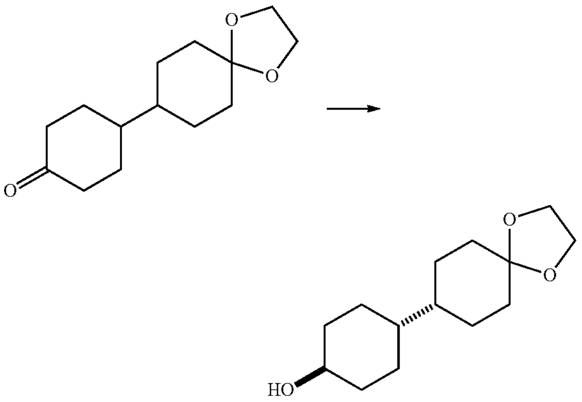

To a stirring suspension of 4-(1,4-dioxaspiro[4.5]decan-8-yl)cyclohexanone (1.18 g, 4.95 mmol) in MeOH (10 mL) was added sodium borohydride (375 mg, 9.90 mmol) at 0° C. The resulting reaction mixture was stirred for 3 h then quenched with water (50 mL). The aqueous layer was extracted with DCM (50 mL), acidified with 1 M HCl (10 mL) then reextracted with DCM (20 mL). The organic layers were combined and solvents evaporated. The residue was dissolved in toluene (20 mL), heated to 60° C. then allowed to slowly cool to room temperature. The precipitate was collected by filtration and washed with hexane to afford 795 mg (67%) of (1r,4r)-4-(1,4-dioxaspiro[4.5]decan-8-yl)cyclohexanol as a white solid.

8-((1r,4r)-4-ethoxycyclohexyl)-1,4-dioxaspiro[4.5]decane

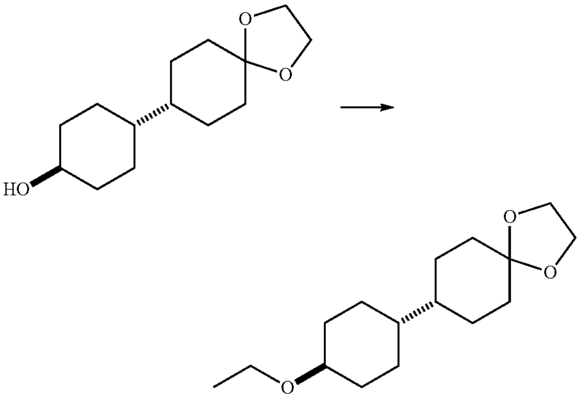

To a stirring solution of (1r,4r)-4-(1,4-dioxaspiro[4.5]decan-8-yl)cyclohexanol (795 mg, 3.31 mmol) in THF (12 mL) at 0° C. was added sodium hydride (159 mg of a 60% dispersion in mineral oil, 3.97 mmol). The resulting reaction mixture was stirred at 0° C. for 10 min. Iodoethane (794 μL, 9.92 mmol) was then added and the mixture was stirred at room temperature overnight. Further sodium hydride (80 mg of a 60% dispersion in mineral oil, 1.99 mmol) and iodethane (400 μL, 4.99 mmol) were added. The mixture was stirred at room temperature overnight. EA (20 mL), water (5 mL) and saturated $NH_4Cl$ solution (10 mL) were added and the layers were separated. The aqueous was extracted with EA (2×30 mL). The combined organic layers were washed with 1 M HCl (10 mL), dried over $MgSO_4$, filtered and solvents evaporated. The residue was purified by column chromatography (EA/Iso-hexane) to afford 546 mg (58%) 8-((1r,4r)-4-ethoxycyclohexyl)-1,4-dioxaspiro[4.5]decane as a clear colourless oil.

(1'r,4'r)-4'-ethoxy-[1,1'-bi(cyclohexan)]-4-one

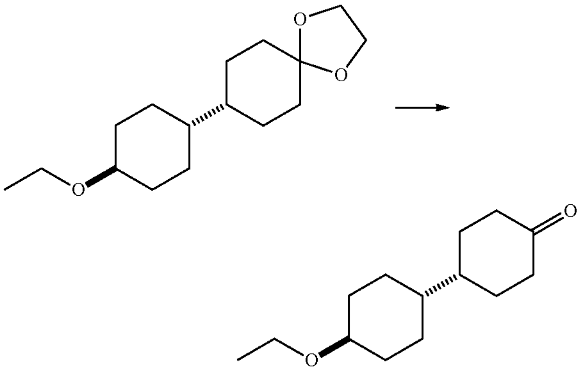

To a stirring solution of 8-((1r,4r)-4-ethoxycyclohexyl)-1,4-dioxaspiro[4.5]decane (546 mg, 2.03 mmol) in a mixture of acetone (4 mL) and water (2 mL) was added TFA (3 mL, 38.9 mmol). The resulting reaction mixture was stirred at room temperature for 72 h. The reaction mixture was concentrated in vacuo and azeotroped with toluene. The residue was purified by column chromatography (EA/isohexane) to afford 330 mg (69%) of (1'r,4'r)-4'-ethoxy-[1,1'-bi(cyclohexan)]-4-one as a colourless oil. Molecular formula: $C_{14}H_{24}O_2$. $^1$H NMR (400 MHz, Chloroform-d) δ 3.52 (q, J=7.0 Hz, 2H), 3.19-3.13 (m, 1H), 2.41-2.26 (m, 4H), 2.13-2.00 (m, 4H), 1.80-1.76 (m, 2H), 1.52-1.40 (m, 3H), 1.27-1.15 (m, 6H), 1.11-0.98 (m, 2H).

Compound 84 was prepared from (S)-1-(3-(4-(5-bromopyrimidin-2-yl)phenyl)-2-(5-(tert-butyl)thiophene-2-carboxamido)propanoyl)azetidine-3-carboxylic acid INT-71 and (1'r,4'r)-4'-ethoxy-[1,1'-bi(cyclohexan)]-4-one using General Procedure 37.

2-methyl-4-(1,4-dioxaspiro[4.5]decan-8-yl)cyclohexan-1-one

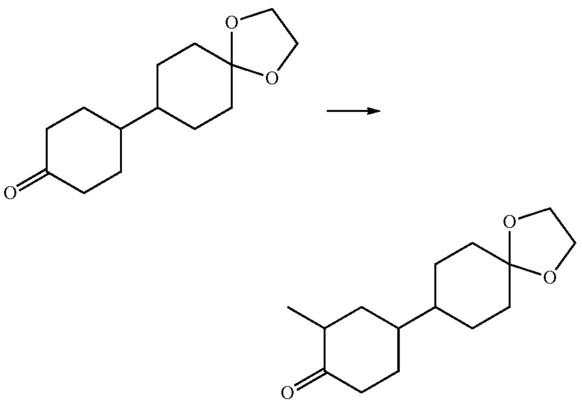

To a stirring solution of LDA (4.62 mL of a 2.0 M solution in THF/heptane/ethylbenzene, 9.23 mmol) in THF (20 mL) at −78° C. was added slowly 4-(1,4-dioxaspiro[4.5]decan-8-yl)cyclohexanone (2.0 g, 8.39 mmol) in THF (15 mL). The resulting reaction mixture was stirred at −78° C. for 1 h and a solution of iodomethane (0.577 mL, 9.23 mmol) in THF (10 mL) was added. The reaction mixture was stirred at −78° C. for 1 h, allowed to warm to room temperature over 2 h and saturated aqueous $NH_4Cl$ (40 mL) was added. The reaction mixture was extracted with $Et_2O$ (100 mL) and the organic layer washed with water (100 mL) and brine (100 mL). The organic was then dried over $MgSO_4$ and solvents evaporated. The residue was purified by column chromatography (EA/iso-hexane) to afford 1.30 g (58%) of 2-methyl-4-(1,4-dioxaspiro[4.5]decan-8-yl)cyclohexanone as an off-white solid.

(Z)-8-(3-methyl-4-propylidenecyclohexyl)-1,4-dioxaspiro[4.5]decane

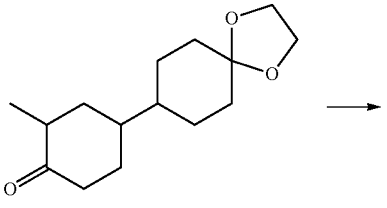

-continued

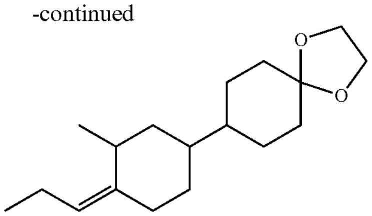

To a stirring solution of triphenyl(propyl)phosphonium bromide (1.17 g, 3.04 mmol) in THF (10 mL) was added potassium tert-butoxide (341 mg, 3.04 mmol). The resulting reaction mixture was stirred at room temperature for 1 h then a solution of 2-methyl-4-(1,4-dioxaspiro[4.5]decan-8-yl)cyclohexanone (590 mg, 2.34 mmol) in THF (5 mL) was added dropwise. The reaction mixture was stirred at room temperature for 16 h. The solvents were evaporated. The residue was treated with $Et_2O$ (50 mL) and stirred for 1 h. The mixture was filtered, washed with further $Et_2O$ and solvents evaporated. The residue was purified by column chromatography (EA/Iso-hexane) to afford 457 mg (70%) of (Z)-8-(3-methyl-4-propylidenecyclohexyl)-1,4-dioxaspiro[4.5]decane as a colourless oil.

8-(3-methyl-4-propylcyclohexyl)-1,4-dioxaspiro[4.5]decane

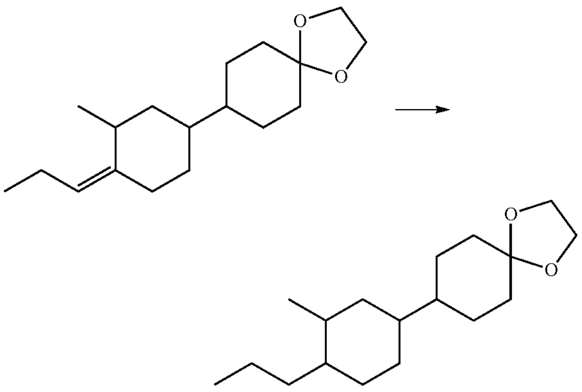

To a stirring solution of 8-(3-methyl-4-propylidenecyclohexyl)-1,4-dioxaspiro[4.5]decane (760 mg, 2.73 mmol) in MeOH/THF (1:1, 20 mL) was added 10% Pd/C (76 mg). The resulting reaction mixture was hydrogenated at 50° C. The mixture was filtered and solvents were evaporated to afford 769 mg (99%) of 8-(3-methyl-4-propylcyclohexyl)-1,4-dioxaspiro[4.5]decane as a colourless oil.

3'-methyl-4'-propyl-[1,1'-bi(cyclohexan)]-4-one

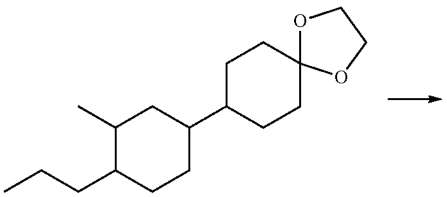

-continued

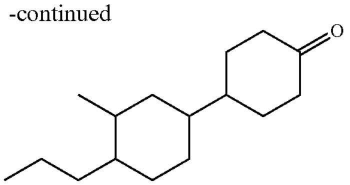

To a stirring solution of 8-(3-methyl-4-propylcyclohexyl)-1,4-dioxaspiro[4.5]decane (769 mg, 2.74 mmol) in a mixture of acetone (5 mL) and water (2.5 mL) was added TFA (5 mL, 64.9 mmol). The resulting reaction mixture was stirred at room temperature overnight. The reaction mixture was added to EA (200 mL) and $H_2O$ (150 mL). The layers were separated. The organic layer was washed with brine (150 mL) and saturated aqueous $NaHCO_3$ (150 mL), dried over $MgSO_4$, filtered and solvents evaporated. The residue was purified by column chromatography (EA/Iso-hexane) to afford 580 mg (89%) of 3'-methyl-4'-propyl-[1,1'-bi(cyclohexan)]-4-one as a colourless oil.

3'-methyl-4'-propyl-[1,1'-bi(cyclohexan)]-3-en-4-yl trifluoromethanesulfonate

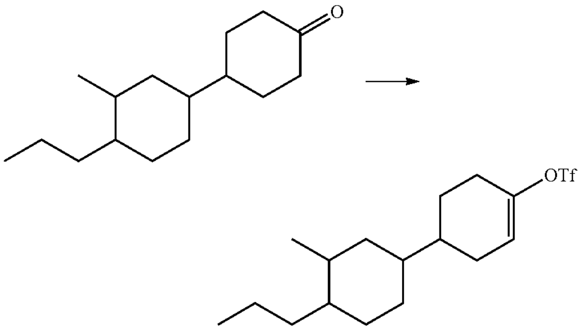

To a stirring solution of LDA (795 μL of a 2.0 M solution in THF/heptane/ethylbenzene, 1.59 mmol) in THF (4 mL) at −78° C. was added 3'-methyl-4'-propyl-[1,1'-bi(cyclohexan)]-4-one (289 mg, 1.22 mmol) in THF (4 mL). The reaction mixture was stirred at −78° C. for 30 min and then 1,1,1-trifluoro-N-phenyl-N-((trifluoromethyl)sulfonyl) methanesulfonamide (480 mg, 1.35 mmol) in THF (4 mL) was added. The reaction mixture was stirred at −78° C. for 30 min then at room temperature for 1 h. A saturated aqueous solution of $NaHCO_3$ (20 mL) was added to the reaction mixture and the aqueous layer was extracted with EA (2×20 mL). The combined organic layers were dried over $MgSO_4$ and solvents evaporated. The residue was purified by column chromatography (EA/iso-hexane) to afford 270 mg (59%) of 3'-methyl-4'-propyl-[1,1'-bi(cyclohexan)]-3-en-4-yl trifluoromethanesulfonate as a colourless oil.

4,4,5,5-tetramethyl-2-(3'-methyl-4'-propyl-[1,1'-bi (cyclohexan)]-3-en-4-yl)-1,3,2-dioxaborolane

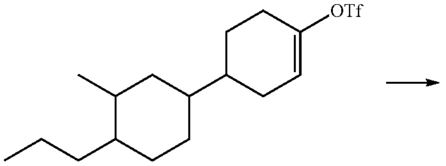

-continued

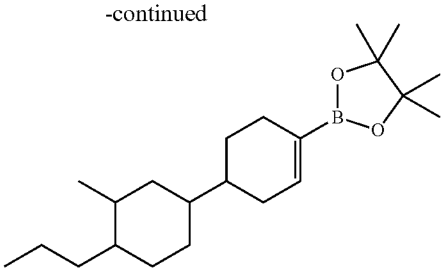

To a stirring solution of 3'-methyl-4'-propyl-[1,1'-bi(cyclohexan)]-3-en-4-yl trifluoromethanesulfonate (335 mg, 0.91 mmol) in dioxane (8 mL) were added 4,4,4',4',5,5,5',5'-octamethyl-2,2'-bi(1,3,2-dioxaborolane) (231 mg, 0.91 mmol) and potassium acetate (268 mg, 2.73 mmol). The resulting reaction mixture was heated at 40° C. and degassed. $PdCl_2$(dppf) (13.31 mg, 0.02 mmol) was added. The reaction mixture was heated at 90° C. over 3 h. The reaction mixture was partitioned between EA (20 mL) and water (20 mL). The aqueous layer was extracted with EA (20 mL). The combined organic layers were dried over $MgSO_4$ and solvents evaporated. The residue was purified by column chromatography (EA/iso-hexanes) to afford 165 mg (51%) of 4,4,5,5-tetramethyl-2-(3'-methyl-4'-propyl-[1,1'-bi (cyclohexan)]-3-en-4-yl)-1,3,2-dioxaborolane as a colourless oil. Molecular formula: $C_{22}H_{39}BO_2$. $^1H$ NMR (400 MHz, DMSO-$d_6$) δ 6.44 (s, 1H), 2.20-2.00 (m, 2H), 1.97-1.85 (m, 1H), 1.83-0.95 (m, 27H), 0.93-0.65 (8H).

Compound 85 was prepared from (S)-1-(3-(4-(5-bromopyrimidin-2-yl)phenyl)-2-(5-(tert-butyl)thiophene-2-carboxamido)propanoyl)azetidine-3-carboxylic acid INT-71 and 4,4,5,5-tetramethyl-2-(3'-methyl-4'-propyl-[1,1'-bi(cyclohexan)]-3-en-4-yl)-1,3,2-dioxaborolane using General Procedure 10.

8-(4-(2-methylpropylidene)cyclohexyl)-1,4-dioxaspiro[4.5]decane

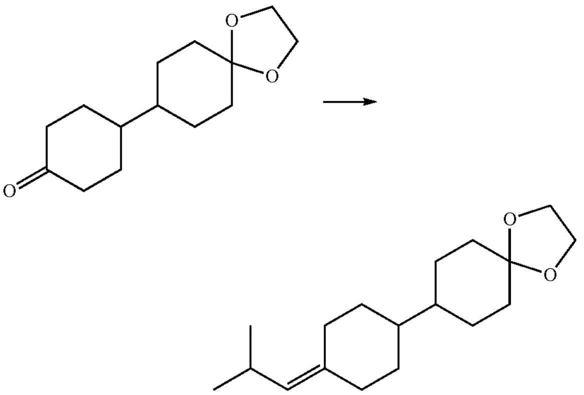

To a stirring solution of isobutyltriphenylphosphonium bromide (5.66 g, 14.18 mmol) in THF (45 mL) was added potassium tert-butoxide (1.591 g, 14.18 mmol) portionwise. The resulting reaction mixture was stirred at room temperature for 1 h then 4-(1,4-dioxaspiro[4.5]decan-8-yl)cyclohexanone (2.6 g, 10.91 mmol) was added portionwise. The reaction mixture was stirred at rt for 72 h. The solvents were evaporated. The residue was treated with $Et_2O$ (60 mL) and stirred for 1 h. The mixture was filtered, washed with further $Et_2O$ and the filtrate was evaporated. The residue was purified by column chromatography (EA/Iso-hexane) to afford 1.63 g (51%) of 8-(4-(2-methylpropylidene)cyclohexyl)-1,4-dioxaspiro[4.5]decane as a colourless oil.

8-(4-iso-butylcyclohexyl)-1,4-dioxaspiro[4.5]decane

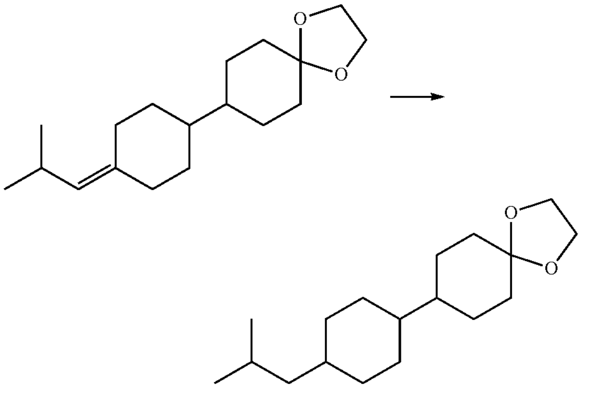

To a stirring solution of 8-(4-(2-methylpropylidene)cyclohexyl)-1,4-dioxaspiro[4.5]decane (1.97 g, 6.37 mmol) in IPA (14 mL) were added phenylsilane (0.786 mL, 6.37 mmol) and a solution of tert-butyl hydroperoxide (1.74 mL of a 5-6 M solution in decane, 9.55 mmol). The resulting mixture was degassed then tris(2,2,6,6-tetramethyl-3,5-heptanedionato)manganese(III) (0.385 g, 0.65 mmol) was added and the mixture was degassed for 30 seconds only. The reaction mixture was stirred for 2 h at room temperature and the solvent evaporated. The residue was purified by column chromatography (EA/iso-hexanes) to afford 680 mg (38%) of 8-(4-iso-butylcyclohexyl)-1,4-dioxaspiro[4.5]decane as a white solid.

4'-iso-butyl-[1,1'-bi(cyclohexan)]-4-one

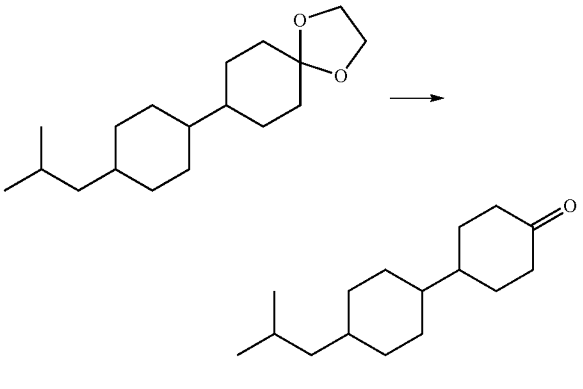

To a stirring solution of 8-(4-iso-butylcyclohexyl)-1,4-dioxaspiro[4.5]decane (630 mg, 2.25 mmol) in a mixture of acetone (4 mL) and water (2 mL) was added trifluoroacetic acid (3 mL, 38.9 mmol). The reaction mixture was stirred at room temperature overnight and the solvents were evaporated. The reaction mixture was added to EA (200 mL) and $H_2O$ (150 mL) and the layers separated. The organic layer was washed with brine (150 mL) and saturated aqueous $NaHCO_3$ (150 mL), dried over $MgSO_4$, filtered and solvents evaporated. The residue was purified by column chromatography (EA/Iso-hexane) to afford 399 mg (74%) of 4'-iso-butyl-[1,1'-bi(cyclohexan)]-4-one as a white solid.

4'-iso-butyl-[1,1'-bi(cyclohexan)]-3-en-4-yl trifluoromethanesulfonate

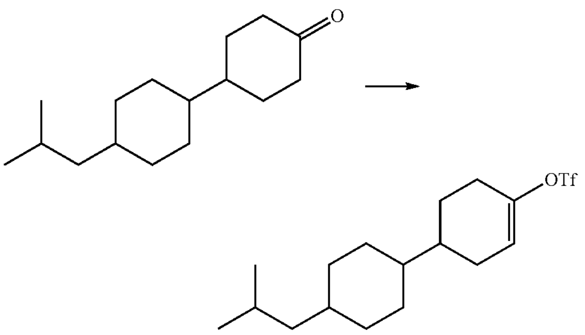

To a stirring solution of LDA (495 μL of a solution of 2.0 M in THF/heptane/ethylbenzene, 0.99 mmol) in THF (3 mL) at −78° C. was added a solution of 4'-iso-butyl-[1,1'-bi(cyclohexan)]-4-one (180 mg, 0.76 mmol) in THF (3 mL). The reaction mixture was stirred at −78° C. for 30 min and then a solution of N-(5-chloropyridin-2-yl)-1,1,1-trifluoro-N-((trifluoromethyl)sulfonyl)methanesulfonamide (359 mg, 0.91 mmol) in THF (3 mL) was added. The reaction mixture was stirred at −78° C. for 30 min then at room temperature. A saturated solution of $NaHCO_3$ (20 mL) was added to the reaction mixture and the aqueous layer was extracted with EA (2×20 mL). The combined organic layers were dried over $MgSO_4$ and solvents evaporated. The residue was purified by column chromatography (EA/iso-hexane) to afford 163 mg (58%) of 4'-iso-butyl-[1,1'-bi(cyclohexan)]-3-en-4-yl trifluoromethanesulfonate as a colourless oil.

2-(4'-iso-butyl-[1,1'-bi(cyclohexan)]-3-en-4-yl)-4,4,5,5-tetramethyl-1,3,2-dioxaborolane

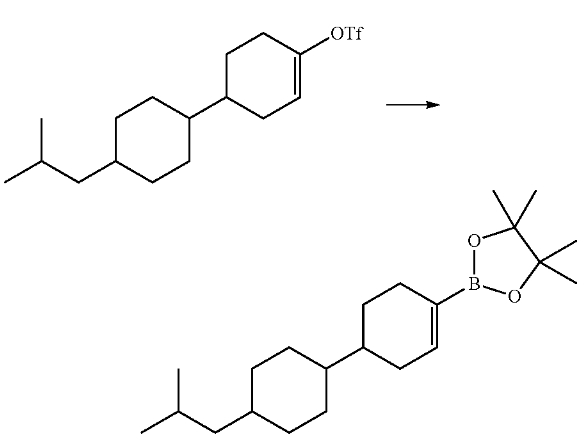

To a stirring solution of 4'-isobutyl-[1,1'-bi(cyclohexan)]-3-en-4-yl trifluoromethanesulfonate (155 mg, 0.42 mmol) in dioxane (4 mL) were added 4,4,4',4',5,5,5',5'-octamethyl-2,2'-bi(1,3,2-dioxaborolane) (112 mg, 0.44 mmol) and potassium acetate (124 mg, 1.26 mmol). The resulting reaction mixture was heated to 40° C. and degassed. $PdCl_2$(dppf) (6.16 mg, 8.41 μmol) was added and the mixture again degassed then heated to 90° C. for 3 h. The reaction mixture was partitioned with EA (20 mL) and water (20 mL). The aqueous layer was extracted once more with EA (20 mL). The combined organic layers were dried over $MgSO_4$, filtered and solvents evaporated. The residue was purified by column chromatography (EA/iso-hexane) to give 78 mg (51%) of 2-(4'-iso-butyl-[1,1'-bi(cyclohexan)]-3-en-4-yl)-4,4,5,5-tetramethyl-1,3,2-dioxaborolane as a colourless oil. Molecular formula: $C_{22}H_{39}BO_2$. $^1H$ NMR (400 MHz, DMSO-$d_6$) δ 6.44 (s, 1H), 2.16-2.04 (m, 2H), 1.98-1.86 (m, 1H), 1.79-0.90 (m, 27H), 0.88-0.80 (m, 8H).

Compound 86 was prepared from (S)-1-(3-(4-(5-bromopyrimidin-2-yl)phenyl)-2-(5-(tert-butyl)thiophene-2-carboxamido)propanoyl)azetidine-3-carboxylic acid INT-71 and 2-(4'-iso-butyl-[1,1'-bi(cyclohexan)]-3-en-4-yl)-4,4,5,5-tetramethyl-1,3,2-dioxaborolane using General Procedure 10.

(1RS,1's,4'RS)-3-methyl-4'-propyl-[1,1'-bi(cyclohexan)]-4-one

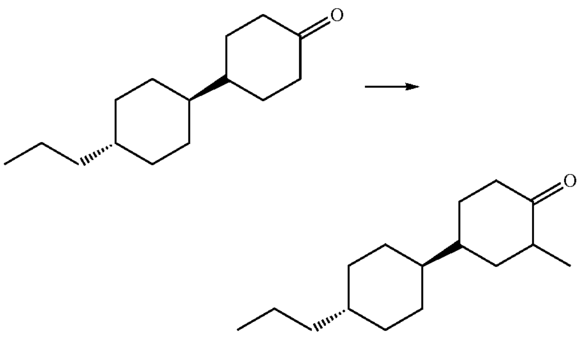

To a stirring solution of LDA (5.67 mL of a 2.0 M solution in THF/heptane/ethylbenzene, 11.33 mmol) in THF (20 mL) at −78° C. was added slowly trans-4'-propyl-[1,1'-bi(cyclohexan)]-4-one (2.1 g, 9.44 mmol) in THF (15 mL). The reaction mixture was stirred at −78° C. for 1 h and a solution of iodomethane (0.709 mL, 11.33 mmol) in THF (10 mL) was added. The reaction mixture was stirred at −78° C. for 1 h, allowed to warm to room temperature over 2 h and saturated aqueous $NH_4Cl$ (40 mL) was added. The reaction mixture was diluted with $Et_2O$ (100 mL) and the organic layer washed with water (100 mL) and brine (100 mL). The organic was then dried over $MgSO_4$, filtered and solvents evaporated. The crude product was purified by column chromatography (EA/Iso-hexane) to afford 1.50 g (67%) of (1RS,1's,4'RS)-3-methyl-4'-propyl-[1,1'-bi(cyclohexan)]-4-one as a pale yellow oil. Molecular formula: $C_{16}H_{28}O$. $^1H$ NMR (400 MHz, DMSO-d6) δ 2.47-2.35 (m, 1H), 2.25 (app t, J=6.7 Hz, 1H), 2.20-2.06 (m, 1H), 2.04-1.9 (m, 1H), 1.97-1.60 (m, 6H), 1.55-1.46 (m, 1H), 1.40-1.23 (m, 3H), 1.19-0.80 (m, 14H).

Compound 87 was prepared from (S)-1-(3-(4-(5-bromopyrimidin-2-yl)phenyl)-2-(5-(tert-butyl)thiophene-2-carboxamido)propanoyl) azetidine-3-carboxylic acid INT-71 and (1RS,1's,4'RS)-3-methyl-4'-propyl-[1,1'-bi(cyclohexan)]-4-one using General Procedure 37.

8-(4-(methoxymethylene)cyclohexyl)-1,4-dioxaspiro[4.5]decane

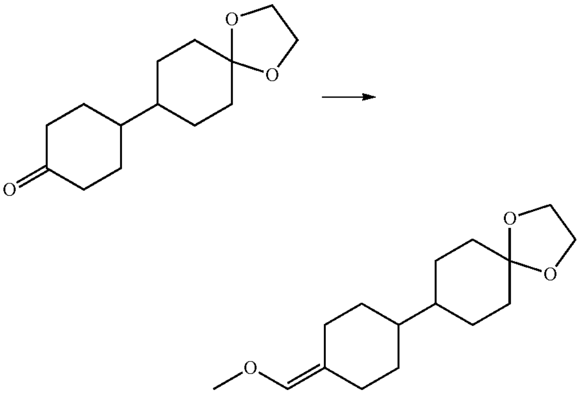

To a stirring solution of (methoxymethyl)triphenylphosphonium chloride (3.74 g, 10.91 mmol) in THF (16 mL) was added potassium tert-butoxide (1.224 g, 10.91 mmol) portionwise. The solution was stirred at room temperature for 50 min then a solution of 4-(1,4-dioxaspiro[4.5]decan-8-yl)cyclohexanone (2 g, 8.39 mmol) in THF (16 mL) was added slowly. The reaction mixture was stirred for 3.5 h. The solvent was removed under vacuum. The residue was treated with $Et_2O$ (44 mL) and stirred for 1 h. The mixture was filtered, washed with $Et_2O$ (2×50 mL) and the filtrate was evaporated. The crude product was purified by column chromatography (EA/Iso-hexane) to afford 1.8 g (76%) of 8-(4-(methoxymethylene)cyclohexyl)-1,4-dioxaspiro[4.5]decane as a colourless oil.

8-((4-(methoxymethyl)cyclohexyl)-1,4-dioxaspiro[4.5]decane

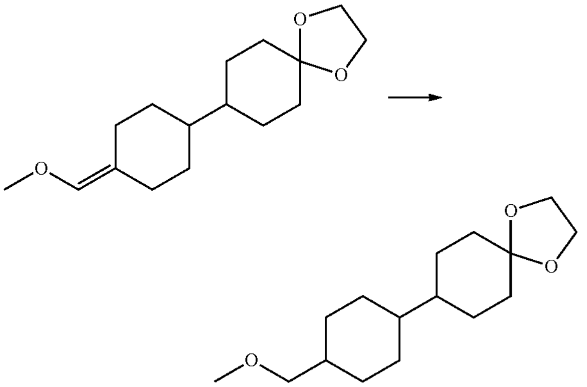

To a stirring solution of 8-(4-(methoxymethylene)cyclohexyl)-1,4-dioxaspiro[4.5]decane (1.8 g, 6.76 mmol) in EtOH (20 mL) was added 5% Palladium on activated carbon (Johnson and Matthey paste Type 58, 0.132 g, 1.24 mmol). The reaction was left stirring under 3 bar hydrogen pressure at room temperature for 16 h. The mixture was filtered through celite and rinsed with EtOH (150 mL). The solvent was evaporated to afford 1.8 g (99%) of 8-((1r,4r)-4-(methoxymethyl)cyclohexyl)-1,4-dioxaspiro[4.5]decane as a colourless oil.

4'-(methoxymethyl)-[1,1'-bi(cyclohexan)]-4-one

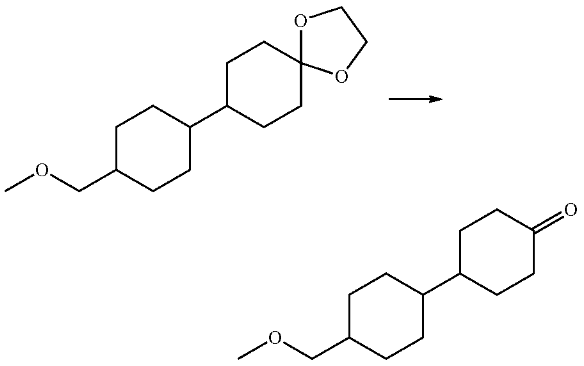

To a stirring solution of 8-(4-(methoxymethyl)cyclohexyl)-1,4-dioxaspiro[4.5]decane (1.8 g, 6.71 mmol) in a mixture of acetone (10 mL) and water (5 mL) was added TFA (7.23 mL, 94 mmol). The reaction mixture was stirred at room temperature for 2 h. The solvents were evaporated to afford 1.65 g (97%) of 4'-(methoxymethyl)-[1,1'-bi(cyclohexan)]-4-one as a colourless oil.

4'-(methoxymethyl)-[1,1'-bi(cyclohexan)]-3-en-4-yl trifluoromethanesulfonate

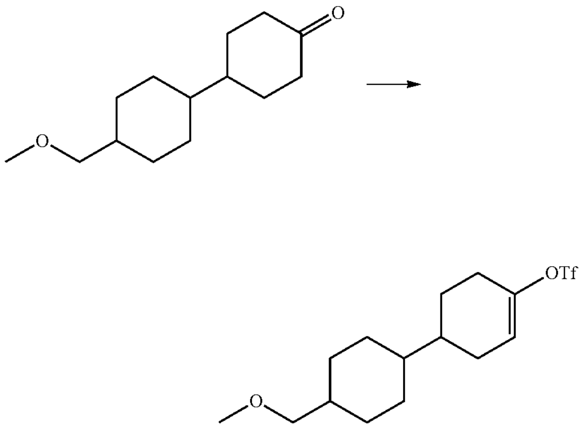 [SMILES: CCCC1CCC(C2CCC(=O)CC2)CC1C ; CCCC1CCC(C2CC=C(OS(=O)(=O)C(F)(F)F)CC2)CC1C]

To a solution of diisopropylamine (1.09 mL, 7.77 mmol) in THF (10 mL) was added n-BuLi (3.11 mL, 7.77 mmol) at −20° C. The mixture was cooled to −78° C. A solution of 4'-(methoxymethyl)-[1,1'-bi(cyclohexan)]-4-one (1.65 g, 6.47 mmol) in THF (10 mL) was added slowly followed by 1,1,1-trifluoro-N-phenyl-N-((trifluoromethyl)sulfonyl) methanesulfonamide (2.43 g, 6.80 mmol). The resultant mixture was stirred at −78° C. for 1.75 h then stirred at room temperature for 16 h. A saturated solution of $NaHCO_3$ (20 mL) was added to the reaction mixture and the aqueous layer was extracted with EA (2×30 mL). The organic layers were washed with brine (30 mL), dried over $MgSO_4$, filtered and the solvent evaporated to afford 2.31 g (100%) of 4'-(methoxymethyl)-[1,1'-bi(cyclohexan)]-3-en-4-yl trifluoromethanesulfonate as an orange oil.

2-(4'-(methoxymethyl)-[1,1'-bi(cyclohexan)]-3-en-4-yl)-4,4,5,5-tetramethyl-1,3,2-dioxaborolane

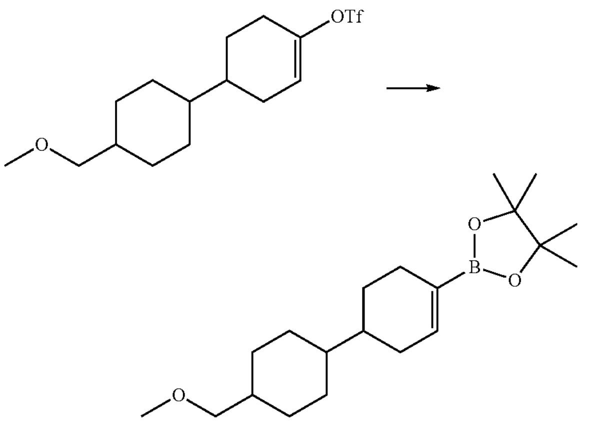

To a stirring solution of 4'-(methoxymethyl)-[1,1'-bi(cyclohexan)]-3-en-4-yl trifluoromethanesulfonate (4.52 g, 6.47 mmol) in DMSO (10 mL) were added 4,4,4',4',5,5,5',5'-octamethyl-2,2'-bi(1,3,2-dioxaborolane) (1.642 g, 6.47 mmol) and potassium acetate (1.904 g, 19.40 mmol). The resulting reaction mixture was warmed to 40° C. and degassed. $PdCl_2dppf$ (0.095 g, 0.13 mmol) was charged and the mixture was further de-gassed. The reaction mixture was heated to 100° C. for 8 h then at room temperature overnight. The mixture was extracted with $Et_2O$ (4×50 mL). The combined organics were washed with water (2×50 mL), brine (50 mL), dried over $MgSO_4$ and evaporated to afford 1.70 g (78%) of 2-(4'-(methoxymethyl)-[1,1'-bi(cyclohexan)]-3-en-4-yl)-4,4,5,5-tetramethyl-1,3,2-dioxaborolane as an orange oil. Molecular formula: $C_{20}H_{35}BO_3$. $^1H$ NMR (400 MHz, Chloroform-d) δ 6.56 (s, 1H), 3.30 (s, 3H), 3.16 (d, J=6.5 Hz, 2H), 2.25-2.0 (m, 3H), 1.85-0.81 (m, 26H)

Compound 88 was prepared from (S)-1-(3-(4-(5-bromopyrimidin-2-yl)phenyl)-2-(5-(tert-butyl)thiophene-2-carboxamido)propanoyl)azetidine-3-carboxylic acid INT-71 and 2-(4'-(methoxymethyl)-[1,1'-bi(cyclohexan)]-3-en-4-yl)-4,4,5,5-tetramethyl-1,3,2-dioxaborolane using General Procedure 10.

Trimethyl(((1RS,1's,4'RS)-3-methyl-4'-propyl-[1,1'-bi(cyclohexan)]-3-en-4-yl)oxy)silane

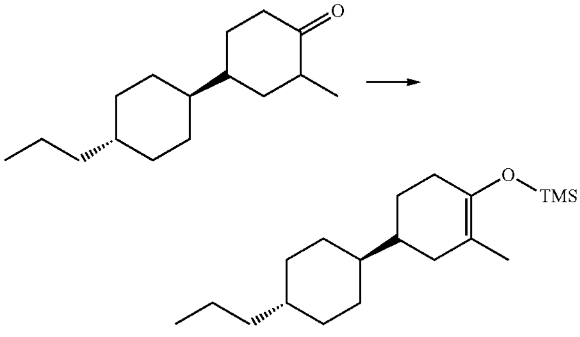

To a stirring solution of racemic (1RS,1's,4'RS)-3-methyl-4'-propyl-[1,1'-bi(cyclohexan)]-4-one (500 mg, 2.12 mmol)

in ACN (20 mL) were added triethylamine (884 μL, 6.35 mmol), chlorotrimethylsilane (403 μL, 3.17 mmol) and sodium iodide (476 mg, 3.17 mmol). The reaction mixture was stirred at room temperature for 16 h. A saturated solution of $NaHCO_3$ (50 mL) was added to the reaction mixture and the aqueous layer was extracted with iso-hexane (3×50 mL). The combined organic layers were washed with brine (100 mL), dried over $MgSO_4$, filtered and solvents evaporated to give 538 mg (74%) of racemic trimethyl(((1RS,1's,4'RS)-3-methyl-4'-propyl-[1,1'-bi(cyclohexan)]-3-en-4-yl)oxy)silane as a yellow oil.

(1RS,1's,4'RS)-3-methyl-4'-propyl-[1,1'-bi(cyclohexan)]-3-en-4-yl trifluoromethane sulfonate

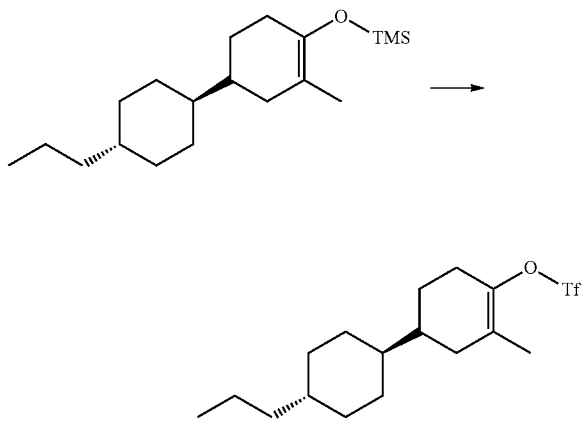

To a stirring solution of racemic trimethyl(((1RS,1's,4'RS)-3-methyl-4'-propyl-[1,1'-bi(cyclohexan)]-3-en-4-yl)oxy)silane (484 mg, 1.41 mmol) in THF (6 mL) at 0° C. was added methyllithium (1147 μL of a 1.6 M solution in $Et_2O$, 1.84 mmol). After 30 min, TMEDA (1065 μL, 7.06 mmol) was added, followed by a solution of 1,1,1-trifluoro-N-phenyl-N-((trifluoromethyl)sulfonyl)methanesulfonamide (656 mg, 1.84 mmol) in THF (3 mL). The reaction was stirred at 0° C. for 1 h then allowed to warm to room temperature. The reaction mixture was quenched with saturated aqueous $NaHCO_3$ (30 mL) and the aqueous layer was extracted with EA (2×30 mL). The combined organic layers were dried over $MgSO_4$, filtered and solvents evaporated. The crude product was purified by column chromatography (EA/Iso-hexane) to afford 224 mg (43%) of racemic (1RS,1's,4'RS)-3-methyl-4'-propyl-[1,1'-bi(cyclohexan)]-3-en-4-yl trifluoromethanesulfonate as a colourless oil.

4,4,5,5-tetramethyl-2-((1RS,1's,4'RS)-3-methyl-4'-propyl-[1,1'-bi(cyclohexan)]-3-en-4-yl)-1,3,2-dioxaborolane

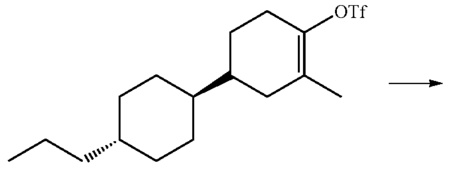

-continued

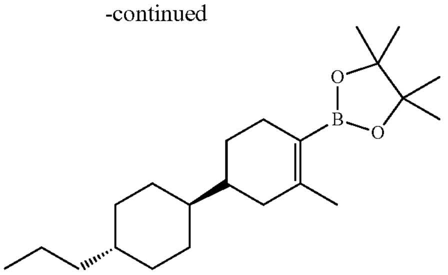

To a stirring solution of racemic (1RS,1's,4'RS)-3-methyl-4'-propyl-[1,1'-bi(cyclohexan)]-3-en-4-yl trifluoromethanesulfonate (260 mg, 0.71 mmol) in dioxane (5 mL) were added 4,4,4',4',5,5,5',5'-octamethyl-2,2'-bi(1,3,2-dioxaborolane) (179 mg, 0.71 mmol) and potassium acetate (208 mg, 2.12 mmol). The resulting reaction mixture was heated to 40° C. and degassed. $PdCl_2$(dppf) (10.33 mg, 0.014 mmol) was added and the mixture again degassed then heated to 90° C. for 3 h. The reaction mixture was partitioned between EA (20 mL) and water (20 mL). The aqueous layer was extracted once more with EA (20 mL). The combined organic layers were dried over $MgSO_4$ and solvents evaporated. The crude product was purified by column chromatography (EA/iso-hexane) to give 146 mg (57%) of racemic 4,4,5,5-tetramethyl-2-((1RS,1's,4'RS)-3-methyl-4'-propyl-[1,1'-bi(cyclohexan)]-3-en-4-yl)-1,3,2-dioxaborolane as a white solid. Molecular formula: $C_{22}H_{39}BO_2$. $^1$H NMR (400 MHz, Chloroform-d) δ 2.28-2.19 (m, 1H), 2.05-1.95 (m, 2H), 1.90 (s, 3H), 1.83-1.68 (m, 6H), 1.35-1.21 (m, 14H), 1.16-0.82 (m, 13H).

Compound 89 was prepared from (S)-1-(3-(4-(5-bromopyrimidin-2-yl)phenyl)-2-(5-(tert-butyl)thiophene-2-carboxamido)propanoyl)azetidine-3-carboxylic acid INT-71 and 4,4,5,5-tetramethyl-2-((1RS,1's,4'RS)-3-methyl-4'-propyl-[1,1'-bi(cyclohexan)]-3-en-4-yl)-1,3,2-dioxaborolane using General Procedure 10.

1-(4-(benzyloxy)phenyl)-4,4-dimethylcyclohexanol

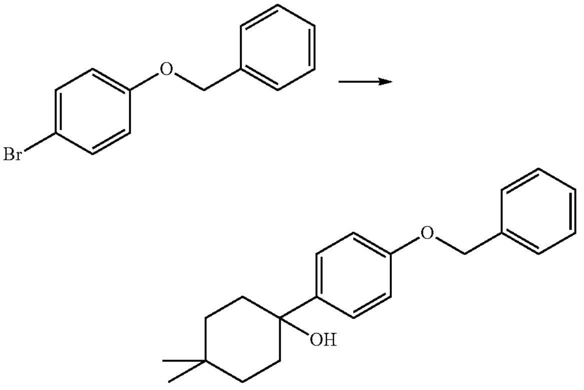

To a stirring suspension of magnesium (1.847 g, 76 mmol) in THF (15 mL) at ~60° C. was added iodine (~20 mg). After 30 min, a solution of 1-(benzyloxy)-4-bromobenzene (10 g, 38.0 mmol) in THF (45 mL) was added slowly to maintain borderline reflux (~2 h addition). The mixture was stirred at ~60° C. for a further 2 h then allowed to cool to room temperature then further cooled to −10° C. whereupon a solution of 4,4-dimethylcyclohexanone (8.5 mL, 34.5 mmol) in THF (15 mL) was added to maintain internal temperature between −5° C. and −10° C. After a further 1 h, the mixture was quenched with $NH_4Cl$ (100 mL) and extracted with diethylether (2×100 mL). The combined organics were dried over $MgSO_4$, filtered and evaporated to afford 10.7 g (100%) of 1-(4-(benzyloxy)phenyl)-4,4-dimethylcyclohexanol as a yellow oil. LCMS-ESI (m/z) calculated for $C_{21}H_{26}O_2$: 310.2. found 293.2 $[M+H-H_2O]^+$, $t_R$=2.90 min (Method 11).

4'-(benzyloxy)-4,4-dimethyl-2,3,4,5-tetrahydro-1,1'-biphenyl

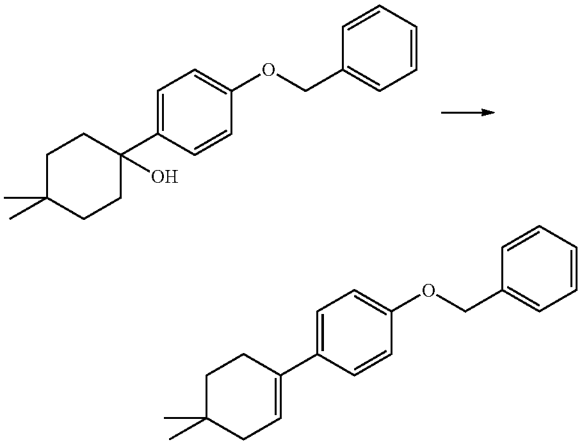

To a stirring solution of 1-(4-(benzyloxy)phenyl)-4,4-dimethylcyclohexanol (10.7 g, 34.5 mmol) in MeOH (135 mL) was added concentrated HCl (15 mL). The resulting reaction mixture was heated to 50° C. for 1 h. The reaction mixture was allowed to cool and the product was collected by filtration, washed with MeOH to afford 4.32 g (39%) of 4'-(benzyloxy)-4,4-dimethyl-2,3,4,5-tetrahydro-1,1'-biphenyl as a yellow solid. LCMS-ESI (m/z) no ionisation, $t_R$=3.26 min (Method 11).

4',4'-dimethyl-[1,1'-bi(cyclohexan)]-4-one

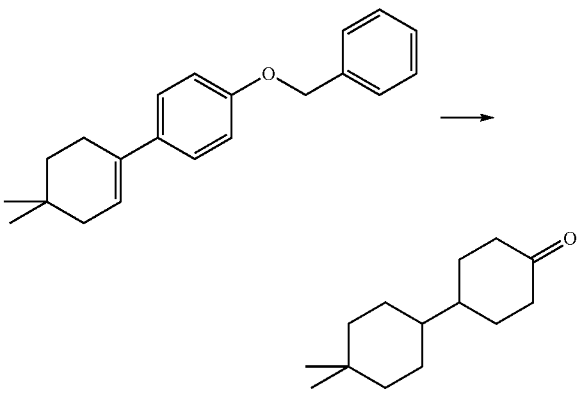

To a stirring solution of 4'-(benzyloxy)-4,4-dimethyl-2,3,4,5-tetrahydro-1,1'-biphenyl (4.32 g, 14.77 mmol) in xylene (55 mL) was added 5% palladium on alumina (Powder Type 325; 1 g). The resulting reaction mixture was purged with nitrogen and hydrogen gas then stirred at 100° C. under hydrogen (5 bars) overnight. The reaction mixture was filtered through a glass microfibre filter, washed with EtOH. The solvents were evaporated. The crude product was purified by column chromatography (EA/iso-hexane) to afford 1.55 g (50%) of 4',4'-dimethyl-[1,1'-bi(cyclohexan)]-4-one as a colourless oil.

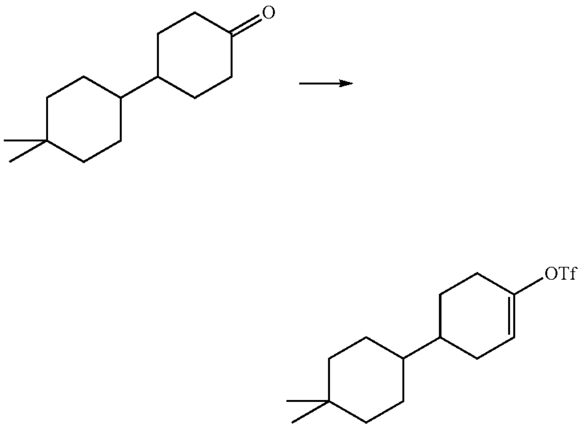

4',4'-dimethyl-[1,1'-bi(cyclohexan)]-3-en-4-yl trifluoromethanesulfonate

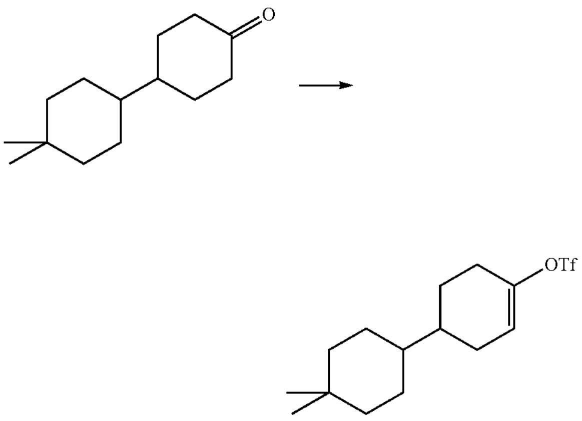

To a stirring solution of diisopropylamine (1.251 mL, 8.93 mmol) in THF (35 mL) was added n-BuLi (3.57 mL, 8.93 mmol) at −20° C. The mixture was cooled to −78° C. 4',4'-dimethyl-[1,1'-bi(cyclohexan)]-4-one (1.55 g, 7.44 mmol) in THF (35 mL) was added slowly followed by 1,1,1-trifluoro-N-phenyl-N-((trifluoromethyl)sulfonyl) methanesulfonamide (2.79 g, 7.81 mmol). The resultant mixture was stirred at −78° C. for 1 h then stirred at room temperature for 16 h. A saturated solution of $NaHCO_3$ (80 mL) was added to the reaction mixture and the aqueous layer was extracted with EA (2×120 mL). The organic layers were combined, dried over $MgSO_4$ and the solvents evaporated. The crude product was purified by column chromatography (EA/iso-hexane) to afford 807 mg (32%) of 4',4'-dimethyl-[1,1'-bi(cyclohexan)]-3-en-4-yl trifluoromethanesulfonate as a colorless oil.

2-(4',4'-dimethyl-[1,1'-bi(cyclohexan)]-3-en-4-yl)-4,4,5,5-tetramethyl-1,3,2-dioxaborolane

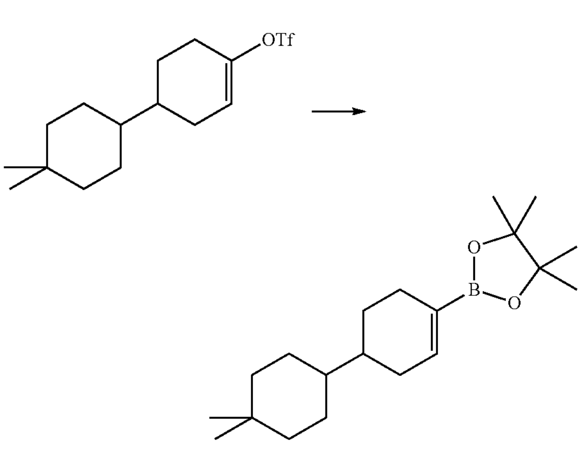

To a stirring solution of 4',4'-dimethyl-[1,1'-bi(cyclohexan)]-3-en-4-yl trifluoromethanesulfonate (807 mg, 2.37 mmol) in dioxane (15 mL) were added 4,4,4',4',5,5,5',5'-octamethyl-2,2'-bi(1,3,2-dioxaborolane) (602 mg, 2.37 mmol) and potassium acetate (698 mg, 7.11 mmol). The resulting reaction mixture was heated to 40° C. and degassed. $PdCl_2$(dppf) (34.7 mg, 0.047 mmol) was added and the mixture again degassed then heated to 90° C. for 4 h. The reaction mixture was partitioned between EA (20 mL) and water (20 mL). The aqueous layer was extracted with EA (3×20 mL). The combined organic layers were dried over MgSO4 and solvents evaporated. The crude product was purified by column chromatography (EA/iso-hexane) to afford 450 mg (57%) of 2-(4',4'-dimethyl-[1,1'-bi(cyclohexan)]-3-en-4-yl)-4,4,5,5-tetramethyl-1,3,2-dioxaborolane as a yellow oil that crystallised upon standing. Molecular formula: $C_{20}H_{35}BO_2$. $^1H$ NMR (400 MHz, Chloroform-d) δ 6.57 (s, 1H), 2.28-1.98 (m, 3H), 1.89-1.73 (m, 2H), 1.59-1.45 (m, 3H), 1.41-1.30 (m, 3H), 1.28-0.95 (m, 17H), 0.88 (s, 3H), 0.85 (s, 3H).

Compound 90 was prepared from (S)-1-(3-(4-(5-bromopyrimidin-2-yl)phenyl)-2-(5-(tert-butyl)thiophene-2-carboxamido)propanoyl)azetidine-3-carboxylic acid INT-71 and 2-(4',4'-dimethyl-[1,1'-bi(cyclohexan)]-3-en-4-yl)-4,4,5,5-tetramethyl-1,3,2-dioxaborolane using General Procedure 10.

(S)-3-(4-(5-bromopyrimidin-2-yl)phenyl)-2-(5-ethylthiophene-2-carboxamido)propanoic acid

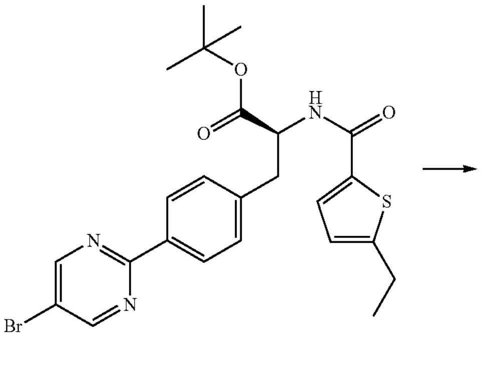

-continued

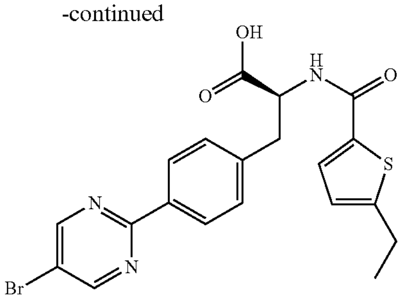

Prepared using General Procedure 8: To a stirring solution of tert-butyl (S)-3-(4-(5-bromopyrimidin-2-yl)phenyl)-2-(5-ethylthiophene-2-carboxamido)propanoate (0.8 g, 1.5 mmol) in DCM (10 mL) was treated with TFA (4 mL). The reaction mixture was stirred at room temperature for 16 hours to complete. The solvent was evaporated and then co-evaporated with toluene (3×20 mL) to remove trace TFA. The residue was suspended in acetonitrile (10 mL) and the solid formed was filtered. The compound was dried under vacuum overnight to afford 0.46 g (68%) of (S)-3-(4-(5-bromopyrimidin-2-yl)phenyl)-2-(5-ethylthiophene-2-carboxamido)propanoic acid as half-white powder. LCMS-ESI (m/z) calculated for $C_{20}H_{18}BrN_3O_3S$: 460.3. found 462.3 $[M+2]^+$, $t_R$=2.76 min (Method 18).

tert-Butyl (S)-1-(3-(4-(5-bromopyrimidin-2-yl)phenyl)-2-(5-ethylthiophene-2-carboxamido)propanoyl) azetidine-3-carboxylate (INT 73)

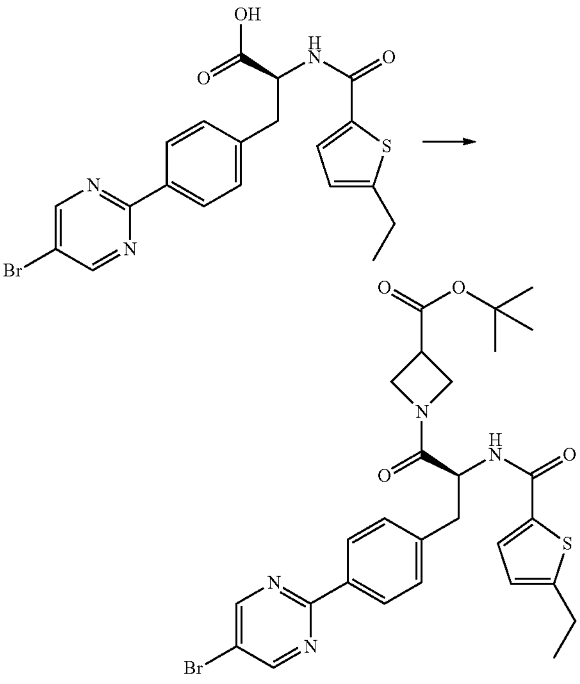

Prepared using General Procedure 7: To a stirred solution of (S)-3-(4-(5-bromopyrimidin-2-yl)phenyl)-2-(5-ethylthiophene-2-carboxamido)propanoic acid (0.43 g, 0.93 mmol) in DMF (5 mL) at 0° C. was added DIPEA (0.6 g, 4.6 mmol) followed by tert-butyl azetidine-3-carboxylate hydrochloride (0.22 g, 1.1 mmol). To the mixture was added HATU (0.88 g, 2.33 mmol). The reaction was allowed to stir at 0° C. for 2 h and then allowed to warm to RT for 16 h. Then the reaction mixture was diluted with saturated sodium bicarbonate solution (5 mL), water (5 mL) and EA (10 mL). The layers were separated and the aqueous layer was extracted with EA (2×10 mL). The combined organic layers were washed with 1N hydrochloric acid, water, brine and then dried over $MgSO_4$ and concentrated. The crude product was purified by column chromatography (0-40% EA/Hexanes) to afford 0.43 g (76%) of tert-butyl (S)-1-(3-(4-(5-bromopyrimidin-2-yl)phenyl)-2-(5-ethylthiophene-2-carboxamido) propanoyl) azetidine-3-carboxylate INT 73. LCMS-ESI (m/z) calculated for $C_{28}H_{31}BrN_4O_4S$: 599.5. found 601.3 [M+2], $t_R$=4.22 min (Method 25).

(1RS,1'r,4'RS)-4'-methyl-[1,1'-bi(cyclohexan)]-3-en-4-yl trifluoromethanesulfonate

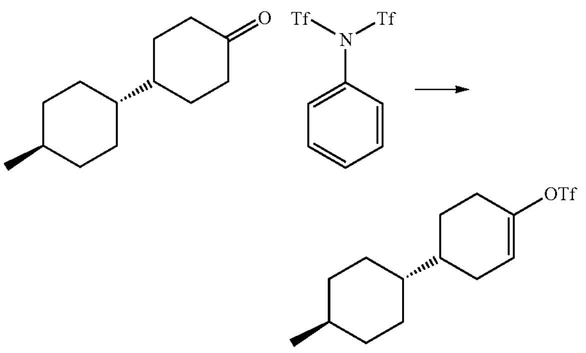

To a stirring solution of diisopropylamine (17.3 mL, 124 mmol) in THF (350 mL) at 0° C. was added butyllithium (41.9 mL of a 2.7 M solution in hexanes, 113 mmol). After 30 min, the mixture was cooled to −78° C. and treated with a solution of (1'r,4'r)-4'-methyl-[1,1'-bi(cyclohexan)]-4-one (20 g, 103 mmol) in THF (100 mL) added over 1 h. After 30 min, a solution of 1,1,1-trifluoro-N-phenyl-N-((trifluoromethyl)sulfonyl)methanesulfonamide (44.1 g, 124 mmol) in THF (180 mL) was added over 1 h. The resultant mixture was allowed to warm slowly to RT. The reaction mixture was carefully quenched with ice/$NaHCO_3$ (200/250 mL) and extracted with EA (2×300 mL). The combined organics were dried over $MgSO_4$ and solvents evaporated. Column chromatography (EA/iso-hexanes) gave 30.7 g (91%) of racemic (1RS,1'r,4'RS)-4'-methyl-[1,1'-bi(cyclohexan)]-3-en-4-yl trifluoromethanesulfonate.

4,4,5,5-tetramethyl-2-((1RS,1'r,4RS)-4'-methyl[1,1'-bi(cyclohexan)]-3-en-4-yl)-1,3,2-dioxaborolane

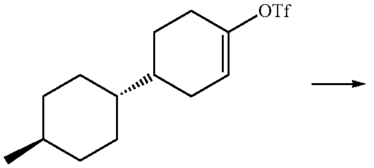

-continued

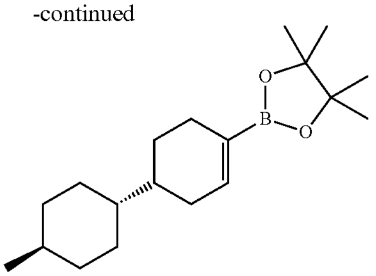

To a stirring solution of racemic (1RS,1'r,4'RS)-4'-methyl-[1,1'-bi(cyclohexan)]-3-en-4-yl trifluoromethanesulfonate (30.7 g, 94 mmol) and 4,4,4',4',5,5,5',5'-octamethyl-2,2'-bi(1,3,2-dioxaborolane) (26.3 g, 103 mmol) in dioxane (400 mL) at 40° C. was added potassium acetate (27.7 g, 282 mmol) and the mixture degassed. $PdCl_2$(dppf) (1.377 g, 1.881 mmol) was added and heated to 100° C. for 4 h. The mixture was allowed to cool then quenched with water (500 mL) and extracted with EA (3×700 mL). The combined organic extracts were dried over $MgSO_4$ and solvents evaporated. Column chromatography (EA/iso-hexanes) gave 12.1 g (42%) of racemic 4,4,5,5-tetramethyl-2-((1RS,1'r,4'RS)-4'-methyl-[1,1'-bi(cyclohexan)]-3-en-4-yl)-1,3,2-dioxaborolane. Molecular formula: $C_{19}H_{33}BO_2$. $^1H$ NMR (400 MHz, Chloroform-d) δ 6.60-6.57 (m, 1H), 2.36-1.96 (m, 3H), 1.95-1.67 (m, 6H), 1.40-0.78 (m, 23H).

Compound 91 was prepared from INT-73 using General Procedure 10 with racemic 4,4,5,5-tetramethyl-2-((1RS,1'r,4'RS)-4'-methyl-[1,1'-bi(cyclohexan)]-3-en-4-yl)-1,3,2-dioxaborolane followed by General Procedure 8.

Compound 92 was prepared from INT-73 using General Procedure 10 with 2-(4',4'-dimethyl-[1,1'-bi(cyclohexan)]-3-en-4-yl)-4,4,5,5-tetramethyl-1,3,2-dioxaborolane and then General Procedure 8.

(Z)—N'—((1RS,1'r,4'RS)-4'-ethyl-[1,1'-bi(cyclohexan)]-4-ylidene)-4-methylbenzene sulfonohydrazide

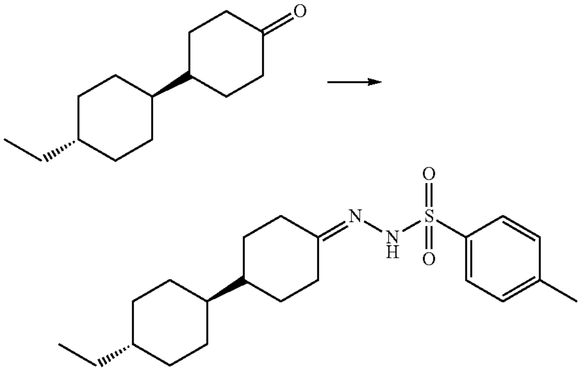

A stirring mixture of (1'r,4'r)-4'-ethyl-[1,1'-bi(cyclohexan)]-4-one (100 g, 470 mmol) and 4-methylbenzenesulfonohydrazide (90 g, 470 mmol) in EtOH (1700 mL) was heated at 100° C. for 3 h. The reaction mixture was allowed to cool down to room temperature. The precipitate was collected by filtration, washed with cold EtOH (100 mL) and dried in the vacuum oven at 50° C. to afford 170 g (94%) of racemic (Z)—N'-((1RS,1'r,4'RS)-4'-ethyl-[1,1'-bi(cyclohexan)]-4-ylidene)-4-methylbenzenesulfonohydrazide as a white solid.

2-((1RS,1'r,4'RS)-4'-ethyl-[1,1'-bi(cyclohexan)]-3-en-4-yl)-4,4,5,5-tetramethyl-1,3,2-dioxaborolane

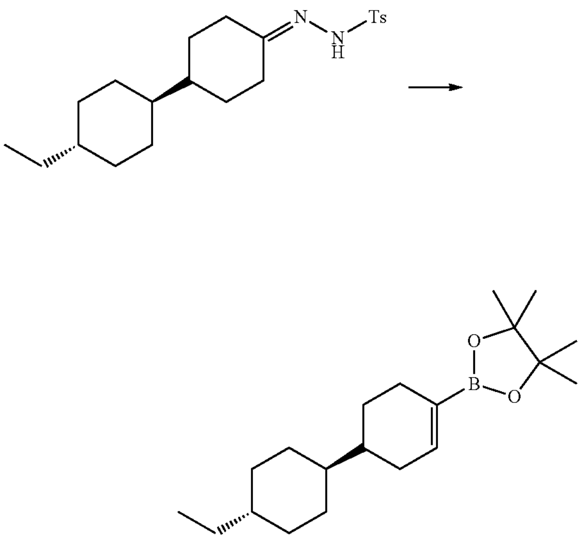

A stirring mixture of racemic (Z)—N'-((1RS,1'r,4'RS)-4'-ethyl-[1,1'-bi(cyclohexan)]-4-ylidene)-4-methylbenzenesulfonohydrazide (47 g, 125 mmol) and N1,N1,N2,N2-tetramethylethane-1,2-diamine (381 mL, 2496 mmol) in isohexanes (400 mL) was cooled to −78° C. and then treated after 15 min with n-BuLi (200 mL of a 2.5 M solution, 499 mmol). After 20 min, the cooling bath was removed. After a further 2 h stirring, the mixture was cooled to −78° C. and 2-isopropoxy-4,4,5,5-tetramethyl-1,3,2-dioxaborolane (105 mL, 499 mmol) was added slowly. The reaction mixture was stirred at −78° C. and then left to warm up to room temperature overnight. The reaction mixture was quenched with $NH_4Cl$ (400 mL). The reaction mixture was partitioned between water (2.5 L) and $Et_2O$ (1.5 L). The organic layer was dried over $MgSO_4$, filtered and solvents evaporated. The residue was treated with MeOH (200 mL) and cooled down using an ice-water bath. The solid formed was collected by filtration to afford 23.78 g (59%) of racemic 2-((1RS,1'r,4'RS)-4'-ethyl-[1,1'-bi(cyclohexan)]-3-en-4-yl)-4,4,5,5-tetramethyl-1,3,2-dioxaborolane as an off-white solid. Molecular formula: $C_{20}H_{35}BO_2$. $^1H$ NMR (400 MHz, DMSO-$d_6$) δ 6.43 (s, 1H), 2.17-2.04 (m, 2H), 1.98-1.86 (m, 1H), 1.84-1.65 (m, 6H), 1.31-0.77 (m, 25H).

Compound 93 was prepared from INT-73 using General Procedure 10 with racemic 2-((1RS,1'r,4'RS)-4'-ethyl-[1,1'-bi(cyclohexan)]-3-en-4-yl)-4,4,5,5-tetramethyl-1,3,2-dioxaborolane followed by General Procedure 8.

tert-Butyl 1-((S)-2-(((benzyloxy)carbonyl)amino)-3-(4-(5-((1RS,1'r,4'RS)-4'-ethyl-[1,1'-bi(cyclohexan)]-3-en-4-yl)pyrimidin-2-yl)phenyl)propanoyl)azetidine-3-carboxylate

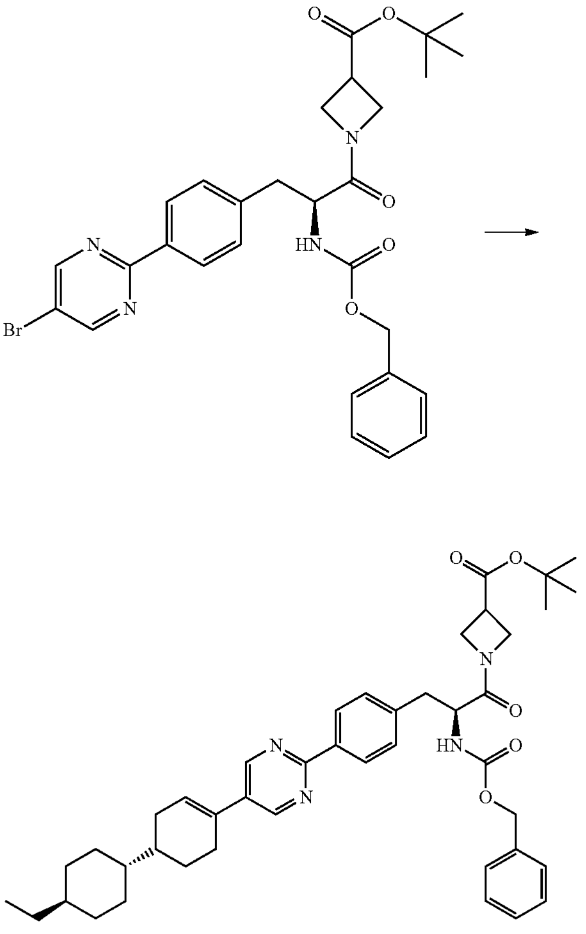

Prepared using General Procedure 10: To a stirring solution of tert-butyl (S)-1-(2-(((benzyloxy)carbonyl)amino)-3-(4-(5-bromopyrimidin-2-yl)phenyl) propanoyl) azetidine-3-carboxylate (1.1 g, 1.9 mmol) and racemic 2-((1RS,1'r,4'RS)-4'-ethyl-[1,1'-bi(cyclohexan)]-3-en-4-yl)-4,4,5,5-tetramethyl-1,3,2-dioxaborolane (0.7 g, 2.2 mmol) in 3:1 dioxanes: $H_2O$ (14 mL) was added sodium carbonate, decahydrate (1.1 g, 3.7 mmol). The mixture was degassed using nitrogen bubbling and then $PdCl_2$(dppf) (0.14 g, 0.2 mmol) was added and the mixture was heated at 70° C. After 3 h, the reaction mixture was diluted with DCM and washed with brine. The organic layer was dried ($Na_2SO_4$) and purified by column chromatography (EA/hex) to provide 1.3 g (99%) of a mixture of diastereomers tert-butyl 1-((S)-2-(((benzyloxy)carbonyl)amino)-3-(4-(5-((1RS,1'r,4'RS)-4'-ethyl-[1,1'-bi(cyclohexan)]-3-en-4-yl)pyrimidin-2-yl)phenyl)propanoyl) azetidine-3-carboxylate. LCMS-ESI (m/z) calculated for $C_{43}H_{54}N_4O_5$: 706.9. found 707.4 $[M+H]^+$, $t_R$=5.3 min (Method 25).

tert-butyl 1-((S)-2-amino-3-(4-(5-((1RS,1'r,4'RS)-4'-ethyl-[1,1'-bi(cyclohexan)]-3-en-4-yl)pyrimidin-2-yl)phenyl)propanoyl)azetidine-3-carboxylate (INT-74)

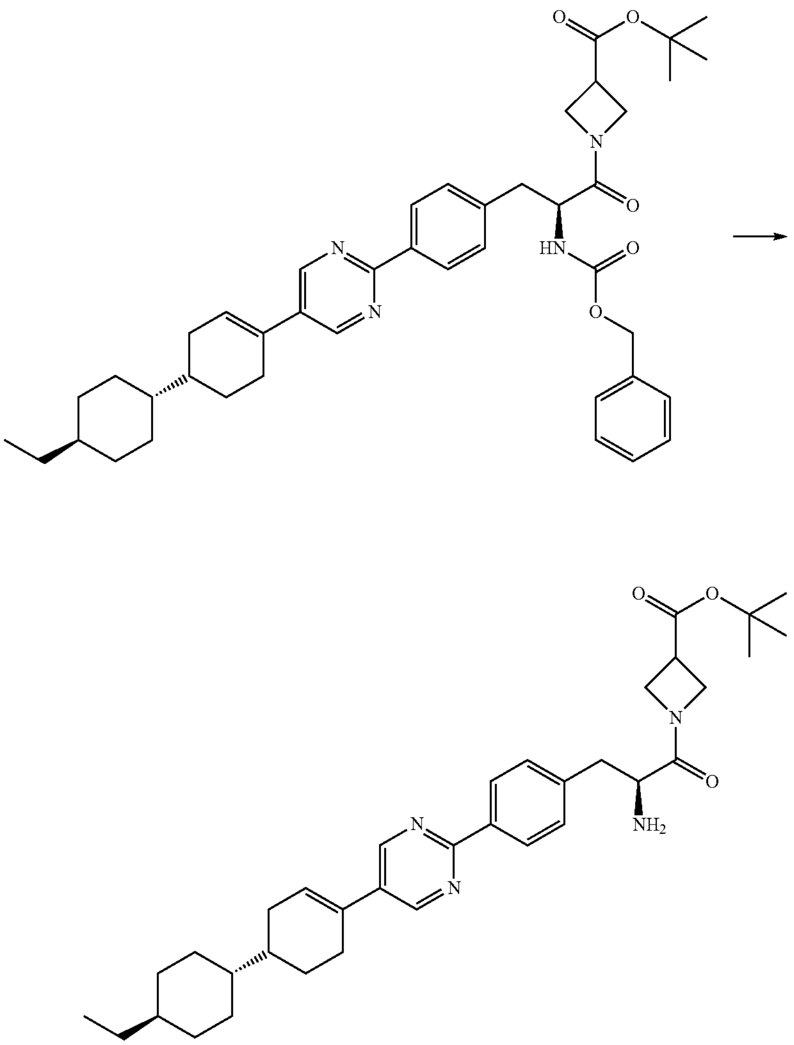

Prepared using General Procedure 18. To a stirring solution of mixture of diastereomers of tert-butyl 1-((S)-2-(((benzyloxy)carbonyl)amino)-3-(4-(5-((1RS, 1'r,4'RS)-4'-ethyl-1-[1,1'-bi(cyclohexan)]-3-en-4-yl)pyrimidin-2-yl)phenyl)propanoyl)azetidine-3-carboxylate (100 mg, 0.14 mmol) in EA (6 mL) was added Pd/C (10 mg, 0.01 mmol) and the reaction was flushed with hydrogen gas three times. The reaction mixture was stirred under an atmosphere of hydrogen for 36 hours, then concentrated, dissolved in MeOH, filtered through Celite, and again concentrated to give 76 mg (95%) of a mixture of diastereomers tert-butyl 1-((S)-2-amino-3-(4-(5-((1RS,1'r,4'RS)-4'-ethyl-[1,1'-bi(cyclohexan)]-3-en-4-yl)pyrimidin-2-yl)phenyl)propanoyl)azetidine-3-carboxylate INT-74. LCMS-ESI (m/z) calculated for $C_{35}H_{48}N_4O_3$: 572.8 found 573.4 [M+H]+, $t_R$=5.02 min (Method 25).

Compounds 94-104 were prepared from INT-74 using General Procedure 7 with the respective carboxylic acid followed by General Procedure 8.

Compounds 105-108 were prepared from Compound 119 using General Procedure 7 with the respective amine followed by General Procedure 8.

(S)-2-(((benzyloxy)carbonyl)amino)-3-(4-(5-bromopyrimidin-2-yl)phenyl)propanoic acid

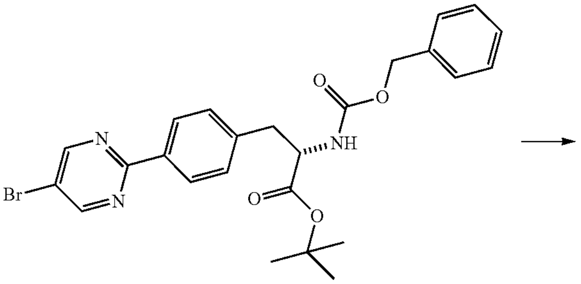

-continued

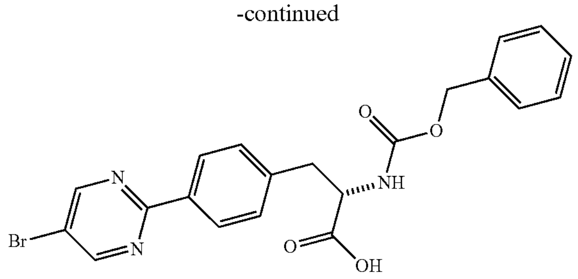

Prepared using General Procedure 8: To a stirring solution of (S)-tert-butyl 2-(((benzyloxy)carbonyl)amino)-3-(4-(5-bromopyrimidin-2-yl)phenyl)propanoate INT-7 (12 g, 23.42 mmol) in DCM (210 mL) was added TFA (150 mL). After 3 h, the mixture was diluted with DCM (100 mL) and poured onto ice water (500 mL). The organic phase was separated, washed with water (2×100 mL), dried over $MgSO_4$ and solvents evaporated to give 10.7 g (100%) of (S)-2-(((benzyloxy)carbonyl)amino)-3-(4-(5-bromopyrimidin-2-yl)phenyl)propanoic acid (12.16 g, 23.45 mmol, 100% yield). LCMS-ESI (m/z) calculated for $C_{21}H_{18}BrN_3O_4$: 455.1. found 456.1 $[M+H]^+$, $t_R$=6.08 min (Method 10).

(S)-benzyl (3-(4-(5-bromopyrimidin-2-yl)phenyl)-1-(methylsulfonamido)-1-oxopropan-2-yl)carbamate

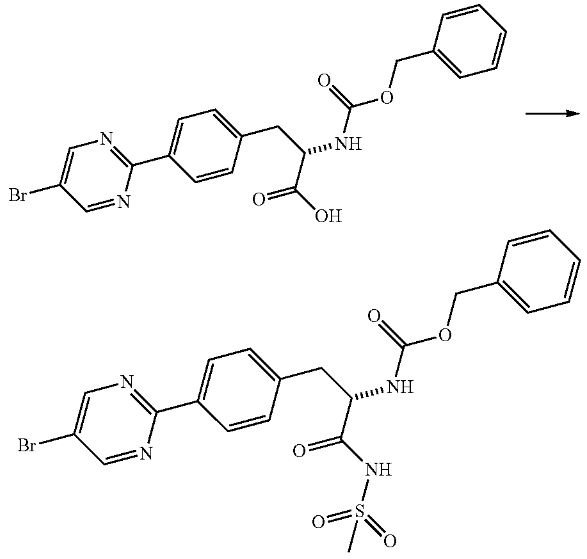

Prepared using General Procedure 7: To a stirring solution of (S)-2-(((benzyloxy)carbonyl)amino)-3-(4-(5-bromopyrimidin-2-yl)phenyl)propanoic acid (12.16 g, 23.45 mmol) in DCM (250 mL) was added methanesulfonamide (22.31 g, 235 mmol), DMAP (5.73 g, 46.9 mmol) and DIEA (20.48 mL, 117 mmol) followed by EDC (6.29 g, 32.8 mmol). The reaction mixture was allowed to stir at room temperature for 3 days then quenched into ice-water (200 mL), acidified with 1 M HCl (250 mL) and extracted with DCM (400 mL). The organic layer was washed with 0.1 M HCl (3×200 mL), dried over $MgSO_4$, filtered and solvents evaporated to afford 10.5 g (84%) of (S)-benzyl (3-(4-(5-bromopyrimidin-2-yl)phenyl)-1-(methylsulfonamido)-1-oxopropan-2-yl) carbamate. LCMS-ESI (m/z) calculated for $C_{22}H_{21}BrN_4O_5S$: 532.0. found 533.0 $[M+H]^+$, $t_R$=2.34 min (Method 11).

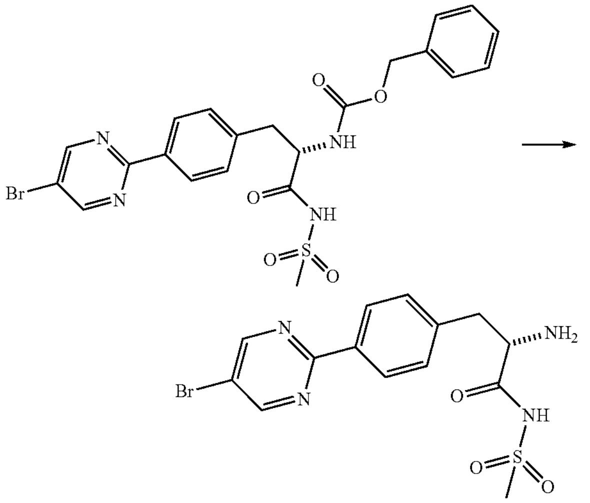

To stirring hydrogen bromide (107 mL of a 33% solution in AcOH, 591 mmol) was added (S)-benzyl (3-(4-(5-bromopyrimidin-2-yl)phenyl)-1-(methylsulfonamido)-1-oxopropan-2-yl)carbamate (10.5 g, 19.70 mmol). After 2 h, diethyl ether (100 mL) was added and the precipitate collected by filtration, washing with iso-hexanes (4×50 mL) to afford 9.5 g (100%) of (S)-2-amino-3-(4-(5-bromopyrimidin-2-yl)phenyl)-N-(methylsulfonyl)propanamide as the HBr salt. LCMS-ESI (m/z) calculated for $C_{14}H_{15}BrN_4O_3S$: 398.0. found 399.1 $[M+H]^+$, $t_R$=1.21 min (Method 11).

(S)—N-(3-(4-(5-bromopyrimidin-2-yl)phenyl)-1-(methylsulfonamido)-1-oxopropan-2-yl)-5-(tert-butyl)thiophene-2-carboxamide

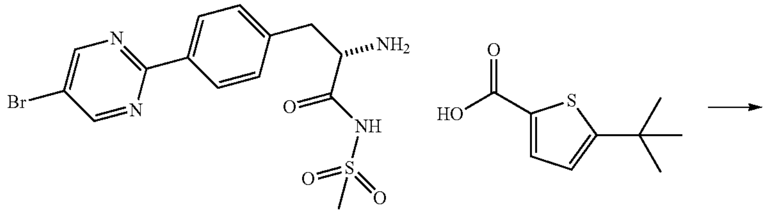

-continued

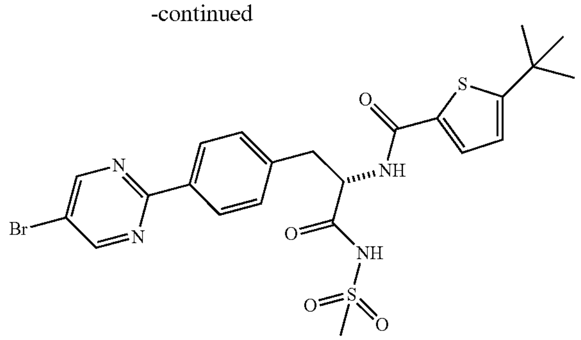

Prepared using General Procedure 7: To a stirring solution of 5-(tert-butyl)thiophene-2-carboxylic acid (4.56 g, 23.53 mmol) and DIEA (21.72 mL, 118 mmol) in DMF (95 mL) was added portionwise HATU (8.95 g, 23.53 mmol). After 30 min, the yellow solution was added to a stirring solution of (S)-2-amino-3-(4-(5-bromopyrimidin-2-yl)phenyl)-N-(methylsulfonyl)propanamide, HBr (9.5 g, 19.61 mmol) in DMF (190 mL). After 1.5 h, ice-water (190 mL) was added. After 10 min acetic acid (8.97 mL, 157 mmol) was added. After a further 10 min, more water added (300 mL). The mixture was allowed to stir at room temperature for 15 min. The precipitate was collected by filtration washed successively with water (2×100 mL), iso-hexanes (2×100 mL), water (2×100 mL) and iso-hexanes (2×100 mL) to give 11.1 g (100%) of (S)—N-(3-(4-(5-bromopyrimidin-2-yl)phenyl)-1-(methylsulfonamido)-1- oxopropan-2-yl)-5-(tert-butyl)thiophene-2-carboxamide. LCMS-ESI (m/z) calculated for $C_{23}H_{25}BrN_4O_4S_2$: 564.1. found 565.1 $[M+H]^+$, $t_R$=2.58 min (Method 11).

5-(tert-butyl)-N—((S)-3-(4-(5-((1RS,1'r,4'RS)-4'-ethyl-[1,1'-bi(cyclohexan)]-3-en-4-yl)pyrimidin-2-yl)phenyl)-1-(methylsulfonamido)-1-oxopropan-2-yl)thiophene-2-carboxamide (Compound 109)

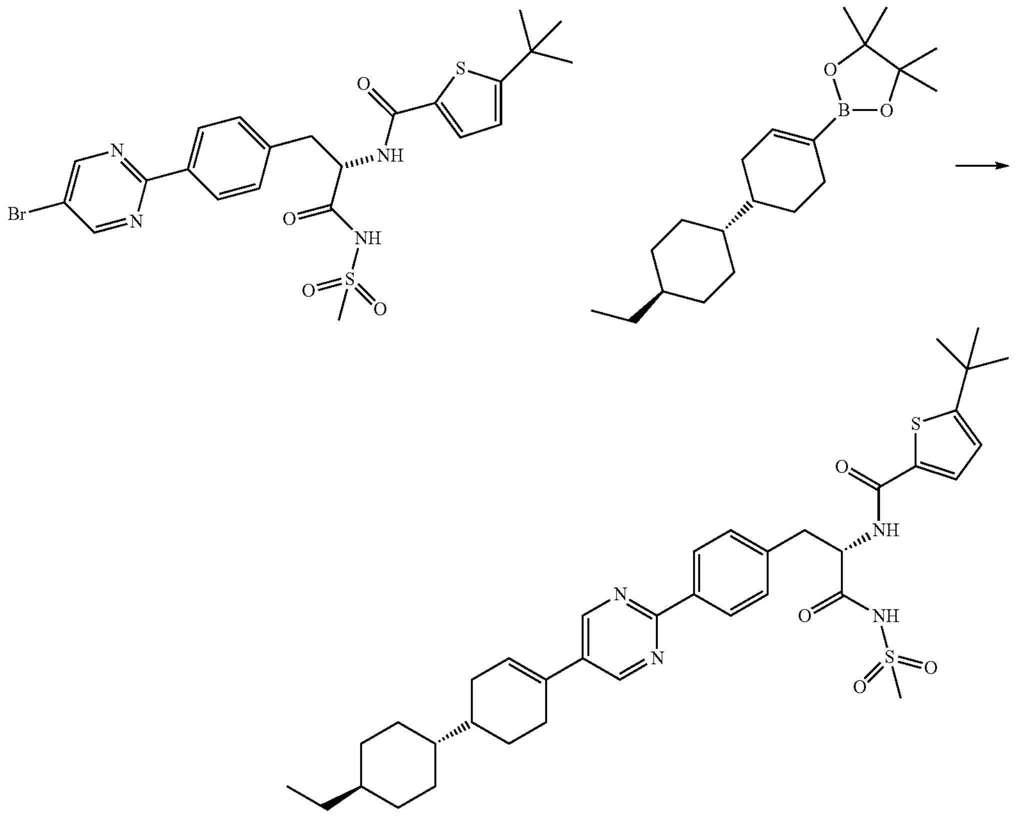

Prepared using General Procedure 10: To a stirring solution of (S)—N-(3-(4-(5-bromopyrimidin-2-yl)phenyl)-1-(methylsulfonamido) 1-oxopropan-2-yl)-5-(tert-butyl)thiophene-2-carboxamide (5.25 g, 9.28 mmol) and racemic 2-((1RS,1'r,4'RS)-4'-ethyl-[1,1'-bi(cyclohexan)]-3-en-4-yl)-4,4,5,5-tetramethyl-1,3,2-dioxaborolane (3.55 g, 11.14 mmol) in dioxane (200 mL) was added sodium hydrogencarbonate (25.8 mL of a 0.9 M aqueous solution, 23.21 mmol). The mixture was warmed to 40° C., de-gassed, then treated with $PdCl_2dppf$ (0.303 g, 0.371 mmol) then heated under reflux for 6 h. The mixture was allowed to cool then poured onto 1 M HCl (200 mL) and extracted with EA (3×200 mL). The combined organic extracts were washed with brine (200 mL), dried over $MgSO_4$, filtered and solvents evaporated. The residue was purified by column chromatography (AcOH/EA/DCM/iso-hexanes) then re-slurried from ACN. The residue was further purified by reverse phase column chromatography (RP Flash C18, ACN/water/formic acid) to afford 4.25 g (68%) of a mixture of diastereomers 5-(tert-butyl)-N—((S)-3-(4-(5-((1RS,1'r,4'RS)-4'-ethyl-[1,1'-bi(cyclohexan)]-3-en-4-yl)pyrimidin-2-yl)phenyl)-1-(methylsulfonamido)-1-oxopropan-2-yl)thiophene-2-carboxamide. LCMS-ESI (m/z) calculated for $C_{37}H_{48}N_4O_4S_2$: 676.3. found 677.3 $[M+H]^+$, $t_R$=3.39 min (Method 11). Chiral analysis (Chiral Method 1) showed >95% single peak. $^1H$ NMR (400 MHz, DMSO-$d_6$) δ 12.18 (s, 1H), 8.91 (s, 2H), 8.70-8.68 (m, 1H), 8.45-8.19 (m, 2H), 7.67 (d, J=3.9 Hz, 1H), 7.51 (d, J=8.3 Hz, 2H), 6.93 (d, J=3.8 Hz, 1H), 6.49-6.34 (m, 1H), 4.75-4.69 (m, 1H), 3.24-3.17 (m, 4H), 3.06 (dd, J=13.6, 10.8 Hz, 1H), 2.49-2.19 (m, 3H), 2.00-1.92 (m, 2H), 1.87-1.70 (m, 4H), 1.38-1.29 (m, 11H), 1.23-0.95 (m, 6H), 0.91-0.82 (m, 5H).

(S)-1-((S)-3-(4-(5-bromopyrimidin-2-yl)phenyl)-2-(5-(tert-butyl)thiophene-2-carboxamido)propanoyl) pyrrolidine-3-carboxylic acid

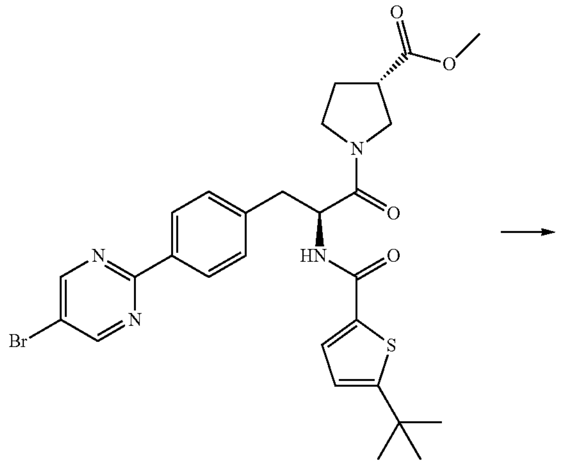

-continued

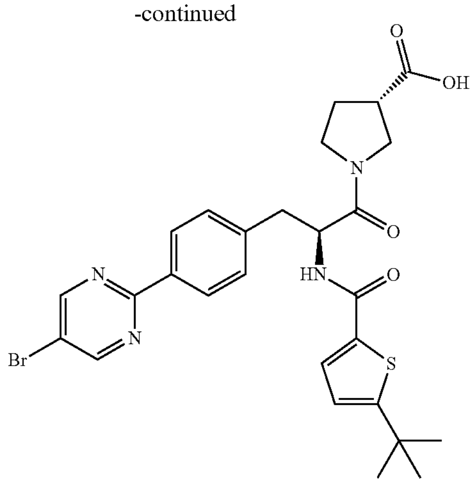

A solution of sulfuric acid (119 mL, 2228 mmol) in acetic acid (300 mL) and water (300 mL) was prepared and allowed to cool to room temperature. This was added to a stirred solution of methyl 1-((S)-3-(4-(5-bromopyrimidin-2-yl)phenyl)-2-(5-(tert-butyl)thiophene-2-carboxamido)propanoyl)pyrrolidine-3-carboxylate INT-35 (44.5 g, 74.3 mmol) in dioxane (500 mL). After 16 h, the mixture was poured into ice water (1 L) and extracted with DCM (2×1 L). The combined organic extracts were washed with water (2×1 L), dried over $MgSO_4$ and solvents evaporated. Column chromatography (AcOH/EA/DCM/iso-hexanes) gave clean product and mixed fractions. These mixed fractions were further purified by column chromatography (AcOH/EA/DCM/iso-hexanes) and the clean products combined and re-slurried from ACN to afford 26.3 g (60%) of (S)-1-((S)-3-(4-(5-bromopyrimidin-2-yl)phenyl)-2-(5-(tert-butyl)thiophene-2-carboxamido) propanoyl)pyrrolidine-3-carboxylic acid. LCMS-ESI (m/z) calculated for $C_{27}H_{29}BrN_4O_4S$: 584.1. found 585.1 $[M+H]^+$, $t_R$=2.48 min (Method 11).

(S)-1-((S)-2-(5-(tert-butyl)thiophene-2-carboxamido)-3-(4-(5-((1RS,1'r,4'RS)-4'-ethyl-[1,1'-bi(cyclohexan)]-3-en-4-yl)pyrimidin-2-yl)phenyl)propanoyl)pyrrolidine-3-carboxylic acid (Compound 110)

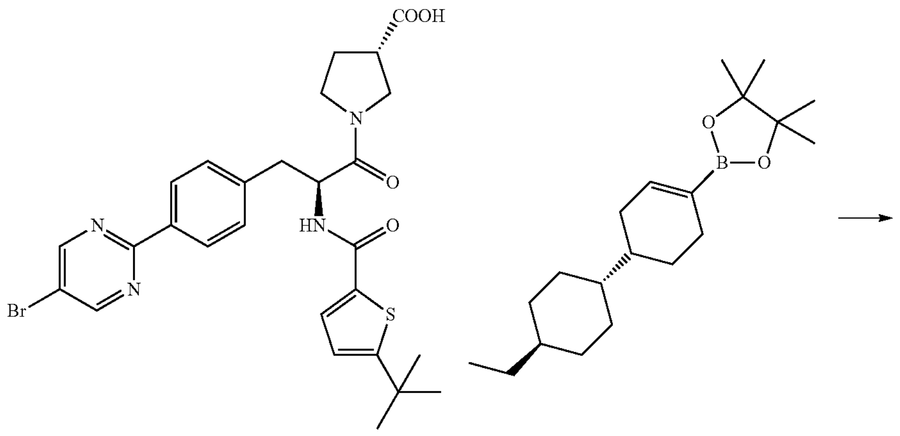

-continued

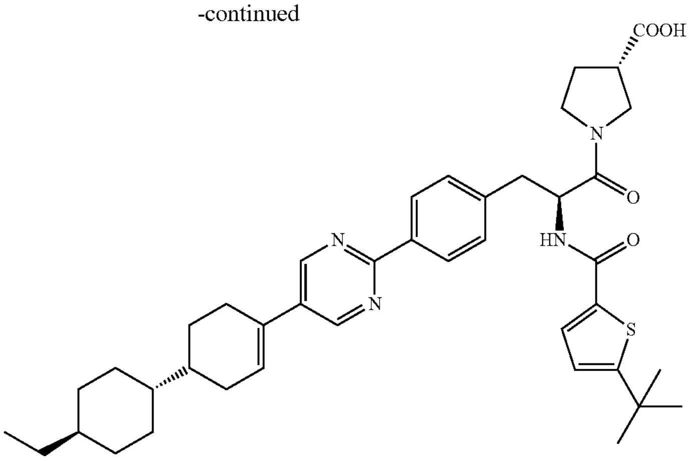

Prepared using General Procedure 10: To a stirring solution of (S)-1-((S)-3-(4-(5-bromopyrimidin-2-yl)phenyl)-2-(5-(tert-butyl)thiophene-2-carboxamido) propanoyl) pyrrolidine-3-carboxylic acid (5.7 g, 9.74 mmol) and racemic 2-((1RS,1'r,4'RS)-4'-ethyl-[1,1'-bi(cyclohexan)]-3-en-4-yl)-4,4,5,5-tetramethyl-1,3,2-dioxaborolane (3.41 g, 10.71 mmol) in dioxane (150 mL), was added $NaHCO_3$ (32.5 mL of a 0.9 M aqueous solution, 29.2 mmol) and the mixture degassed. $PdCl_2$(dppf) (0.356 g, 0.487 mmol) was added and the mixture heated under reflux. After 3 h, the mixture was allowed to cool then poured onto a mixture of ice-water (75 mL) and 1 M HCl (125 mL). The precipitate was collected by filtration, washing with water (50 mL). The solid was re-slurried from ACN (150 mL) then purified by column chromatography (AcOH/THF/DCM/iso-hexanes). The product was again re-slurried from ACN (200 mL) to afford 4.74 g (70%) of a mixture of diastereomers (S)-1-((S)-2-(5-(tert-butyl)thiophene-2-carboxamido)-3-(4-(5-((1RS,1'r, 4'RS)-4'-ethyl-[1,1'-bi(cyclohexan)]-3-en-4-yl)pyrimidin-2-yl)phenyl)propanoyl)pyrrolidine-3-carboxylic acid. LCMS-ESI (m/z) calculated for $C_{41}H_{52}N_4O_4S$: 696.4; no m/z observed, $t_R$=11.05 min (Method 10). Chiral analysis (Chiral Method 1) showed >95% single peak. $^1H$ NMR (400 MHz, DMSO-$d_6$) δ 12.53 (s, 1H), 8.91 (d, J=0.8 Hz, 2H), 8.78 (t, J=8.2 Hz, 1H), 8.27 (d, J=8.0 Hz, 2H), 7.73 (d, J=3.9 Hz, 1H), 7.44 (dd, J=8.5, 2.3 Hz, 2H), 6.92 (dd, J=3.9, 0.9 Hz, 1H), 6.51-6.37 (m, 1H), 5.00-4.73 (m, 1H), 3.88-3.83 (m, 0.5H), 3.72-3.66 (m, 0.5H), 3.62-3.36 (m, 2H), 3.17-2.87 (m, 3H), 2.49-2.19 (m, 3H), 2.13-1.69 (m, 8H), 1.36-1.32 (m, 11H), 1.23-0.67 (m, 12H).

Compounds 111-114 and 116 were prepared from Compound 123 using General Procedure 7 using the respective amine followed by General Procedure 8.

Compound 115 was prepared from Compound 123 using General Procedure 7.

tert-butyl (tert-butoxycarbonyl)-L-tyrosinate

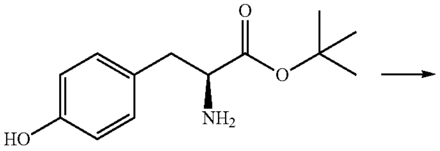

-continued

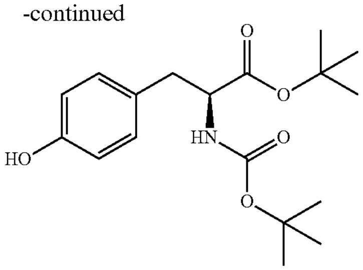

To a stirring solution of sodium bicarbonate (37.4 g, 445 mmol) in water (1 L) was added (S)-tert-butyl 2-amino-3-(4-hydroxyphenyl)propanoate (96 g, 405 mmol) and acetone (850 mL). A solution of di-tert-butyl dicarbonate (97 g, 445 mmol) in acetone (220 mL) was then added slowly over 2 h. After a further 16 h, the mixture was treated with water (1.7 L) then treated with a solution of AcOH (30 mL) in water (300 mL) added slowly. The mixture was extracted with EA (1 L) and the organics dried over $Na_2SO_4$ and partially concentrated. The residue was re-slurried with iso-hexanes (1 L). The precipitate was collected by filtration, washing with iso-hexanes (100 mL) to afford 128.4 g (94%) of tert-butyl (tert-butoxycarbonyl)-L-tyrosinate. LCMS-ESI (m/z) calculated for $C_{18}H_{27}NO_5$: 337.2. found 360.2 $[M+Na]^+$, $t_R$=5.93 min (Method 10).

tert-butyl (S)-2-((tert-butoxycarbonyl)amino)-3-(4-(((trifluoromethyl)sulfonyl)oxy)phenyl)propanoate

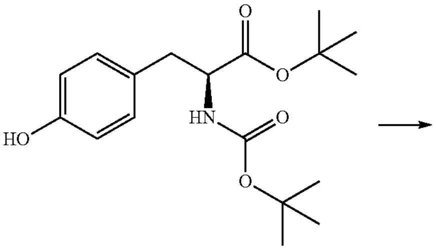

-continued

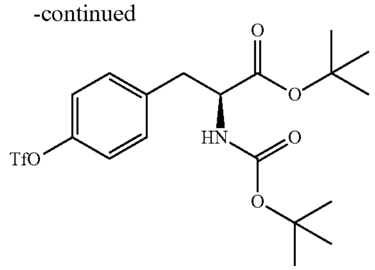

To a stirred solution of tert-butyl (tert-butoxycarbonyl)-L-tyrosinate (145 g, 429 mmol) in DCM (1.5 L) was added DIEA (95 mL, 514 mmol) then 1,1,1-trifluoro-N-phenyl-N-((trifluoromethyl)sulfonyl)methanesulfonamide (7.66 g, 21.5 mmol). After 16 h, additional 1,1,1-trifluoro-N-phenyl-N-((trifluoromethyl)sulfonyl)methanesulfonamide (7.66 g, 21.5 mmol) was added. After a further 3 h, additional 1,1,1-trifluoro-N-phenyl-N-((trifluoromethyl)sulfonyl) methanesulfonamide (153.11 g, 429 mmol) was added. After a further 20 h, the mixture was washed successively with a solution of citric acid monohydrate (105 g, 500 mmol) in water (1.5 L) then saturated aqueous sodium bicarbonate (1 L). The organics were dried over $Na_2SO_4$ and solvents evaporated to afford tert-butyl (S)-2-((tert-butoxycarbonyl) amino)-3-(4-(((trifluoromethyl)sulfonyl)oxy)phenyl)propanoate, overweight with phenyltriflimide and used crude for the next step. LCMS-ESI (m/z) calculated for $C_{19}H_{26}F_3NO_7S$: 469.1. found 492.2 $[M+Na]^+$, $t_R$=2.87 min (Method 11).

tert-Butyl (S)-2-((tert-butoxycarbonyl)amino)-3-(4-(4,4,5,5-tetramethyl-1,3,2-dioxaborolan-2-yl)phenyl) propanoate

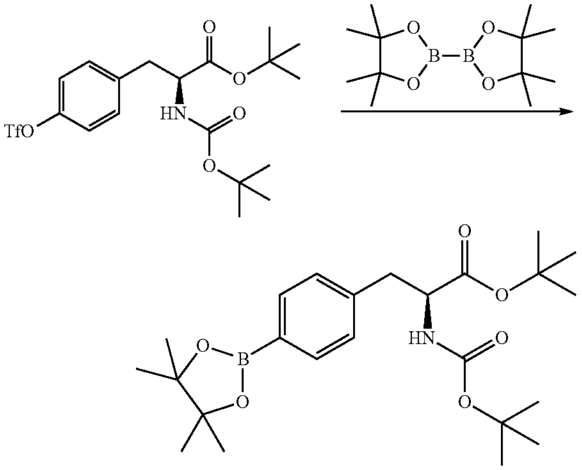

A stirred mixture of tert-butyl (S)-2-((tert-butoxycarbonyl)amino)-3-(4-(((trifluoromethyl)sulfonyl)oxy)phenyl) propanoate (crude from previous step, assumed 429 mmol), potassium acetate (126 g, 1287 mmol) and 4,4,4',4',5,5,5',5'-octamethyl-2,2'-bi(1,3,2-dioxaborolane) (109 g, 429 mmol) in DMSO (750 mL) was warmed to 40° C. and de-gassed. The $PdCl_2dppf$ (6.28 g, 8.58 mmol) was charged, the mixture again de-gassed, then heated to 100° C. After 2.5 h, the mixture was allowed to cool then extracted with $Et_2O$ (3×750 mL). The combined organics were washed with water (2×600 mL then 1×1 L), dried over $Na_2SO_4$ and solvents evaporated to afford 188.9 g (98%) of tert-butyl (S)-2-((tert-butoxycarbonyl)amino)-3-(4-(4,4,5,5-tetramethyl-1,3,2-dioxaborolan-2-yl)phenyl) propanoate as a brown solid used directly for the next step. LCMS-ESI (m/z) calculated for $C_{24}H_{38}BNO_6$: 447.3. found 470.3 $[M+Na]^+$, $t_R$=2.99 min (Method 11). $^1H$ NMR (400 MHz, DMSO-$d_6$) δ 7.63-7.55 (m, 2H), 7.25 (d, J=7.8 Hz, 2H), 7.15 (d, J=8.1 Hz, 1H), 4.01 (ddd, J=9.7, 8.1, 5.5 Hz, 1H), 3.05-2.78 (m, 2H), 1.36 (s, 9H), 1.34 (s, 9H), 1.29 (s, 12H).

tert-butyl (S)-3-(4-(5-bromopyrimidin-2-yl)phenyl)-2-((tert-butoxycarbonyl amino) propanoate

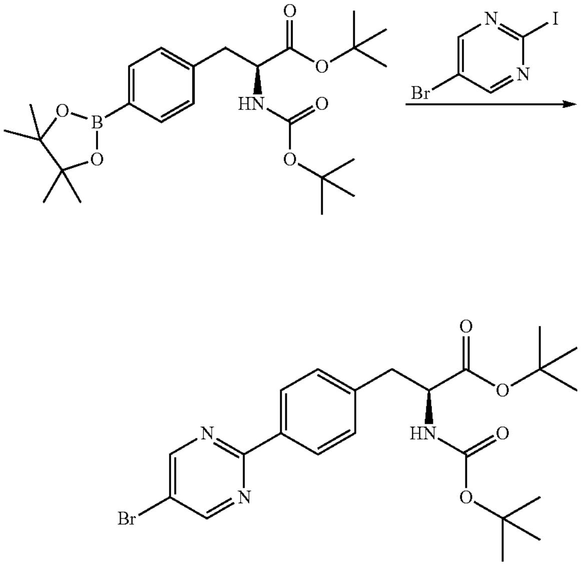

A stirred solution of sodium carbonate decahydrate (242 g, 844 mmol) in water (0.9 L) was treated with (S)-tert-butyl 2-((tert-butoxycarbonyl)amino)-3-(4-(4,4,5,5-tetramethyl-1,3,2-dioxaborolan-2-yl)phenyl)propanoate (188.9 g, 422 mmol) and 5-bromo-2-iodopyrimidine (120 g, 422 mmol) in dioxane (1.8 L) and the resulting mixture warmed to 40° C. and de-gassed by bubbling with $N_2$. The $PdCl_2dppf$ (6.18 g, 8.44 mmol) was charged and the mixture heated under gentle reflux for 6 h. The mixture was allowed to cool to 40° C. then treated with water (1.8 L) and cooled to 20° C. The precipitate was collected by filtration. The reaction vessel was washed out with acetone (250 mL) and this solution treated with water (300 mL) to afford a second crop of precipitate that was combined with the bulk material. The precipitated solid was washed successively with water (2×500 mL) and iso-hexanes (2×500 mL). This was then slurried in EtOH (550 mL) and heated under reflux for 30 min. The suspension was cooled to 20° C. and the precipitate collected by filtration, washing with EtOH (200 mL) to afford 146.8 g (73%) of tert-butyl (S)-3-(4-(5-bromopyrimidin-2-yl)phenyl)-2-((tert-butoxycarbonyl)amino) propanoate as a fine beige powder. LCMS-ESI (m/z) calculated for $C_{22}H_{28}BrN_3O_4$: 477.1. found 500.1 [M+Na], $t_R$=2.18 min (Method 6). $^1H$ NMR (400 MHz, DMSO-$d_6$) δ 9.00 (s, 2H), 8.25-8.12 (m, 2H), 7.34 (d, J=8.2 Hz, 2H), 7.18 (d, J=8.0 Hz, 1H) 4.05-3.94 (m, 1H), 3.06-2.73 (m, 2H), 1.28 (m, 18H).

tert-butyl (S)-2-amino-3-(4-(5-bromopyrimidin-2-yl) phenyl)propanoate (INT-79)

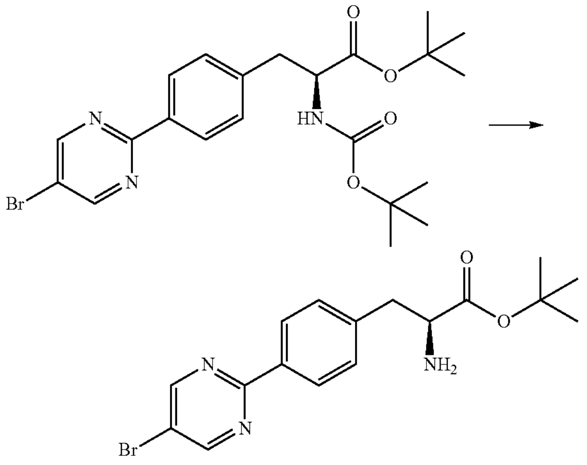

To a stirred solution of (S)-tert-butyl 3-(4-(5-bromopyrimidin-2-yl)phenyl)-2-((tert-butoxycarbonyl)amino)propanoate (146.77 g, 307 mmol) in DCM (500 mL) was added hydrogen chloride (614 mL of a 5-6 N solution in IPA, ~3.1 mol). After 1 h, the product was collected by filtration, washing with IPA (100 mL) then ether (2×100 mL) to afford 122.3 g (96%) of tert-butyl (S)-2-amino-3-(4-(5-bromopyrimidin-2-yl)phenyl)propanoate (hydrochloride salt). LCMS-ESI (m/z) calculated for $C_{17}H_{20}BrN_3O_2$*HCl: 377.1. found 378.1 $[M+H]^+$, $t_R$=2.99 min (Method 10). $^1H$ NMR (400 MHz, DMSO-$d_6$) δ 9.09 (s, 2H), 8.61 (br s, 3H), 8.39-8.25 (m, 2H), 7.57-7.37 (m, 2H), 4.21 (br s, 1H), 3.42-3.19 (m, 1H), 3.09 (dd, J=14.0, 8.4 Hz, 1H), 1.31 (s, 9H).

The product was dissolved in $CHCl_3$/MeOH and washed with saturated aqueous sodium bicarbonate to afford the free base.

Compounds 117 and 118 were prepared from (S)-tert-butyl 2-amino-3-(4-(5-bromopyrimidin-2-yl)phenyl)propanoate INT-79 using General Procedures 7, 8, 7, 4 and 10 sequentially.

Compound 119 was prepared from INT-17 using General Procedures 10 then 8.

8-cyclohexyl-1,4-dioxaspiro[4.5]decane

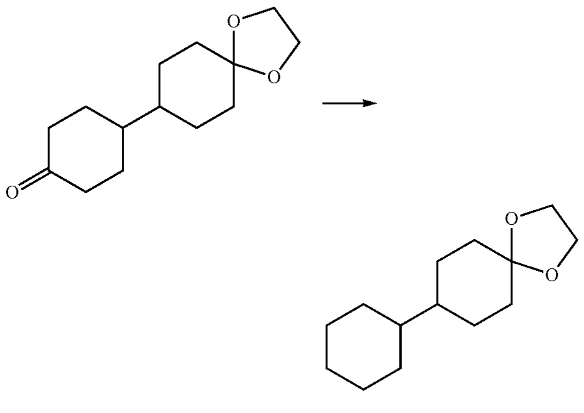

To a stirring solution of 4-(1,4-dioxaspiro[4.5]decan-8-yl)cyclohexanone (1 g, 4.20 mmol) in diethylene glycol (15 mL) were added hydrazine (3.92 mL, 62.9 mmol) and potassium hydroxide (2.354 g, 42.0 mmol). The reaction mixture was heated up to 160° C. for 16 h then up to 210° C. for 1 h. The reaction mixture was cooled down to room temperature and quenched with a solution of $NH_4Cl$ (120 mL). The aqueous layer was extracted with EA (3×80 mL). The combined organic layers were dried over $MgSO_4$, filtered and solvents evaporated. The crude product was purified by column chromatography (EA/Iso-hexane) to afford 728 mg (77%) of 8-cyclohexyl-1,4-dioxaspiro[4.5] decane as a white solid.

[1,1'-bi(cyclohexan)]-4-one

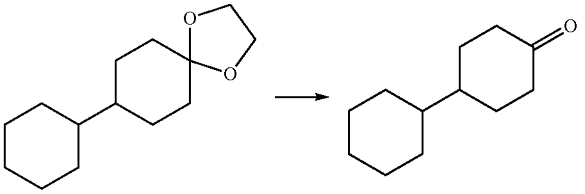 [SMILES: C1CCC(C2CCC3(CC2)OCCO3)CC1 ; O=C1CCC(C2CCCCC2)CC1]

To a stirring solution of 8-cyclohexyl-1,4-dioxaspiro[4.5] decane (724 mg, 3.23 mmol) in a mixture of acetone (4 mL) and water (2 mL) was added trifluoroacetic acid (3 mL, 38.9 mmol). The reaction mixture was stirred at room temperature for 4 h. The solvents were evaporated. The crude product was purified by column chromatography (EA/Iso-hexane) to afford 582 mg (100%) of [1,1'-bi(cyclohexan)]-4-one as a colourless oil.

[1,1'-bi(cyclohexan)]-3-en-4-yl trifluoromethanesulfonate

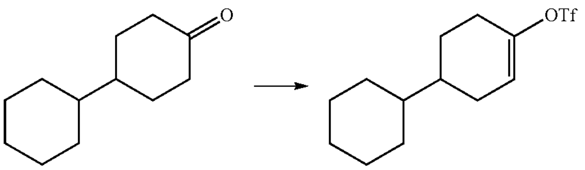 [SMILES: O=C1CCC(C2CCCCC2)CC1 ; O=S(=O)(OC1=CCC(C2CCCCC2)CC1)C(F)(F)F]

To a stirring solution of [1,1'-bi(cyclohexan)]-4-one (622 mg, 3.45 mmol) in THF (10 mL) at −78° C. was added 1,1,1-trifluoro-N-phenyl-N-((trifluoromethyl)sulfonyl) methanesulfonamide (1233 mg, 3.45 mmol) and lithium bis(trimethylsilyl)amide (3.8 mL of a 1 M solution in THF, 3.80 mmol). The solution was stirred for 2 h at −78° C. then stirred at room temperature for 72 h. A saturated solution of $NaHCO_3$ (20 mL) was added to the reaction mixture and the aqueous layer was extracted with EA (3×30 mL). The organic layers were dried over $MgSO_4$ and the solvents evaporated. The crude product was purified by column chromatography (EA/iso-hexane) to afford 519 mg (48%) of [1,1'-bi(cyclohexan)]-3-en-4-yl trifluoromethanesulfonate as a colorless oil.

2-([1,1'-bi(cyclohexan)]-3-en-yl)-4,4,5,5-tetramethyl-1,3,2-dioxaborolane

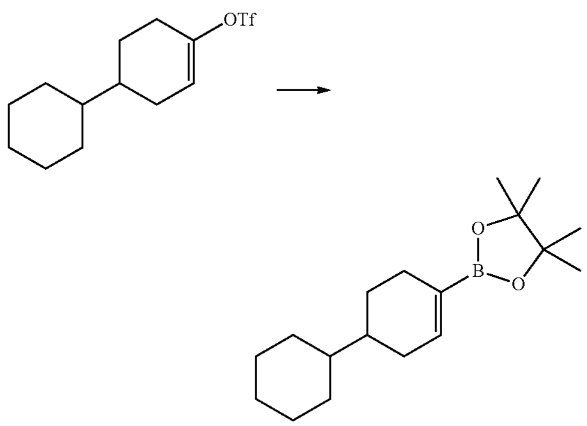

A stirring solution of [1,1'-bi(cyclohexan)]-3-en-4-yl trifluoromethanesulfonate (519 mg, 1.66 mmol), 4,4,4',4',5,5,5',5'-octamethyl-2,2'-bi(1,3,2-dioxaborolane) (422 mg, 1.66 mmol) and potassium acetate (489 mg, 4.98 mmol) in dioxane (10 mL) was heated to 40° C. and degassed. $PdCl_2$(dppf) (24.32 mg, 0.033 mmol) was added and the mixture again degassed then heated to 90° C. for 3 h. The reaction mixture was partitioned between EA (20 mL) and water (20 mL). The aqueous layer was extracted once more with EA (20 mL). The combined organic layers were dried over MgSO4, filtered and solvents evaporated. The crude product was purified by column chromatography (EA/isohexane) to afford 100 mg (20%) of 2-([1,1'-bi(cyclohexan)]-3-en-4-yl)-4,4,5,5-tetramethyl-1,3,2-dioxaborolane as a colourless oil. Molecular formula: $C_{18}H_{31}BO_2$. $^1H$ NMR (400 MHz, DMSO-$d_6$) δ 5.70 (m, 1H), 1.43-1.27 (m, 2H), 1.32-1.27 (m, 1H), 1.08-0.81 (m, 7H), 0.53-0.12 (m, 20H).

Compound 120 was prepared from (S)-tert-butyl 3-(4-(5-bromopyrimidin-2-yl)phenyl)-2-(5-(tert-butyl)thiophene-2-carboxamido)propanoate INT-17 using General Procedure 8 followed by General Procedure 10 using 2-([1,1'-bi(cyclohexan)]-3-en-4-yl)-4,4,5,5-tetramethyl-1,3,2-dioxaborolane.

8-(4-propylphenyl)-1,4-dioxaspiro[4.5]decan-8-ol

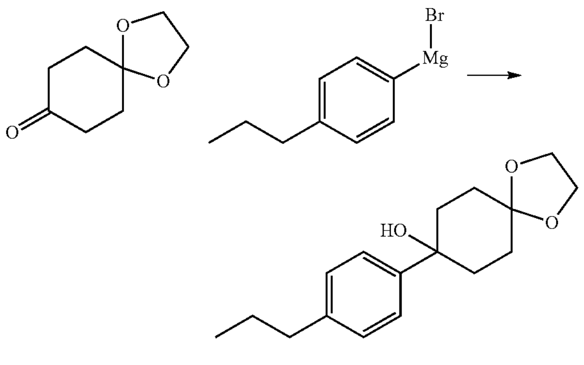

To a stirring solution of 1,4-dioxaspiro[4.5]decan-8-one (1 g, 6.40 mmol) in THF (10 mL) was added (4-propylphenyl)magnesium bromide (23 mL of a 0.5 M solution in THF, 11.50 mmol). The reaction heated under reflux for 5 h. The mixture was allowed to cool then quenched into saturated aqueous $NH_4Cl$ and extracted with EA (2×40 mL). The combined organic extracts were dried over $MgSO_4$ and solvents evaporated. Column chromatography (EA/isohexanes) gave 1.38 g 77% of 8-(4-propylphenyl)-1,4-dioxaspiro[4.5]decan-8-ol as a white solid.

8-(4-propylphenyl)-1,4-dioxaspiro[4.5]dec-7-ene

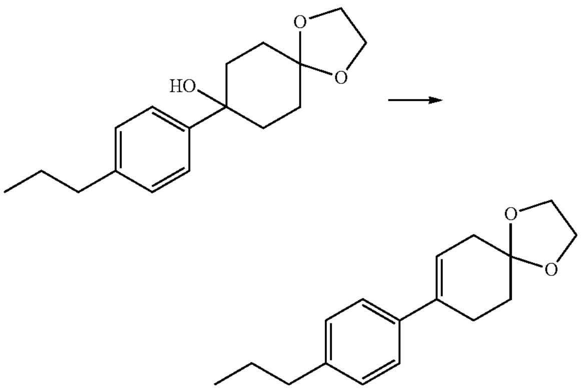

To a stirring mixture of 8-(4-propylphenyl)-1,4-dioxaspiro[4.5]decan-8-ol (1.38 g, 4.99 mmol) in THF (24 mL) was added Burgess reagent (2.38 g, 9.99 mmol). The mixture was heated at 50° C. for 3 h. The solvent was evaporated and the reaction mixture partitioned between water (30 mL) and DCM (50 mL). Solvents were evaporated and the residue purified by column chromatography (EA/isohexanes) to afford 1.21 g (93%) of 8-(4-propylphenyl)-1,4-dioxaspiro[4.5]dec-7-ene (1.21 g, 4.64 mmol, 93% yield) as a colourless oil.

8-(4-propylphenyl)-1,4-dioxaspiro[4.5]decane

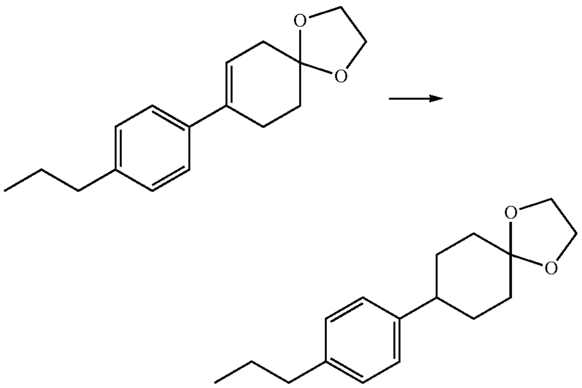

To a stirring solution of 8-(4-propylphenyl)-1,4-dioxaspiro[4.5]dec-7-ene (1.208 g, 4.68 mmol) in EtOH (30 mL) was added Palladium on carbon (10% Johnson and Matthey Paste Type 39, 200 mg) and the mixture hydrogenated under 5 bar for 4 h. The mixture was filtered through Celite and solvents evaporated to afford 1.18 g (96%) of 8-(4-propylphenyl)-1,4-dioxaspiro[4.5]decane.

4-(4-propylphenyl)cyclohexanone

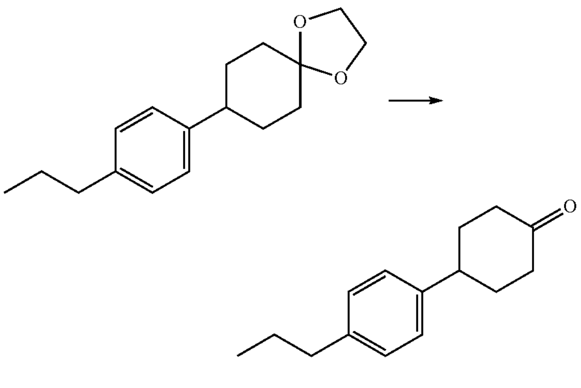

To a stirring solution of 8-(4-propylphenyl)-1,4-dioxaspiro[4.5]decane (1.12 g, 4.30 mmol) in acetone (6 mL) and water (3 mL) was added TFA (4.5 mL, 58.4 mmol). After 16 h, solvents were evaporated and the residue purified by column chromatography (EA/iso-hexanes) to afford product and recovered starting material. The recovered starting material was re-submitted to the reaction conditions above and products combined to afford 678 mg (69%) of 4-(4-propylphenyl)cyclohexanone.

4'-propyl-1,2,3,6-tetrahydro-[1,1'-biphenyl]-4-yl trifluoromethanesulfonate

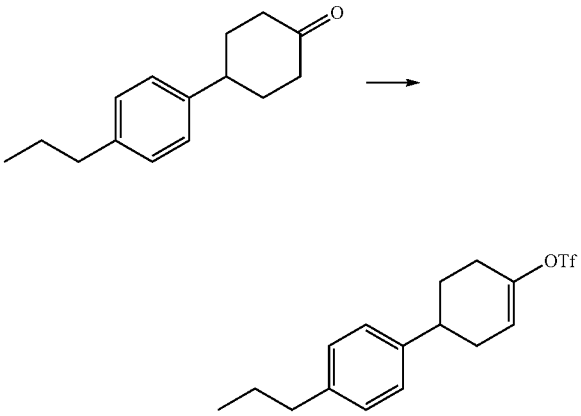

To a stirring solution of diisopropylamine (0.53 mL, 3.76 mmol) in THF (15 mL) at −20° C. was added butyllithium (1.5 mL of a 2.5 M solution in hexanes, 3.76 mmol). The mixture was cooled to −78° C. whereupon a solution of 4-(4-propylphenyl)cyclohexanone (678 mg, 3.13 mmol) in THF (15 mL) was added slowly followed by 1,1,1-trifluoro-N-phenyl-N-((trifluoromethyl)sulfonyl)methanesulfonamide (1176 mg, 3.29 mmol). After 1 h, the mixture was allowed to warm to room temperature. The mixture was quenched into $NaHCO_3$ (40 mL) and extracted with EA (3×50 mL). The combined organic extracts were dried over $MgSO_4$ and solvents evaporated. Column chromatography (EA/iso-hexanes) gave 506 mg (46%) of 4'-propyl-1,2,3,6-tetrahydro-[1,1'-biphenyl]-4-yl trifluoromethanesulfonate.

4,4,55-tetramethyl-2-(4'-propyl-1,2,3,6-tetrahydro-[1,1'-biphenyl]-4-yl)-1,3,2-dioxaborolane

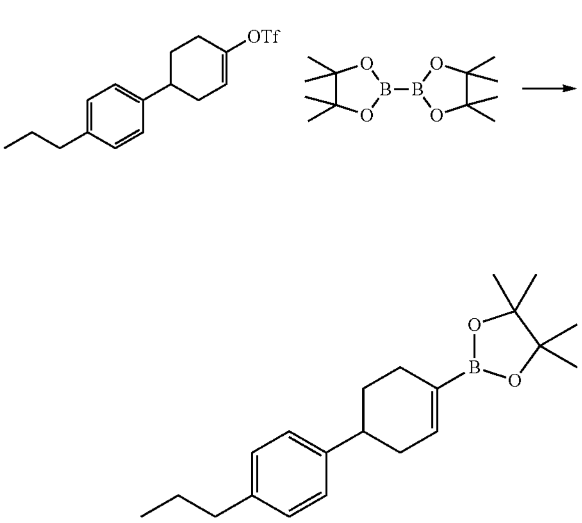

To a stirring solution of 4'-propyl-1,2,3,6-tetrahydro-[1,1'-biphenyl]-4-yl trifluoromethanesulfonate (506 mg, 1.452 mmol) and 4,4,4',4',5,5,5',5'-octamethyl-2,2'-bi(1,3,2-dioxaborolane) (369 mg, 1.452 mmol) in dioxane (8 mL) was added potassium acetate (428 mg, 4.36 mmol). The mixture was heated to 40° C. and degassed then treated with $PdCl_2$(dppf) (21 mg, 0.029 mmol) and heated to 90° C. for 4 h. The mixture was allowed to cool then diluted with water (20 mL) and extracted with EA (4×20 mL). The combined organic extracts were dried over $MgSO_4$ and solvents evaporated. Column chromatography gave 146 mg (31%) of 4,4,5,5-tetramethyl-2-(4'-propyl-1,2,3,6-tetrahydro-[1,1'-biphenyl]-4-yl)-1,3,2-dioxaborolane. Molecular formula: $C_{21}H_{31}BO_2$. $^1H$ NMR (400 MHz, Chloroform-d) δ 7.17-7.10 (m, 4H), 6.76-6.57 (m, 1H), 2.87-2.68 (m, 1H), 2.61-2.54 (m, 2H), 2.47-2.16 (m, 3H), 1.96 (ddd, J=10.2, 5.2, 2.7 Hz, 1H), 1.77-1.60 (m, 3H), 1.30-1.24 (m, 13H), 0.96 (t, J=7.3 Hz, 3H).

Compound 121 was prepared from (S)-tert-butyl 3-(4-(5-bromopyrimidin-2-yl)phenyl)-2-(5-(tert-butyl)thiophene-2-carboxamido)propanoate INT-17 using General Procedure 8 followed by General Procedure 10 using 4,4,5,5-tetramethyl-2-(4'-propyl-1,2,3,6-tetrahydro-[1,1'-biphenyl]-4-yl)-1,3,2-dioxaborolane.

Compound 122 was prepared from (S)-tert-butyl 3-(4-(5-bromopyrimidin-2-yl)phenyl)-2-(5-(tert-butyl)thiophene-2-carboxamido)propanoate INT-17 using General Procedure 8 followed by General Procedure 10 using 2-(4',4'-dimethyl-[1,1'-bi(cyclohexan)]-3-en-4-yl)-4,4,5,5-tetramethyl-1,3,2-dioxaborolane.

(S)-2-(5-(tert-butyl)thiophene-2-carboxamido)-3-(4-(5-((1RS,1'r,4'RS)-4'-methyl-[1,1'-bi(cyclohexan)]-3-en-4-yl)pyrimidin-2-yl)phenyl)propanoic acid (Compound 123)

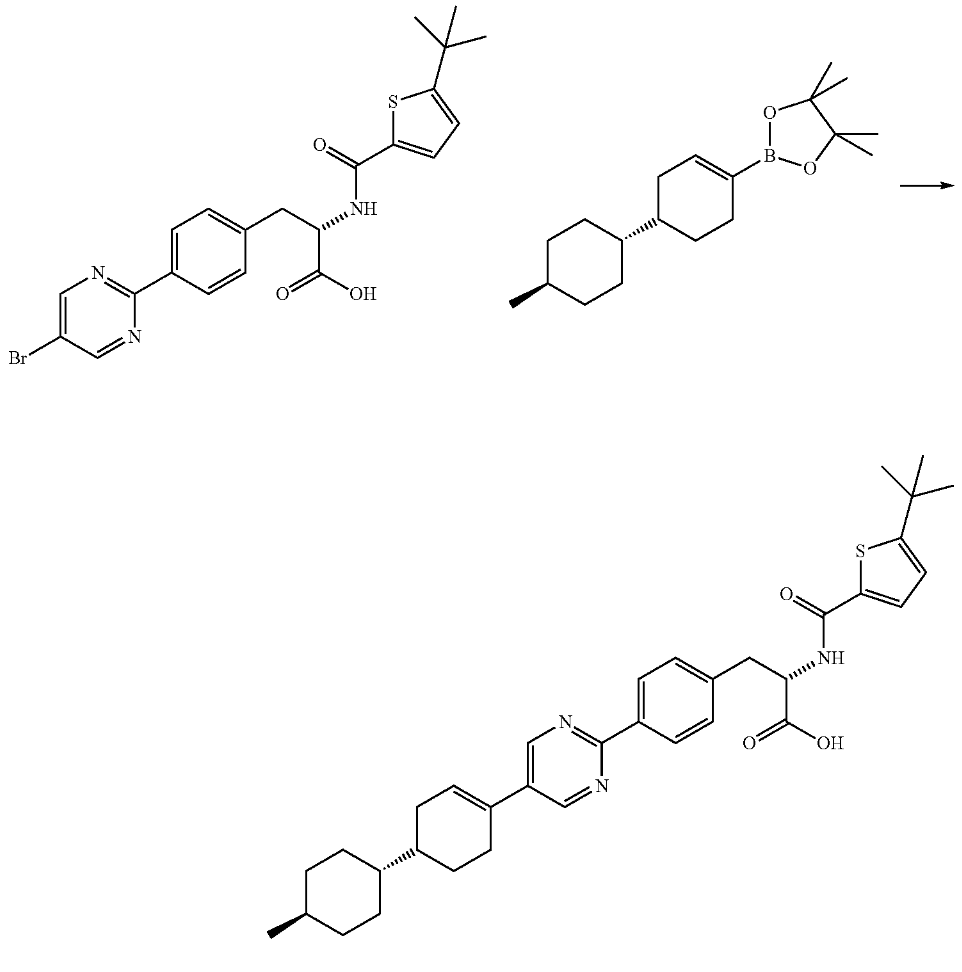

Prepared using General Procedure 10: To a stirred solution of (S)-3-(4-(5-bromopyrimidin-2-yl)phenyl)-2-(5-(tert-butyl)thiophene-2-carboxamido) propanoic acid (6.13 g, 12.55 mmol) and racemic 4,4,5,5-tetramethyl-2-((1RS,1'r,4'RS)-4'-methyl-[1,1'-bi(cyclohexan)]-3-en-4-yl)-1,3,2-dioxaborolane (4.20 g, 13.81 mmol) in dioxane (100 mL) was added a solution of $NaHCO_3$ (3.16 g, 37.7 mmol) in water (50 mL). This mixture was warmed to 40° C. then de-gassed and treated with $PdCl_2$dppf (0.276 g, 0.377 mmol). The mixture was heated under gentle reflux. After 3 h, the mixture was allowed to cool, diluted with water (100 mL) and DCM (200 mL) then acidified with AcOH. The layers were separated and the aqueous further extracted with DCM (2×100 mL). Solvents were evaporated and the residue purified by column chromatography (AcOH/EA/THF/DCM/iso-hexanes). The product was re-slurried from MeOH to afford 4.57 g (62%) of a mixture of diastereomers (S)-2-(5-(tert-butyl)thiophene-2-carboxamido)-3-(4-(5-((1RS,1'r,4'RS)-4'-methyl-[1,1'-bi(cyclohexan)]-3-en-4-yl)pyrimidin-2-yl)phenyl)propanoic acid. LCMS-ESI (m/z) calculated for $C_{35}H_{43}N_3O_3S$: 585.3; no m/z observed, $t_R$=11.12 min (Method 10). Chiral analysis (Chiral Method 1) showed >95% single peak. $^1$H NMR (400 MHz, DMSO-$d_6$) δ 12.84 (s, 1H), 8.91 (s, 2H), 8.64 (d, J=8.3 Hz, 1H), 8.27 (d, J=8.3 Hz, 2H), 7.63 (d, J=3.9 Hz, 1H), 7.43 (d, J=8.4 Hz, 2H), 6.92 (d, J=3.9 Hz, 1H), 6.44 (s, 1H), 4.80-4.42 (m, 1H), 3.25 (dd, J=13.9, 4.5 Hz, 1H), 3.10 (dd, J=13.9, 10.5 Hz, 1H), 2.55-2.51 (m, 2H), 2.41-2.26 (m, 2H), 2.00-1.92 (m, 2H), 1.85-1.62 (m, 4H), 1.39-1.28 (m, 11H), 1.16-0.70 (m, 8H).

Compound 124 was prepared from (S)-tert-butyl 3-(4-(5-bromopyrimidin-2-yl)phenyl)-2-(5-(tert-butyl)thiophene-2-carboxamido)propanoate R-INT-17 using General Procedures 8, 7, 4 and 4,4,5,5-tetramethyl-2-(4'-propyl-1,2,3,6-tetrahydro-[1,1'-biphenyl]-4-yl)-1,3,2-dioxaborolane in step 10 sequentially.

Compound 125 was prepared from compound 76 using General Procedure 18.

TABLE 1
| Representative Compounds | | | |
|---|---|---|---|
| STRUCTURE | COMPOUND NUMBER | LCMS RETENTION TIME (min) | PURITY METHOD |
| 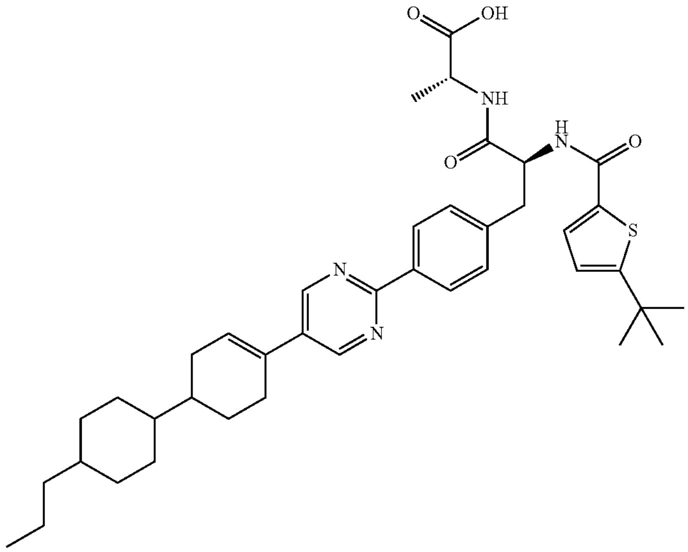 [SMILES: CCCC1CCC(C2CC=C(c3cnc(-c4ccc(C[C@H](NC(=O)c5ccc(C(C)(C)C)s5)C(=O)N[C@H](C)C(=O)O)cc4)nc3)CC2)CC1] | 1 | 12.15 | 11 |
| 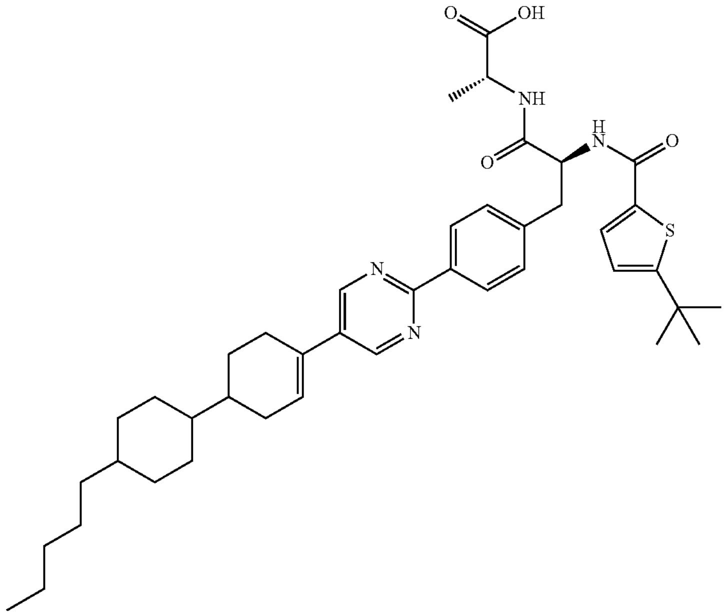 [SMILES: CCCCCC1CCC(C2CC=C(c3cnc(-c4ccc(C[C@H](NC(=O)c5ccc(C(C)(C)C)s5)C(=O)N[C@H](C)C(=O)O)cc4)nc3)CC2)CC1] | 2 | 11.09 | 14 |

TABLE 1-continued
| Representative Compounds | | | |
|---|---|---|---|
| STRUCTURE | COMPOUND NUMBER | LCMS RETENTION TIME (min) | PURITY METHOD |
| 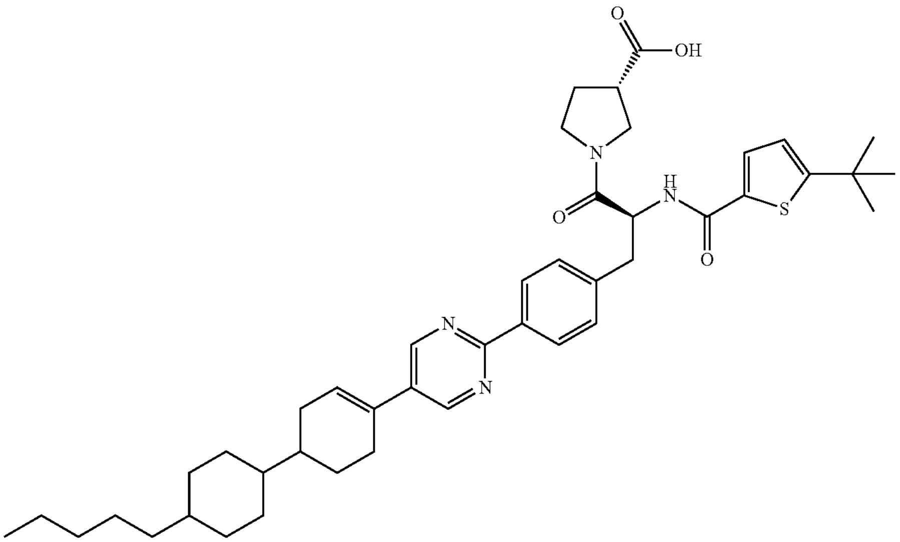 [SMILES: CCCCCC1CCC(C2CC=C(c3cnc(-c4ccc(C[C@H](NC(=O)c5ccc(C(C)(C)C)s5)C(=O)N5CC[C@H](C(=O)O)C5)cc4)nc3)CC2)CC1] | 3 | 13.30 | 14 |
| 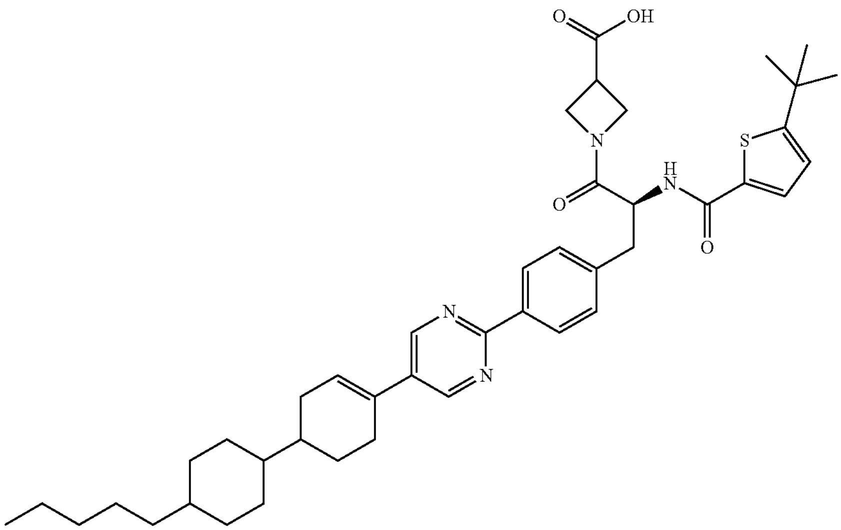 [SMILES: CCCCCC1CCC(C2CC=C(c3cnc(-c4ccc(C[C@H](NC(=O)c5ccc(C(C)(C)C)s5)C(=O)N5CC(C(=O)O)C5)cc4)nc3)CC2)CC1] | 4 | 12.55 | 14 |

TABLE 1-continued
| Representative Compounds | | | |
|---|---|---|---|
| STRUCTURE | COMPOUND NUMBER | LCMS RETENTION TIME (min) | PURITY METHOD |
| 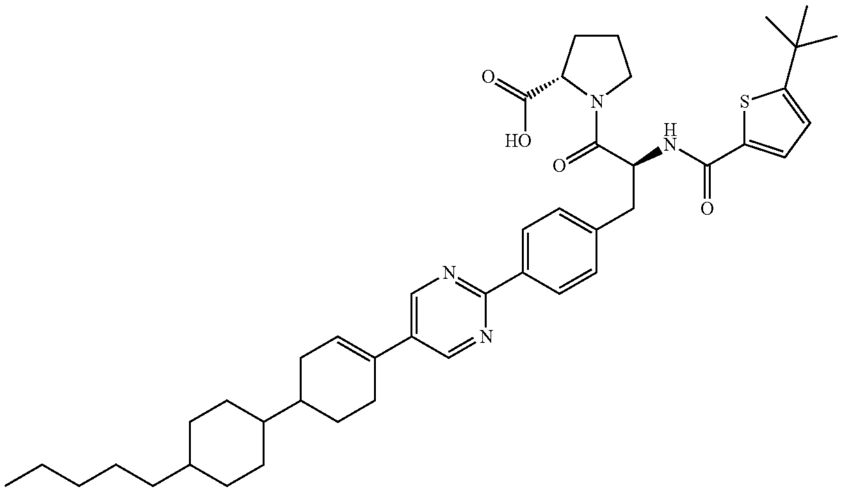 [SMILES: CCCCCC1CCC(C2CC=C(c3cnc(-c4ccc(C[C@H](NC(=O)c5ccc(C(C)(C)C)s5)C(=O)N5CCC[C@H]5C(=O)O)cc4)nc3)CC2)CC1] | 5 | 12.98 | 14 |
| 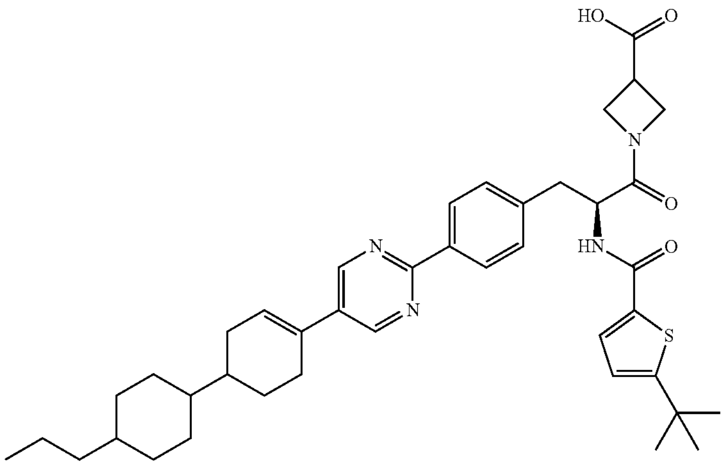 [SMILES: CCCC1CCC(C2CC=C(c3cnc(-c4ccc(C[C@H](NC(=O)c5ccc(C(C)(C)C)s5)C(=O)N5CC(C(=O)O)C5)cc4)nc3)CC2)CC1] | 6 | 11.38 | 14 |

TABLE 1-continued
| Representative Compounds | | | |
|---|---|---|---|
| STRUCTURE | COMPOUND NUMBER | LCMS RETENTION TIME (min) | PURITY METHOD |
| 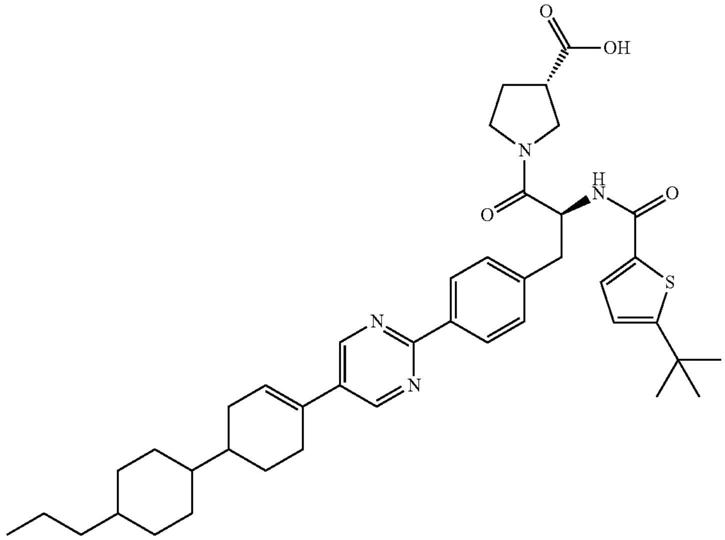 [SMILES: CCCC1CCC(C2CC=C(c3cnc(-c4ccc(C[C@H](NC(=O)c5ccc(C(C)(C)C)s5)C(=O)N5CC[C@H](C(=O)O)C5)cc4)nc3)CC2)CC1] | 7 | 11.84 | 14 |
| 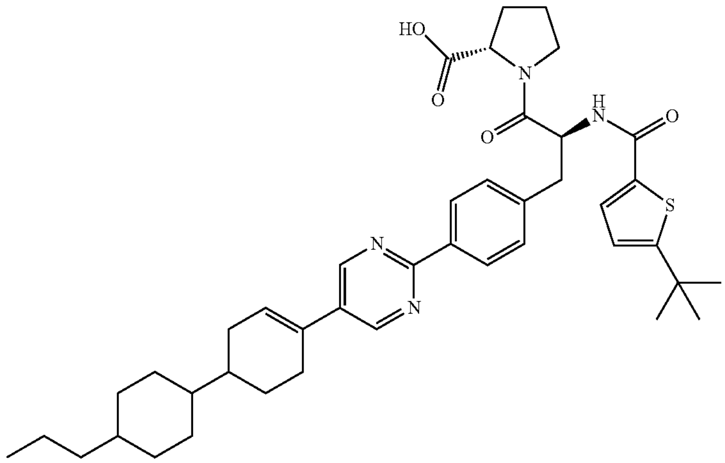 [SMILES: CCCC1CCC(C2CC=C(c3cnc(-c4ccc(C[C@H](NC(=O)c5ccc(C(C)(C)C)s5)C(=O)N5CCC[C@H]5C(=O)O)cc4)nc3)CC2)CC1] | 8 | 11.80 | 14 |
| 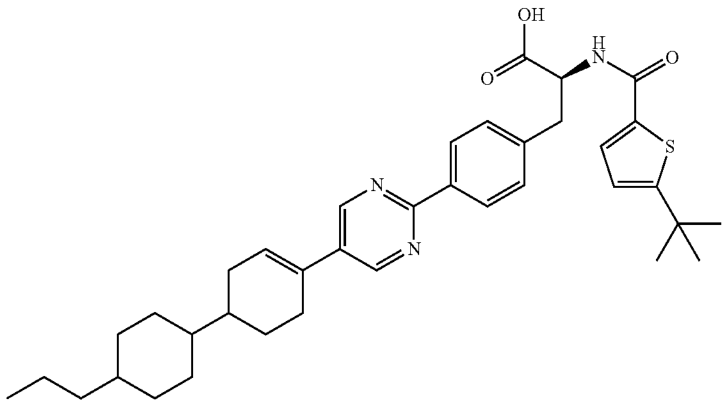 [SMILES: CCCC1CCC(C2CC=C(c3cnc(-c4ccc(C[C@H](NC(=O)c5ccc(C(C)(C)C)s5)C(=O)O)cc4)nc3)CC2)CC1] | 9 | 11.57 | 14 |

TABLE 1-continued
| Representative Compounds | | | |
|---|---|---|---|
| STRUCTURE | COMPOUND NUMBER | LCMS RETENTION TIME (min) | PURITY METHOD |
| 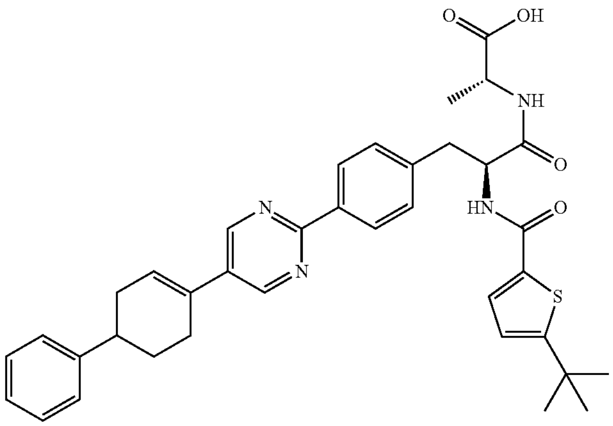 [SMILES: C[C@@H](NC(=O)[C@H](Cc1ccc(-c2ncc(C3=CCC(c4ccccc4)CC3)cn2)cc1)NC(=O)c1ccc(C(C)(C)C)s1)C(=O)O] | 10 | 8.36 | 14 |
| 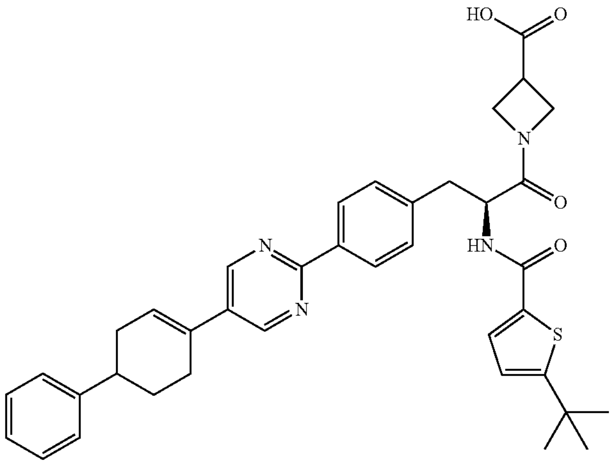 [SMILES: CC(C)(C)c1ccc(C(=O)N[C@@H](Cc2ccc(-c3ncc(C4=CCC(c5ccccc5)CC4)cn3)cc2)C(=O)N2CC(C(=O)O)C2)s1] | 11 | 8.20 | 14 |
| 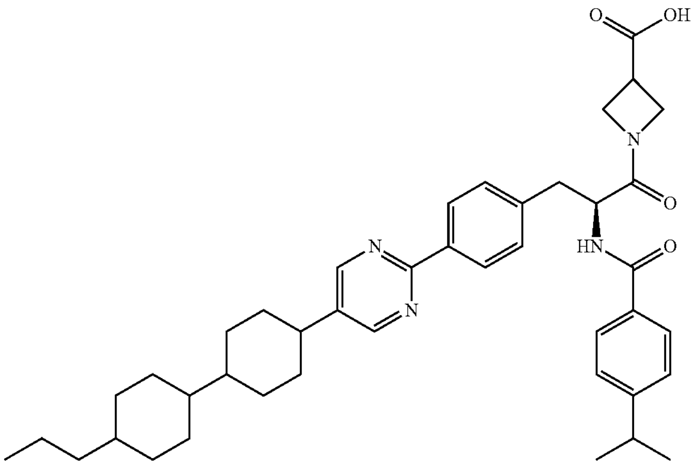 [SMILES: CCCC1CCC(C2CCC(c3cnc(-c4ccc(C[C@H](NC(=O)c5ccc(C(C)C)cc5)C(=O)N5CC(C(=O)O)C5)cc4)nc3)CC2)CC1] | 12 | 11.18 | 14 |

TABLE 1-continued
| Representative Compounds | | | |
|---|---|---|---|
| STRUCTURE | COMPOUND NUMBER | LCMS RETENTION TIME (min) | PURITY METHOD |
| 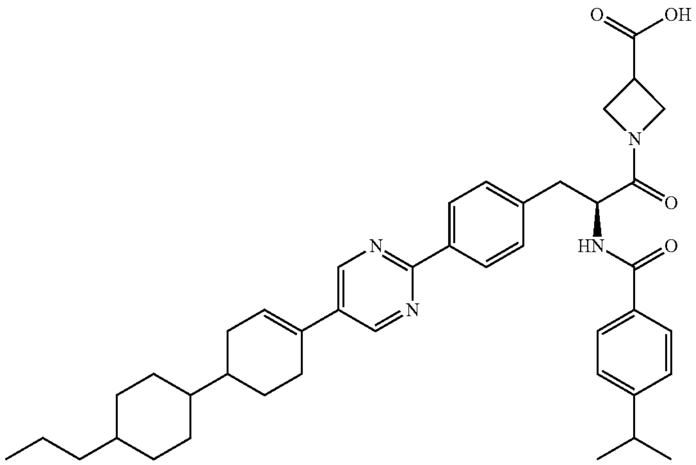 [SMILES: CCCC1CCC(C2CC=C(c3cnc(-c4ccc(C[C@H](NC(=O)c5ccc(C(C)C)cc5)C(=O)N5CC(C(=O)O)C5)cc4)nc3)CC2)CC1] | 13 | 11.36 | 14 |
| 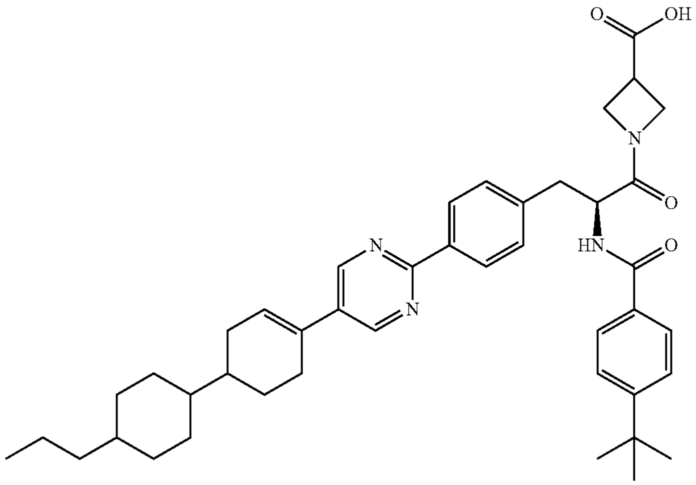 [SMILES: CCCC1CCC(C2CC=C(c3cnc(-c4ccc(C[C@H](NC(=O)c5ccc(C(C)(C)C)cc5)C(=O)N5CC(C(=O)O)C5)cc4)nc3)CC2)CC1] | 14 | 11.54 | 14 |
| 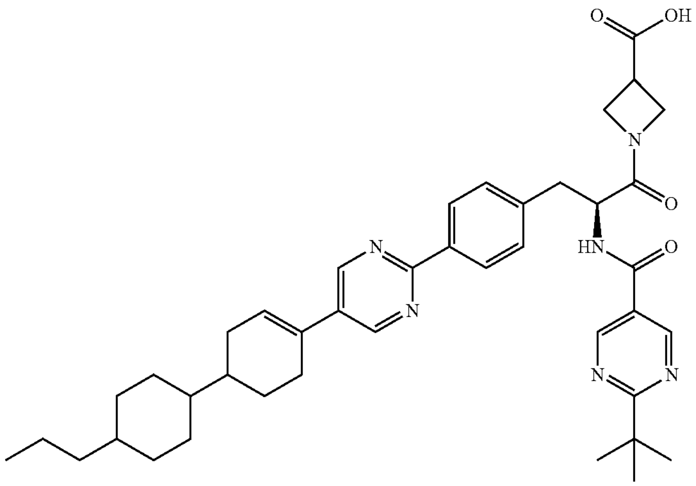 [SMILES: CCCC1CCC(C2CC=C(c3cnc(-c4ccc(C[C@H](NC(=O)c5cnc(C(C)(C)C)nc5)C(=O)N5CC(C(=O)O)C5)cc4)nc3)CC2)CC1] | 15 | 10.83 | 14 |

TABLE 1-continued
| Representative Compounds | | | |
|---|---|---|---|
| STRUCTURE | COMPOUND NUMBER | LCMS RETENTION TIME (min) | PURITY METHOD |
| 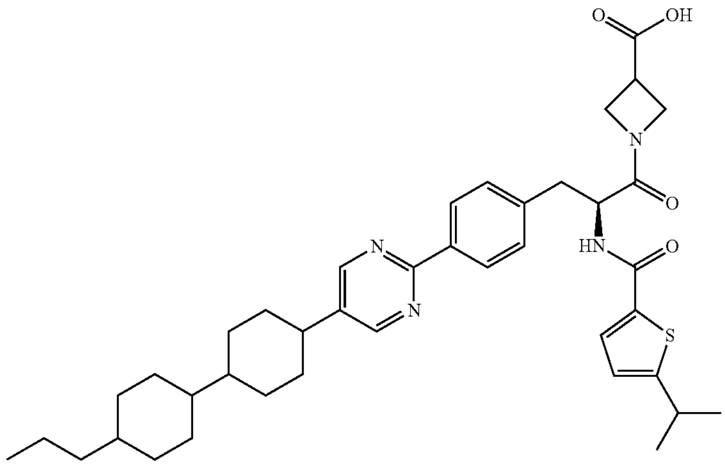 [SMILES: CCCC1CCC(C2CCC(c3cnc(-c4ccc(C[C@H](NC(=O)c5ccc(C(C)C)s5)C(=O)N5CC(C(=O)O)C5)cc4)nc3)CC2)CC1] | 16 | 10.92 | 14 |
| 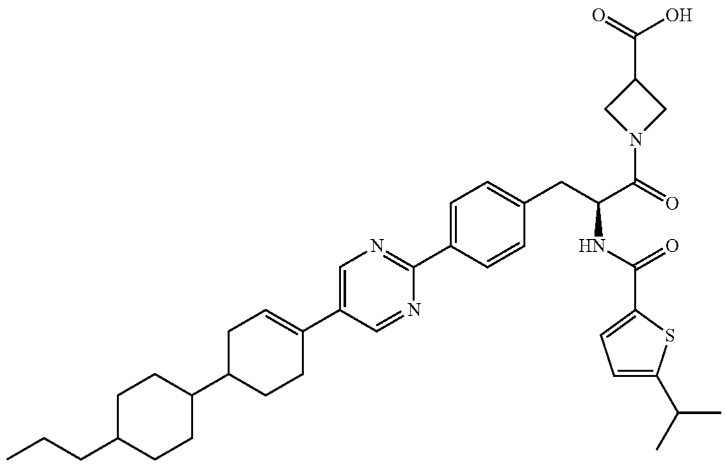 [SMILES: CCCC1CCC(C2CC=C(c3cnc(-c4ccc(C[C@H](NC(=O)c5ccc(C(C)C)s5)C(=O)N5CC(C(=O)O)C5)cc4)nc3)CC2)CC1] | 17 | 11.16 | 14 |
| 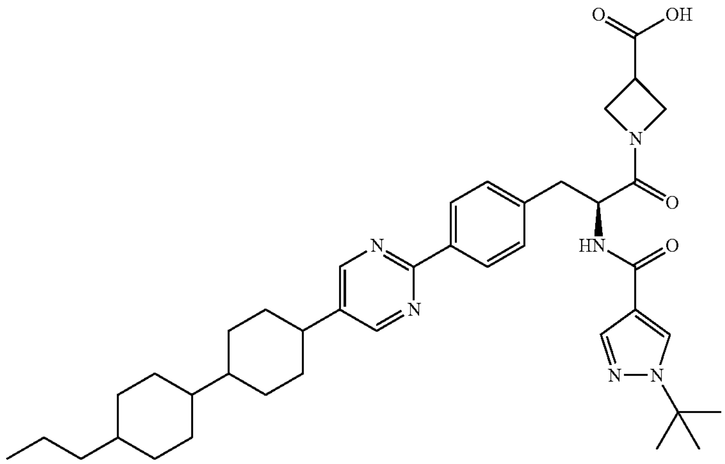 [SMILES: CCCC1CCC(C2CCC(c3cnc(-c4ccc(C[C@H](NC(=O)c5cnn(C(C)(C)C)c5)C(=O)N5CC(C(=O)O)C5)cc4)nc3)CC2)CC1] | 18 | 9.85 | 14 |

TABLE 1-continued
| Representative Compounds | | | |
|---|---|---|---|
| STRUCTURE | COMPOUND NUMBER | LCMS RETENTION TIME (min) | PURITY METHOD |
| 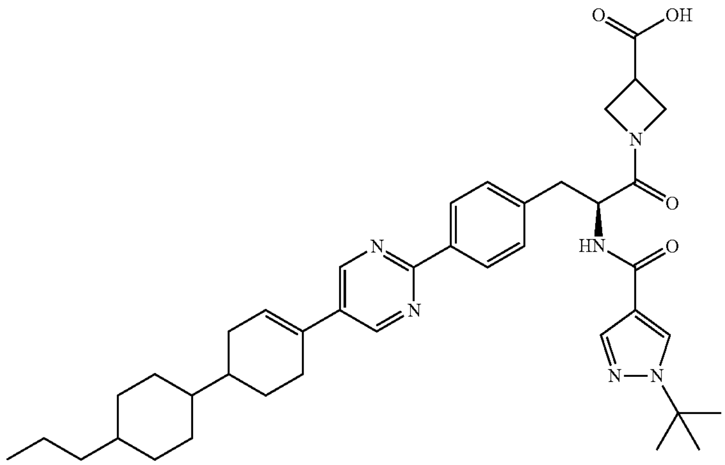 [SMILES: CCCC1CCC(C2CC=C(c3cnc(-c4ccc(C[C@H](NC(=O)c5cnn(C(C)(C)C)c5)C(=O)N5CC(C(=O)O)C5)cc4)nc3)CC2)CC1] | 19 | 10.03 | 14 |
| 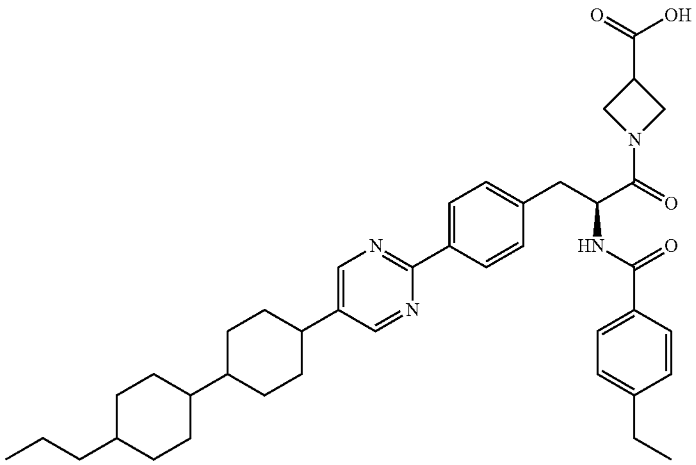 [SMILES: CCCC1CCC(C2CCC(c3cnc(-c4ccc(C[C@H](NC(=O)c5ccc(CC)cc5)C(=O)N5CC(C(=O)O)C5)cc4)nc3)CC2)CC1] | 20 | 10.65 | 14 |
| 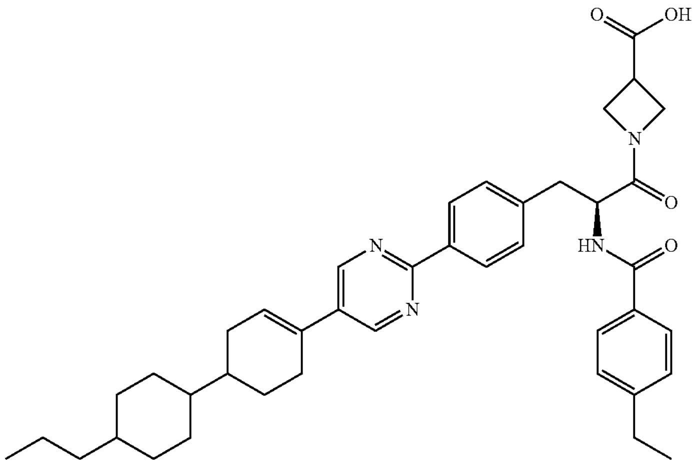 [SMILES: CCCC1CCC(C2CC=C(c3cnc(-c4ccc(C[C@H](NC(=O)c5ccc(CC)cc5)C(=O)N5CC(C(=O)O)C5)cc4)nc3)CC2)CC1] | 21 | 10.80 | 14 |

TABLE 1-continued
| Representative Compounds | | | |
|---|---|---|---|
| STRUCTURE | COMPOUND NUMBER | LCMS RETENTION TIME (min) | PURITY METHOD |
| 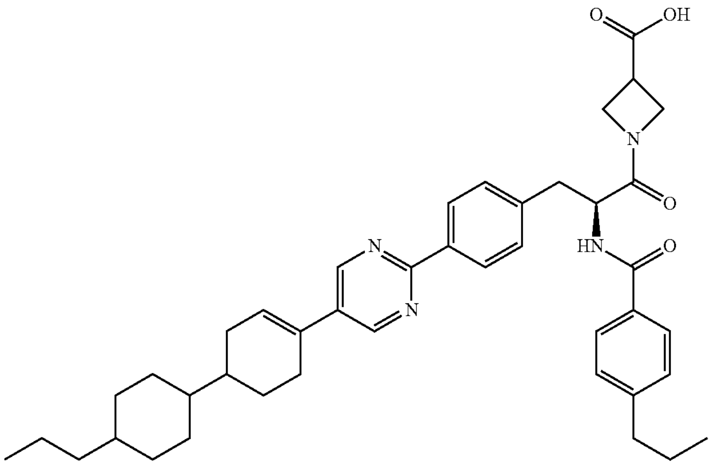 [SMILES: CCCc1ccc(C(=O)N[C@@H](Cc2ccc(-c3ncc(C4=CCC(C5CCC(CCC)CC5)CC4)cn3)cc2)C(=O)N2CC(C(=O)O)C2)cc1] | 22 | 11.30 | 14 |
| 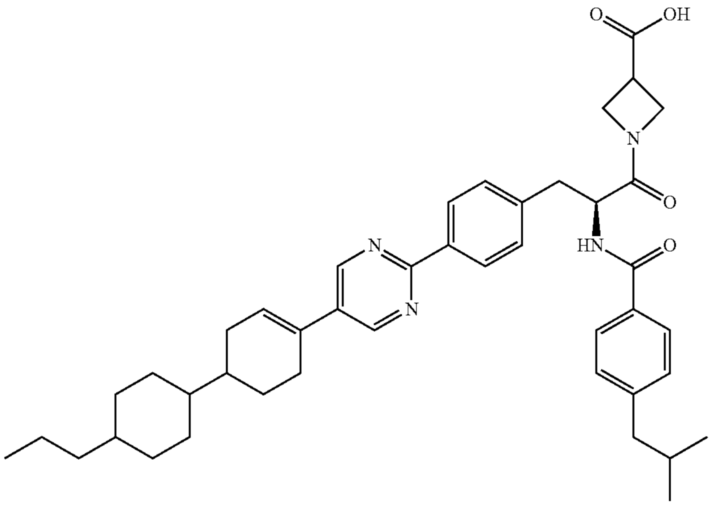 | 23 | 11.70 | 14 |
| 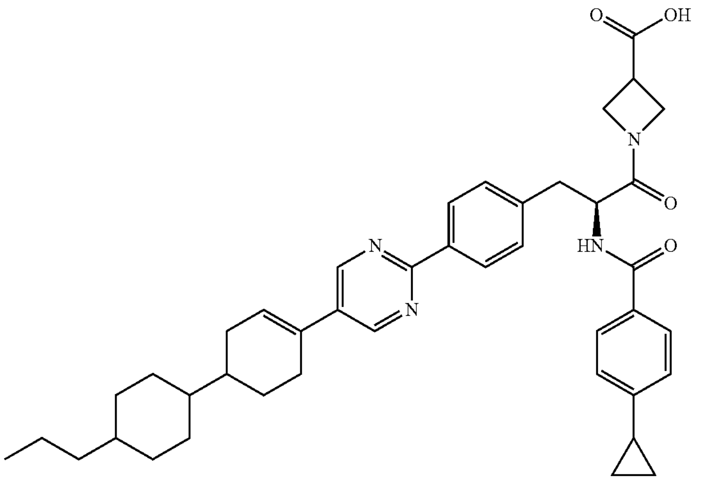 [SMILES: CCCC1CCC(C2CC=C(c3cnc(-c4ccc(C[C@H](NC(=O)c5ccc(C6CC6)cc5)C(=O)N5CC(C(=O)O)C5)cc4)nc3)CC2)CC1] | 24 | 10.90 | 14 |

TABLE 1-continued
| Representative Compounds | | | |
|---|---|---|---|
| STRUCTURE | COMPOUND NUMBER | LCMS RETENTION TIME (min) | PURITY METHOD |
| 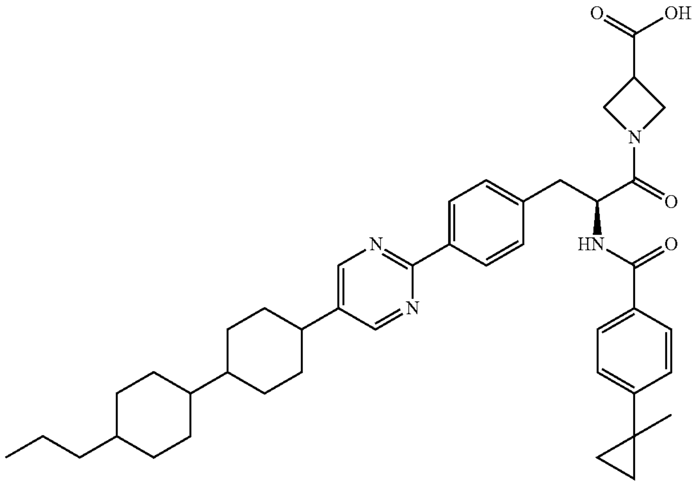 [SMILES: CCCC1CCC(C2CCC(c3cnc(-c4ccc(C[C@H](NC(=O)c5ccc(C6(C)CC6)cc5)C(=O)N5CC(C(=O)O)C5)cc4)nc3)CC2)CC1] | 25 | 11.10 | 14 |
| 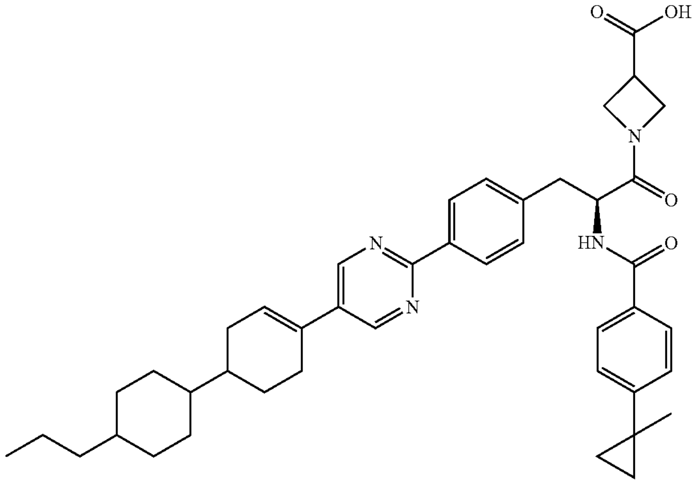 [SMILES: CCCC1CCC(C2CC=C(c3cnc(-c4ccc(C[C@H](NC(=O)c5ccc(C6(C)CC6)cc5)C(=O)N5CC(C(=O)O)C5)cc4)nc3)CC2)CC1] | 26 | 11.30 | 14 |
| 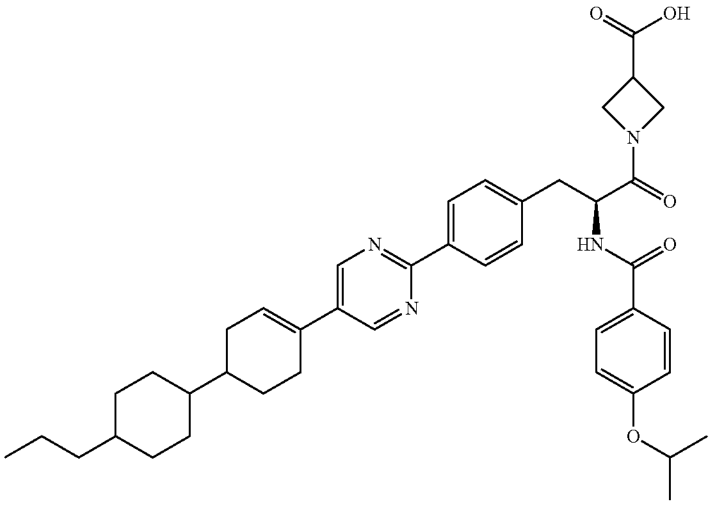 [SMILES: CCCC1CCC(C2CC=C(c3cnc(-c4ccc(C[C@H](NC(=O)c5ccc(OC(C)C)cc5)C(=O)N5CC(C(=O)O)C5)cc4)nc3)CC2)CC1] | 27 | 10.89 | 14 |

TABLE 1-continued
| Representative Compounds | | | |
|---|---|---|---|
| STRUCTURE | COMPOUND NUMBER | LCMS RETENTION TIME (min) | PURITY METHOD |
| 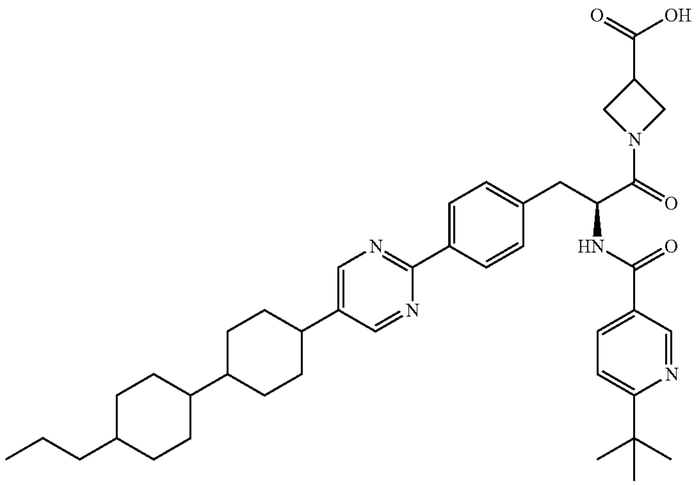 [SMILES: CCCC1CCC(C2CCC(c3cnc(-c4ccc(C[C@H](NC(=O)c5ccc(C(C)(C)C)nc5)C(=O)N5CC(C(=O)O)C5)cc4)nc3)CC2)CC1] | 28 | 10.65 | 14 |
| 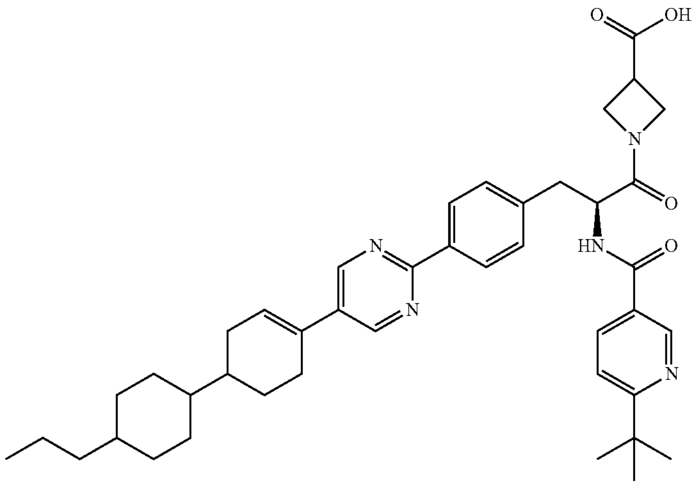 | 29 | 10.76 | 14 |
| 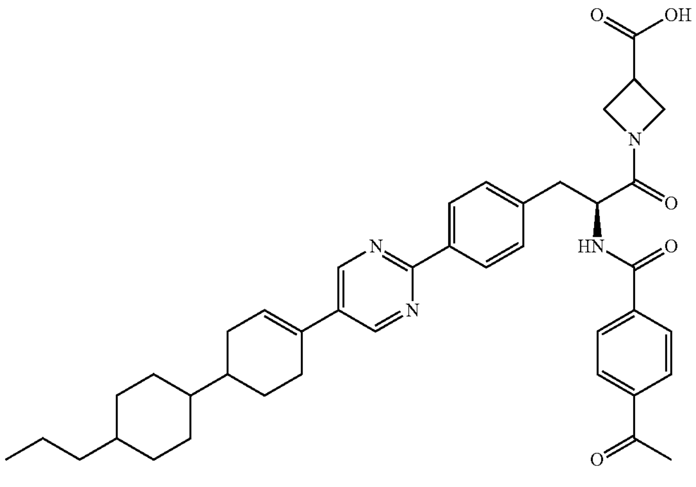 [SMILES: CCCC1CCC(C2CC=C(c3cnc(-c4ccc(C[C@H](NC(=O)c5ccc(C(C)=O)cc5)C(=O)N5CC(C(=O)O)C5)cc4)nc3)CC2)CC1] | 30 | 10.07 | 14 |

TABLE 1-continued
Representative Compounds
| STRUCTURE | COMPOUND NUMBER | LCMS RETENTION TIME (min) | PURITY METHOD |
|---|---|---|---|
| 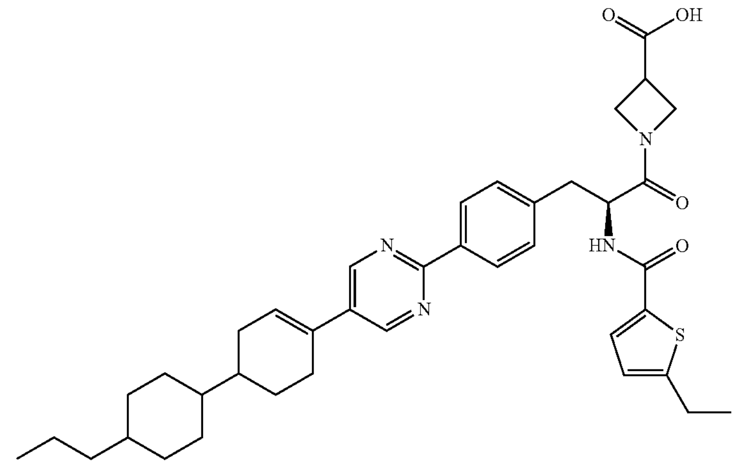 [SMILES: CCCC1CCC(C2CC=C(c3cnc(-c4ccc(C[C@H](NC(=O)c5ccc(CC)s5)C(=O)N5CC(C(=O)O)C5)cc4)nc3)CC2)CC1] | 31 | 10.62 | 14 |
| 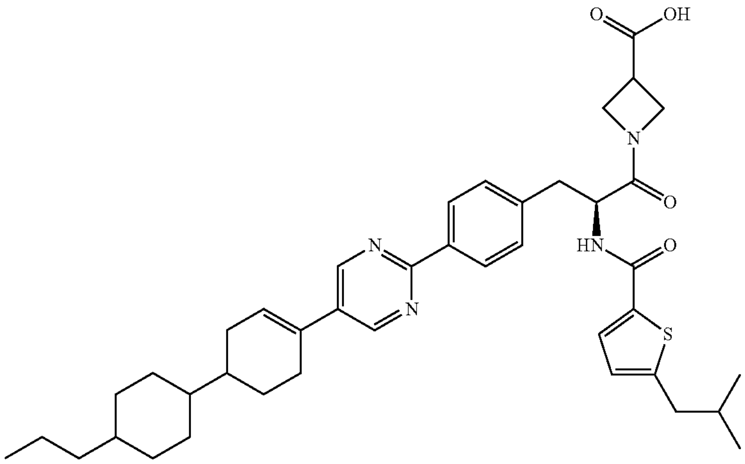 [SMILES: CCCC1CCC(C2CC=C(c3cnc(-c4ccc(C[C@H](NC(=O)c5ccc(CC(C)C)s5)C(=O)N5CC(C(=O)O)C5)cc4)nc3)CC2)CC1] | 32 | 11.76 | 14 |
| 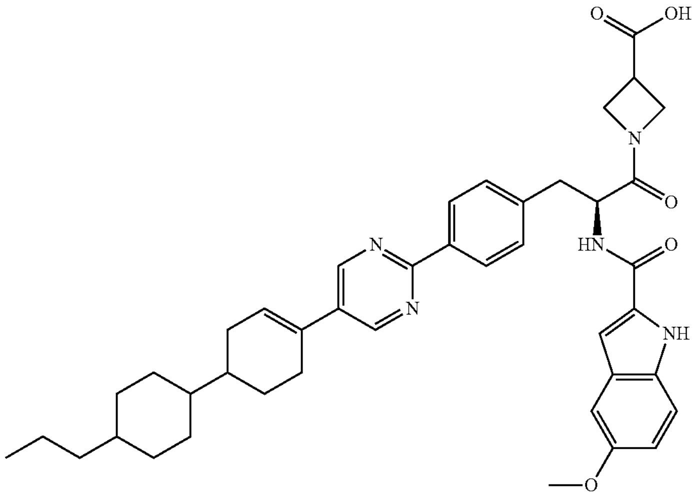 [SMILES: CCCC1CCC(C2CC=C(c3cnc(-c4ccc(C[C@H](NC(=O)c5cc6cc(OC)ccc6[nH]5)C(=O)N5CC(C(=O)O)C5)cc4)nc3)CC2)CC1] | 33 | 10.61 | 14 |

TABLE 1-continued
| Representative Compounds | | | |
|---|---|---|---|
| STRUCTURE | COMPOUND NUMBER | LCMS RETENTION TIME (min) | PURITY METHOD |
| 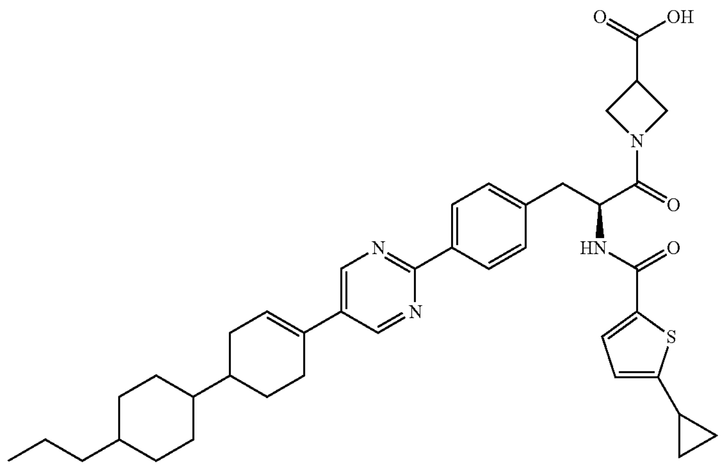 [SMILES: CCCC1CCC(C2CC=C(c3cnc(-c4ccc(C[C@H](NC(=O)c5ccc(C6CC6)s5)C(=O)N5CC(C(=O)O)C5)cc4)nc3)CC2)CC1] | 34 | 10.60 | 14 |
| 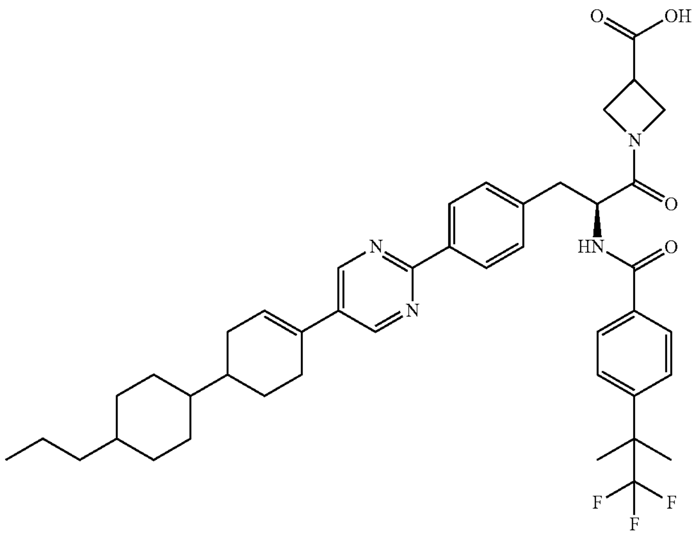 [SMILES: CCCC1CCC(C2CC=C(c3cnc(-c4ccc(C[C@H](NC(=O)c5ccc(C(C)(C)C(F)(F)F)cc5)C(=O)N5CC(C(=O)O)C5)cc4)nc3)CC2)CC1] | 35 | 11.14 | 14 |
| 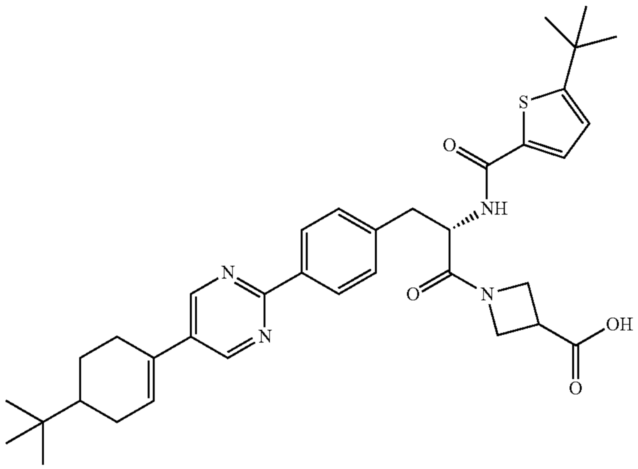 [SMILES: CC(C)(C)c1ccc(C(=O)N[C@@H](Cc2ccc(-c3ncc(C4=CCC(C(C)(C)C)CC4)cn3)cc2)C(=O)N2CC(C(=O)O)C2)s1] | 36 | 9.61 | 10 |

TABLE 1-continued
| Representative Compounds | | | |
|---|---|---|---|
| STRUCTURE | COMPOUND NUMBER | LCMS RETENTION TIME (min) | PURITY METHOD |
| 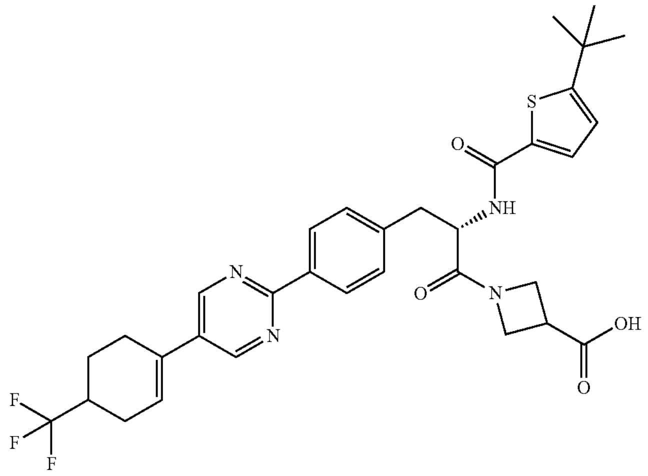 [SMILES: CC(C)(C)c1ccc(C(=O)N[C@@H](Cc2ccc(-c3ncc(C4=CCC(C(F)(F)F)CC4)cn3)cc2)C(=O)N2CC(C(=O)O)C2)s1] | 37 | 7.90 | 10 |
| 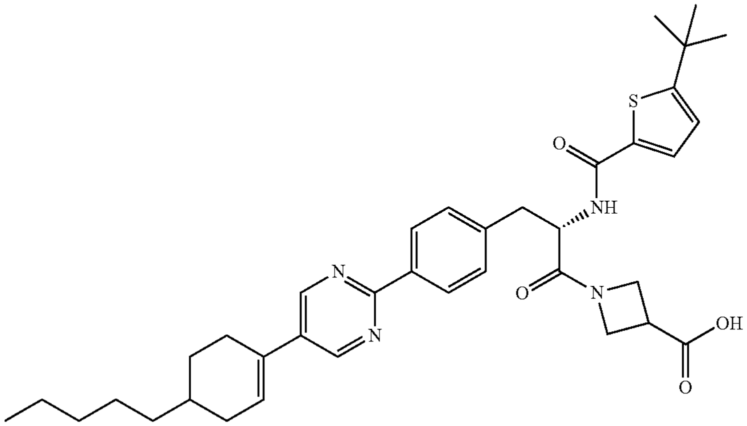 [SMILES: CCCCCC1CC=C(c2cnc(-c3ccc(C[C@H](NC(=O)c4ccc(C(C)(C)C)s4)C(=O)N4CC(C(=O)O)C4)cc3)nc2)CC1] | 38 | 10.40 | 10 |
| 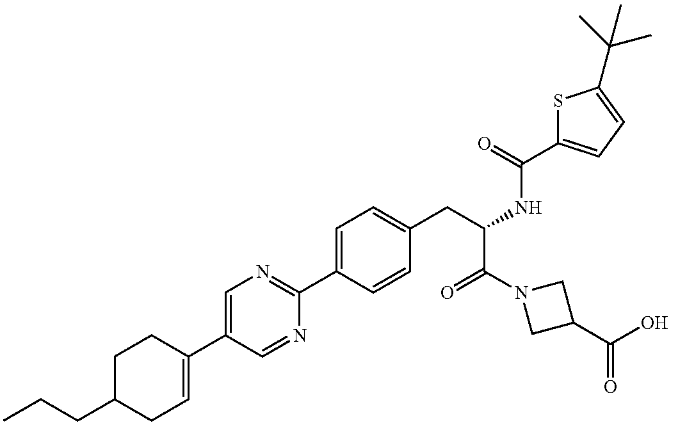 [SMILES: CCCC1CC=C(c2cnc(-c3ccc(C[C@H](NC(=O)c4ccc(C(C)(C)C)s4)C(=O)N4CC(C(=O)O)C4)cc3)nc2)CC1] | 39 | 9.30 | 10 |

TABLE 1-continued
| Representative Compounds | | | |
|---|---|---|---|
| STRUCTURE | COMPOUND NUMBER | LCMS RETENTION TIME (min) | PURITY METHOD |
| 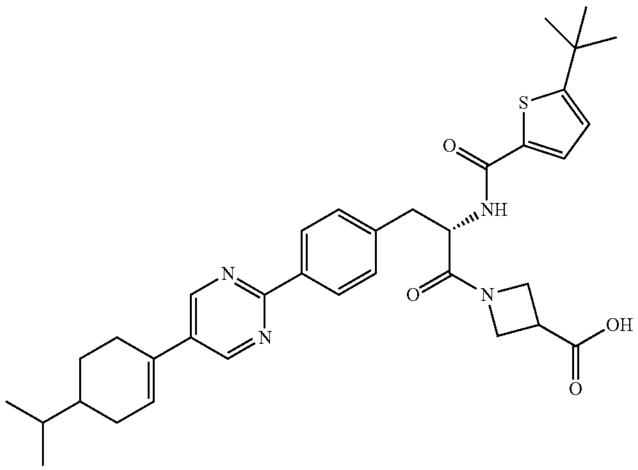 [SMILES: CC(C)C1CC=C(c2cnc(-c3ccc(C[C@H](NC(=O)c4ccc(C(C)(C)C)s4)C(=O)N4CC(C(=O)O)C4)cc3)nc2)CC1] | 40 | 9.20 | 10 |
| 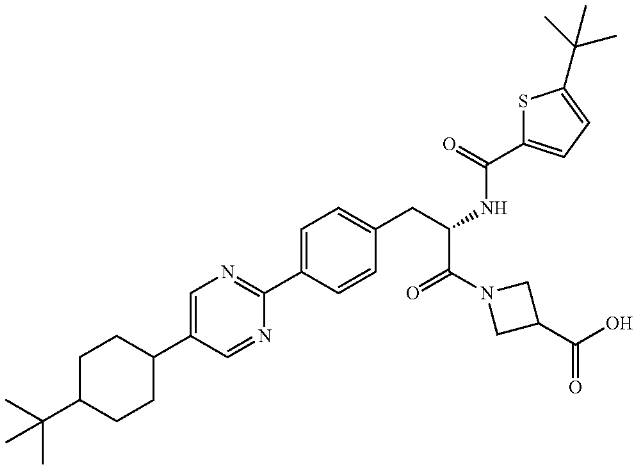 [SMILES: CC(C)(C)c1ccc(C(=O)N[C@@H](Cc2ccc(-c3ncc(C4CCC(C(C)(C)C)CC4)cn3)cc2)C(=O)N2CC(C(=O)O)C2)s1] | 41 | 9.35 | 10 |
| 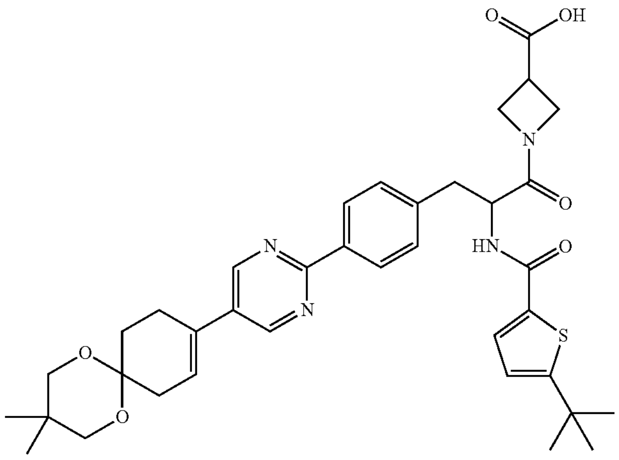 [SMILES: CC1(C)COC2(CC=C(c3cnc(-c4ccc(CC(NC(=O)c5ccc(C(C)(C)C)s5)C(=O)N5CC(C(=O)O)C5)cc4)nc3)CC2)OC1] | 43 | 7.44 | 10 |

TABLE 1-continued
| Representative Compounds | | | |
|---|---|---|---|
| STRUCTURE | COM-POUND NUM-BER | LCMS RETEN-TION TIME (min) | PURITY METH-OD |
| 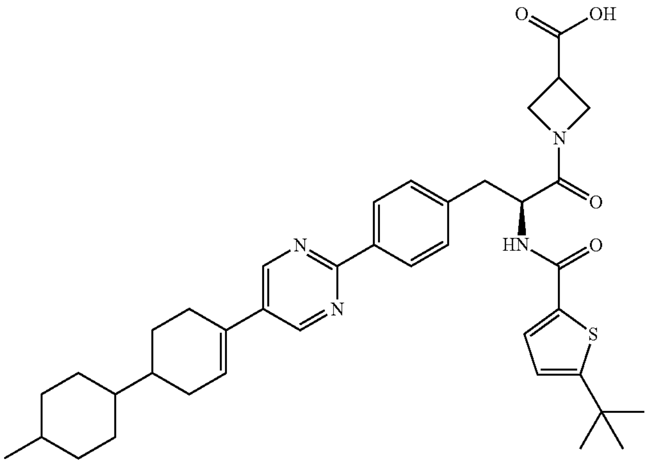 [SMILES: CC1CCC(C2CC=C(c3cnc(-c4ccc(C[C@H](NC(=O)c5ccc(C(C)(C)C)s5)C(=O)N5CC(C(=O)O)C5)cc4)nc3)CC2)CC1] | 44 | 11.03 | 10 |
| 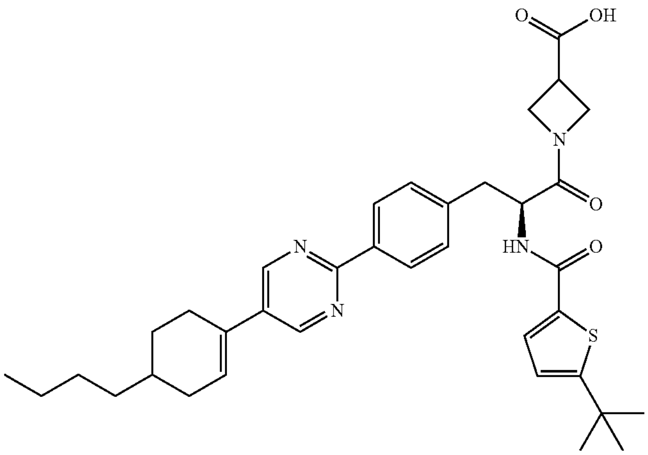 [SMILES: CCCCC1CC=C(c2cnc(-c3ccc(C[C@H](NC(=O)c4ccc(C(C)(C)C)s4)C(=O)N4CC(C(=O)O)C4)cc3)nc2)CC1] | 45 | 9.95 | 10 |
| 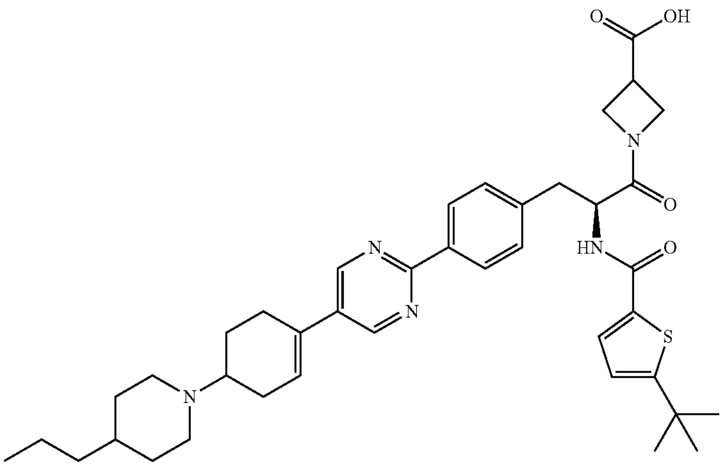 [SMILES: CCCC1CCN(C2CC=C(c3cnc(-c4ccc(C[C@H](NC(=O)c5ccc(C(C)(C)C)s5)C(=O)N5CC(C(=O)O)C5)cc4)nc3)CC2)CC1] | 46 | 4.93 | 10 |

TABLE 1-continued
| Representative Compounds | | | |
|---|---|---|---|
| STRUCTURE | COMPOUND NUMBER | LCMS RETENTION TIME (min) | PURITY METHOD |
| 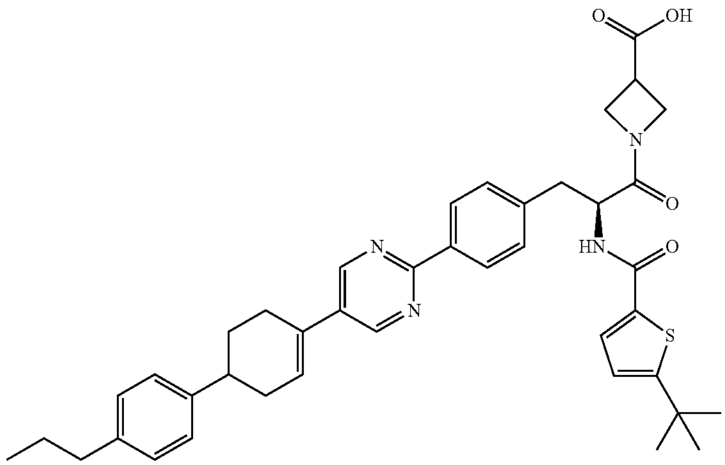 [SMILES: CCCc1ccc(C2CC=C(c3cnc(-c4ccc(C[C@H](NC(=O)c5ccc(C(C)(C)C)s5)C(=O)N5CC(C(=O)O)C5)cc4)nc3)CC2)cc1] | 47 | 10.15 | 10 |
| 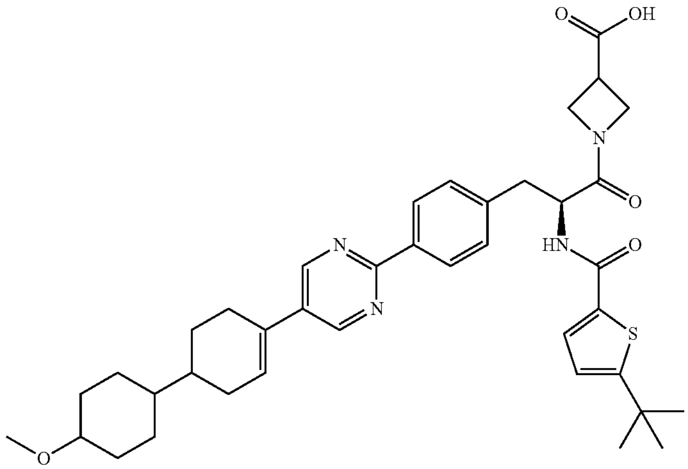 [SMILES: COC1CCC(C2CC=C(c3cnc(-c4ccc(C[C@H](NC(=O)c5ccc(C(C)(C)C)s5)C(=O)N5CC(C(=O)O)C5)cc4)nc3)CC2)CC1] | 48 | 8.72 | 10 |
| 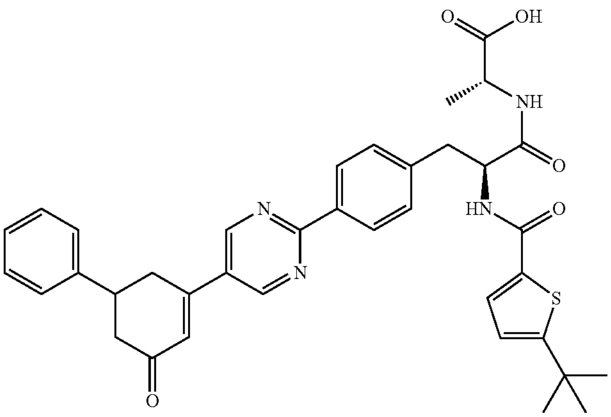 [SMILES: C[C@@H](NC(=O)[C@H](Cc1ccc(-c2ncc(C3=CC(=O)CC(c4ccccc4)C3)cn2)cc1)NC(=O)c1ccc(C(C)(C)C)s1)C(=O)O] | 49 | 7.35 | 10 |

TABLE 1-continued
| Representative Compounds | | | |
|---|---|---|---|
| STRUCTURE | COMPOUND NUMBER | LCMS RETENTION TIME (min) | PURITY METHOD |
| 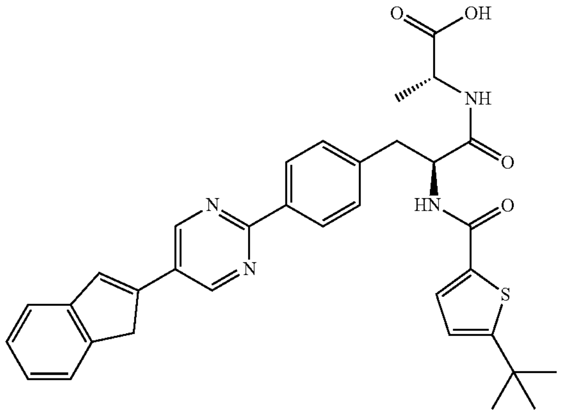 [SMILES: C[C@@H](NC(=O)[C@H](Cc1ccc(-c2ncc(C3=Cc4ccccc4C3)cn2)cc1)NC(=O)c1ccc(C(C)(C)C)s1)C(=O)O] | 50 | 8.08 | 10 |
| 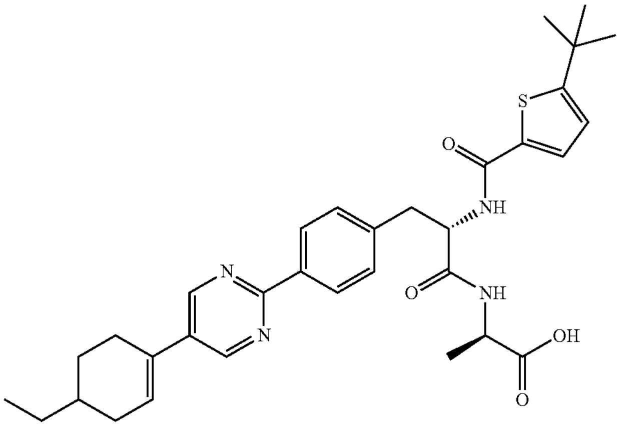 [SMILES: CCC1CC=C(c2cnc(-c3ccc(C[C@H](NC(=O)c4ccc(C(C)(C)C)s4)C(=O)N[C@H](C)C(=O)O)cc3)nc2)CC1] | 51 | 9.04 | 10 |
| 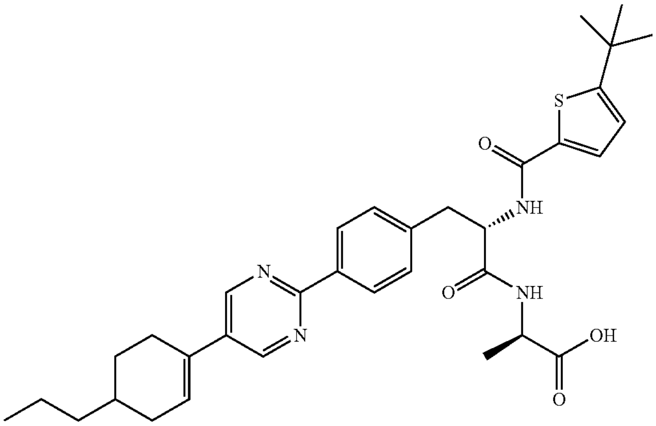 [SMILES: CCCC1CC=C(c2cnc(-c3ccc(C[C@H](NC(=O)c4ccc(C(C)(C)C)s4)C(=O)N[C@H](C)C(=O)O)cc3)nc2)CC1] | 52 | 9.59 | 10 |

TABLE 1-continued
| Representative Compounds | | | |
|---|---|---|---|
| STRUCTURE | COMPOUND NUMBER | LCMS RETENTION TIME (min) | PURITY METHOD |
| 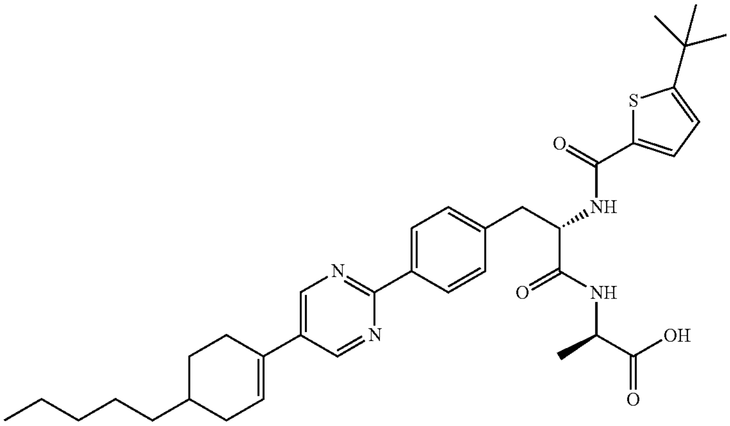 [SMILES: CCCCCC1CC=C(c2cnc(-c3ccc(C[C@H](NC(=O)c4ccc(C(C)(C)C)s4)C(=O)N[C@H](C)C(=O)O)cc3)nc2)CC1] | 53 | 10.60 | 10 |
| 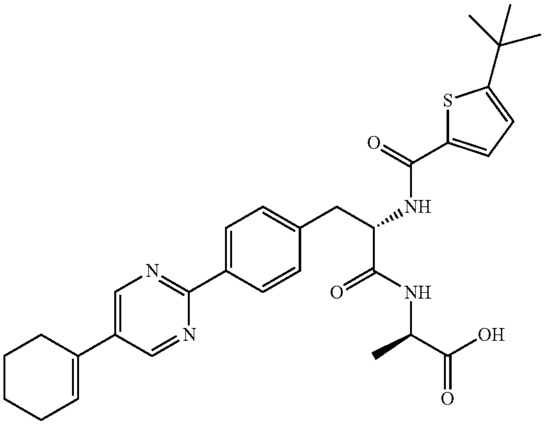 [SMILES: C[C@@H](NC(=O)[C@H](Cc1ccc(-c2ncc(C3=CCCCC3)cn2)cc1)NC(=O)c1ccc(C(C)(C)C)s1)C(=O)O] | 54 | 7.98 | 10 |
| 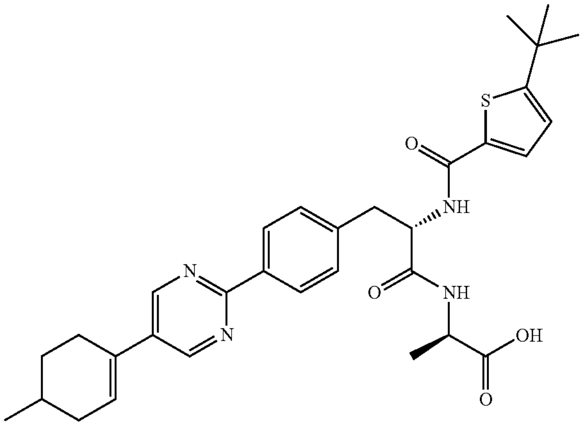 [SMILES: CC1CC=C(c2cnc(-c3ccc(C[C@H](NC(=O)c4ccc(C(C)(C)C)s4)C(=O)N[C@H](C)C(=O)O)cc3)nc2)CC1] | 55 | 8.50 | 10 |

TABLE 1-continued
| Representative Compounds | | | |
|---|---|---|---|
| STRUCTURE | COMPOUND NUMBER | LCMS RETENTION TIME (min) | PURITY METHOD |
| 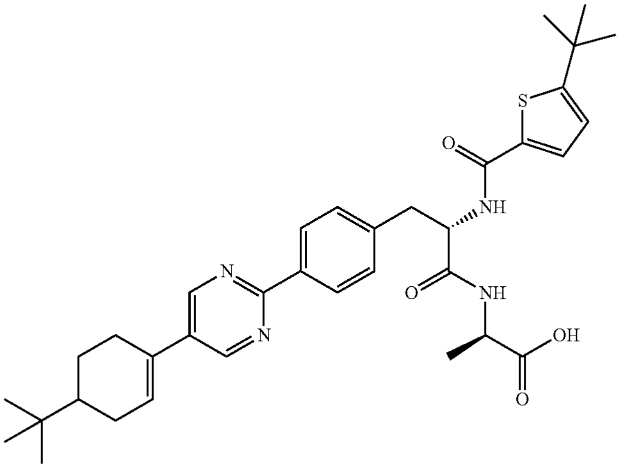 [SMILES: C[C@@H](NC(=O)[C@H](Cc1ccc(-c2ncc(C3=CCC(C(C)(C)C)CC3)cn2)cc1)NC(=O)c1ccc(C(C)(C)C)s1)C(=O)O] | 56 | 9.79 | 10 |
| 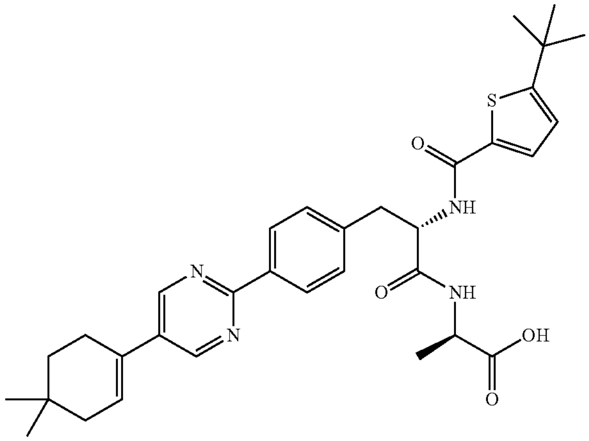 [SMILES: C[C@@H](NC(=O)[C@H](Cc1ccc(-c2ncc(C3=CCC(C)(C)CC3)cn2)cc1)NC(=O)c1ccc(C(C)(C)C)s1)C(=O)O] | 57 | 8.85 | 10 |
| 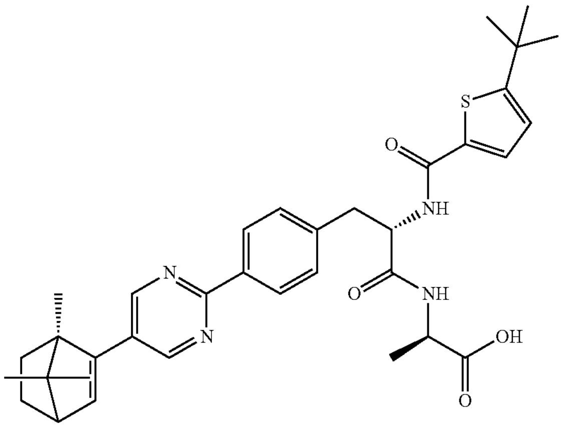 [SMILES: C[C@@H](NC(=O)[C@H](Cc1ccc(-c2ncc(C3=CC4CC[C@]3(C)C4(C)C)cn2)cc1)NC(=O)c1ccc(C(C)(C)C)s1)C(=O)O] | 58 | 9.32 | 10 |

TABLE 1-continued
| Representative Compounds | | | |
|---|---|---|---|
| STRUCTURE | COMPOUND NUMBER | LCMS RETENTION TIME (min) | PURITY METHOD |
| 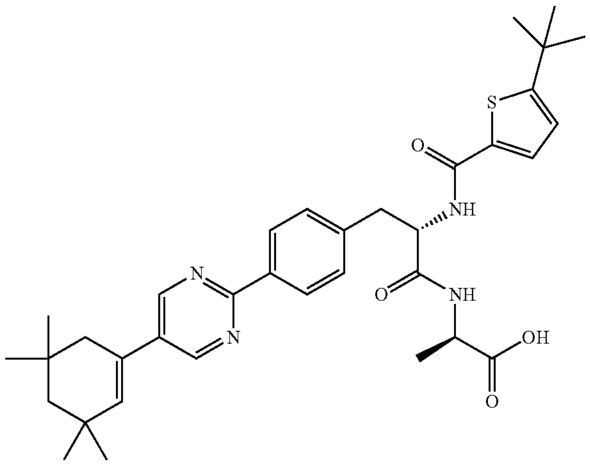 [SMILES: C[C@@H](NC(=O)[C@H](Cc1ccc(-c2ncc(C3=CC(C)(C)CC(C)(C)C3)cn2)cc1)NC(=O)c1ccc(C(C)(C)C)s1)C(=O)O] | 59 | 9.73 | 10 |
| 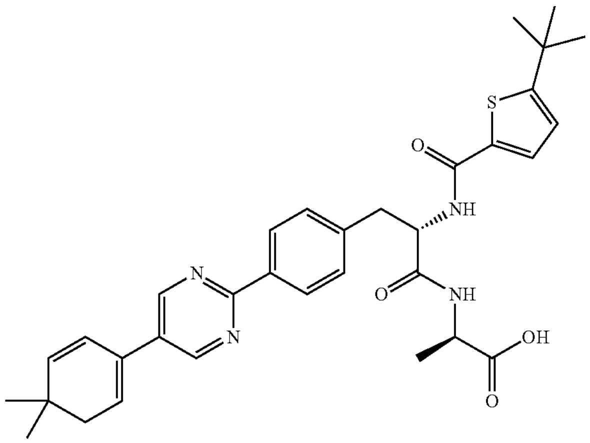 [SMILES: C[C@@H](NC(=O)[C@H](Cc1ccc(-c2ncc(C3=CCC(C)(C)C=C3)cn2)cc1)NC(=O)c1ccc(C(C)(C)C)s1)C(=O)O] | 60 | 8.58 | 10 |
| 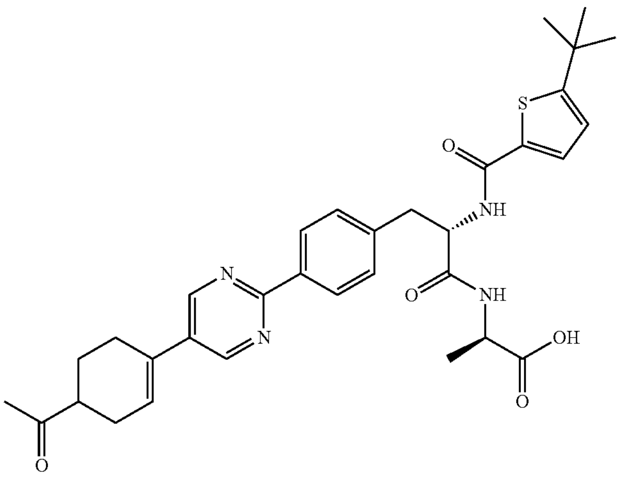 [SMILES: CC(=O)C1CC=C(c2cnc(-c3ccc(C[C@H](NC(=O)c4ccc(C(C)(C)C)s4)C(=O)N[C@H](C)C(=O)O)cc3)nc2)CC1] | 61 | 6.59 | 10 |

TABLE 1-continued
| Representative Compounds | | | |
|---|---|---|---|
| STRUCTURE | COMPOUND NUMBER | LCMS RETENTION TIME (min) | PURITY METHOD |
| 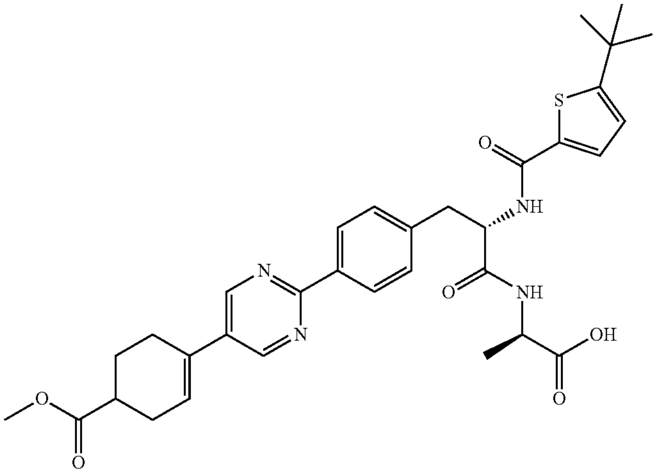 [SMILES: COC(=O)C1CC=C(c2cnc(-c3ccc(C[C@H](NC(=O)c4ccc(C(C)(C)C)s4)C(=O)N[C@H](C)C(=O)O)cc3)nc2)CC1] | 62 | 7.04 | 10 |
| 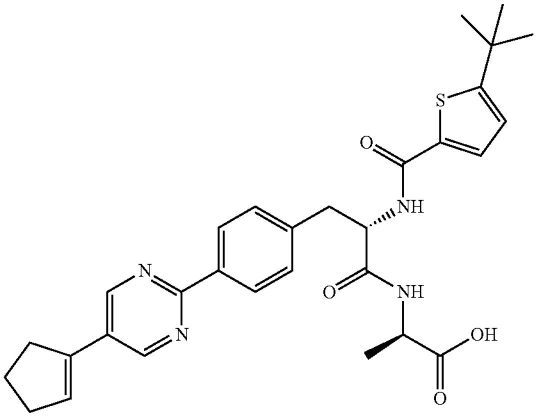 [SMILES: C[C@@H](NC(=O)[C@H](Cc1ccc(-c2ncc(C3=CCCC3)cn2)cc1)NC(=O)c1ccc(C(C)(C)C)s1)C(=O)O] | 63 | 7.65 | 10 |
| 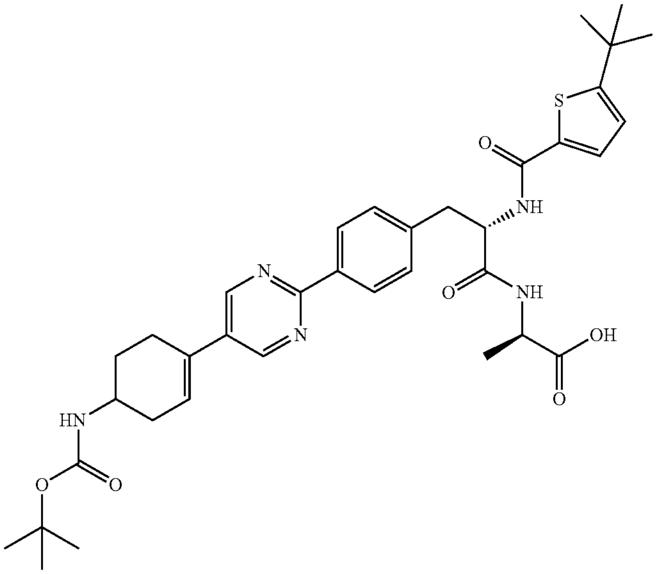 [SMILES: C[C@@H](NC(=O)[C@H](Cc1ccc(-c2ncc(C3=CCC(NC(=O)OC(C)(C)C)CC3)cn2)cc1)NC(=O)c1ccc(C(C)(C)C)s1)C(=O)O] | 64 | 7.53 | 10 |

TABLE 1-continued
| Representative Compounds | | | |
|---|---|---|---|
| STRUCTURE | COMPOUND NUMBER | LCMS RETENTION TIME (min) | PURITY METHOD |
| 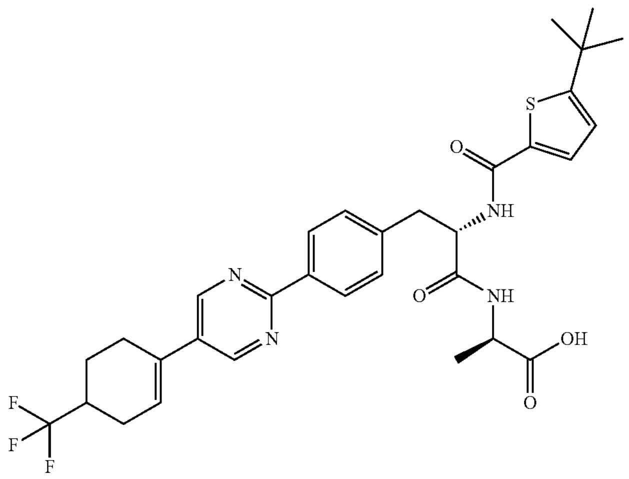 [SMILES: C[C@@H](NC(=O)[C@H](Cc1ccc(-c2ncc(C3=CCC(C(F)(F)F)CC3)cn2)cc1)NC(=O)c1ccc(C(C)(C)C)s1)C(=O)O] | 65 | 8.12 | 10 |
| 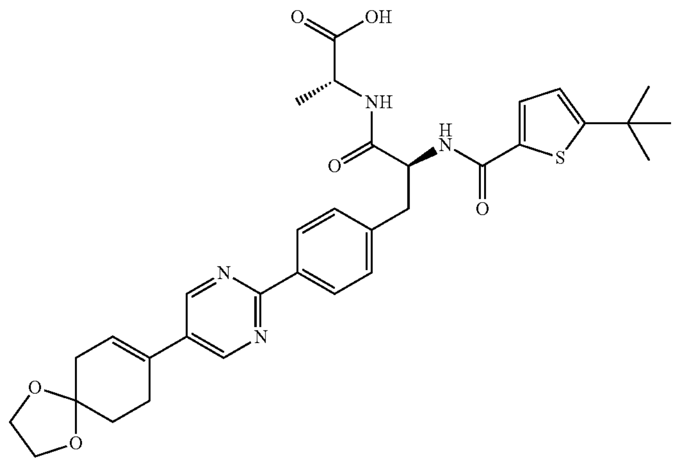 [SMILES: C[C@@H](NC(=O)[C@H](Cc1ccc(-c2ncc(C3=CCC4(CC3)OCCO4)cn2)cc1)NC(=O)c1ccc(C(C)(C)C)s1)C(=O)O] | 66 | 6.48 | 10 |
| 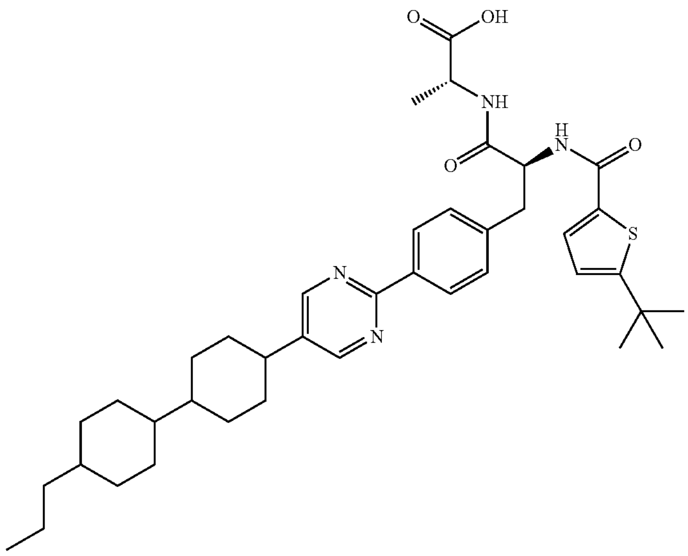 [SMILES: CCCC1CCC(C2CCC(c3cnc(-c4ccc(C[C@H](NC(=O)c5ccc(C(C)(C)C)s5)C(=O)N[C@H](C)C(=O)O)cc4)nc3)CC2)CC1] | 67 | 11.72 | 10 |

TABLE 1-continued
Representative Compounds
| STRUCTURE | COMPOUND NUMBER | LCMS RETENTION TIME (min) | PURITY METHOD |
|---|---|---|---|
| 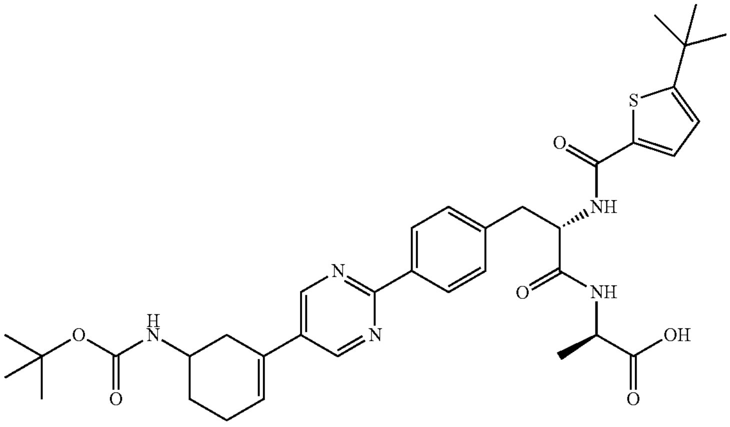 [SMILES: C[C@@H](NC(=O)[C@H](Cc1ccc(-c2ncc(C3=CCCC(NC(=O)OC(C)(C)C)C3)cn2)cc1)NC(=O)c1ccc(C(C)(C)C)s1)C(=O)O] | 69 | 7.60 | 10 |
| 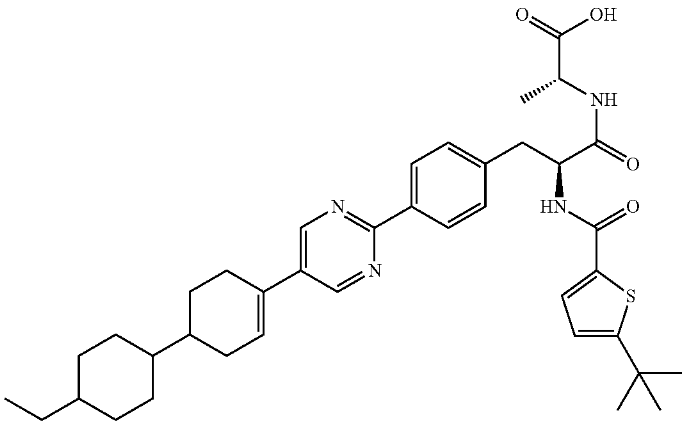 [SMILES: CCC1CCC(C2CC=C(c3cnc(-c4ccc(C[C@H](NC(=O)c5ccc(C(C)(C)C)s5)C(=O)N[C@H](C)C(=O)O)cc4)nc3)CC2)CC1] | 70 | 11.79 | 10 |
| 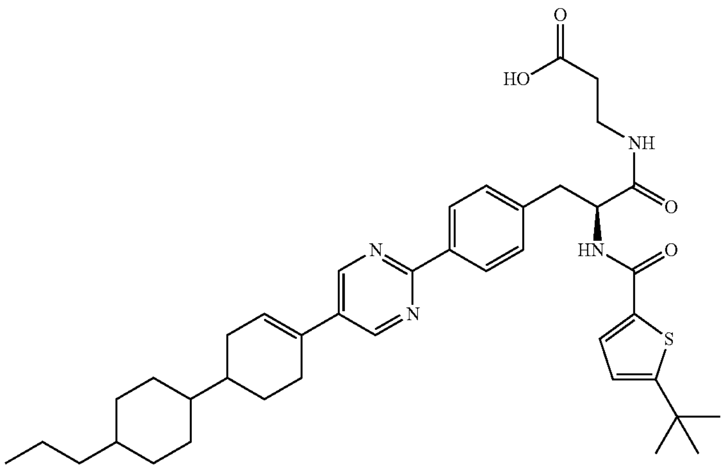 [SMILES: CCCC1CCC(C2CC=C(c3cnc(-c4ccc(C[C@H](NC(=O)c5ccc(C(C)(C)C)s5)C(=O)NCCC(=O)O)cc4)nc3)CC2)CC1] | 71 | 11.56 | 14 |

TABLE 1-continued
| Representative Compounds | | | |
|---|---|---|---|
| STRUCTURE | COMPOUND NUMBER | LCMS RETENTION TIME (min) | PURITY METHOD |
| 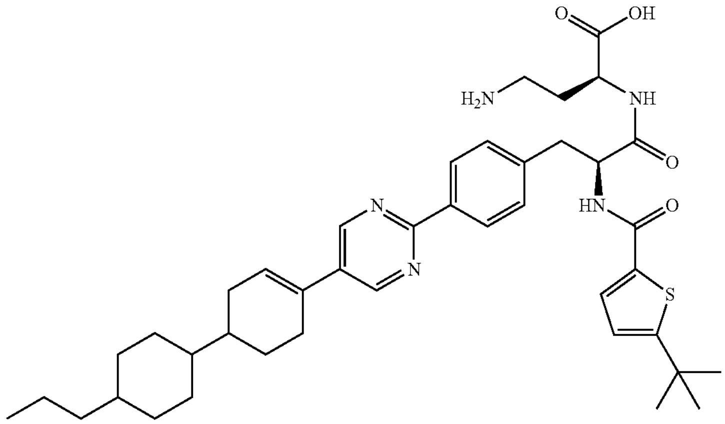 [SMILES: CCCC1CCC(C2CC=C(c3cnc(-c4ccc(C[C@H](NC(=O)c5ccc(C(C)(C)C)s5)C(=O)N[C@@H](CCN)C(=O)O)cc4)nc3)CC2)CC1] | 72 | 11.08 | 14 |
| 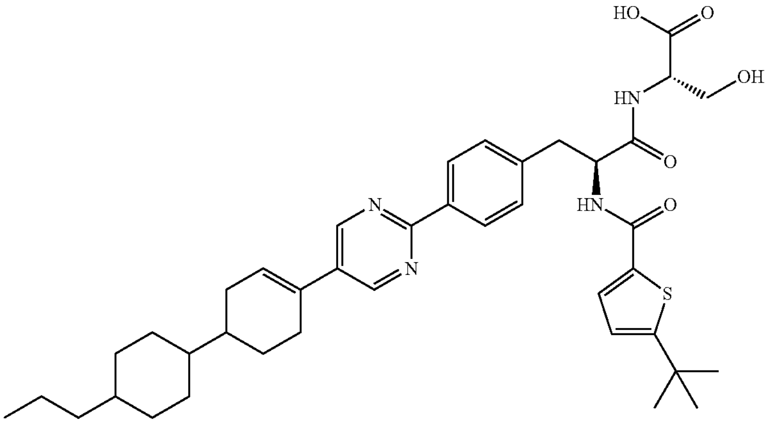 [SMILES: CCCC1CCC(C2CC=C(c3cnc(-c4ccc(C[C@H](NC(=O)c5ccc(C(C)(C)C)s5)C(=O)N[C@@H](CO)C(=O)O)cc4)nc3)CC2)CC1] | 73 | 11.08 | 14 |
| 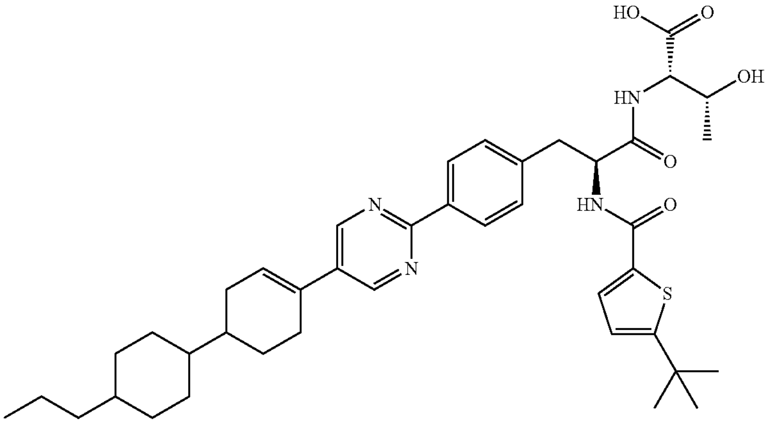 [SMILES: CCCC1CCC(C2CC=C(c3cnc(-c4ccc(C[C@H](NC(=O)c5ccc(C(C)(C)C)s5)C(=O)N[C@H](C(=O)O)[C@@H](C)O)cc4)nc3)CC2)CC1] | 74 | 11.27 | 14 |

TABLE 1-continued
| Representative Compounds | | | |
|---|---|---|---|
| STRUCTURE | COMPOUND NUMBER | LCMS RETENTION TIME (min) | PURITY METHOD |
| 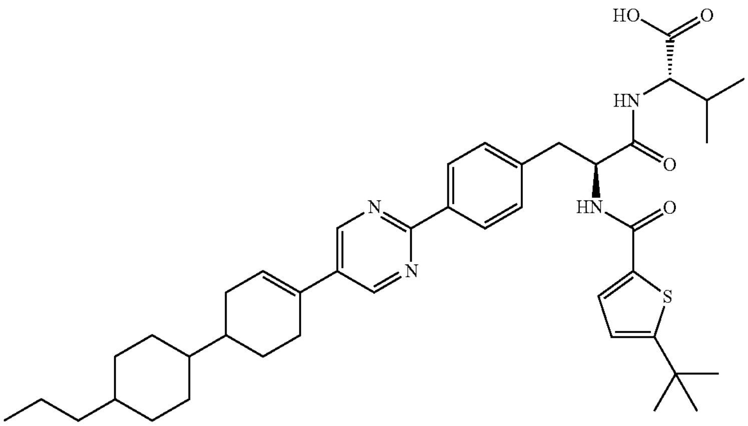 [SMILES: CCCC1CCC(C2CC=C(c3cnc(-c4ccc(C[C@H](NC(=O)c5ccc(C(C)(C)C)s5)C(=O)N[C@H](C(=O)O)C(C)C)cc4)nc3)CC2)CC1] | 75 | 11.80 | 14 |
| 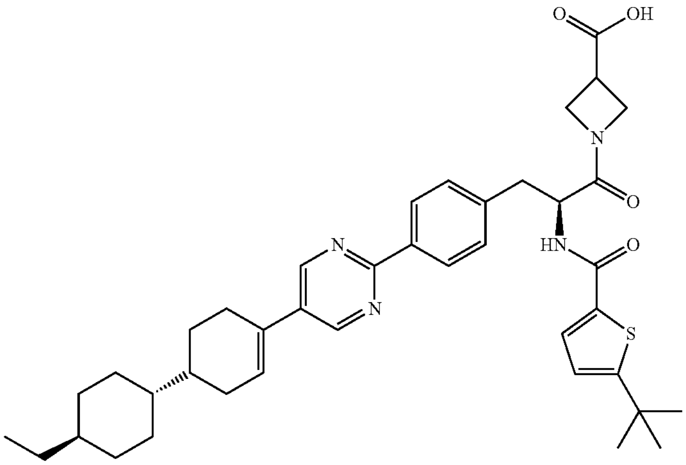 [SMILES: CC[C@H]1CC[C@H](C2CC=C(c3cnc(-c4ccc(C[C@H](NC(=O)c5ccc(C(C)(C)C)s5)C(=O)N5CC(C(=O)O)C5)cc4)nc3)CC2)CC1] | 76 | 11.50 | 10 |
| 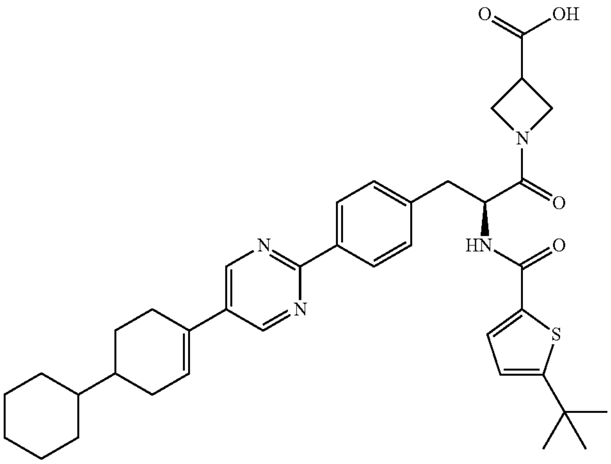 [SMILES: CC(C)(C)c1ccc(C(=O)N[C@@H](Cc2ccc(-c3ncc(C4=CCC(C5CCCCC5)CC4)cn3)cc2)C(=O)N2CC(C(=O)O)C2)s1] | 77 | 11.57 | 10 |

TABLE 1-continued
| Representative Compounds | | | |
|---|---|---|---|
| STRUCTURE | COMPOUND NUMBER | LCMS RETENTION TIME (min) | PURITY METHOD |
| 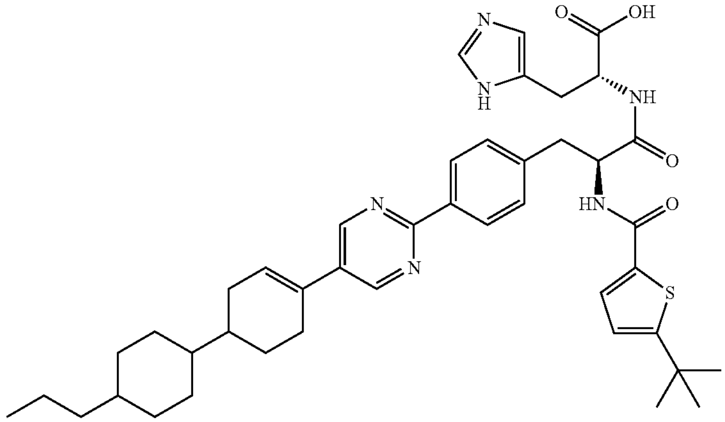 [SMILES: CCCC1CCC(C2CC=C(c3cnc(-c4ccc(C[C@H](NC(=O)c5ccc(C(C)(C)C)s5)C(=O)N[C@H](Cc5cnc[nH]5)C(=O)O)cc4)nc3)CC2)CC1] | 78 | 11.40 | 14 |
| 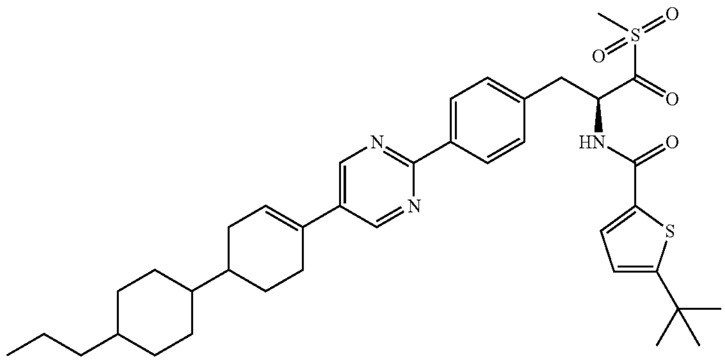 [SMILES: CCCC1CCC(C2CC=C(c3cnc(-c4ccc(C[C@H](NC(=O)c5ccc(C(C)(C)C)s5)C(=O)S(C)(=O)=O)cc4)nc3)CC2)CC1] | 79 | 12.18 | 14 |
| 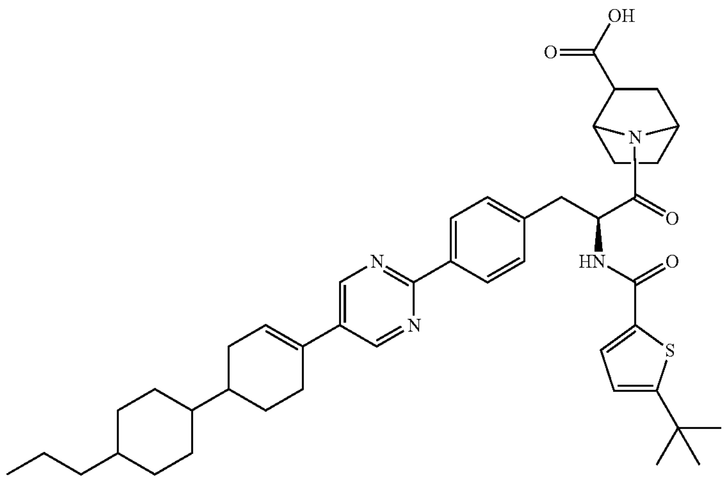 [SMILES: CCCC1CCC(C2CC=C(c3cnc(-c4ccc(C[C@H](NC(=O)c5ccc(C(C)(C)C)s5)C(=O)N5C6CCC5C(C(=O)O)C6)cc4)nc3)CC2)CC1] | 80 | 12.30 | 14 |

TABLE 1-continued
| Representative Compounds | | | |
|---|---|---|---|
| STRUCTURE | COMPOUND NUMBER | LCMS RETENTION TIME (min) | PURITY METHOD |
| 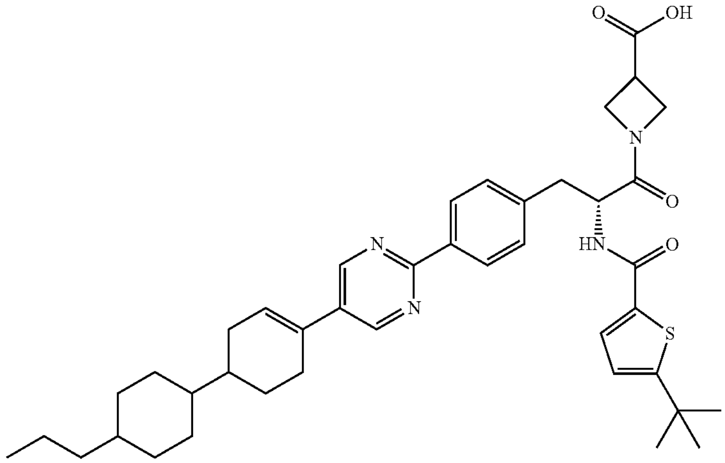 [SMILES: CCCC1CCC(C2CC=C(c3cnc(-c4ccc(C[C@@H](NC(=O)c5ccc(C(C)(C)C)s5)C(=O)N5CC(C(=O)O)C5)cc4)nc3)CC2)CC1] | 81 | 11.83 | 14 |
| 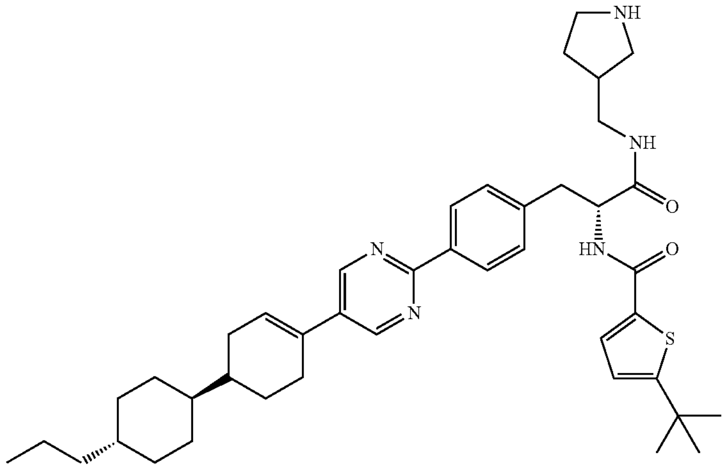 [SMILES: CCC[C@H]1CC[C@H](C2CC=C(c3cnc(-c4ccc(C[C@@H](NC(=O)c5ccc(C(C)(C)C)s5)C(=O)NCC5CCNC5)cc4)nc3)CC2)CC1] | 82 | 8.67 | 10 |
| 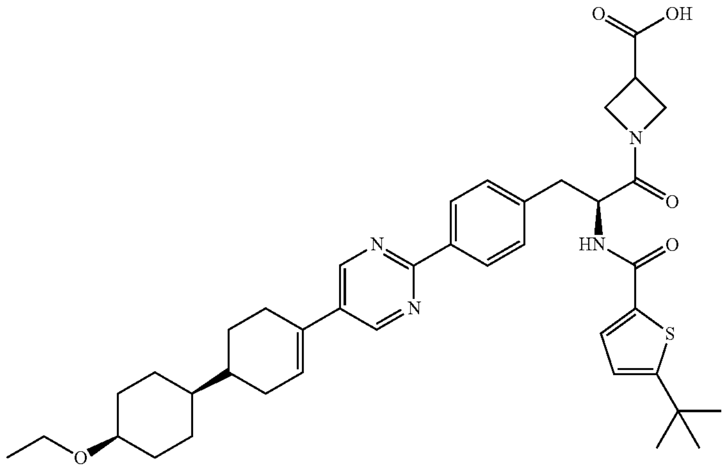 [SMILES: CCO[C@H]1CC[C@@H](C2CC=C(c3cnc(-c4ccc(C[C@H](NC(=O)c5ccc(C(C)(C)C)s5)C(=O)N5CC(C(=O)O)C5)cc4)nc3)CC2)CC1] | 83 | 9.68 | 10 |

TABLE 1-continued
| Representative Compounds | | | |
|---|---|---|---|
| STRUCTURE | COMPOUND NUMBER | LCMS RETENTION TIME (min) | PURITY METHOD |
| 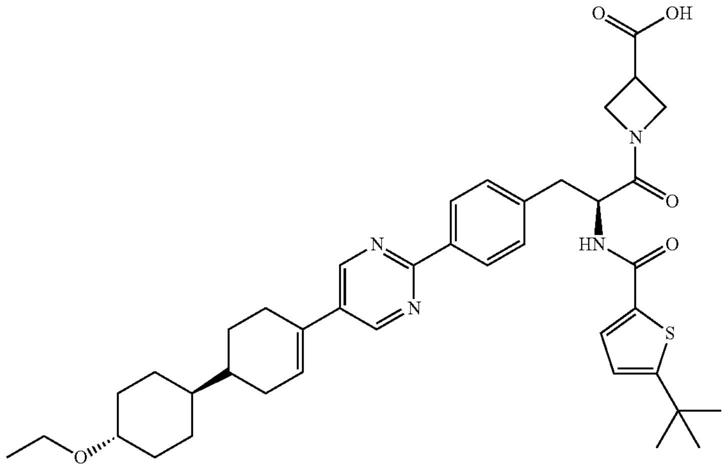 [SMILES: CCO[C@H]1CC[C@H](C2CC=C(c3cnc(-c4ccc(C[C@H](NC(=O)c5ccc(C(C)(C)C)s5)C(=O)N5CC(C(=O)O)C5)cc4)nc3)CC2)CC1] | 84 | 9.20 | 10 |
| 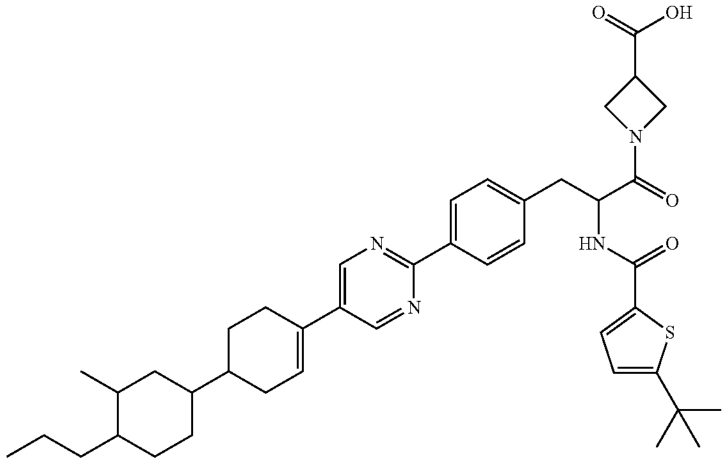 [SMILES: CCCC1CCC(C2CC=C(c3cnc(-c4ccc(CC(NC(=O)c5ccc(C(C)(C)C)s5)C(=O)N5CC(C(=O)O)C5)cc4)nc3)CC2)CC1C] | 85 | 12.21 | 10 |
| 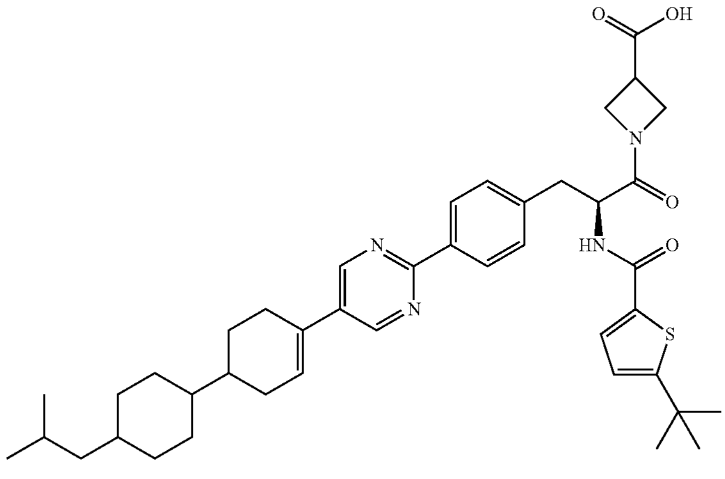 [SMILES: CC(C)CC1CCC(C2CC=C(c3cnc(-c4ccc(C[C@H](NC(=O)c5ccc(C(C)(C)C)s5)C(=O)N5CC(C(=O)O)C5)cc4)nc3)CC2)CC1] | 86 | 12.01 | 10 |

TABLE 1-continued
| Representative Compounds | | | |
|---|---|---|---|
| STRUCTURE | COMPOUND NUMBER | LCMS RETENTION TIME (min) | PURITY METHOD |
| 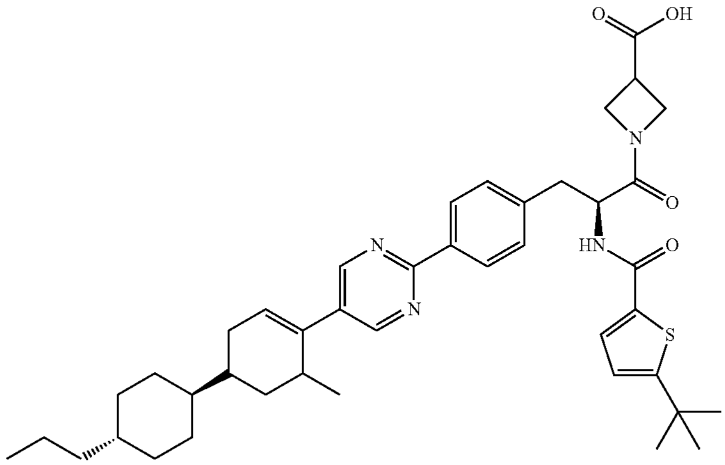 [SMILES: CCC[C@H]1CC[C@H](C2CC=C(c3cnc(-c4ccc(C[C@H](NC(=O)c5ccc(C(C)(C)C)s5)C(=O)N5CC(C(=O)O)C5)cc4)nc3)C(C)C2)CC1] | 87 | 12.11 | 10 |
| 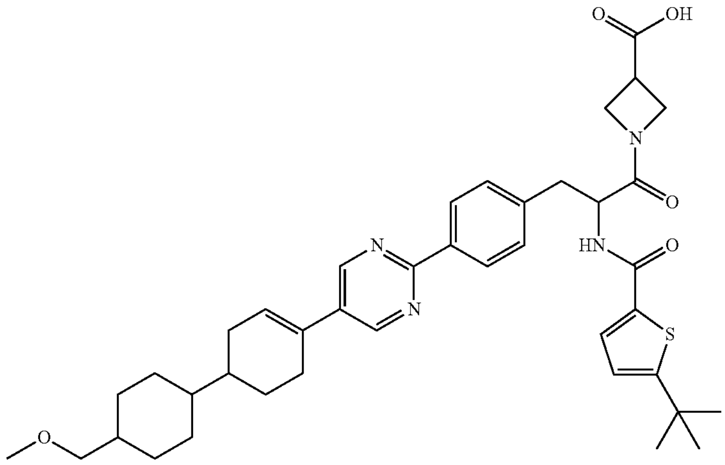 | 88 | 9.46 | 10 |
| 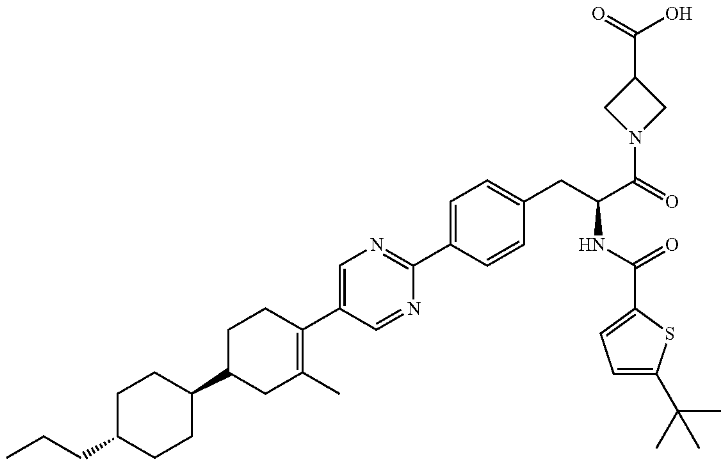 [SMILES: CCC[C@H]1CC[C@H](C2CCC(c3cnc(-c4ccc(C[C@H](NC(=O)c5ccc(C(C)(C)C)s5)C(=O)N5CC(C(=O)O)C5)cc4)nc3)=C(C)C2)CC1] | 89 | 9.88 | 20 |

TABLE 1-continued
| Representative Compounds | | | |
|---|---|---|---|
| STRUCTURE | COMPOUND NUMBER | LCMS RETENTION TIME (min) | PURITY METHOD |
| 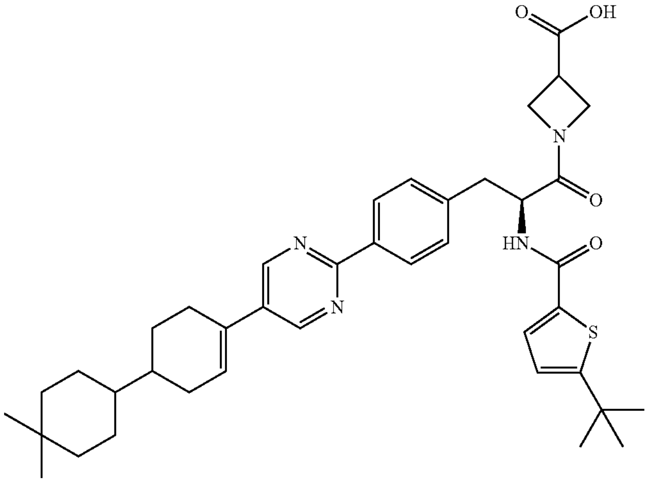 [SMILES: CC1(C)CCC(C2CC=C(c3cnc(-c4ccc(C[C@H](NC(=O)c5ccc(C(C)(C)C)s5)C(=O)N5CC(C(=O)O)C5)cc4)nc3)CC2)CC1] | 90 | 10.60 | 10 |
| 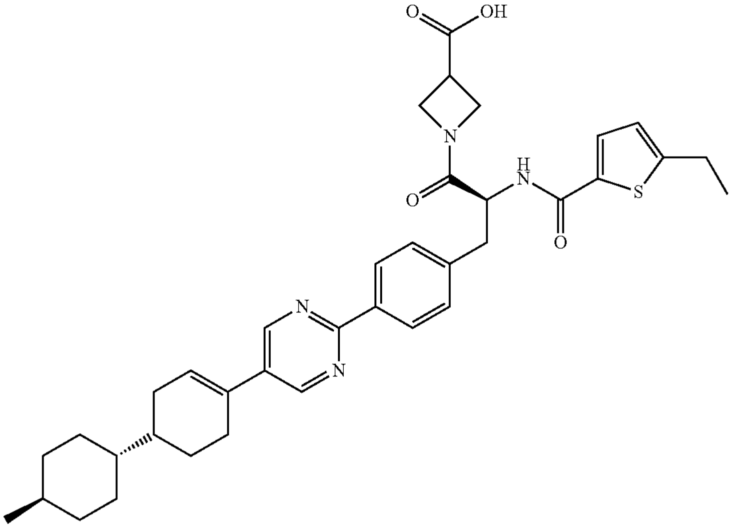 [SMILES: CCc1ccc(C(=O)N[C@@H](Cc2ccc(-c3ncc(C4=CCC([C@H]5CC[C@H](C)CC5)CC4)cn3)cc2)C(=O)N2CC(C(=O)O)C2)s1] | 91 | 8.19 | 20 |

TABLE 1-continued
| Representative Compounds | | | |
|---|---|---|---|
| STRUCTURE | COMPOUND NUMBER | LCMS RETENTION TIME (min) | PURITY METHOD |
| 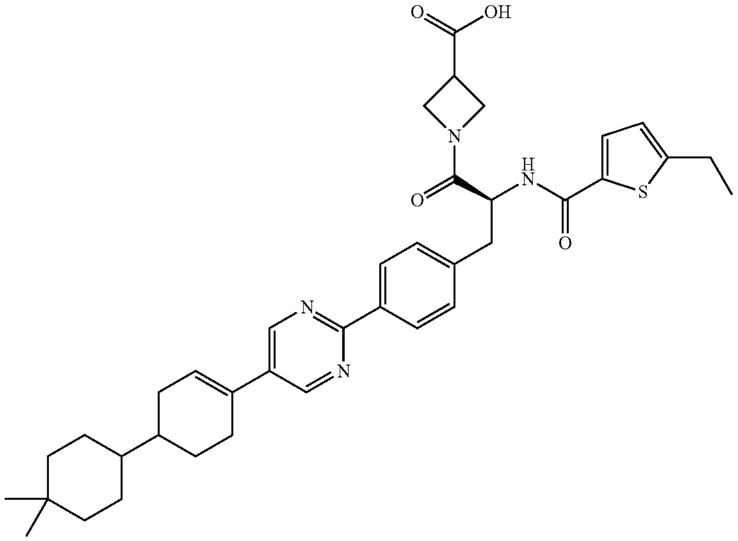 [SMILES: CCc1ccc(C(=O)N[C@@H](Cc2ccc(-c3ncc(C4=CCC(C5CCC(C)(C)CC5)CC4)cn3)cc2)C(=O)N2CC(C(=O)O)C2)s1] | 92 | 8.39 | 20 |
| 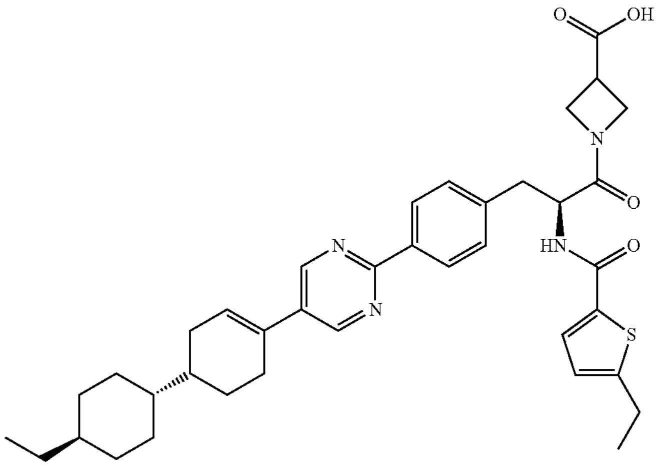 [SMILES: CCc1ccc(C(=O)N[C@@H](Cc2ccc(-c3ncc(C4=CCC([C@H]5CC[C@H](CC)CC5)CC4)cn3)cc2)C(=O)N2CC(C(=O)O)C2)s1] | 93 | 8.57 | 28 |

TABLE 1-continued
| Representative Compounds | | | |
|---|---|---|---|
| STRUCTURE | COMPOUND NUMBER | LCMS RETENTION TIME (min) | PURITY METHOD |
| 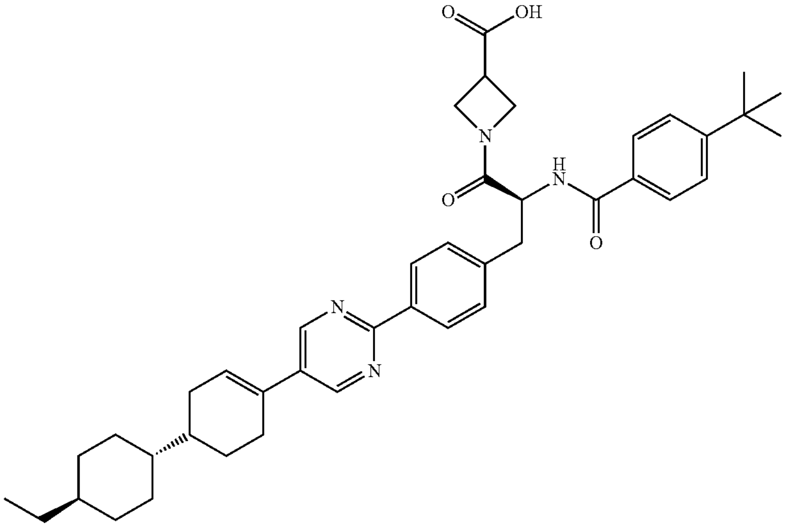 [SMILES: CC[C@H]1CC[C@H](C2CC=C(c3cnc(-c4ccc(C[C@H](NC(=O)c5ccc(C(C)(C)C)cc5)C(=O)N5CC(C(=O)O)C5)cc4)nc3)CC2)CC1] | 94 | 9.24 | 20 |
| 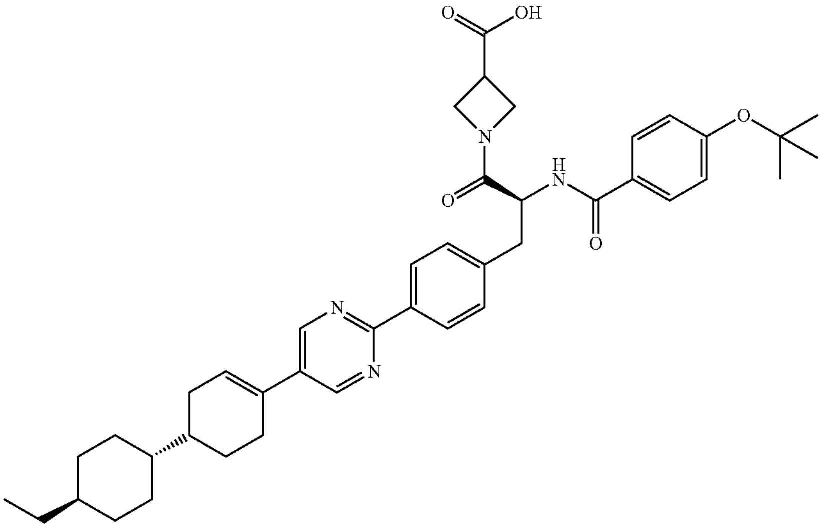 [SMILES: CC[C@H]1CC[C@H](C2CC=C(c3cnc(-c4ccc(C[C@H](NC(=O)c5ccc(OC(C)(C)C)cc5)C(=O)N5CC(C(=O)O)C5)cc4)nc3)CC2)CC1] | 95 | 9.16 | 20 |

TABLE 1-continued
| Representative Compounds | | | |
|---|---|---|---|
| STRUCTURE | COMPOUND NUMBER | LCMS RETENTION TIME (min) | PURITY METHOD |
| 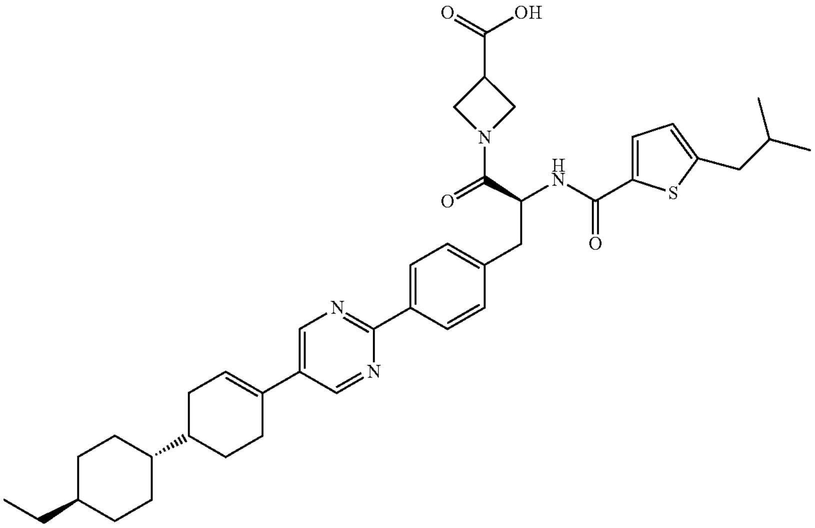 [SMILES: CC[C@H]1CC[C@H](C2CC=C(c3cnc(-c4ccc(C[C@H](NC(=O)c5ccc(CC(C)C)s5)C(=O)N5CC(C(=O)O)C5)cc4)nc3)CC2)CC1] | 96 | 9.20 | 20 |
| 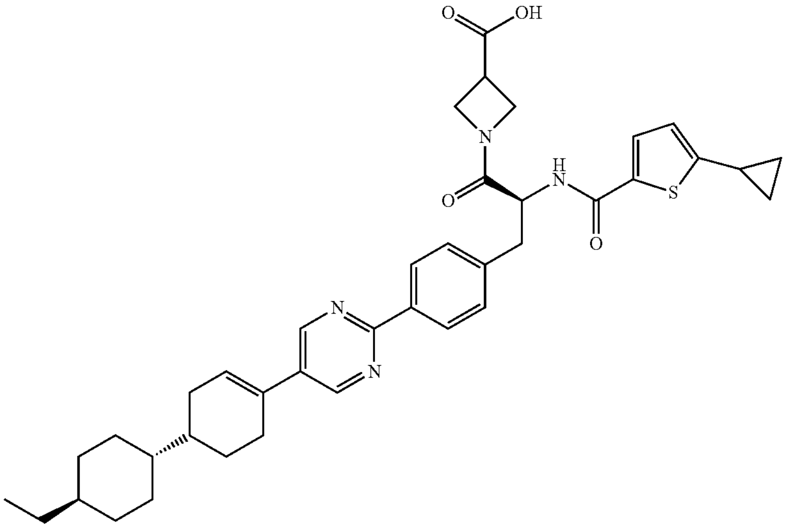 [SMILES: CC[C@H]1CC[C@H](C2CC=C(c3cnc(-c4ccc(C[C@H](NC(=O)c5ccc(C6CC6)s5)C(=O)N5CC(C(=O)O)C5)cc4)nc3)CC2)CC1] | 97 | 8.44 | 20 |

TABLE 1-continued
Representative Compounds
| STRUCTURE | COMPOUND NUMBER | LCMS RETENTION TIME (min) | PURITY METHOD |
|---|---|---|---|
| 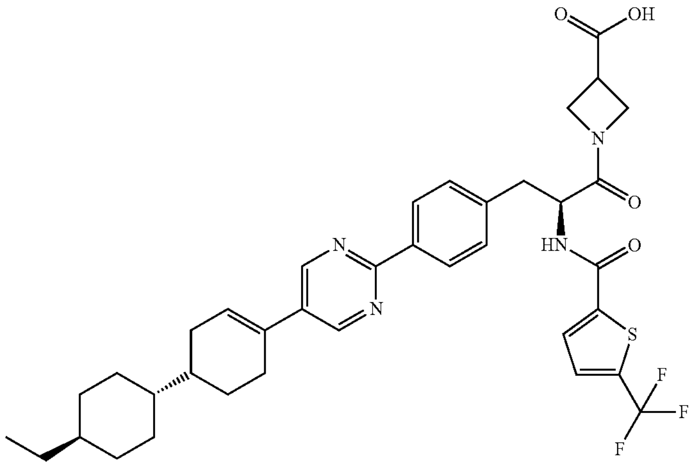 [SMILES: CC[C@H]1CC[C@H](C2CC=C(c3cnc(-c4ccc(C[C@H](NC(=O)c5ccc(C(F)(F)F)s5)C(=O)N5CC(C(=O)O)C5)cc4)nc3)CC2)CC1] | 98 | 8.83 | 20 |
| 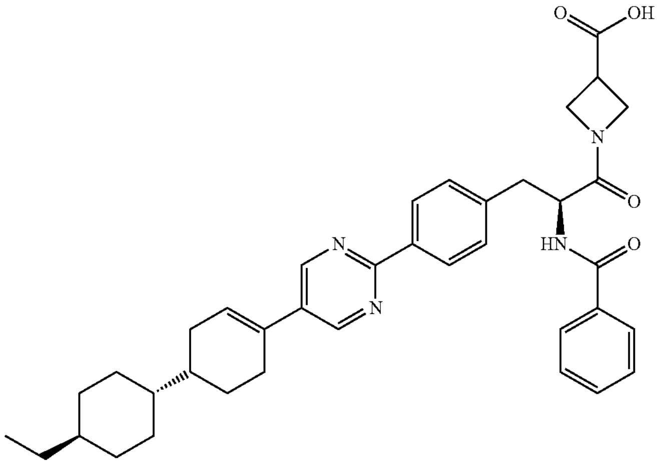 [SMILES: CC[C@H]1CC[C@H](C2CC=C(c3cnc(-c4ccc(C[C@H](NC(=O)c5ccccc5)C(=O)N5CC(C(=O)O)C5)cc4)nc3)CC2)CC1] | 99 | 7.97 | 20 |
| 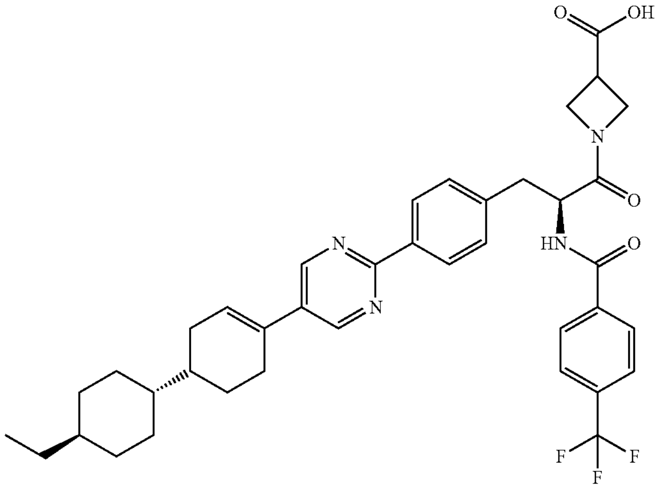 [SMILES: CC[C@H]1CC[C@H](C2CC=C(c3cnc(-c4ccc(C[C@H](NC(=O)c5ccc(C(F)(F)F)cc5)C(=O)N5CC(C(=O)O)C5)cc4)nc3)CC2)CC1] | 100 | 8.80 | 20 |

TABLE 1-continued
| Representative Compounds | | | |
|---|---|---|---|
| STRUCTURE | COMPOUND NUMBER | LCMS RETENTION TIME (min) | PURITY METHOD |
| 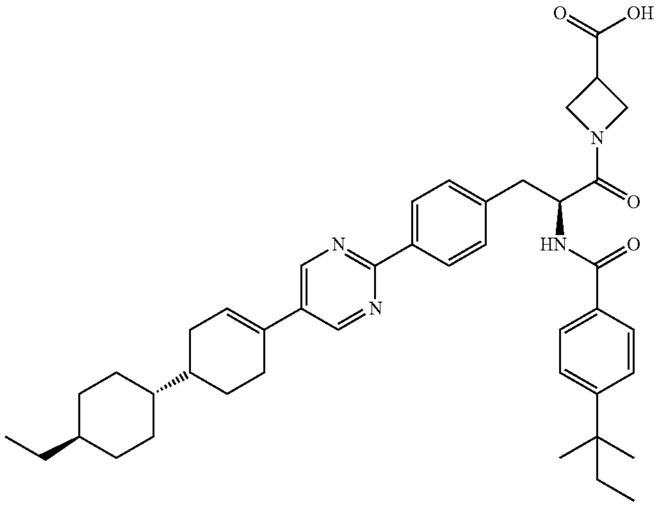 [SMILES: CCC(C)(C)c1ccc(C(=O)N[C@@H](Cc2ccc(-c3ncc(C4=CCC([C@H]5CC[C@H](CC)CC5)CC4)cn3)cc2)C(=O)N2CC(C(=O)O)C2)cc1] | 101 | 9.59 | 20 |
| 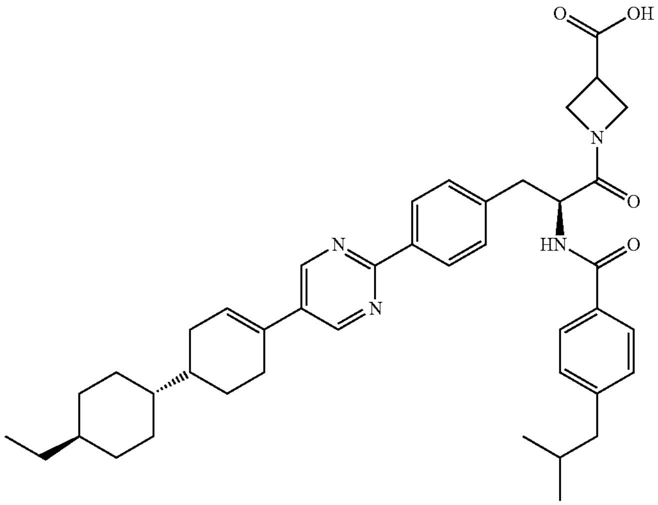 [SMILES: CC[C@H]1CC[C@H](C2CC=C(c3cnc(-c4ccc(C[C@H](NC(=O)c5ccc(CC(C)C)cc5)C(=O)N5CC(C(=O)O)C5)cc4)nc3)CC2)CC1] | 102 | 9.39 | 20 |
| 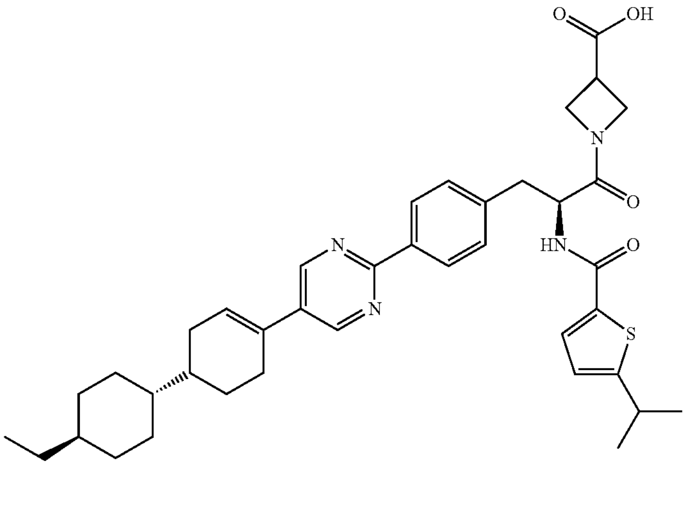 [SMILES: CC[C@H]1CC[C@H](C2CC=C(c3cnc(-c4ccc(C[C@H](NC(=O)c5ccc(C(C)C)s5)C(=O)N5CC(C(=O)O)C5)cc4)nc3)CC2)CC1] | 103 | 8.85 | 20 |

TABLE 1-continued
| Representative Compounds | | | |
|---|---|---|---|
| STRUCTURE | COMPOUND NUMBER | LCMS RETENTION TIME (min) | PURITY METHOD |
| 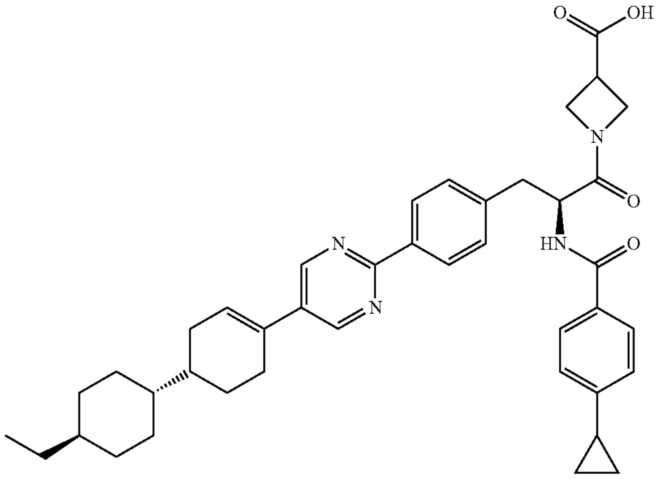 [SMILES: CC[C@H]1CC[C@H](C2CC=C(c3cnc(-c4ccc(C[C@H](NC(=O)c5ccc(C6CC6)cc5)C(=O)N5CC(C(=O)O)C5)cc4)nc3)CC2)CC1] | 104 | 8.66 | 20 |
| 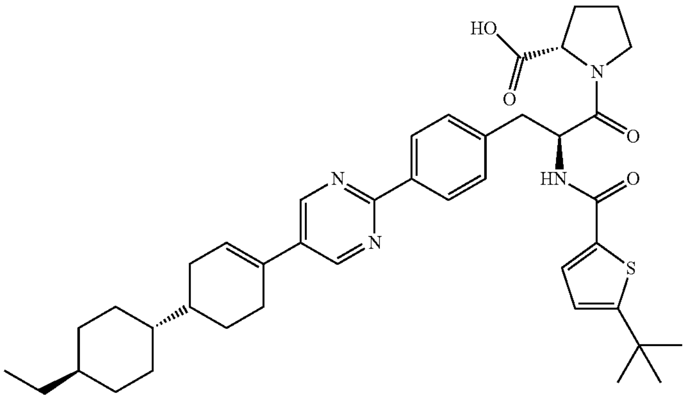 [SMILES: CC[C@H]1CC[C@H](C2CC=C(c3cnc(-c4ccc(C[C@H](NC(=O)c5ccc(C(C)(C)C)s5)C(=O)N5CCC[C@H]5C(=O)O)cc4)nc3)CC2)CC1] | 105 | 9.50 | 28 |
| 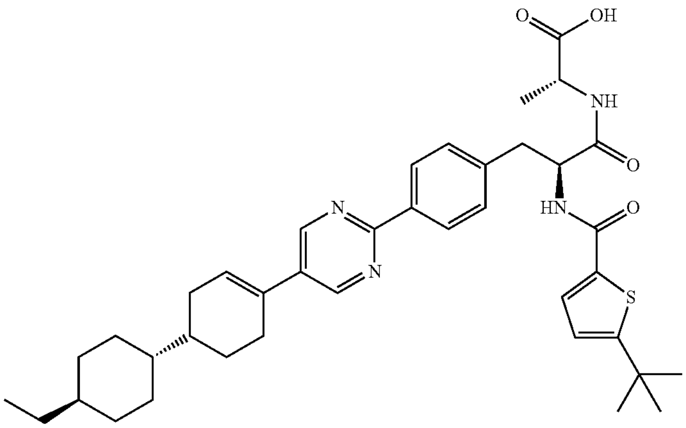 [SMILES: CC[C@H]1CC[C@H](C2CC=C(c3cnc(-c4ccc(C[C@H](NC(=O)c5ccc(C(C)(C)C)s5)C(=O)N[C@H](C)C(=O)O)cc4)nc3)CC2)CC1] | 106 | 9.32 | 28 |

TABLE 1-continued
| Representative Compounds | | | |
|---|---|---|---|
| STRUCTURE | COMPOUND NUMBER | LCMS RETENTION TIME (min) | PURITY METHOD |
| 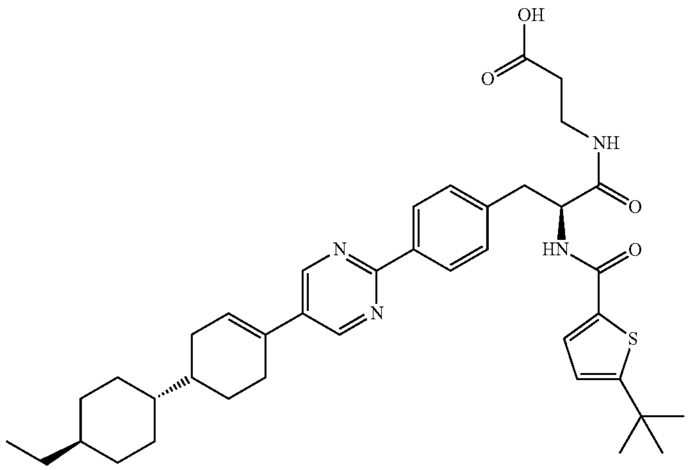 [SMILES: CC[C@H]1CC[C@H](C2CC=C(c3cnc(-c4ccc(C[C@H](NC(=O)c5ccc(C(C)(C)C)s5)C(=O)NCCC(=O)O)cc4)nc3)CC2)CC1] | 107 | 9.65 | 28 |
| 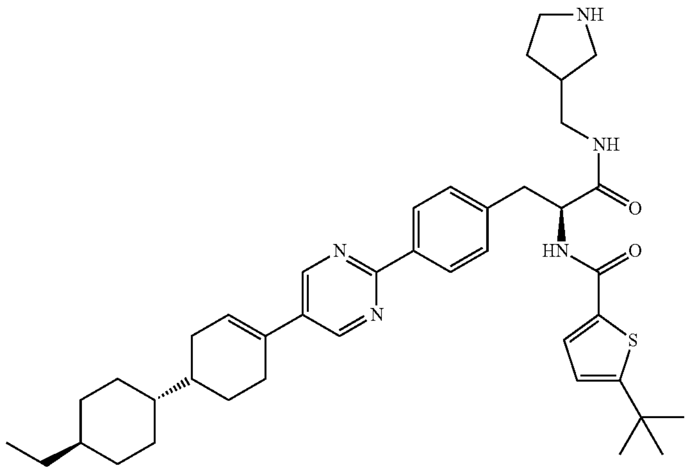 [SMILES: CC[C@H]1CC[C@H](C2CC=C(c3cnc(-c4ccc(C[C@H](NC(=O)c5ccc(C(C)(C)C)s5)C(=O)NCC5CCNC5)cc4)nc3)CC2)CC1] | 108 | 12.55 | 28 |
| 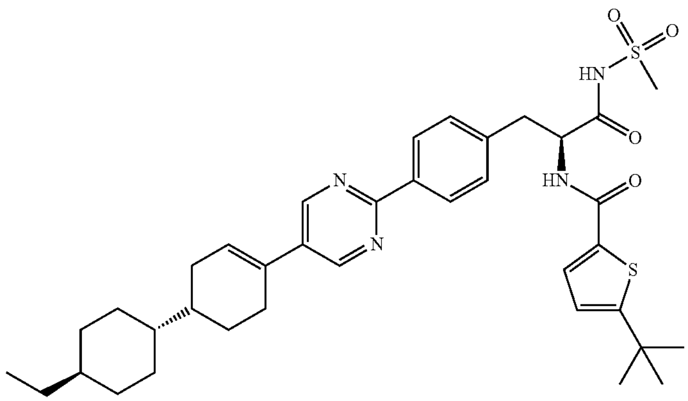 [SMILES: CC[C@H]1CC[C@H](C2CC=C(c3cnc(-c4ccc(C[C@H](NC(=O)c5ccc(C(C)(C)C)s5)C(=O)NS(C)(=O)=O)cc4)nc3)CC2)CC1] | 109 | 9.62 | 28 |

TABLE 1-continued
| Representative Compounds | | | |
|---|---|---|---|
| STRUCTURE | COMPOUND NUMBER | LCMS RETENTION TIME (min) | PURITY METHOD |
| 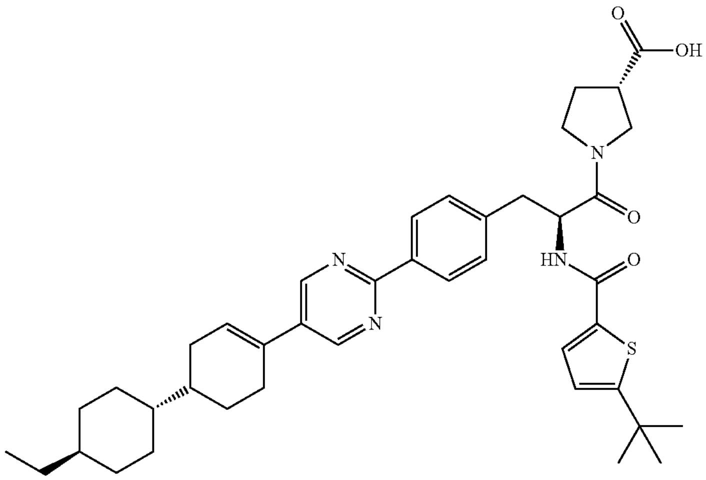 [SMILES: CC[C@H]1CC[C@H](C2CC=C(c3cnc(-c4ccc(C[C@H](NC(=O)c5ccc(C(C)(C)C)s5)C(=O)N5CC[C@H](C(=O)O)C5)cc4)nc3)CC2)CC1] | 110 | 9.56 | 28 |
| 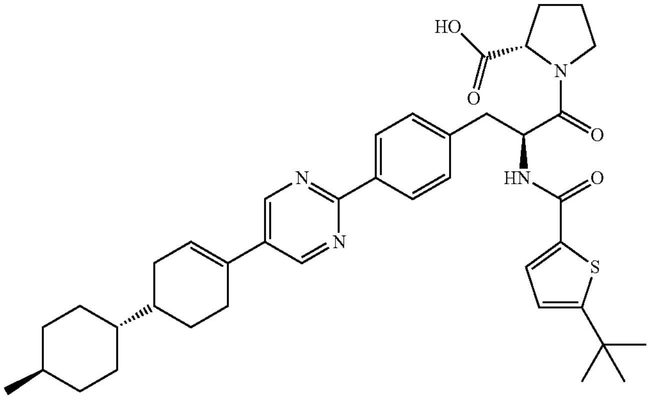 [SMILES: CC(C)(C)c1ccc(C(=O)N[C@@H](Cc2ccc(-c3ncc(C4=CCC([C@H]5CC[C@H](C)CC5)CC4)cn3)cc2)C(=O)N2CCC[C@H]2C(=O)O)s1] | 111 | 9.48 | 28 |
| 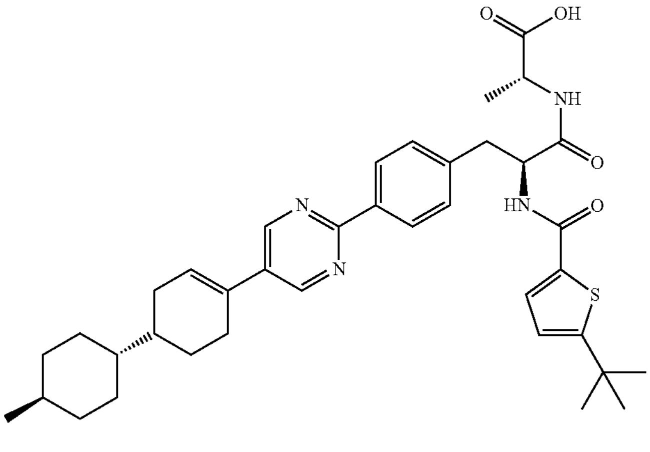 [SMILES: C[C@@H](NC(=O)[C@H](Cc1ccc(-c2ncc(C3=CCC([C@H]4CC[C@H](C)CC4)CC3)cn2)cc1)NC(=O)c1ccc(C(C)(C)C)s1)C(=O)O] | 112 | 9.01 | 28 |

TABLE 1-continued
| Representative Compounds | | | |
|---|---|---|---|
| STRUCTURE | COMPOUND NUMBER | LCMS RETENTION TIME (min) | PURITY METHOD |
| 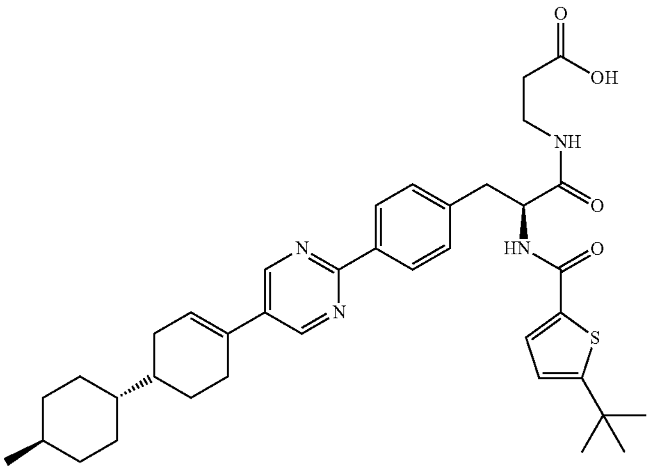 [SMILES: CC(C)(C)c1ccc(C(=O)N[C@@H](Cc2ccc(-c3ncc(C4=CCC([C@H]5CC[C@H](C)CC5)CC4)cn3)cc2)C(=O)NCCC(=O)O)s1] | 113 | 9.94 | 28 |
| 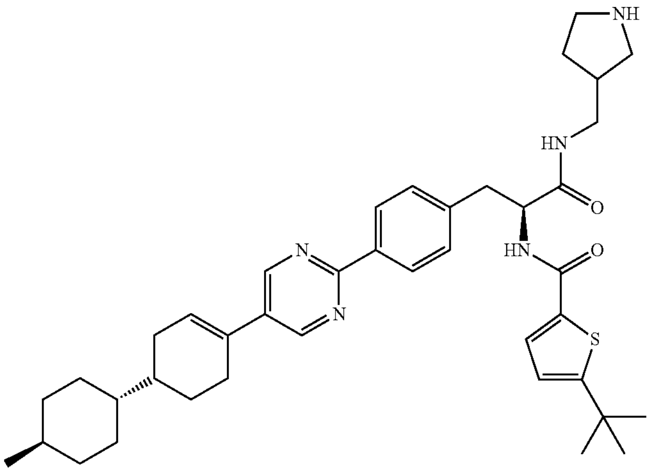 [SMILES: CC(C)(C)c1ccc(C(=O)N[C@@H](Cc2ccc(-c3ncc(C4=CCC([C@H]5CC[C@H](C)CC5)CC4)cn3)cc2)C(=O)NCC2CCNC2)s1] | 114 | 12.32 | 28 |
| 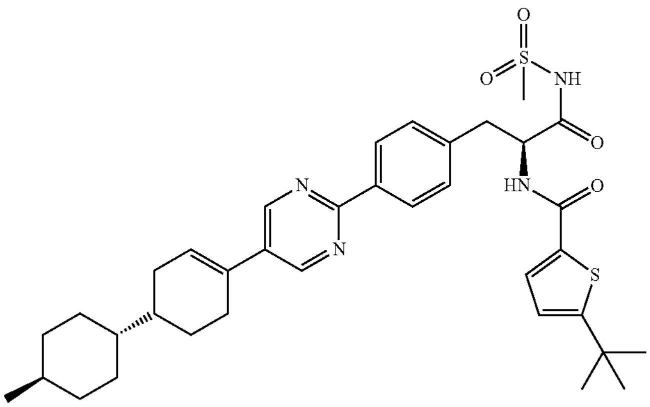 [SMILES: CC(C)(C)c1ccc(C(=O)N[C@@H](Cc2ccc(-c3ncc(C4=CCC([C@H]5CC[C@H](C)CC5)CC4)cn3)cc2)C(=O)NS(C)(=O)=O)s1] | 115 | 9.32 | 28 |

TABLE 1-continued
| Representative Compounds | | | |
|---|---|---|---|
| STRUCTURE | COMPOUND NUMBER | LCMS RETENTION TIME (min) | PURITY METHOD |
| 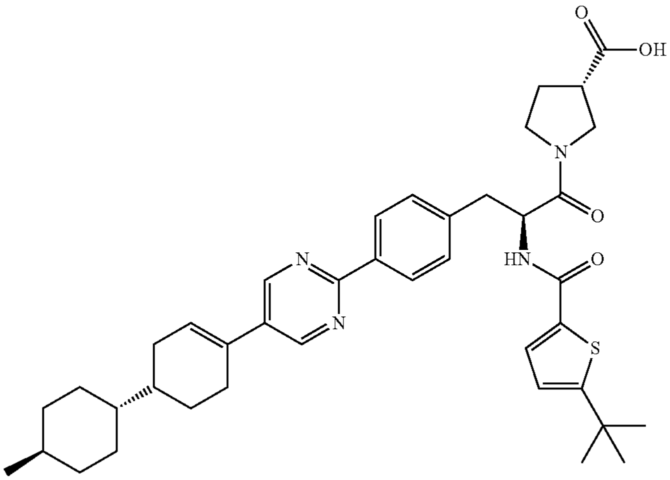 [SMILES: CC(C)(C)c1ccc(C(=O)N[C@@H](Cc2ccc(-c3ncc(C4=CCC([C@H]5CC[C@H](C)CC5)CC4)cn3)cc2)C(=O)N2CC[C@H](C(=O)O)C2)s1] | 116 | 9.71 | 28 |
| 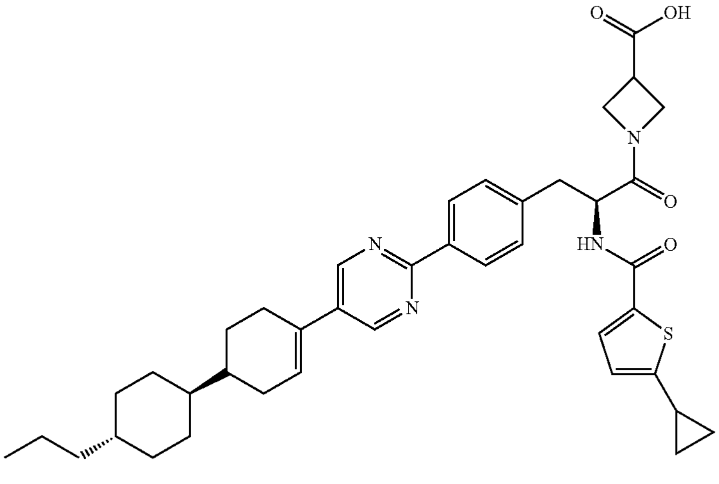 [SMILES: CCC[C@H]1CC[C@H](C2CC=C(c3cnc(-c4ccc(C[C@H](NC(=O)c5ccc(C6CC6)s5)C(=O)N5CC(C(=O)O)C5)cc4)nc3)CC2)CC1] | 117 | 10.75 | 10 |
| 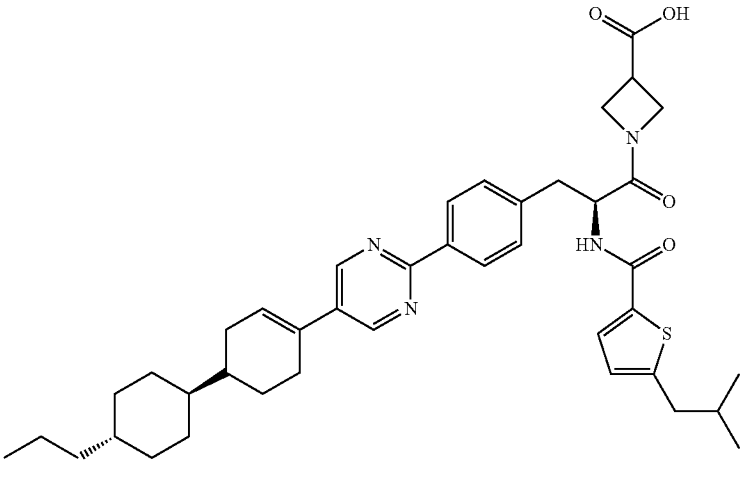 [SMILES: CCC[C@H]1CC[C@H](C2CC=C(c3cnc(-c4ccc(C[C@H](NC(=O)c5ccc(CC(C)C)s5)C(=O)N5CC(C(=O)O)C5)cc4)nc3)CC2)CC1] | 118 | 11.43 | 10 |

TABLE 1-continued
Representative Compounds
| STRUCTURE | COMPOUND NUMBER | LCMS RETENTION TIME (min) | PURITY METHOD |
|---|---|---|---|
| 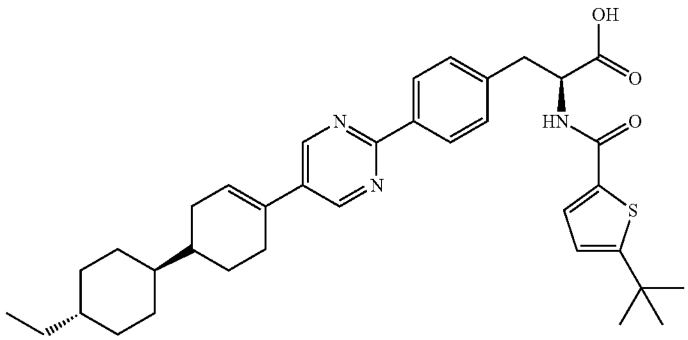 [SMILES: CC[C@H]1CC[C@H](C2CC=C(c3cnc(-c4ccc(C[C@H](NC(=O)c5ccc(C(C)(C)C)s5)C(=O)O)cc4)nc3)CC2)CC1] | 119 | 4.38 | 14 |
| 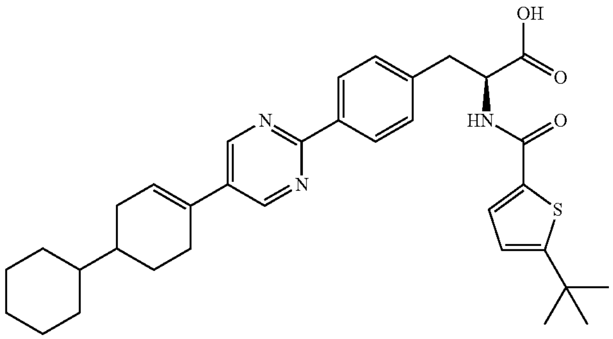 [SMILES: CC(C)(C)c1ccc(C(=O)N[C@@H](Cc2ccc(-c3ncc(C4=CCC(C5CCCCC5)CC4)cn3)cc2)C(=O)O)s1] | 120 | 11.34 | 10 |
| 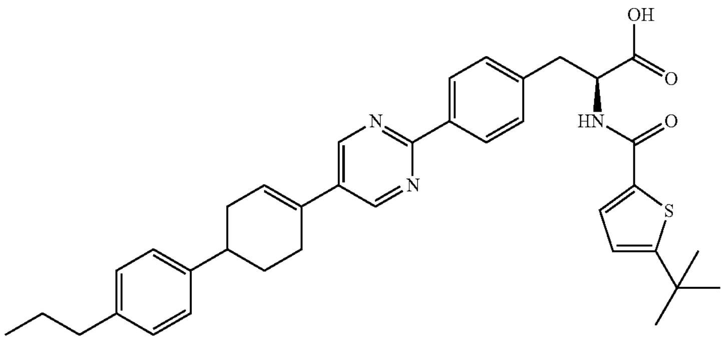 [SMILES: CCCc1ccc(C2CC=C(c3cnc(-c4ccc(C[C@H](NC(=O)c5ccc(C(C)(C)C)s5)C(=O)O)cc4)nc3)CC2)cc1] | 121 | 10.79 | 10 |
| 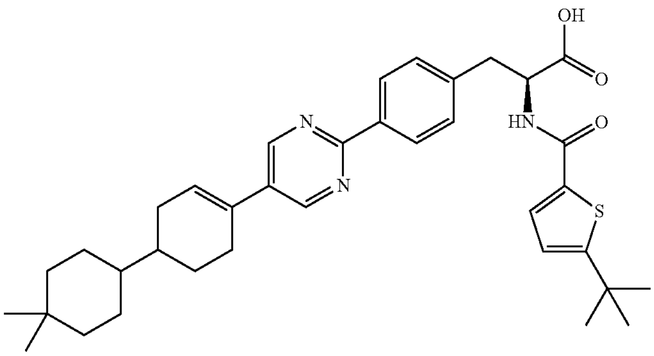 [SMILES: CC1(C)CCC(C2CC=C(c3cnc(-c4ccc(C[C@H](NC(=O)c5ccc(C(C)(C)C)s5)C(=O)O)cc4)nc3)CC2)CC1] | 122 | 12.01 | 10 |

TABLE 1-continued
Representative Compounds
| STRUCTURE | COMPOUND NUMBER | LCMS RETENTION TIME (min) | PURITY METHOD |
|---|---|---|---|
| 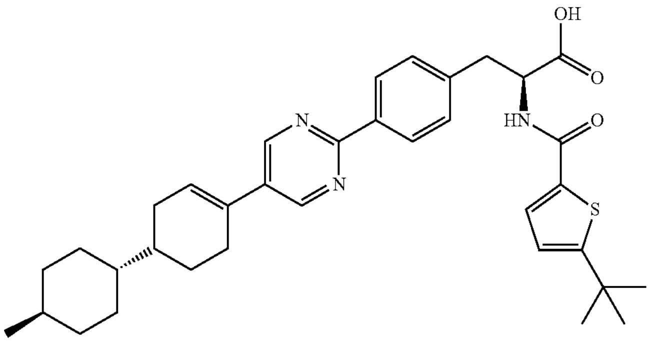 [SMILES: CC(C)(C)c1ccc(C(=O)N[C@@H](Cc2ccc(-c3ncc(C4=CCC([C@H]5CC[C@H](C)CC5)CC4)cn3)cc2)C(=O)O)s1] | 123 | 11.12 | 10 |
| 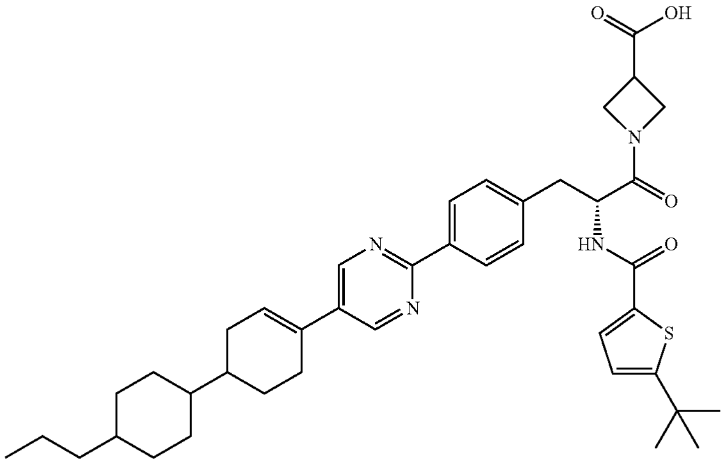 [SMILES: CCCC1CCC(C2CC=C(c3cnc(-c4ccc(C[C@@H](NC(=O)c5ccc(C(C)(C)C)s5)C(=O)N5CC(C(=O)O)C5)cc4)nc3)CC2)CC1] | 124 | 11.95 | 10 |
| 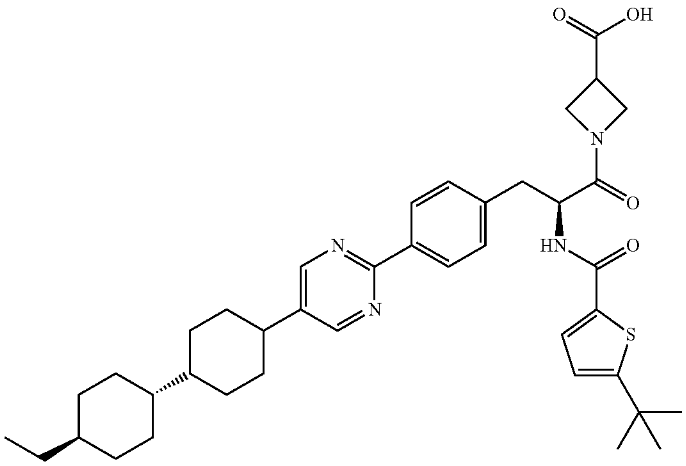 [SMILES: CC[C@H]1CC[C@H](C2CCC(c3cnc(-c4ccc(C[C@H](NC(=O)c5ccc(C(C)(C)C)s5)C(=O)N5CC(C(=O)O)C5)cc4)nc3)CC2)CC1] | 125 | 9.57 | 28 |

BIOLOGICAL ASSAYS

Assay Procedures

GLP-1 PAM Shift cAMP Assay: Dose Response of Peptide Ligand in Presence of Fixed Concentration of Compound.

A GLP-1R expressing CRE-bla CHO-K1 cell line was purchased from Invitrogen. Cells were seeded into 384-well white flat bottom plates at 5000 cells/well/20 μL growth media (DMEM-High glucose, 10% dialyzed FBS, 0.1 mM NEAA, 25 mM Hepes, 100 U/mL penicillin/100 g/mL streptomycin, 5 μg/mL Blasticidin, 600 μg/mL Hygromycin) and incubated for 18 h at 37° C. in 5% $CO_2$. Growth medium was replaced with 12 μL assay buffer (Hanks Balanced Salt solution, 10 mM Hepes, 0.1% BSA, pH 7.4). A 5× peptide dose response curve (12-point) was generated in assay buffer containing 1.5 mM IBMX, 12.5% DMSO, and 50 μM compound. Peptide ligand was GLP-1(9-36). The 5× peptide dose response plus compound mix was added (3 μL) and cells were incubated for 30 min at 37° C. Direct detection of cAMP was carried out using DiscoveRx HitHunter cAMP kit according to manufacturer's instructions and luminescence was read using a SpectraMax M5 plate reader. Luminescence was analyzed by non-linear regression to determine the $EC_{50}$ and Emax. A GLP-1(7-36) dose response was included to determine maximum efficacy.

$EC_{20}$ GLP-1(9-36) PAM cAMP Assay: Dose Response of Compound in the Presence of Fixed Concentration of GLP-1 (9-36).

GLP-1R CRE-bla CHO-K1 cells cultured in growth medium (DMEM-High glucose, 10% dialyzed FBS, 0.1 mM NEAA, 25 mM Hepes, 100 U/mL penicillin/100 μg/mL streptomycin, 5 μg/mL Blasticidin, 600 μg/mL Hygromycin) were trypsinized and plated in suspension into 384 well white flat bottom plates at 5000 cells/well in 12 μL assay buffer (Hanks Balanced Salt solution, 10 mM Hepes, 0.1% BSA, 10 pH 7.4). A 5× compound dose response curve (12-point) was generated in assay buffer containing 1.5 mM IBMX, 4% DMSO. GLP-1(9-36) was diluted to 4.2 μM in assay buffer containing 1.5 mM IBMX and 4% DMSO. The 5× compound dose response was added (3 μL), followed by 0.5 μL of GLP-1(9-36) and cells were incubated for 30 min at 37° C. Direct detection of cAMP was carried out using DiscoveRx HitHunter cAMP kit according to manufacturer's instructions and luminescence was read using a SpectraMax M5 plate reader. Luminescence was converted to total cAMP using a cAMP standard curve and data was analyzed by non-linear regression to determine the $EC_{50}$ and Emax.

Peptide Sequences

GLP-1(7-36): HAEGTFTSDVS SYLEGQAAKEFIAWLVKGR-$NH_2$ (SEQ ID NO: 2) GLP-1(9-36): EGTFTSDVSSYLEGQAAKEFIAWLVKGR-$NH_2$ (SEQ ID NO: 3) GLP-1(7-36) was purchased from GenScript. GLP-1(9-36) was purchased from Biopeptide Co., Inc.

GLP-1 Activity

Activity data for representative GLP-1 modulators are displayed in Table 2. The $EC_{20}$GLP-1(9-36) PAM Activity range is denoted as follows: + denotes activity <0.5 μM, ++ denotes activity between 0.5 and 2.5 μM, +++ denotes activity between 2.5 and 5 μM, and ++++ denotes activity 5 to 10 μM.

TABLE 2

| GLP-1 Activity | |
|---|---|
| COMPOUND NUMBER | $EC_{20}$ GLP-1(9-36) PAM $EC_{50}$ |
| 1 | + |
| 2 | ++++ |
| 3 | + |
| 4 | + |
| 5 | ++ |
| 6 | + |
| 7 | + |
| 8 | + |
| 9 | ++ |
| 10 | + |
| 11 | + |
| 12 | +++ |
| 13 | + |
| 14 | + |
| 15 | + |
| 16 | ++ |
| 17 | + |
| 18 | ++++ |
| 19 | ++ |
| 20 | ++++ |
| 21 | + |
| 22 | + |
| 23 | + |
| 24 | + |
| 25 | +++ |
| 26 | + |
| 27 | + |
| 28 | ++++ |
| 29 | ++ |
| 30 | ++ |
| 31 | + |
| 32 | + |
| 33 | ++ |
| 34 | + |
| 35 | ++ |
| 36 | + |
| 37 | ++ |
| 38 | ++ |
| 39 | ++ |
| 40 | ++ |
| 41 | ++++ |
| 43 | ++++ |
| 44 | + |
| 45 | ++ |
| 46 | +++ |
| 47 | + |
| 48 | ++ |
| 49 | ++++ |
| 50 | ++ |
| 51 | ++ |
| 52 | ++ |
| 53 | ++ |
| 54 | ++++ |
| 55 | +++ |
| 56 | + |
| 57 | ++ |
| 58 | +++ |
| 59 | + |
| 60 | ++ |
| 61 | + |
| 62 | + |
| 63 | ++ |
| 64 | +++ |
| 65 | ++ |
| 66 | +++ |
| 67 | + |
| 69 | +++ |
| 70 | + |
| 71 | + |
| 72 | +++ |
| 73 | + |
| 74 | + |
| 75 | ++ |
| 76 | + |
| 77 | + |

TABLE 2-continued

| GLP-1 Activity | |
|---|---|
| COMPOUND NUMBER | $EC_{20}$ GLP-1(9-36) PAM $EC_{50}$ |
| 78 | ++ |
| 79 | + |
| 80 | ++ |
| 81 | ++ |
| 82 | ++ |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | ++ |
| 96 | + |
| 97 | + |
| 98 | + |
| 99 | ++ |
| 100 | + |
| 101 | + |
| 102 | ++ |
| 103 | + |
| 104 | + |
| 105 | + |
| 106 | + |
| 107 | + |
| 108 | ++ |
| 109 | + |
| 110 | + |
| 111 | + |
| 112 | + |
| 113 | + |
| 114 | ++ |
| 115 | + |
| 116 | + |
| 117 | + |
| 118 | + |
| 119 | ++ |
| 120 | ++ |
| 121 | + |
| 122 | ++ |
| 123 | + |
| 124 | ++ |
| 125 | ++ |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A compound having the structure of Formula I-R or I-S:

I-R

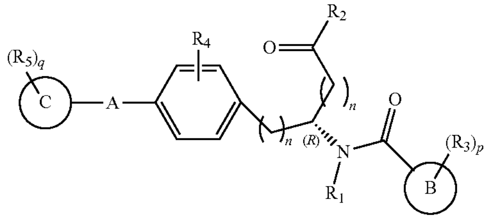

I-S

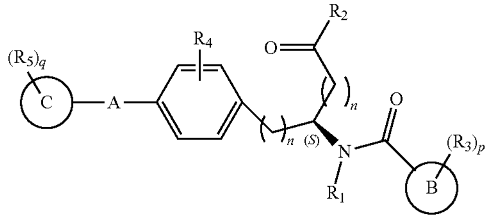

or a pharmaceutically acceptable enantiomer, diastereomer, racemate, salt, hydrate or solvate thereof;

wherein

A is pyrimidinyl, pyridinyl, pyridazinyl or pyrazinyl, each of which may be optionally substituted with one or more of $R_4$;

B is phenyl or heterocycle;

C is a nonaromatic carbocyclyl or nonaromatic carbocyclylalkyl;

each $R_1$ is independently H or $C_{1-4}$ alkyl;

$R_2$ is —OH, —O—$R_8$, —N($R_1$)—$SO_2$—$R_7$, —$NR_{41}R_{42}$, N($R_1$)—($CR_aR_b$)$_m$—$COOR_8$, —N($R_1$)—($CR_aR_b$)$_m$—CO—N($R_1$)($R_{40}$), —N($R_1$)—($CR_aR_b$)$_m$—N($R_1$)C(O)O($R_8$), —N($R_1$)—($CR_aR_b$)$_m$—N($R_1$)($R_{40}$), —N($R_1$)—($CR_aR_b$)$_m$—CO—N($R_1$)-heterocyclyl, or —N($R_1$)—($CR_aR_b$)$_m$-heterocyclyl, which heterocyclyl may be optionally (singly or multiply) substituted with $R_7$;

each $R_3$ and $R_4$ is independently H, halo, alkyl, alkyl substituted (singly or multiply) with $R_{31}$, alkoxy, haloalkyl, perhaloalkyl, haloalkoxy, perhaloalkoxy, aryl, heterocyclyl, —OH, —$OR_7$, —CN, —$NO_2$, —$NR_1R_7$, —C(O)$R_7$, —(O)$NR_1R_7$, —$NR_1$C(O)$R_7$, —$SR_7$, —S(O)$R_7$, —S(O)$_2R_7$, —OS(O)$_2R_7$, —S(O)$_2NR_1R_7$, —$NR_1$S(O)$_2R_7$, —($CR_aR_b$)$_m$$NR_1R_7$, —($CR_aR_b$)$_m$O($CR_aR_b$)$_m$$R_7$, —($CR_aR_b$)$_m$$NR_1$($CR_aR_b$)$_m$$R_7$ or —($CR_aR_b$)$_m$$NR_1$($CR_aR_b$)$_m$$COOR_8$; or any two $R_3$ or $R_4$ groups on the same carbon atom taken together form oxo;

$R_5$ is $R_7$, —($CR_aR_b$)$_m$—($CR_aR_b$)$_m$—$R_7$, or -(-$L_3$-($CR_aR_b$)$_r$-$L_3$-$R_7$, wherein the carbon atoms of any two adjacent —($CR_aR_b$)$_m$ or ($CR_aR_b$)$_r$ groups may be taken together to form a double bond (—C($R_a$)═C($R_a$)—) or triple bond (—C≡C—);

$R_6$ is H, alkyl, aryl, heteroaryl, heterocyclyl, heterocycloalkyl, any of which may be optionally substituted (singly or multiply) with $R_7$ or —($CR_aR_b$)$_m$-$L_2$-($CR_aR_b$)$_m$—$R_7$;

each $R_7$ is independently $R_{10}$; a ring moiety selected from cycloalkyl, aryl, aralkyl, heterocyclyl or heterocyclylalkyl, where such ring moiety is optionally (singly or multiply) substituted with $R_{10}$; or when a carbon atom bears two $R_7$ groups such two $R_7$ groups are taken together to form oxo or thioxo, or are taken together to form a ring moiety selected from cycloalkyl, aryl, heterocyclyl or heterocyclylalkyl, wherein such ring moiety is optionally singly or multiply substituted with $R_{10}$;

each $R_8$ is independently H, alkyl, haloalkyl, aryl, —($CR_aR_b$)$_m$-$L_2$-($CR_aR_b$)$_m$—$R_1$ or -(-$L_3$-($CR_aR_b$)$_r$-)$_s$-$L_3$-$R_1$;

each $R_{10}$ is independently H, halo, alkyl, haloalkyl, haloalkoxy, perhaloalkyl, perhaloalkoxy, —($CR_aR_b$)$_m$OH, —($CR_aR_b$)$_m$$OR_8$, —($CR_aR_b$)$_m$CN, —($CR_aR_b$)$_m$NH(C═NH)$NH_2$, —($CR_aR_b$)$_m$$NR_1R_8$, —($CR_aR_b$)$_m$O($CR_aR_b$)$_m$$R_8$, —($CR_aR_b$)$_m$$NR_1$($CR_aR_b$)$_m$$R_8$, —($CR_aR_b$)$_m$C(O)$R_8$, —($CR_aR_b$)$_m$C(O)$OR_8$, —($CR_aR_b$)$_m$C(O)$NR_1R_8$, —($CR_aR_b$)$_m$$NR_1$($CR_aR_b$)$_m$C(O)$OR_8$, —($CR_aR_b$)$_m$$NR_1$C(O)$R_8$, —($CR_aR_b$)$_m$C(O)$NR_1$S(O)$_2R_8$, —($CR_aR_b$)$_m$$SR_8$, —($CR_aR_b$)$_m$S(O)$R_8$, —($CR_aR_b$)—S(O)$_2R_8$, —($CR_aR_b$)$_m$S(O)$_2NR_1R_8$ or —($CR_aR_b$)$_m$$NR_1$S(O)$_2R_8$;

each $R_{31}$ is independently H, halo, hydroxyl, —$NR_{41}R_{42}$, or alkoxy;

each $R_{40}$ is independently H, $R_7$, alkyl which may be optionally (singly or multiply) substituted with $R_7$, or $R_{40}$ and $R_1$ taken together with the N atom to which they are attached form a 3- to 7-membered heterocyclyl which may be optionally (singly or multiply) substituted with $R_7$;

each $R_{41}$ and $R_{42}$ is independently $R_{40}$, —($CHR_{40}$)$_n$—C(O)O—$R_{40}$, —($CHR_{40}$)$_n$—C(O)—$R_{40}$, —($CH_2$)$_n$—N($R_1$)($R_7$), aryl or heteroaryl any of which aryl or heteroaryl may be optionally (singly or multiply) substituted with $R_7$; or any two $R_{41}$ and $R_{42}$ taken together with the N atom to which they are attached form a 3- to 7-membered heterocyclyl which may be optionally (singly or multiply) substituted with $R_7$;

each $R_a$ and $R_b$ is independently H, halo, alkyl, alkoxy, aryl, aralkyl, heterocyclyl, heterocyclylalkyl (any of which alkyl, alkoxy, aryl, aralkyl, heterocyclyl or heterocyclylalkyl may be optionally (singly or multiply) substituted with $R_7$), $—(CHR_{40})_mC(O)OR_{40}$, $—(CHR_{40})_mOR_{40}$, $—(CHR_{40})_mSR_{40}$, $—(CHR_{40})_m NR_{41}R_{42}$, $—(CHR_{40})_mC(O)NR_{41}R_{42}$, $—(CHR_{40})_mC(O)N(R_1)(CHR_{40})_mNR_{41}R_{42}$, $—(CHR_{40})_mC(O)N(R_1)(CHR_{40})_mC(O)NR_{41}R_{42}$, $—(CHR_{40})_mC(O)N(R_1)—(CHR_{40})_mC(O)OR_{40}$, or $—(CHR_{40})_m—S—S—R_{40}$; or any two $R_a$ and $R_b$ taken together with the carbon atom(s) to which they are attached form a cycloalkyl or heterocyclyl optionally substituted (singly or multiply) with $R_7$; or $R_1$ and any one of $R_a$ or $R_b$ taken together with the atoms to which they are attached form heterocyclyl optionally substituted (singly or multiply) with $R_7$;

$L_2$ is independently, from the proximal to distal end of the structure of Formula I-R or I-S, null, —O—, —OC(O)—, $—NR_1—$, $—C(O)NR_1—$, $—N(R_1)—C(O)—$, $—S(O_2)—$, —S(O)—, —S—, —C(O)— or $—S(O_2)—N(R_1)—$;

each $L_3$ is independently null, —O—, or $—N(R_1)—$ each m is independently 0, 1, 2, 3, 4, 5 or 6;

each n is independently 0 or 1 or 2;

p is 0, 1, 2 or 3;

q is 0, 1, 2 or 3;

each r is independently 2, 3, or 4; and each s is independently 1, 2, 3, or 4.

2. The compound of claim 1 having the following structure:

I-R/S (1)

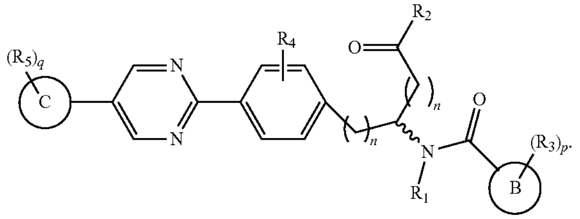

3. The compound of claim 1 having the following structure:

I-R/S (2)

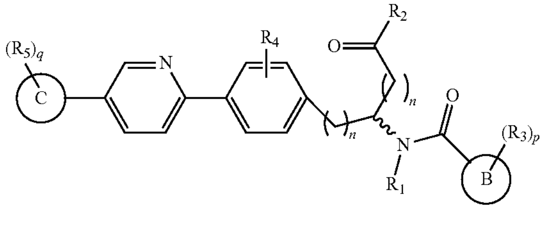

or

-continued

I-R/S (3)

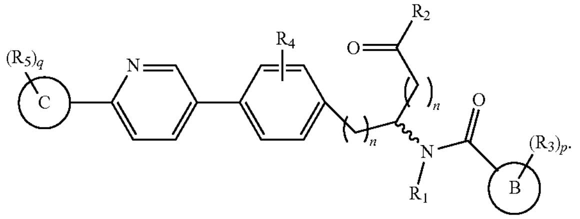

4. The compound of claim 1 having the following structure:

I-R/S (4)

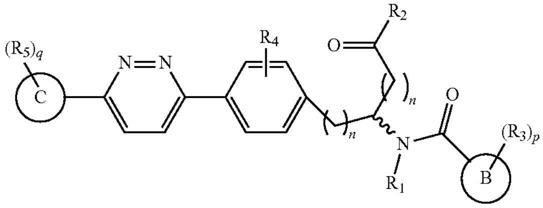

or

I-R/S (5)

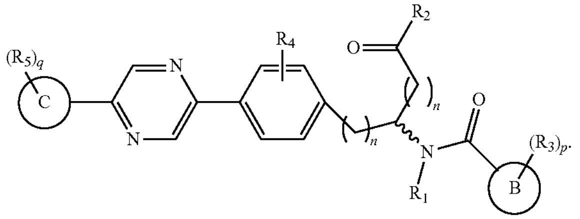

5. The compound of claim 1 having the following structure:

I-R/S (7)

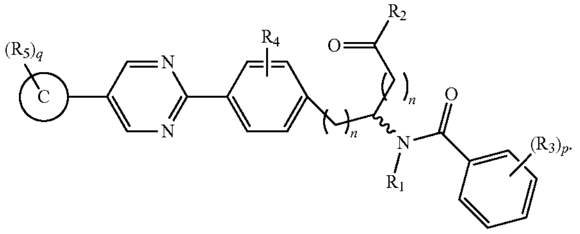

6. The compound of claim 1 having the following structure:

I-R/S (8)

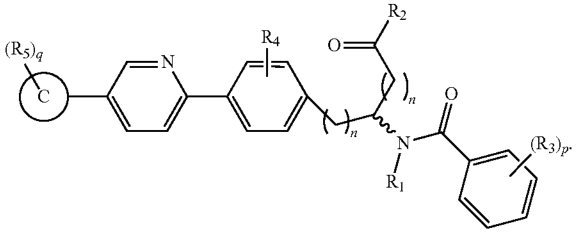

7. The compound of claim 1 having the following structure:

I-R/S (9)

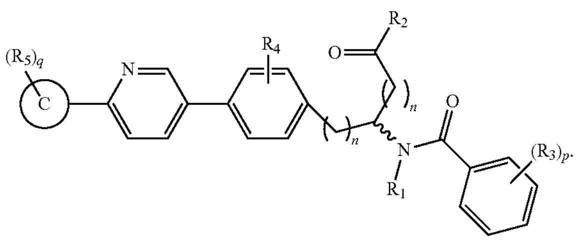

8. The compound of claim 1 having the following structure:

I-R/S (10)

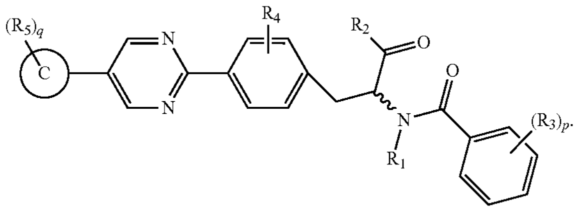

9. The compound of claim 1 having the following structure:

I-R/S (11)

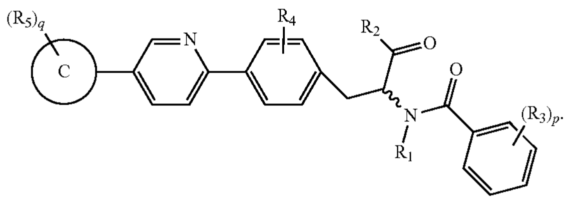

10. The compound of claim 1 having the following structure:

I-R/S (12)

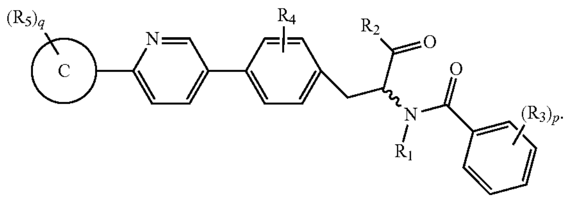

11. The compound of claim 1 having the following structure:

I-R/S (16)

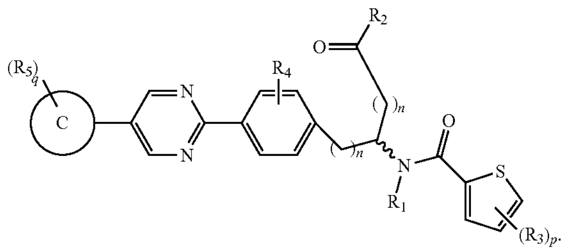

12. The compound of claim 1 having the following structure:

I-R/S (17)

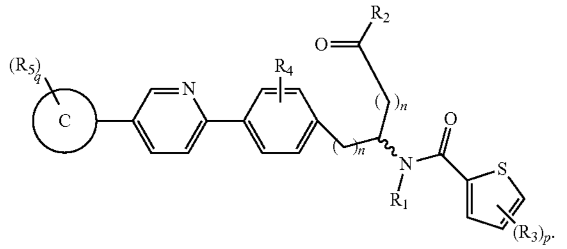

13. The compound of claim 1 having the following structure:

I-R/S (18)

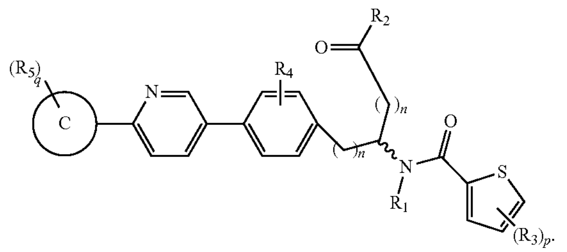

14. The compound of claim 1 having the following structure:

I-R/S (19)

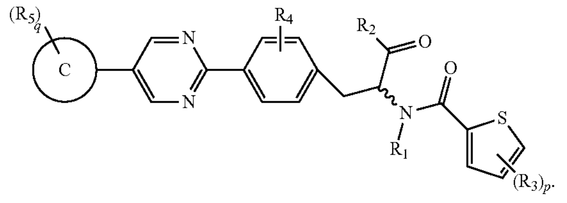

15. The compound of claim 1 having the following structure:

I-R/S (20)

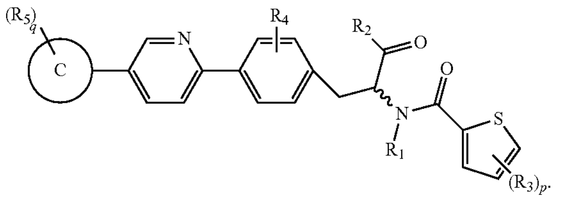

16. The compound of claim 1 having the following structure:

I-R/S (21)

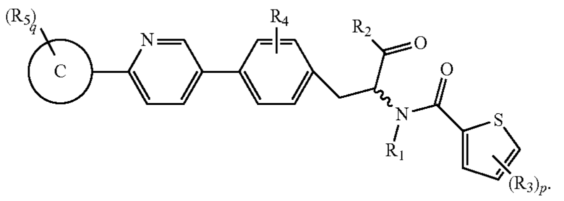

17. The compound of claim 1 wherein B is pyrimidinyl.

18. The compound of claim 1 wherein B is pyrazolyl.

19. The compound of claim 1 wherein B is pyridinyl.

20. The compound of claim 1 wherein B is indolyl.

21. The compound of claim 1 wherein C is nonaromatic carbocyclyl.

22. The compound of claim 21 wherein nonaromatic carbocyclyl is cycloalkenyl.

23. The compound of claim 21 wherein nonaromatic carbocyclyl is cycloalkenyl.

24. The compound of claim 1 wherein C is selected from:

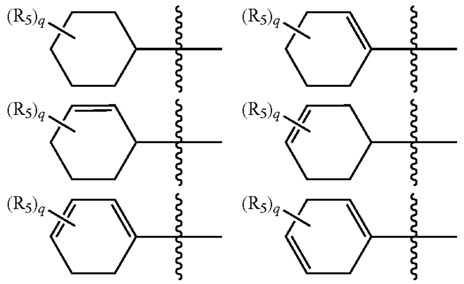

-continued

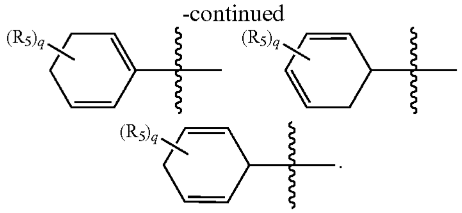

25. The compound of claim 1 having the following structure:

I-R/S (22)

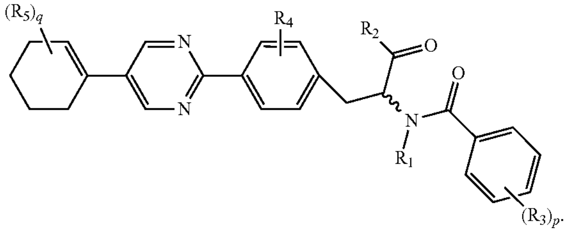

26. The compound of claim 1 having the following structure:

I-R/S (23)

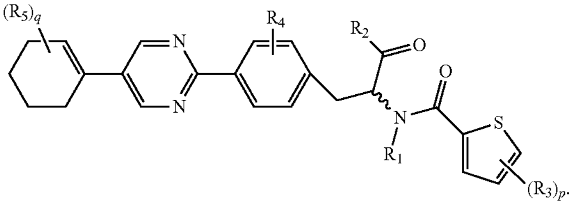

27. The compound of claim 26 wherein $R_1$ is H.

28. The compound of claim 26 wherein $R_4$ is H.

29. The compound of claim 26 wherein q is one.

30. The compound of claim 29 wherein $R_5$ is alkyl.

31. The compound of claim 26 wherein p is one.

32. The compound of claim 31 wherein $R_3$ is alkyl.

33. The compound of claim 32 wherein alkyl is a straight or branched alkyl.

34. The compound of claim 32 wherein alkyl is cycloalky.

35. The compound of claim 1 having the following structure:

I-R/S (24)

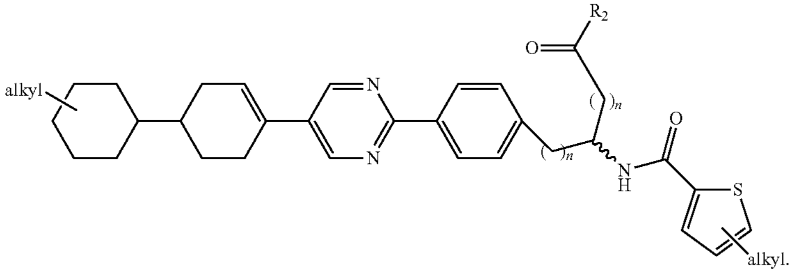

36. The compound of claim 1 having the following structure:

I-R/S (25)

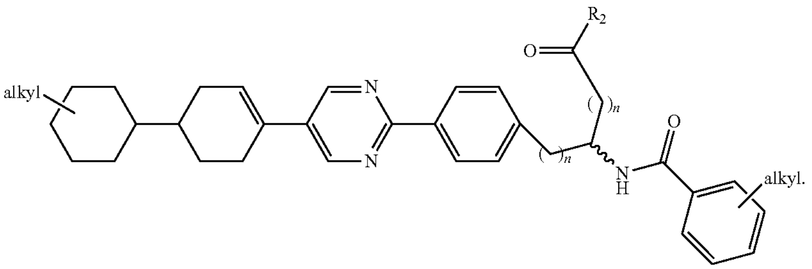

37. The compound of claim 1 having the following structure:

I-R/S (26)

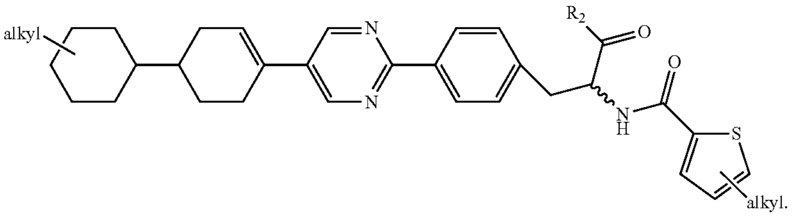

38. The compound of claim 1 having the following structure:

I-R/S (27)

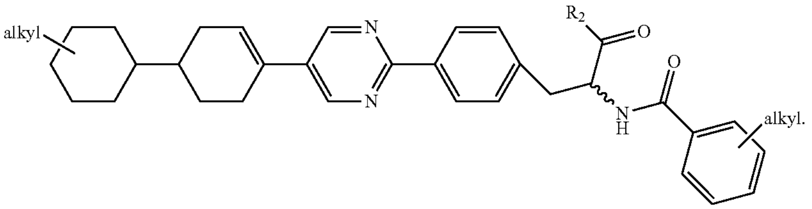

39. The compound of any one of claims 35-38 wherein each alkyl is independently a $C_1$-$C_8$ straight or branched alkyl.

40. The compound of claim 39 wherein each alkyl is independently methyl, ethyl, n-propyl, iso-propyl, n-butyl, iso-butyl, sec-butyl or tert-butyl.

41. The compound of any one of claims 35-38 wherein $R_2$ is $-N(R_1)(CR_aR_b)_mCOOR_8$.

42. The compound of claim 41 wherein m is 2, $R_1$ is hydrogen, each occurrence of $R_a$ and $R_b$ are hydrogen, and $R_8$ is hydrogen.

43. The compound of claim 41 wherein m is 1, $R_1$, $R_b$ and $R_8$ are hydrogen, and $R_a$ is as defined in claim 1.

44. The compound of claim 41 wherein m is 2, a single $R_a$ is hydrogen and the other $R_a$ is as defined in claim 1, each occurrence of $R_b$ is hydrogen, and $R_1$ and $R_8$ are hydrogen.

45. The compound claim 44 wherein the other $R_a$ is alkyl optionally substituted with $R_7$.

46. The compound of claim 45 wherein the other $R_a$ is a straight or branched alkyl selected from methyl, ethyl, n-propyl, iso-propyl, n-butyl, iso-butyl, sec-butyl and tert-butyl.

47. The compound of claim 46 wherein the other $R_a$ is methyl.

48. The compound claim 44 wherein the other $R_a$ is cycloalkyl selected from isopropyl, cyclobutyl, cyclopentyl and cyclohexyl.

49. The compound of claim 44 wherein the other $R_a$ is heterocyclyl optionally substituted with $R_7$ or heterocyclylalkyl optionally substituted with $R_7$.

50. The compound of claim 44 wherein the other $R_a$ is aryl optionally substituted with $R_7$ or aralkyl optionally substituted with $R_7$.

51. The compound of claim 44 wherein the other $R_a$ is $-(CHR_{40})_mC(O)OR_{40}$, $-(CHR_{40})_mOR_{40}$, $-(CHR_{40})_mSR_{40}$, $-(CHR_{40})_mNR_{41}R_{42}$, $-(CHR_{40})_mC(O)NR_{41}R_{42}$, $-(CHR_{40})_mC(O)N(R_1)(CHR_{40})_m-NR_{41}R_{42}$, $-(CHR_{40})_mC(O)N(R_1)(CHR_{40})_m-C(O)NR_{41}R_{42}$, $-(CHR_{40})_mC(O)N(R_1)(CHR_{40})_m-C(O)OR_{40}$, or $-(CHR_{40})_m-S-S-R_{40}$.

52. The compound of claim 41 wherein m is 1, $R_b$ is hydrogen and $R_1$ and $R_a$ taken together with the atoms to which they are attached form a heterocyclyl optionally substituted with $R_7$.

53. The compound of claim 41 wherein m is 2, $R_b$ of the second $(CR_aR_b)$ group is hydrogen and $R_1$ and $R_a$ of the second $(CR_aR_b)$ group taken together with the atoms to which they are attached form a heterocyclyl optionally substituted with $R_7$.

54. The compound of any one of claims 35-38 wherein $R_2$ is —OH.

55. The compound of any one of claims 35-38 wherein $R_2$ is —$N(R_1)$—$SO_2$—$R_8$.

56. The compound of any one of claims 35-38 wherein $R_2$ is —$N(R_1)(R_{42})$.

57. The compound of claim 56 wherein $R_{41}$ and $R_{42}$ are independently $R_{40}$, —$(CHR_{40})_n$—$C(O)OR_{40}$, —$(CHR_{40})_n$—$C(O)R_{40}$, —$(CH_2)_nN(R_1)(R_7)$, aryl optionally substituted with $R_7$, or heteroaryl optionally substituted with $R_7$.

58. The compound of claim 56 wherein $R_{41}$ is hydrogen and $R_{42}$ is alkyl optionally substituted with $R_7$.

59. The compound of claim 56 wherein $R_{41}$ is hydrogen and $R_{42}$ is —$(CHR_{40})_nC(O)OR_{40}$, —$(CHR_{40})_n(O)R_{40}$, —$(CH_2)_nN(R_1)(R_7)$, aryl optionally substituted with $R_7$, or heteroaryl optionally substituted with $R_7$.

60. The compound of of claim 56 wherein $R_{41}$ and $R_{42}$ taken together with the N atom to which they are attached form a 3- to 7-membered heterocyclyl optionally substituted with $R_7$.

61. The compound of any one of claims 35-38 wherein $R_2$ is $N(R_1)(CR_aR_b)_mCON(R_1)(R_{40})$.

62. The compound of claim 61 wherein m is 1, $R_b$ is hydrogen and $R_1$ and $R_a$ taken together with the atoms to which they are attached form a heterocyclyl optionally substituted with $R_7$.

63. The compound of claim 61 wherein m is 2, $R_b$ of the second $(CR_aR_b)$ group is hydrogen and $R_1$ and $R_a$ of the second $(CR_aR_b)$ group taken together with the atoms to which they are attached form a heterocyclyl optionally substituted with $R_7$.

64. The compound of any one of claims 35-38 wherein $R_2$ is —$N(R_1)(CR_aR_b)_mN(ROC(O)OR_8$, —$N(R_1)(CR_aR_b)_mN(R_1)(R_7)$, —$N(R_1)(CR_aR_b)_mCON(R_1)$-heterocyclyl, or —$(CR_aR_b)_mN(R_1)$heterocyclyl.

65. The compound of claim 1, wherein the compound has the structure of any one of the following compounds:

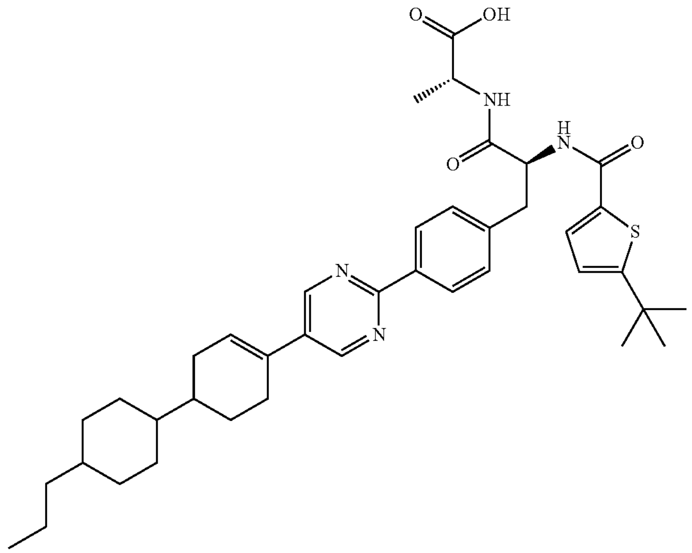 [SMILES: CCCC1CCC(C2CC=C(c3cnc(-c4ccc(C[C@H](NC(=O)c5ccc(C(C)(C)C)s5)C(=O)N[C@H](C)C(=O)O)cc4)nc3)CC2)CC1]

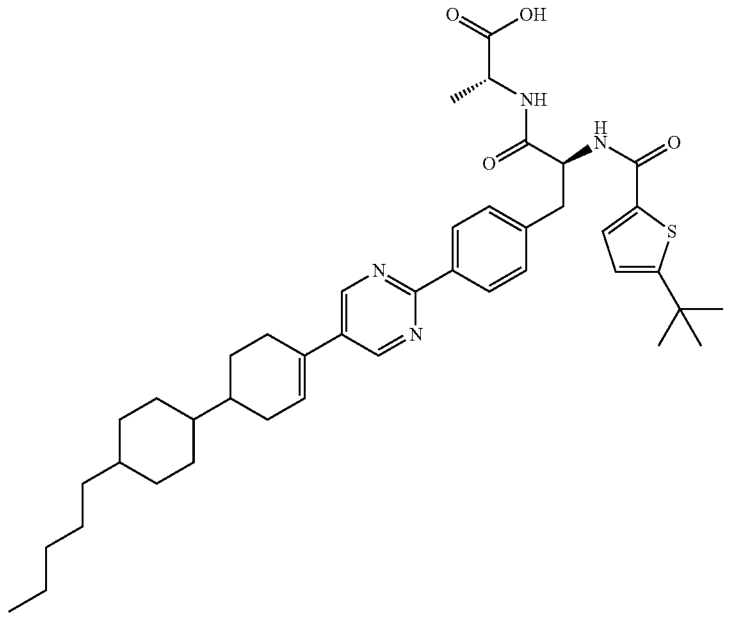

-continued
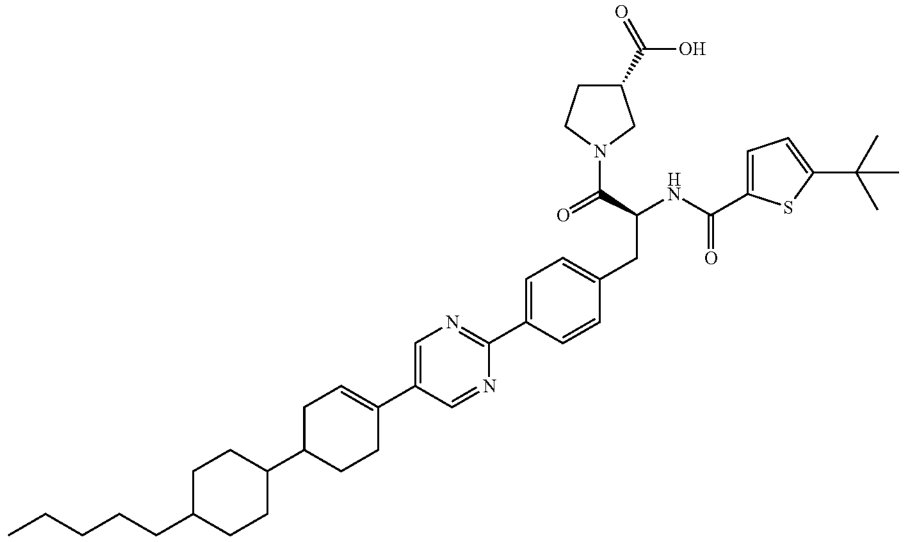
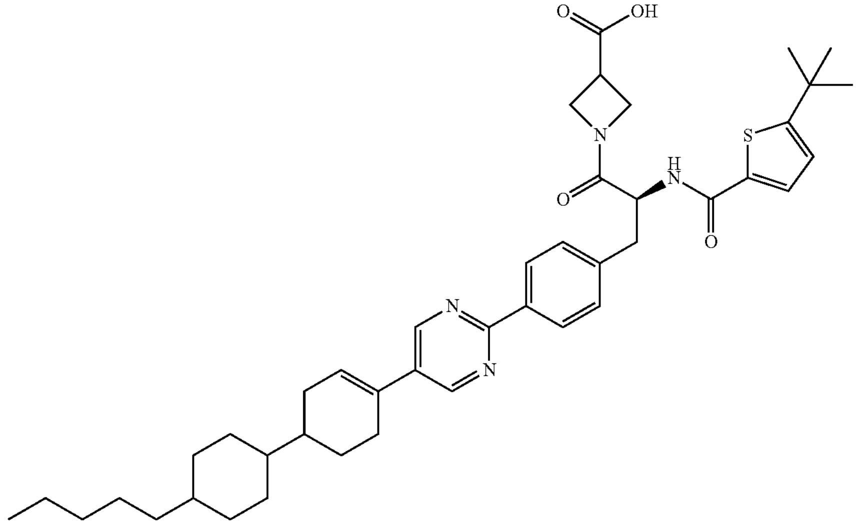
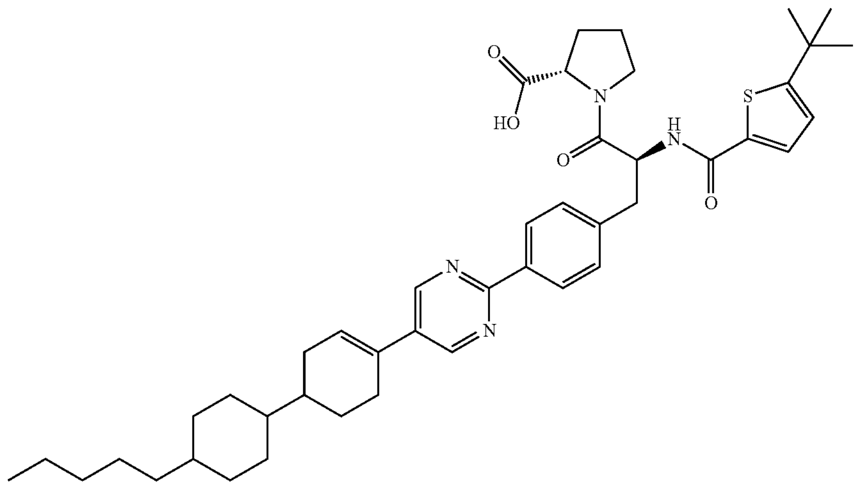

-continued
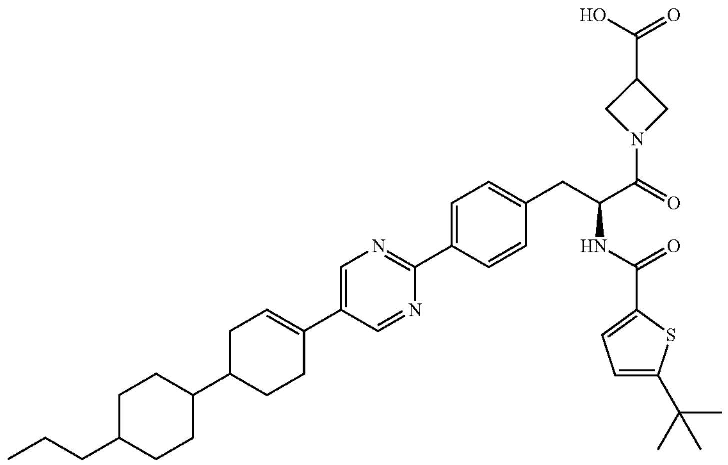 [SMILES: CCCC1CCC(C2CC=C(c3cnc(-c4ccc(C[C@H](NC(=O)c5ccc(C(C)(C)C)s5)C(=O)N5CC(C(=O)O)C5)cc4)nc3)CC2)CC1]
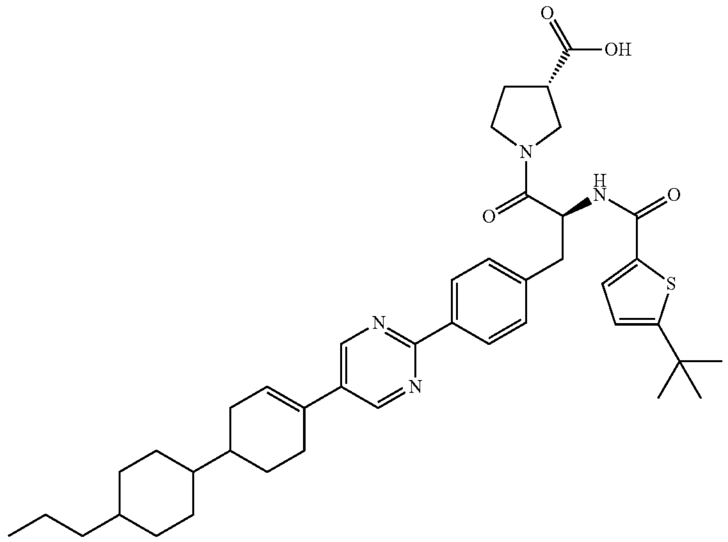 [SMILES: CCCC1CCC(C2CC=C(c3cnc(-c4ccc(C[C@H](NC(=O)c5ccc(C(C)(C)C)s5)C(=O)N5CC[C@H](C(=O)O)C5)cc4)nc3)CC2)CC1]
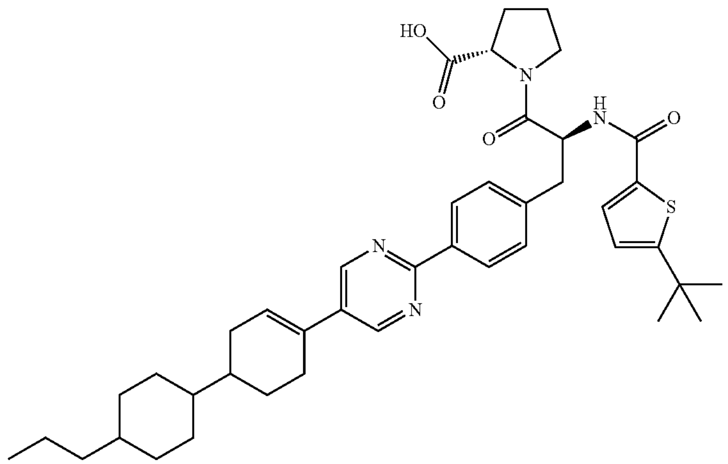

-continued
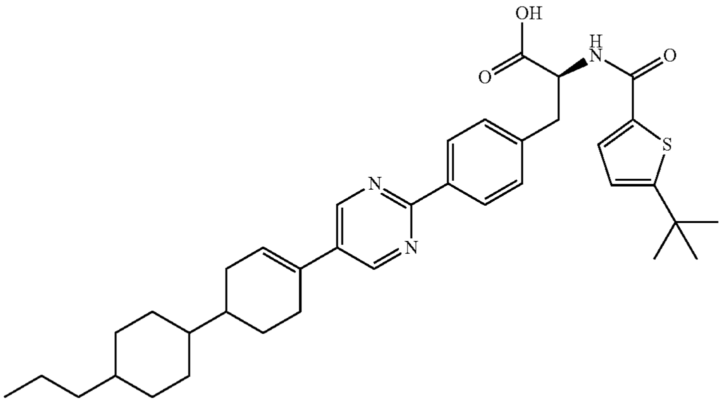
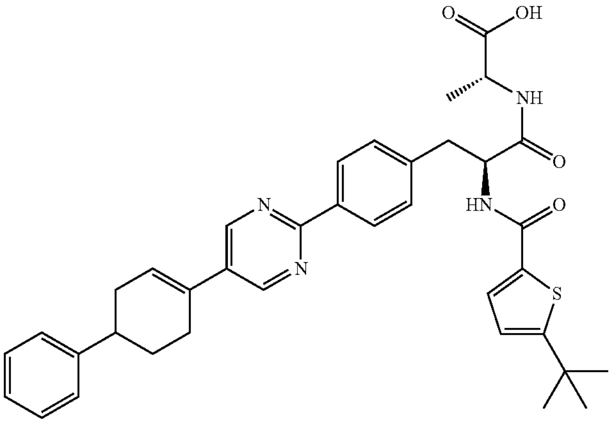
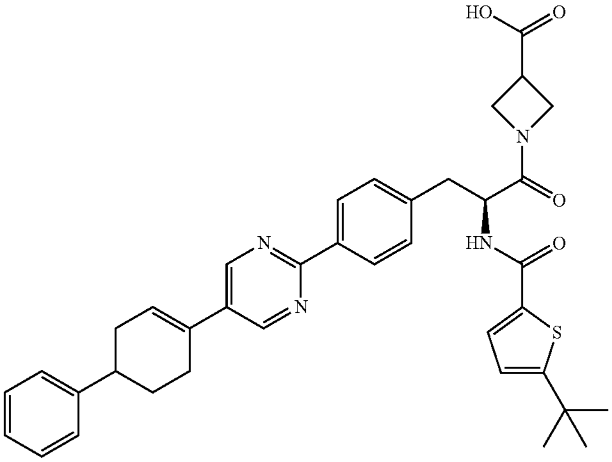

-continued
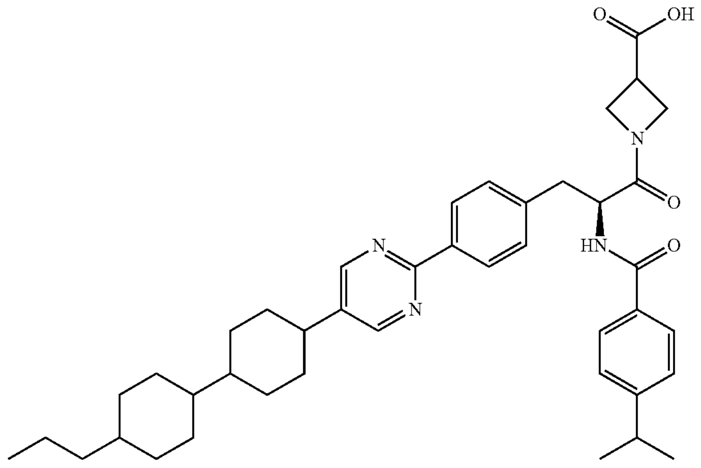
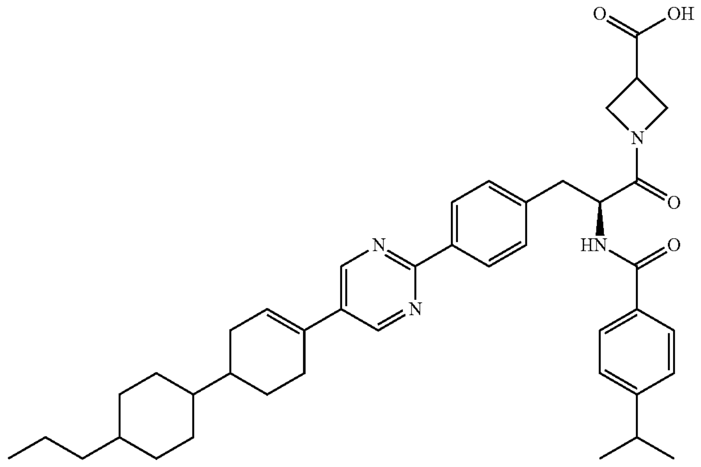
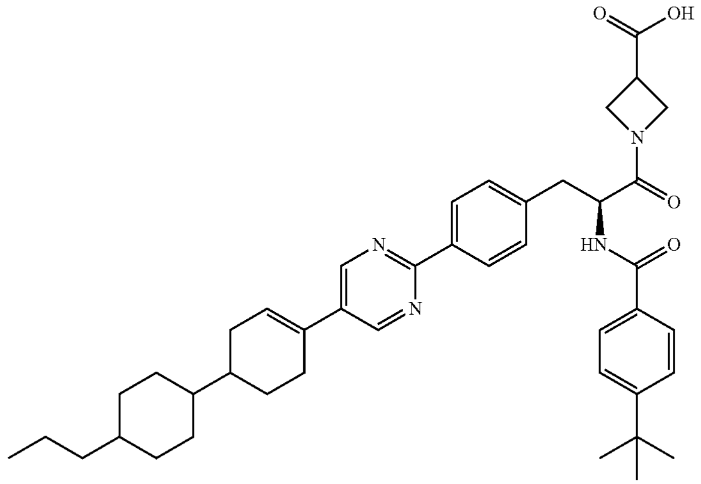

-continued
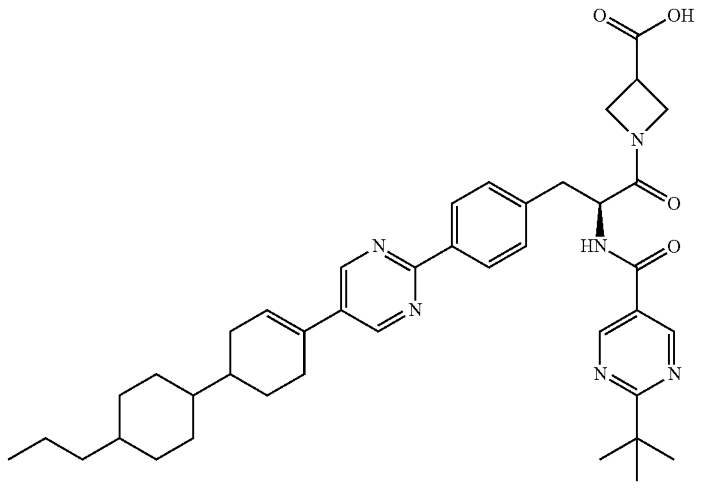
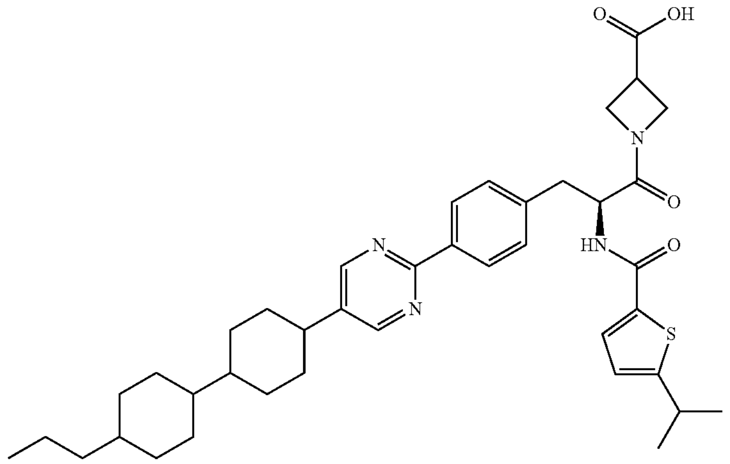
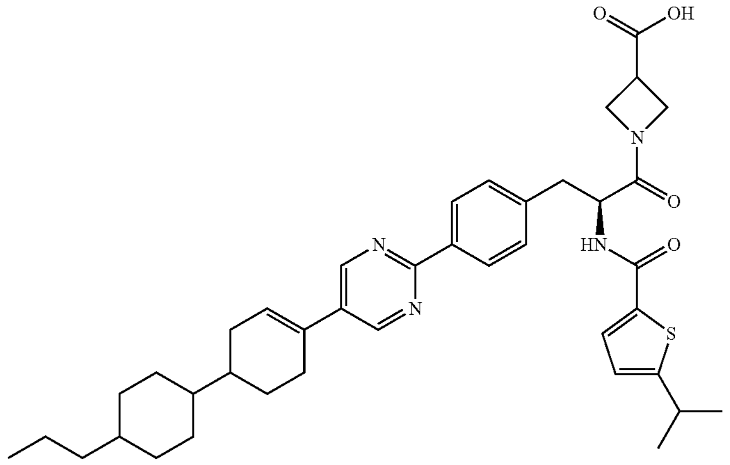

-continued
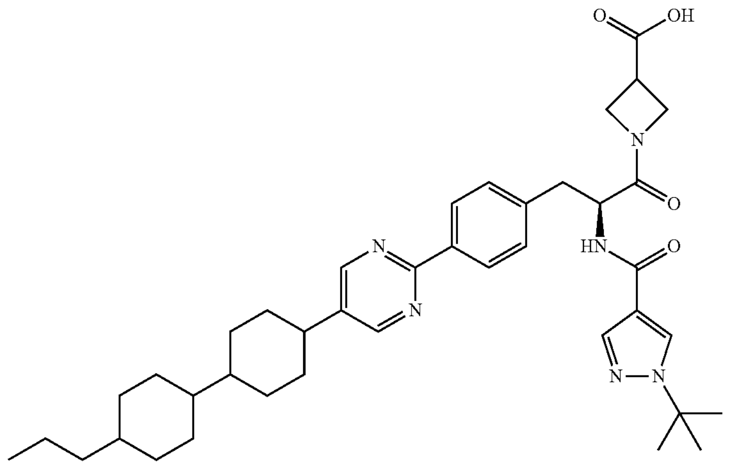
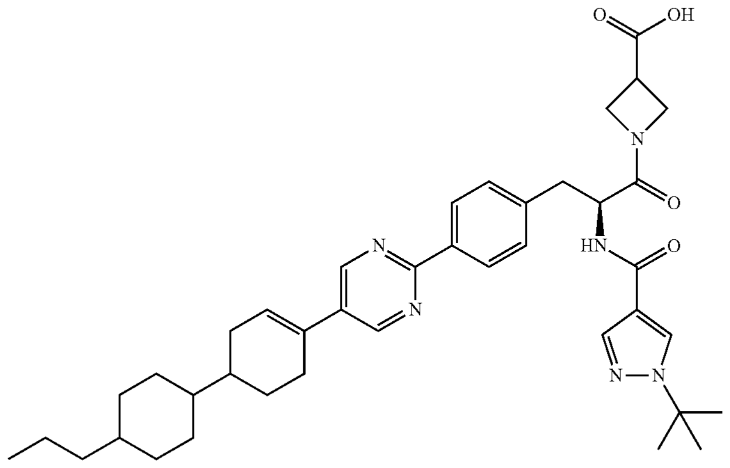
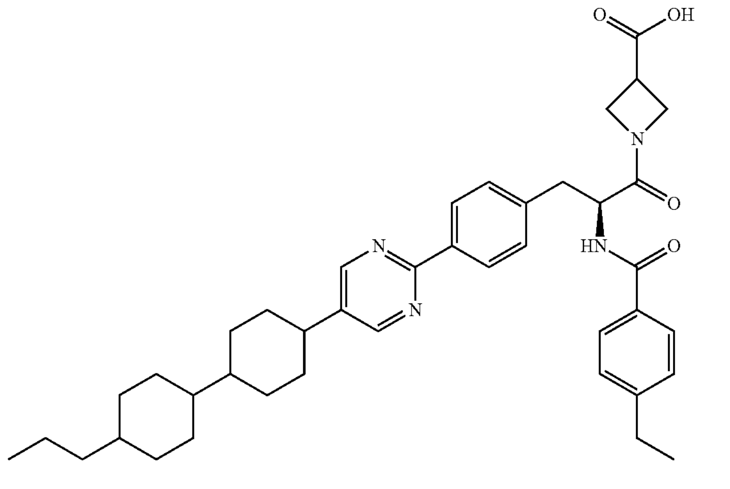

-continued
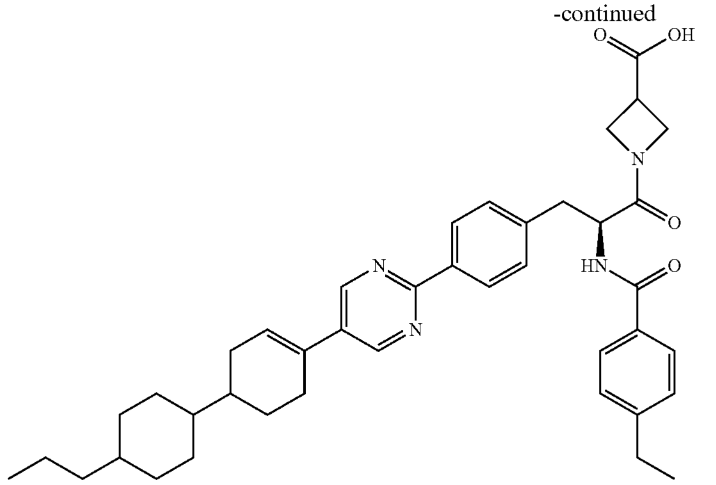
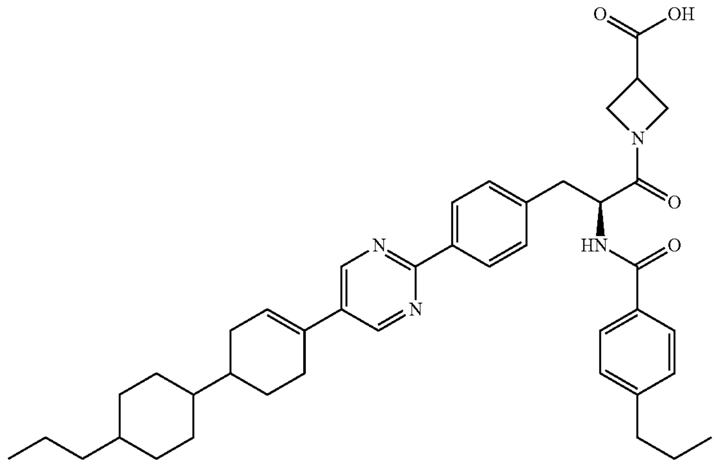
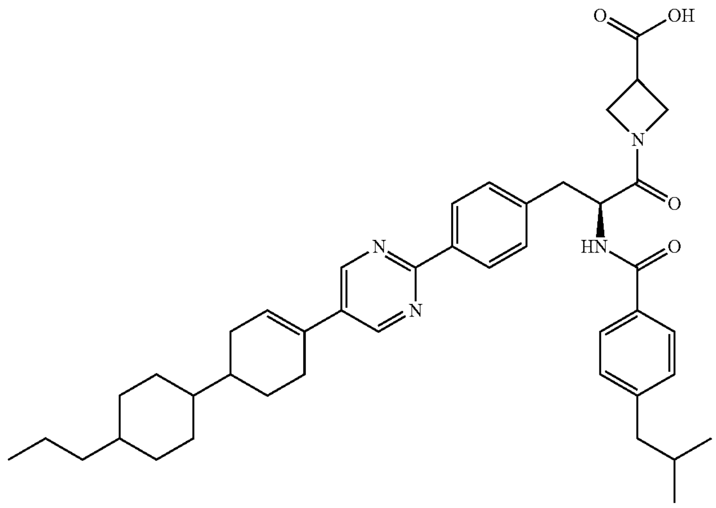

-continued
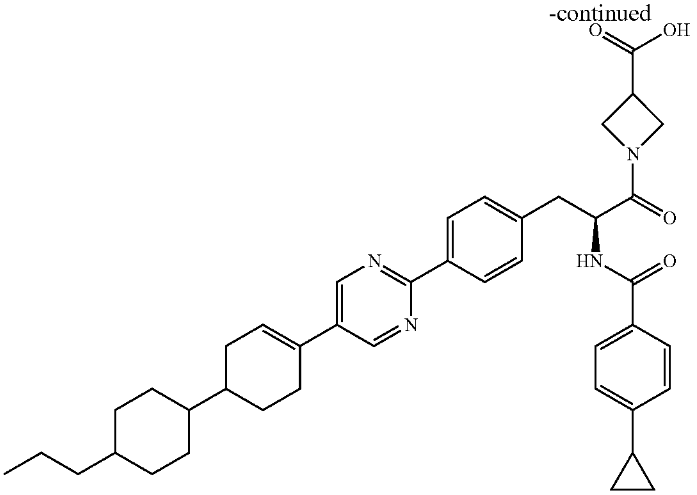
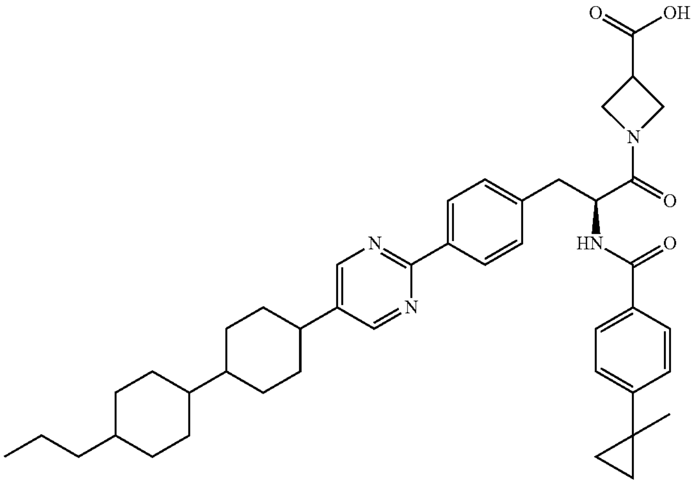
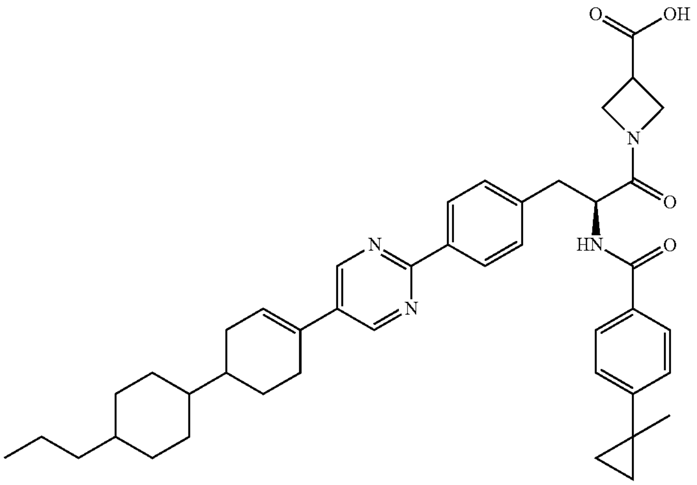

-continued
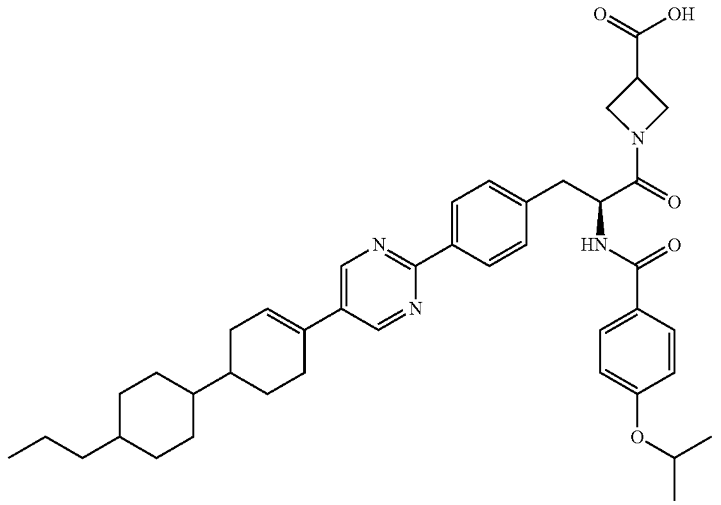
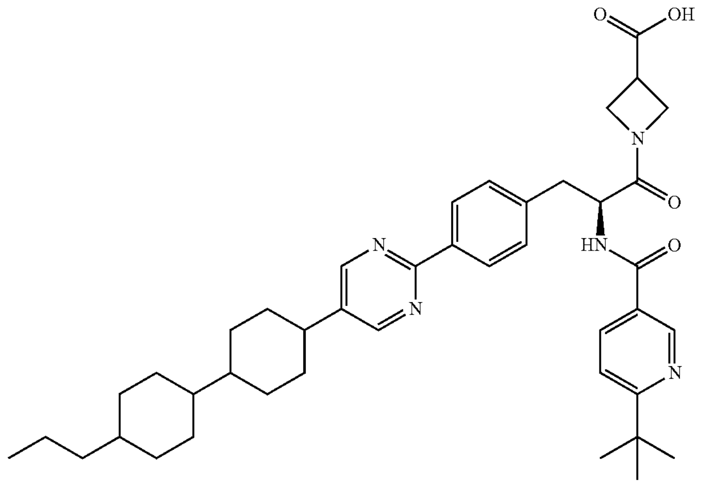
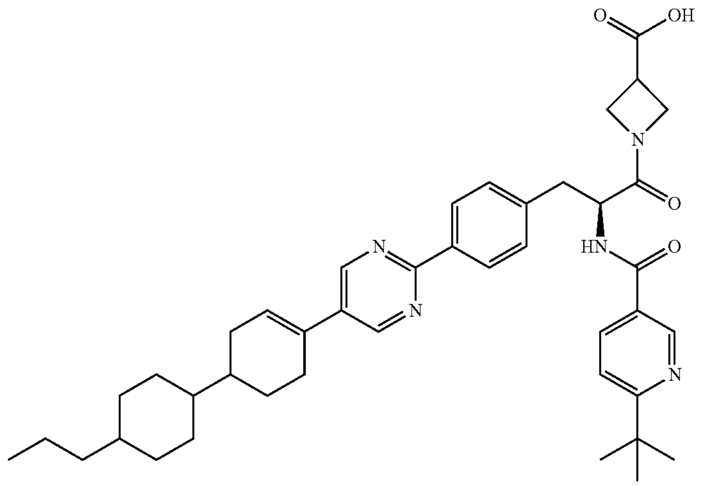

-continued
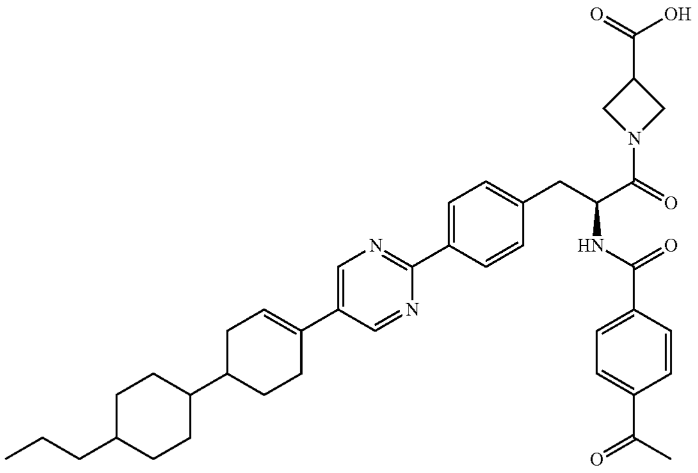
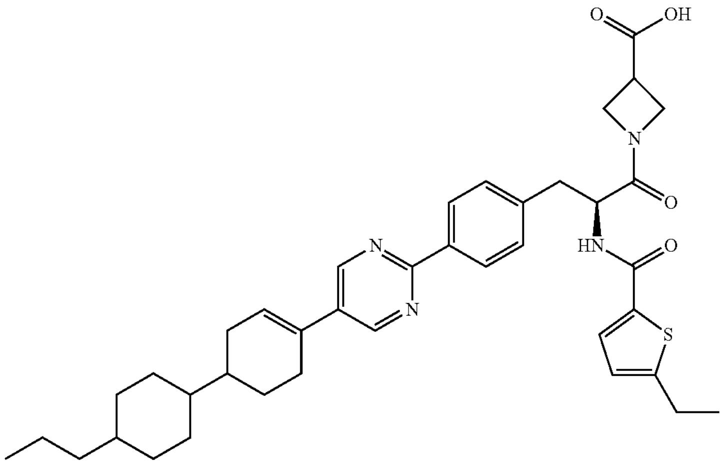
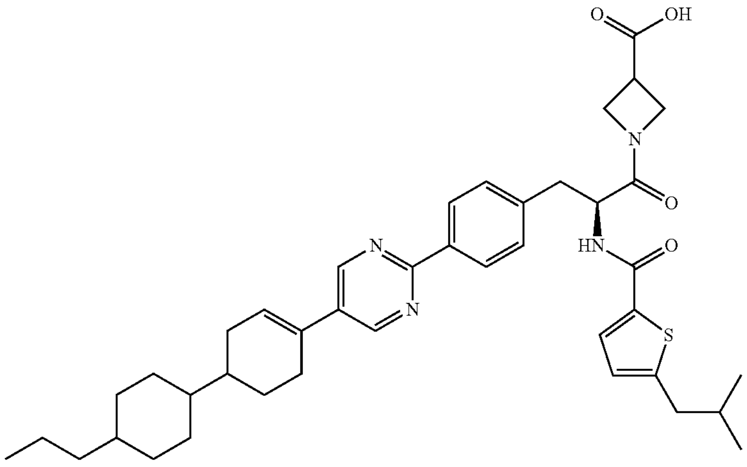

-continued
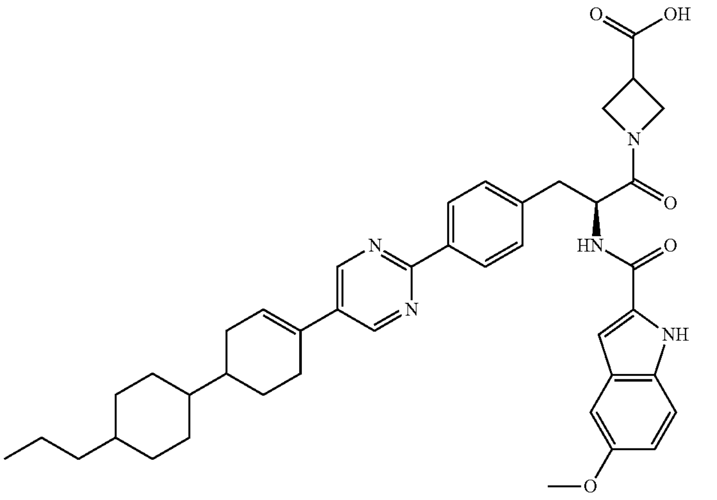
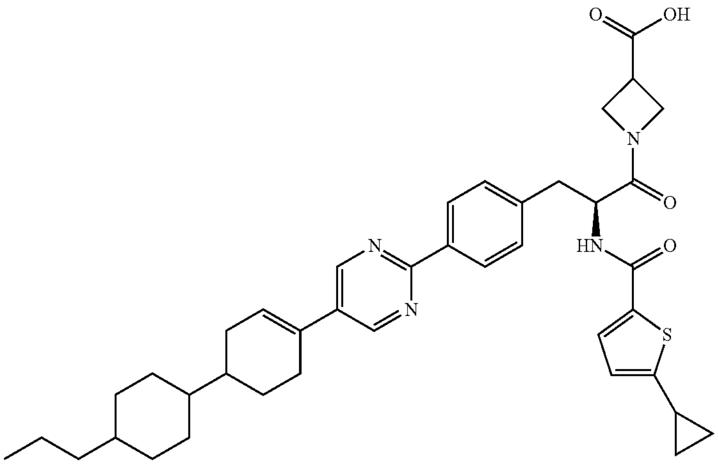
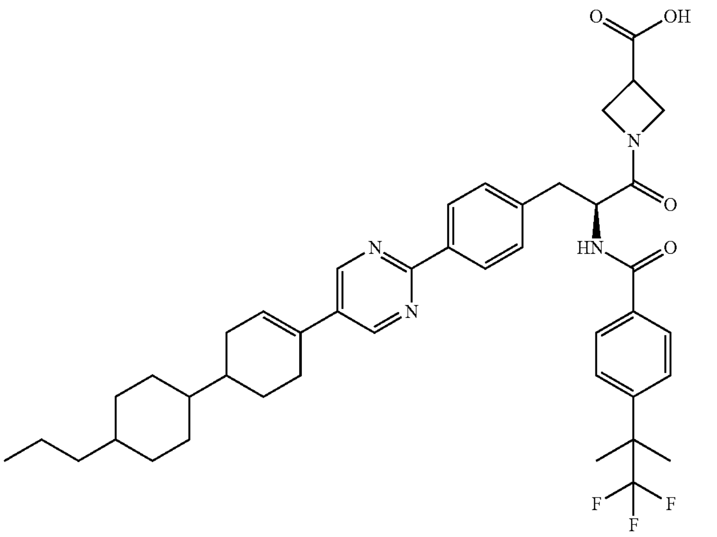

-continued
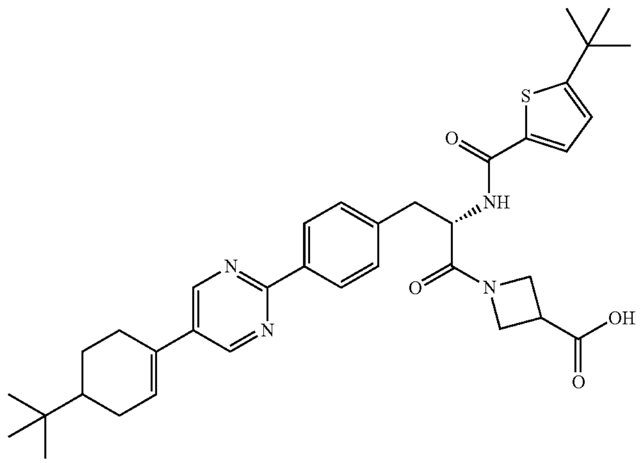
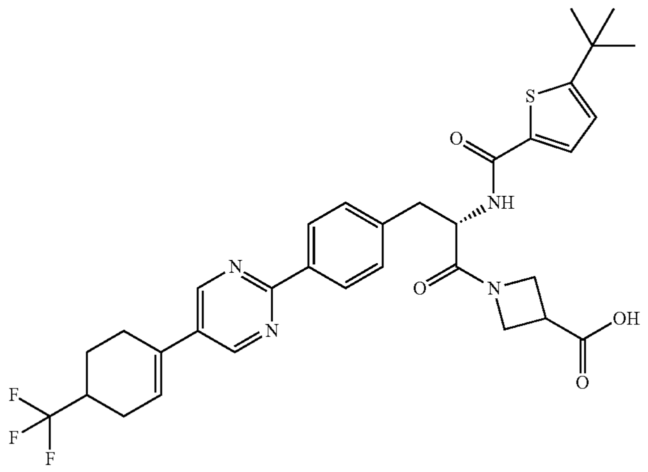
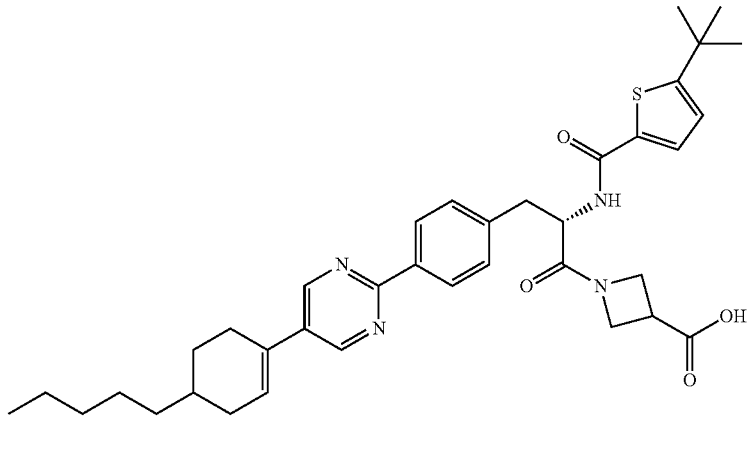

-continued
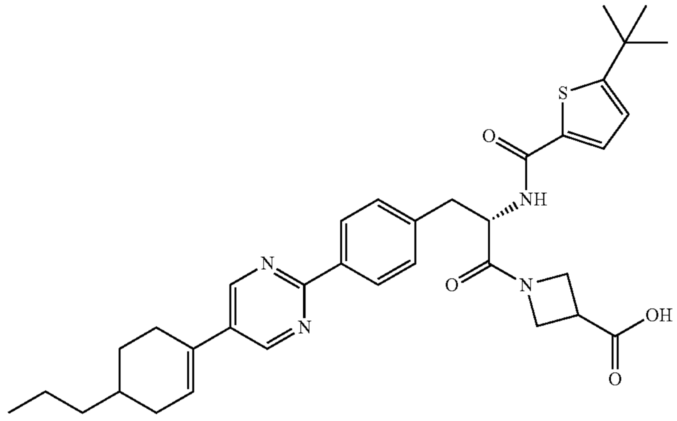
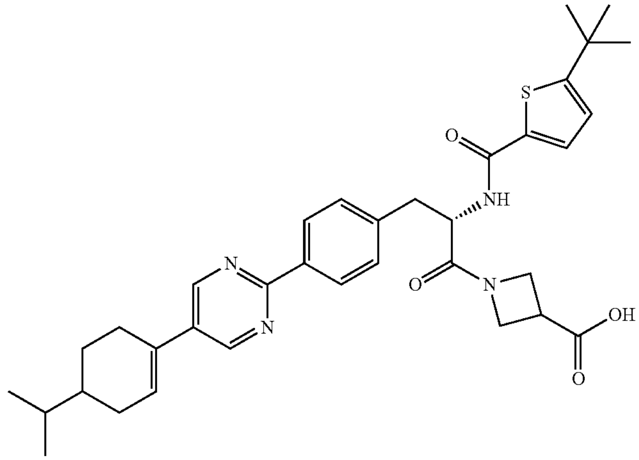
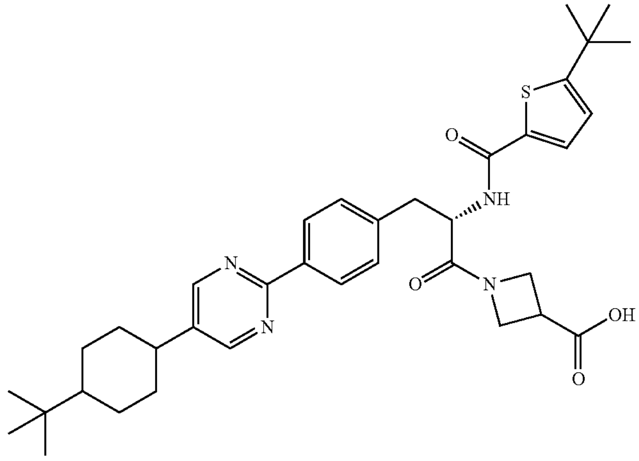

-continued
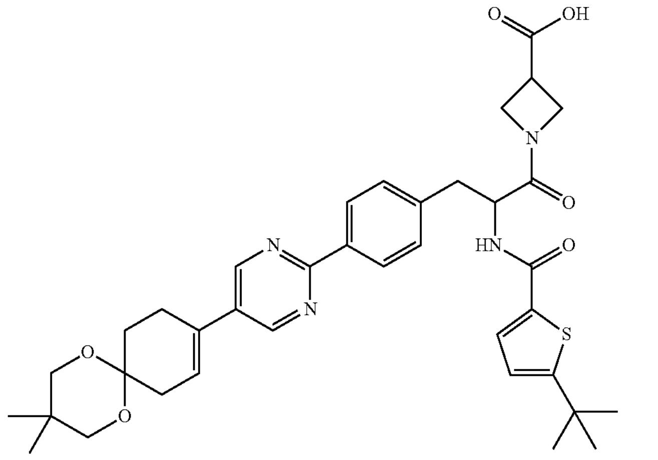
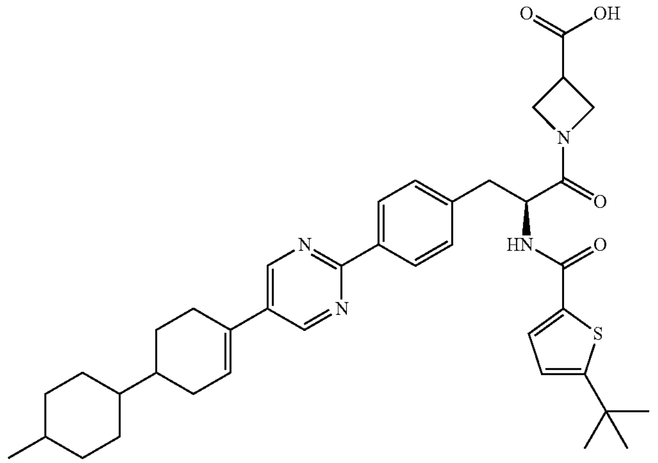 [SMILES: CC1CCC(C2CC=C(c3cnc(-c4ccc(C[C@H](NC(=O)c5ccc(C(C)(C)C)s5)C(=O)N5CC(C(=O)O)C5)cc4)nc3)CC2)CC1]
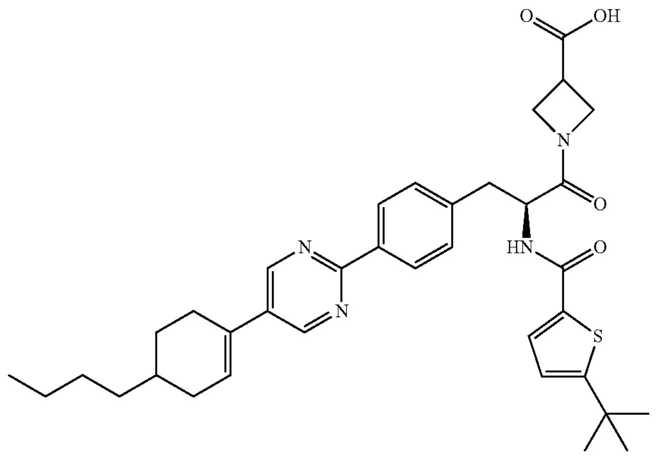

-continued
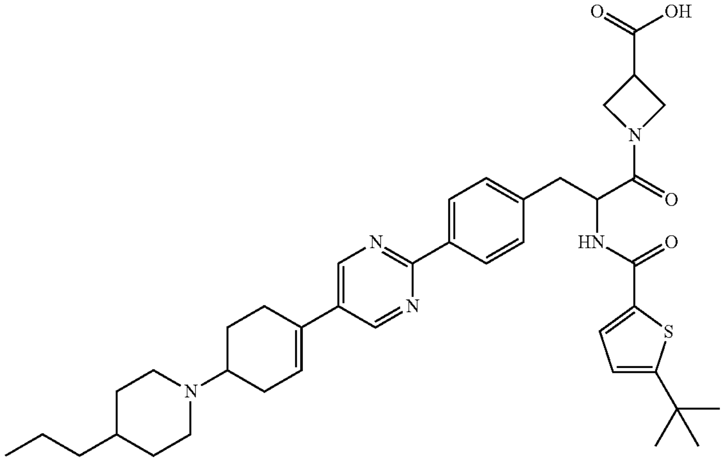
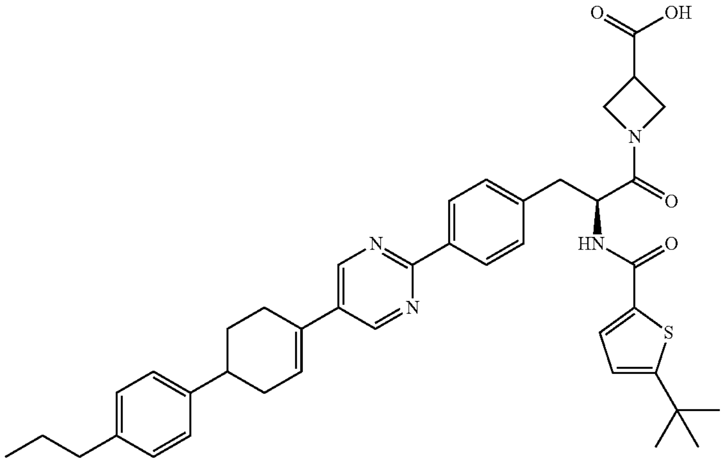
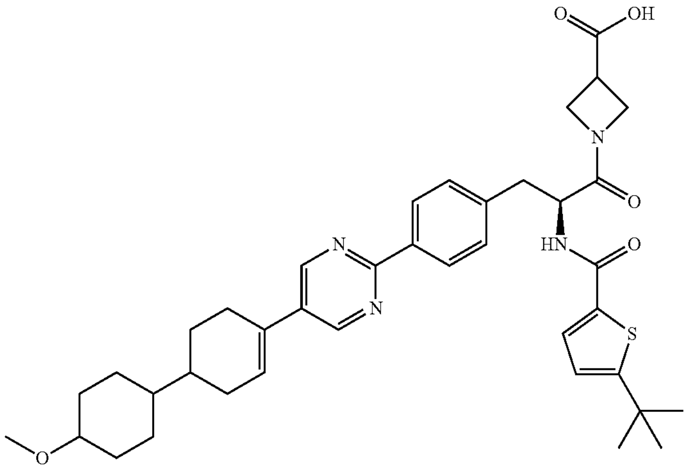

-continued
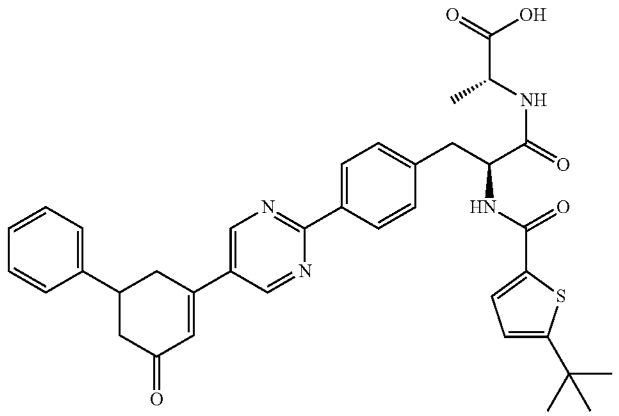
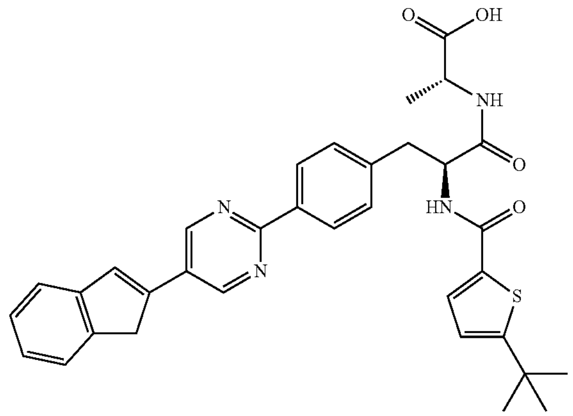
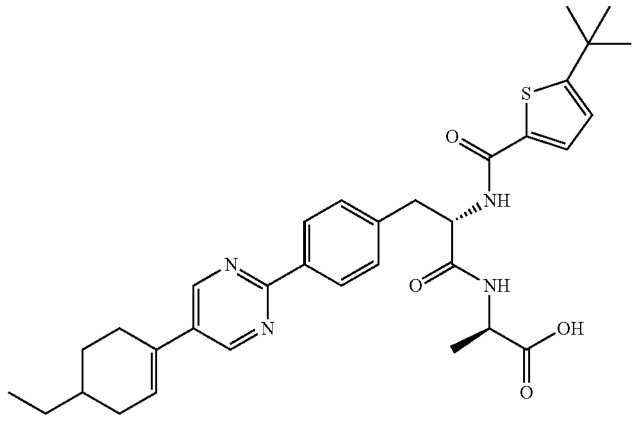
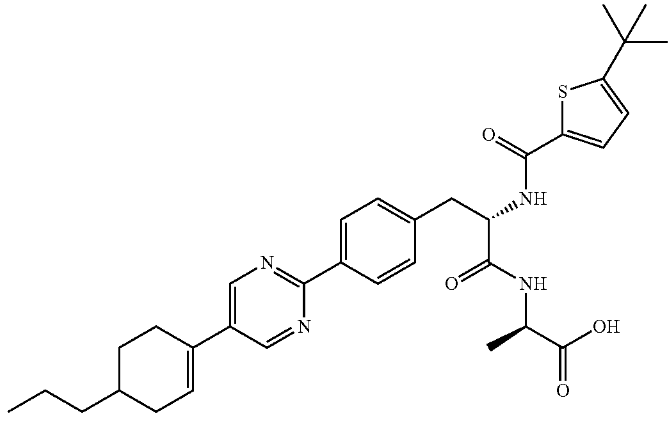
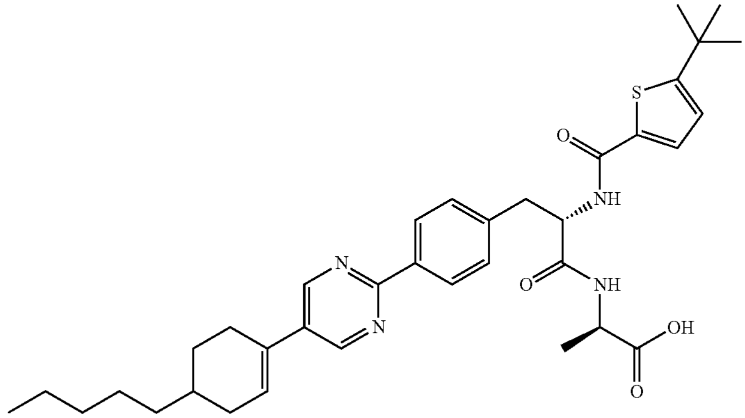

-continued
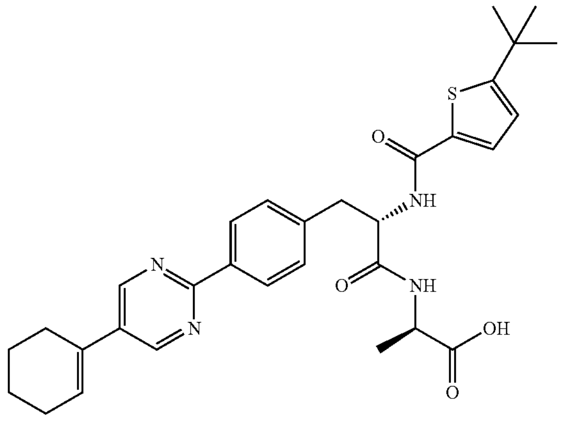
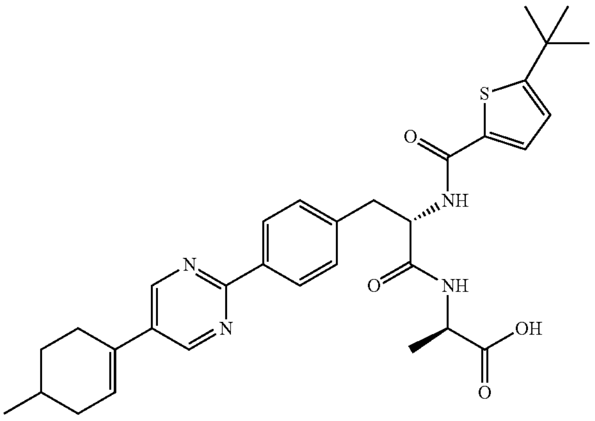
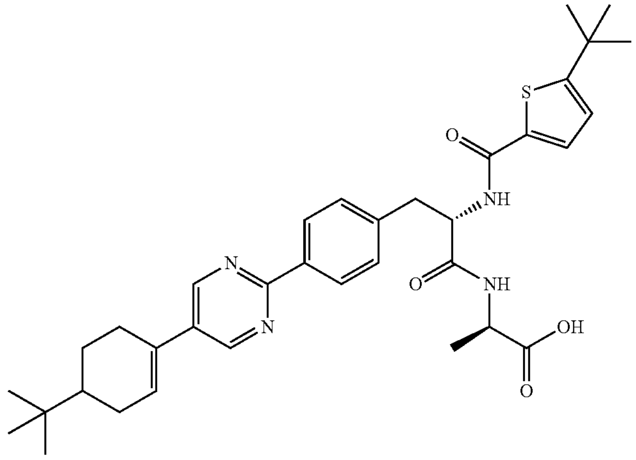
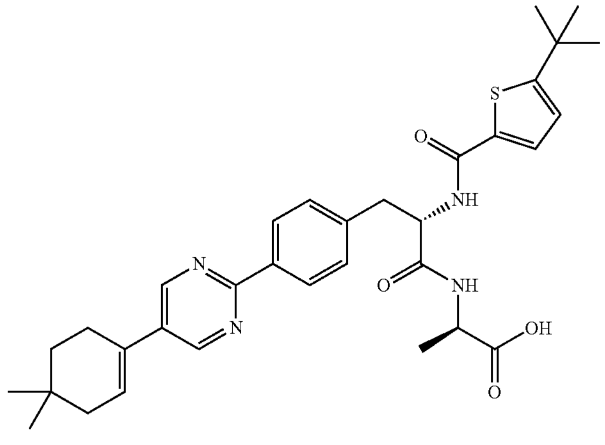
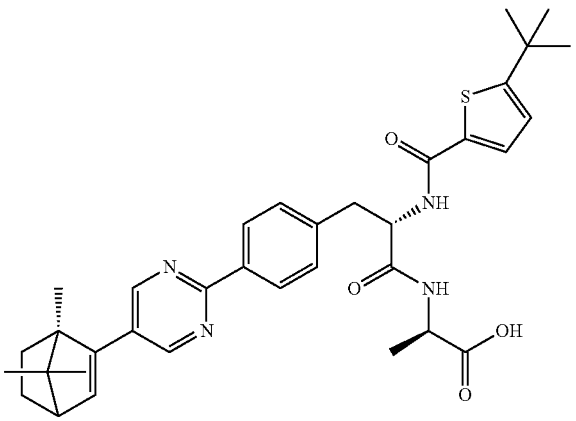

-continued
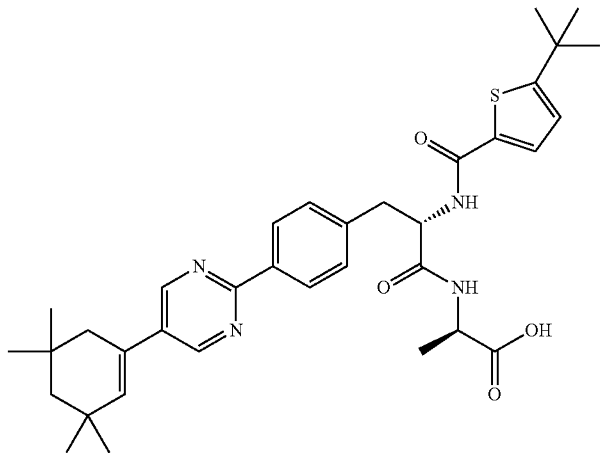
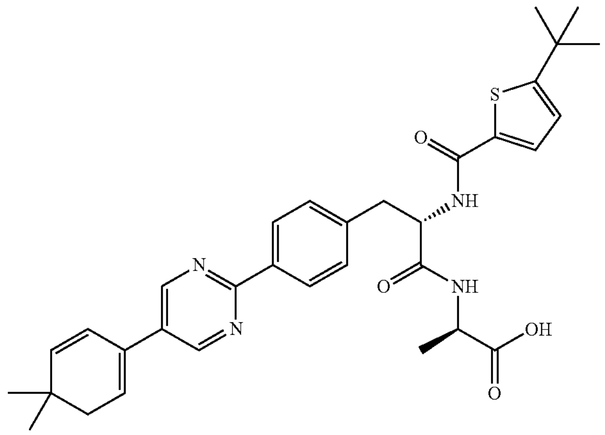
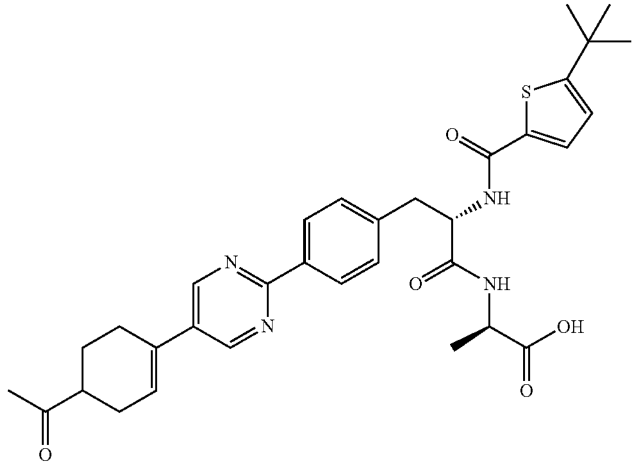

-continued
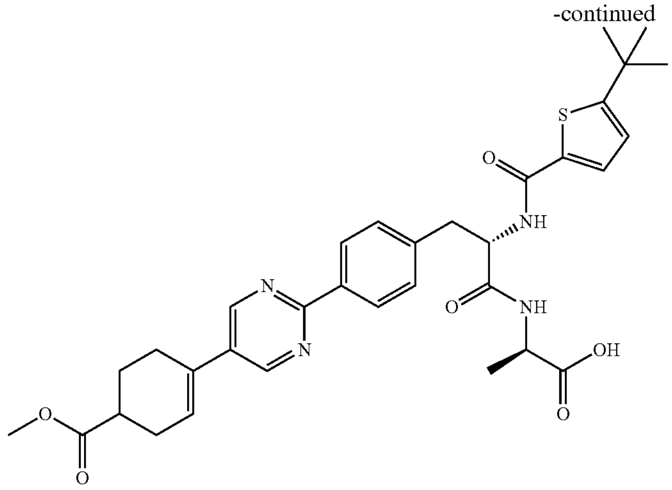
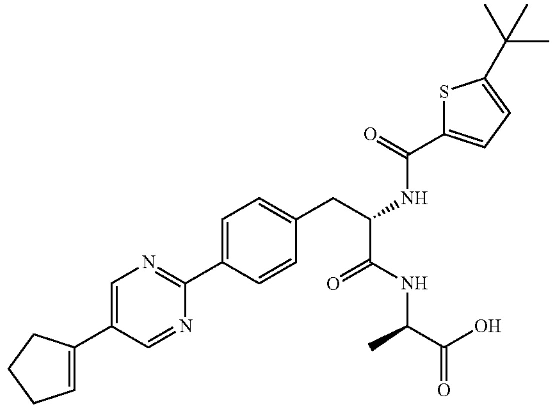
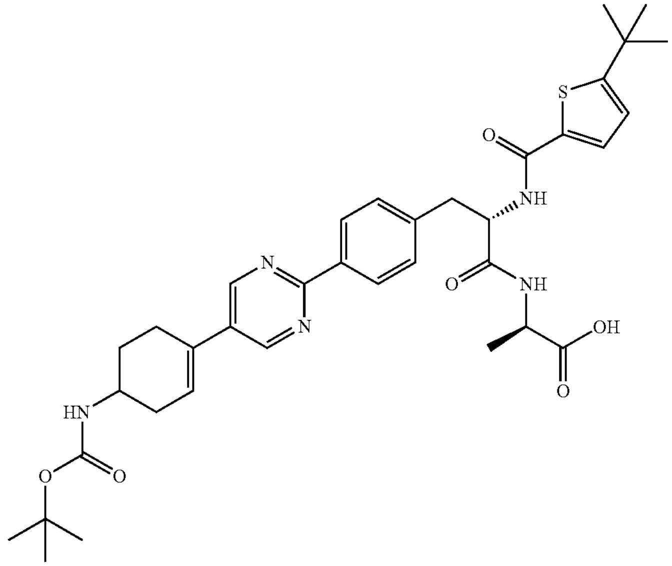

-continued
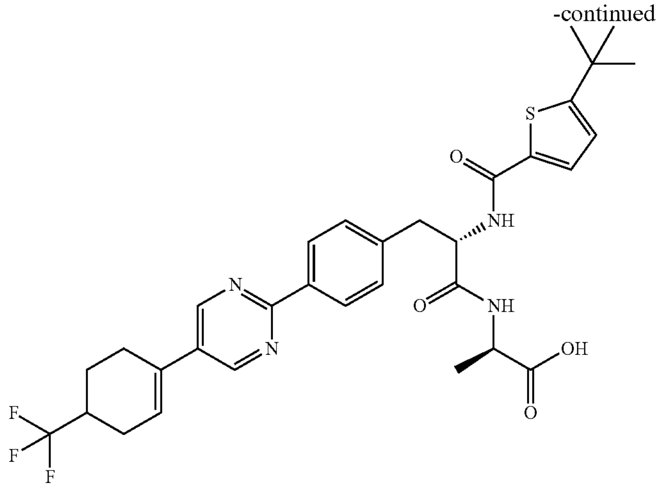
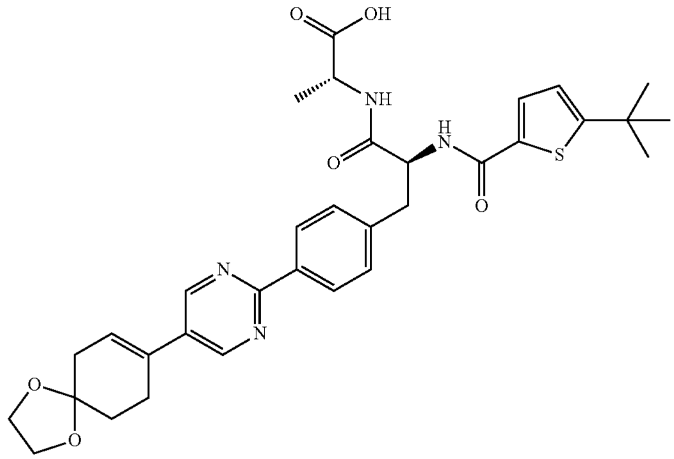
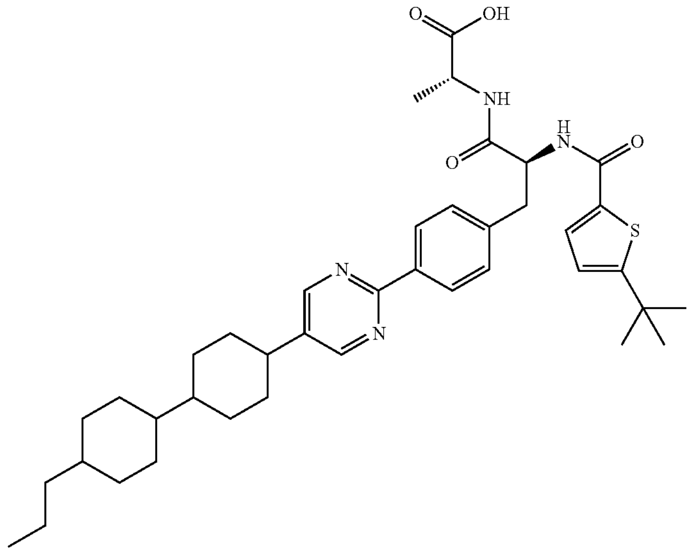

-continued
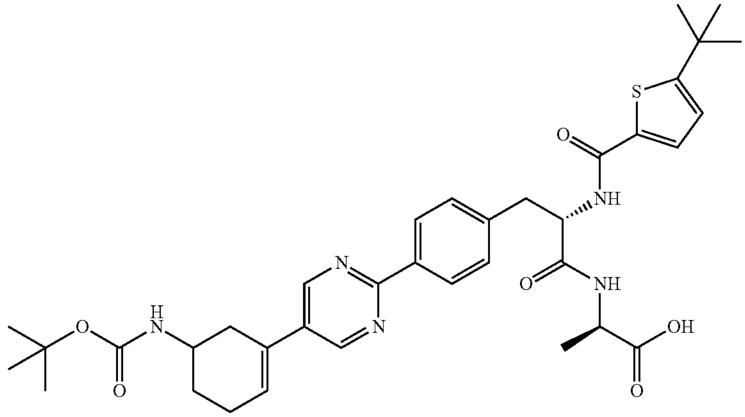
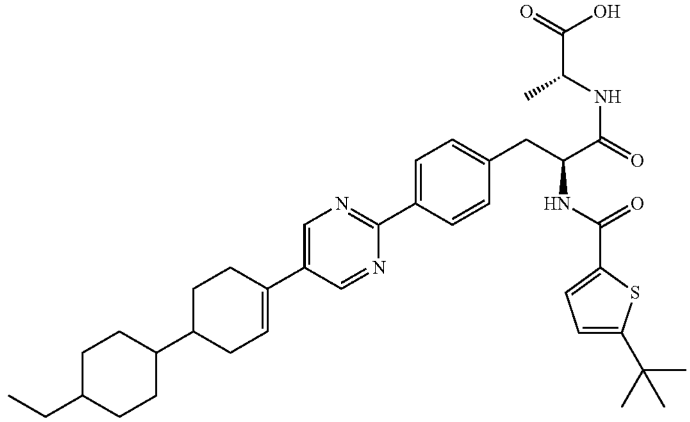 [SMILES: CCC1CCC(C2CC=C(c3cnc(-c4ccc(C[C@H](NC(=O)c5ccc(C(C)(C)C)s5)C(=O)N[C@H](C)C(=O)O)cc4)nc3)CC2)CC1]
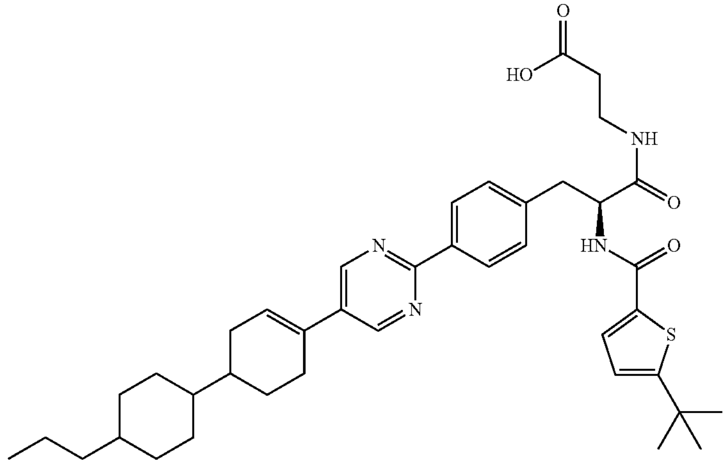
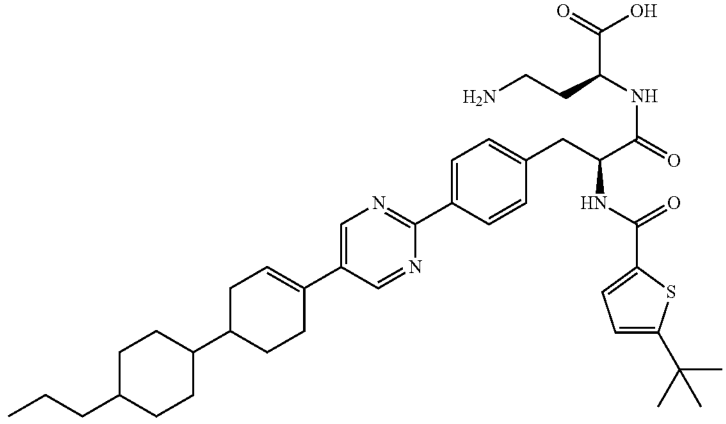

-continued
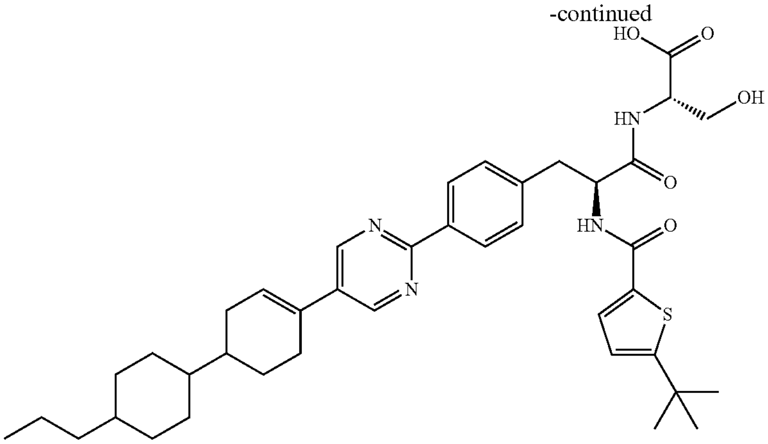
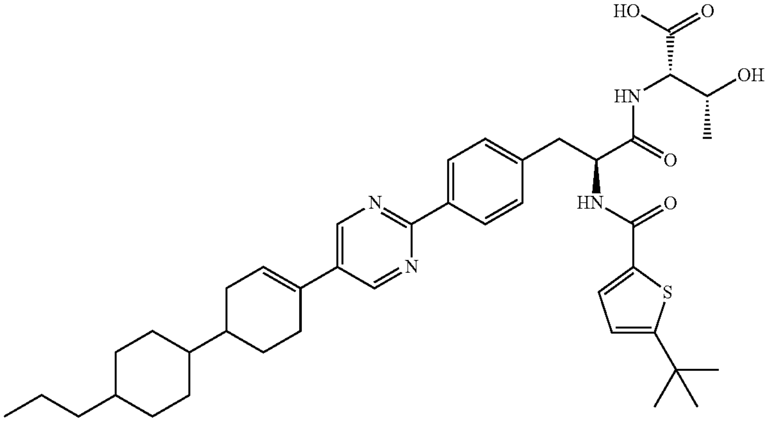
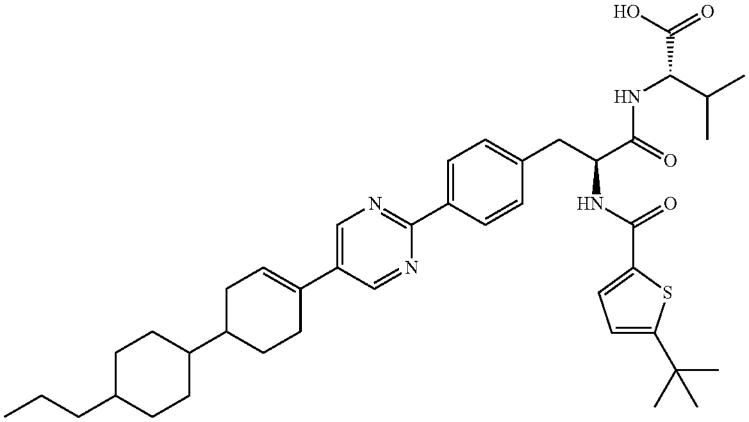
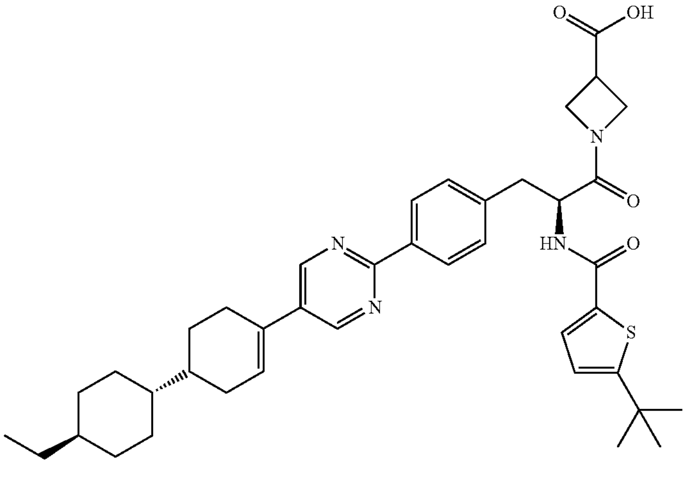 [SMILES: CC[C@H]1CC[C@H](C2CC=C(c3cnc(-c4ccc(C[C@H](NC(=O)c5ccc(C(C)(C)C)s5)C(=O)N5CC(C(=O)O)C5)cc4)nc3)CC2)CC1]

-continued
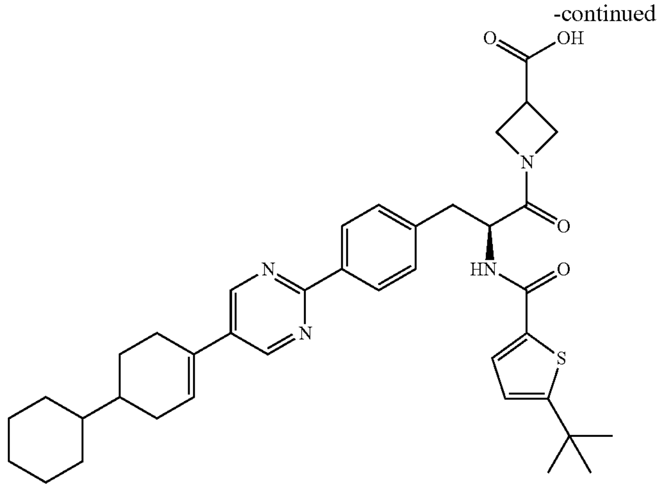
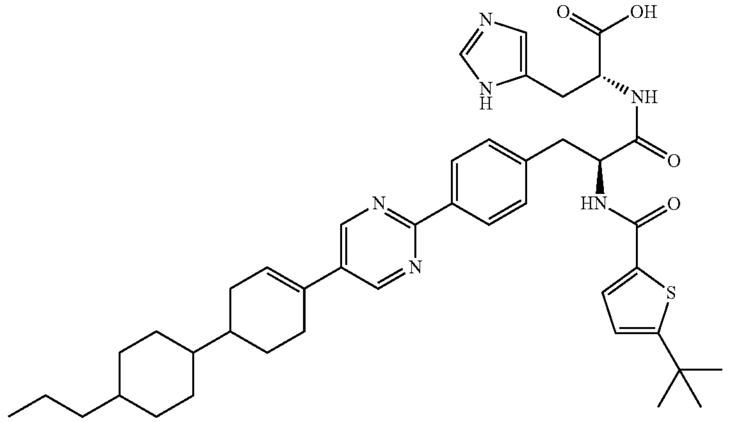
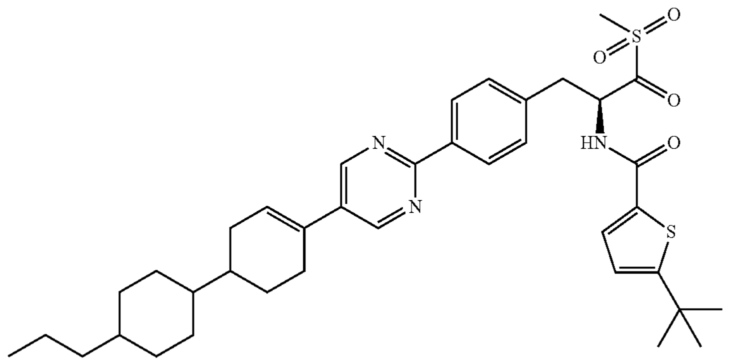
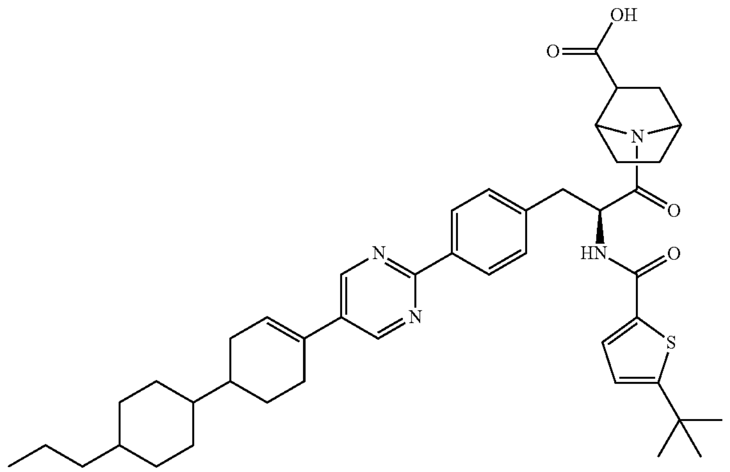

-continued
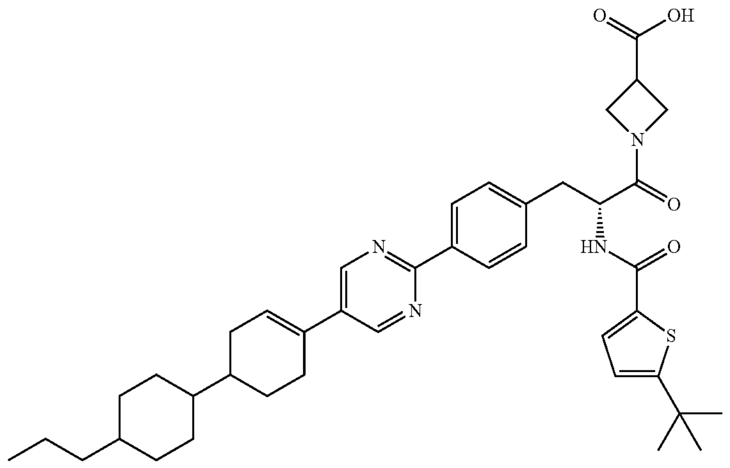
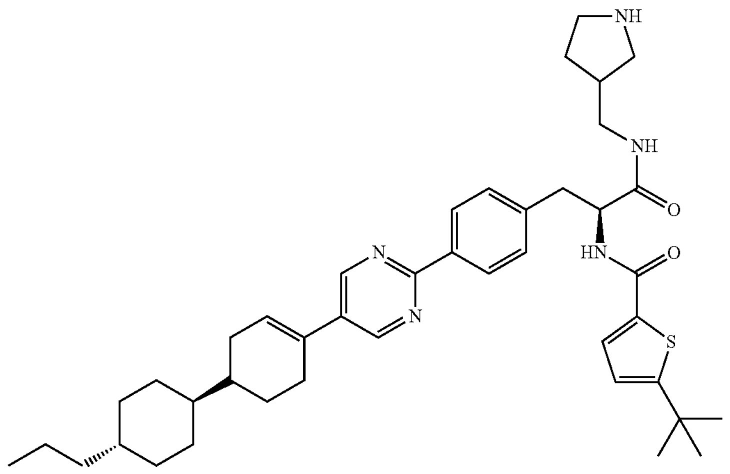
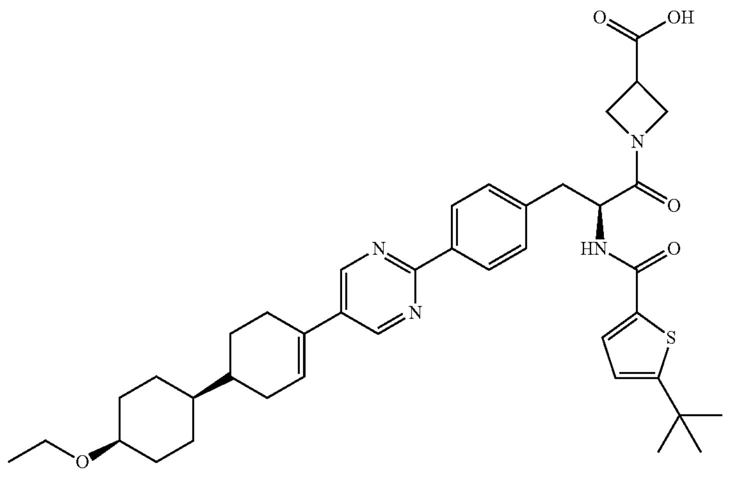

-continued
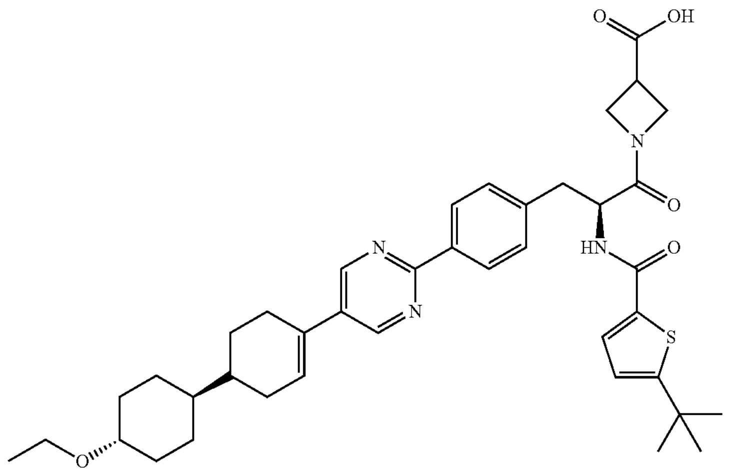
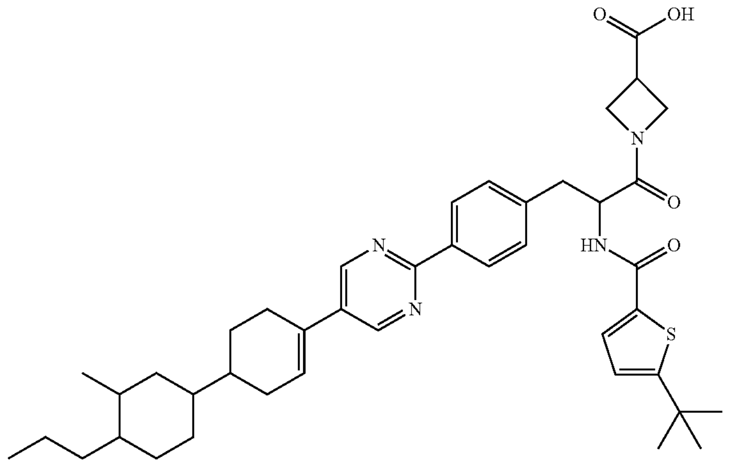
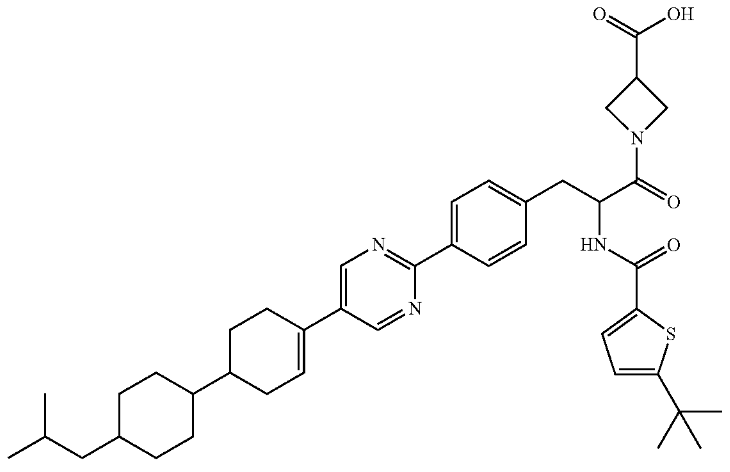

-continued
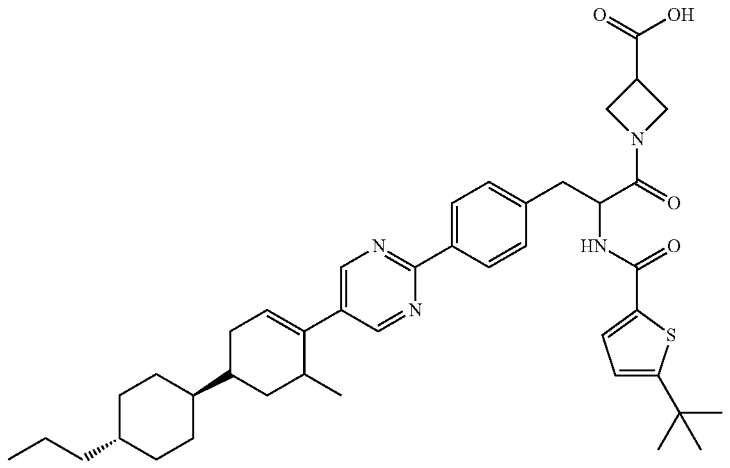
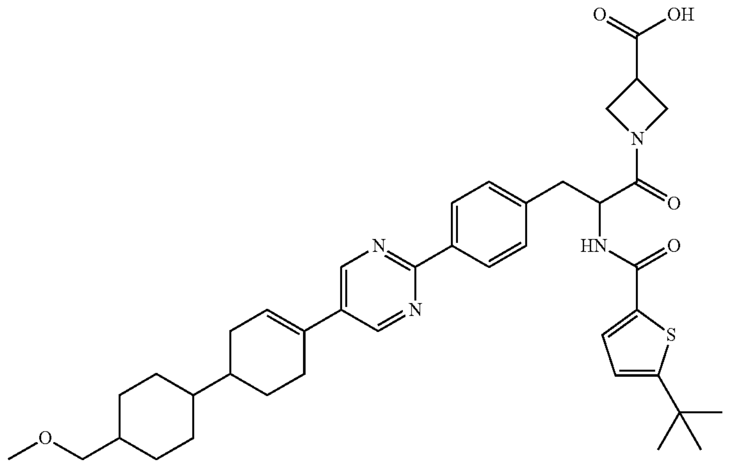
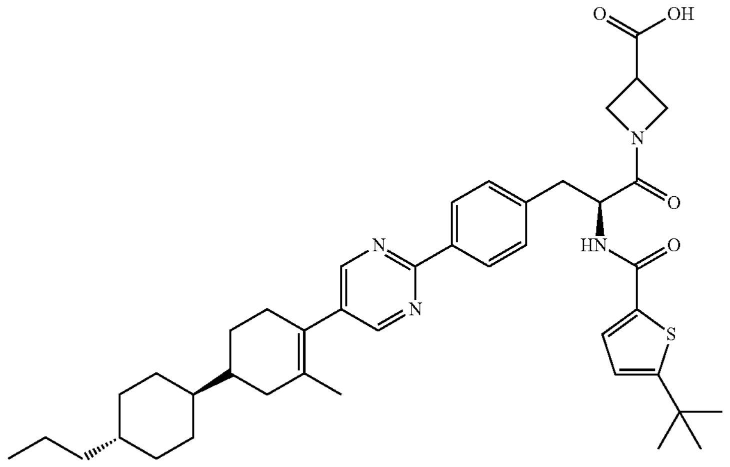

-continued
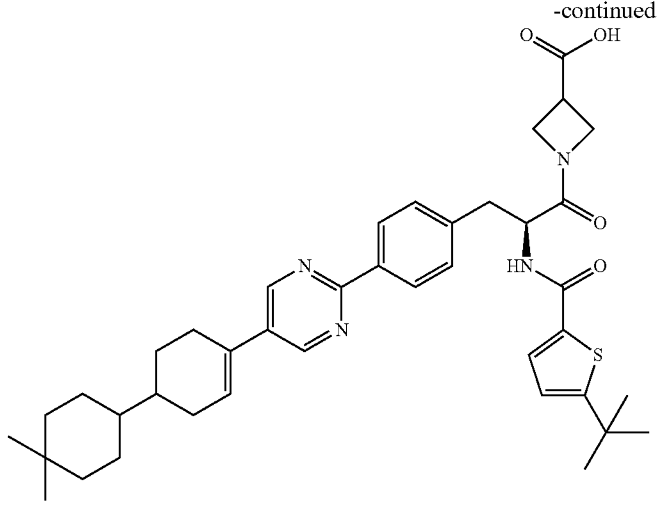
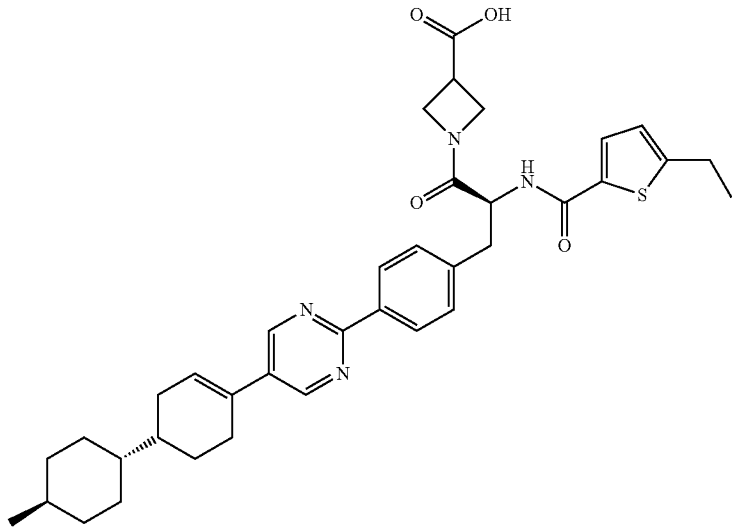
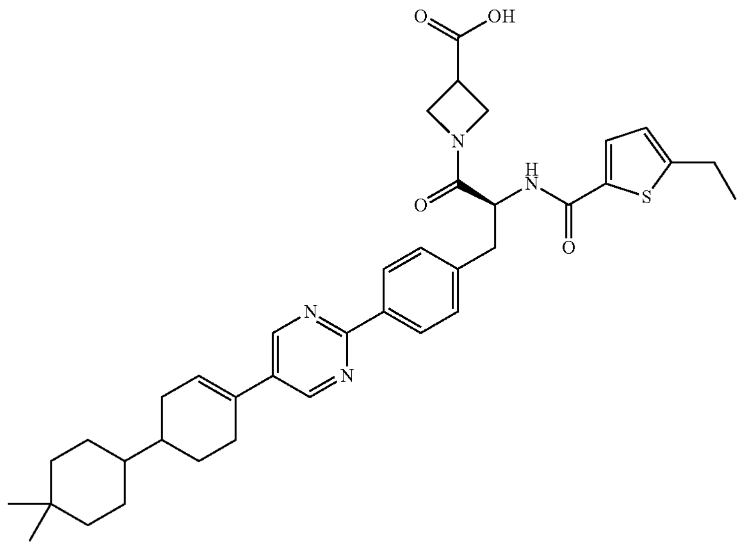

-continued
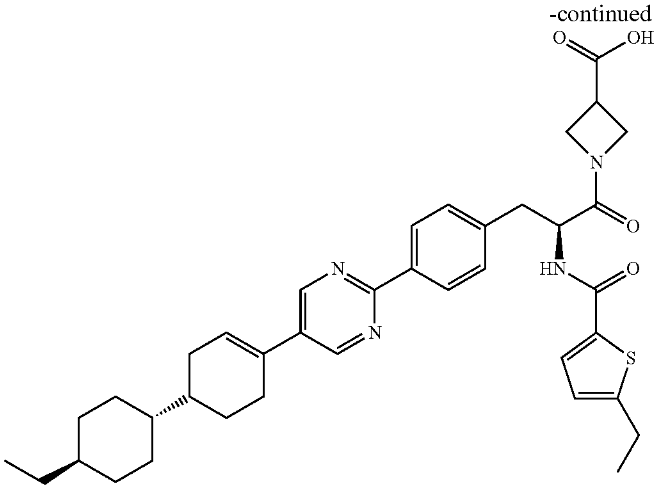
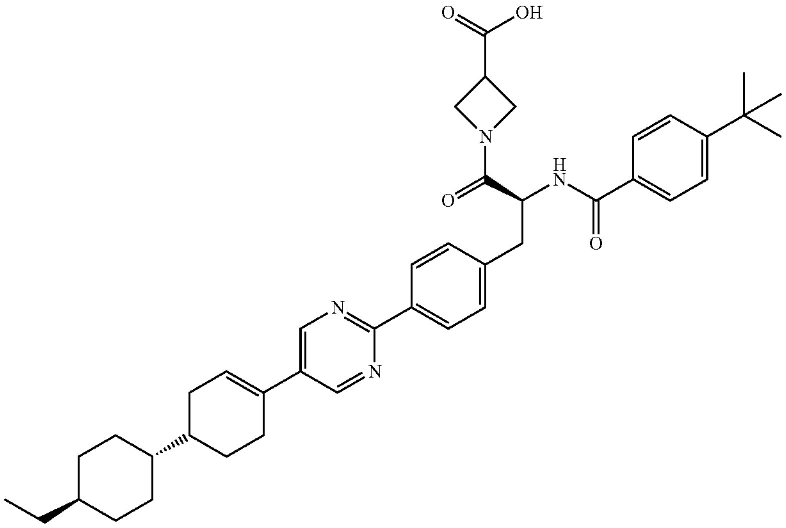
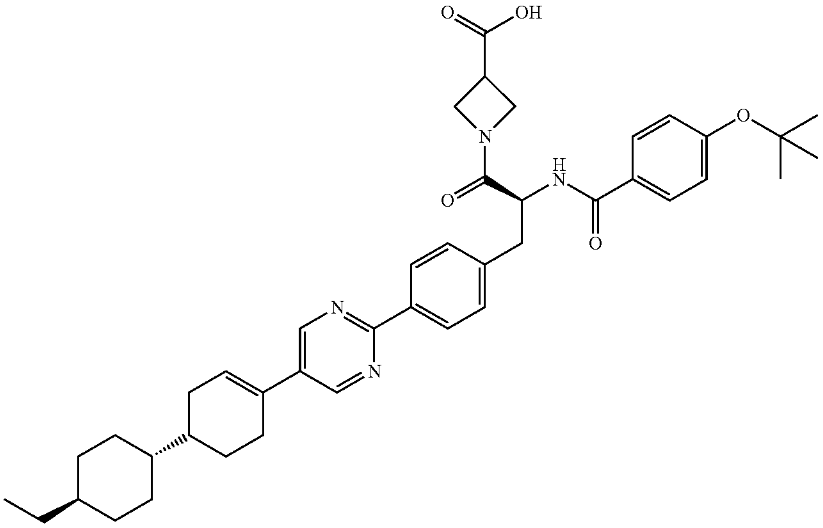

-continued
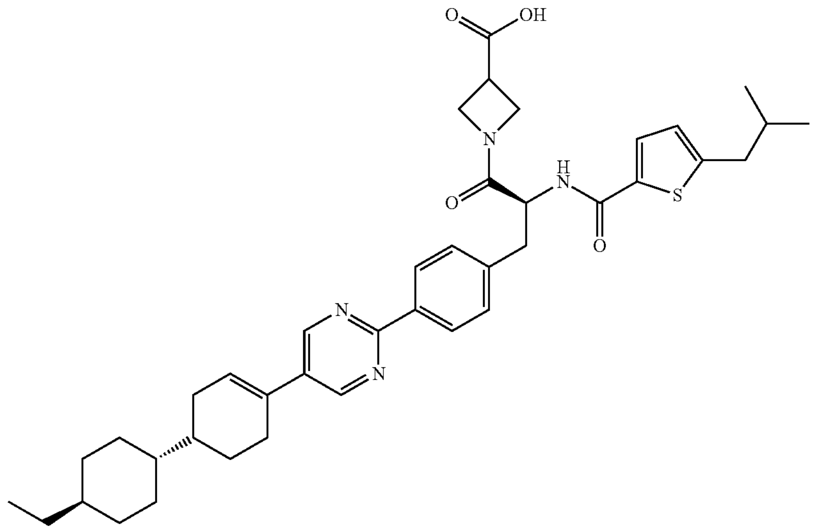
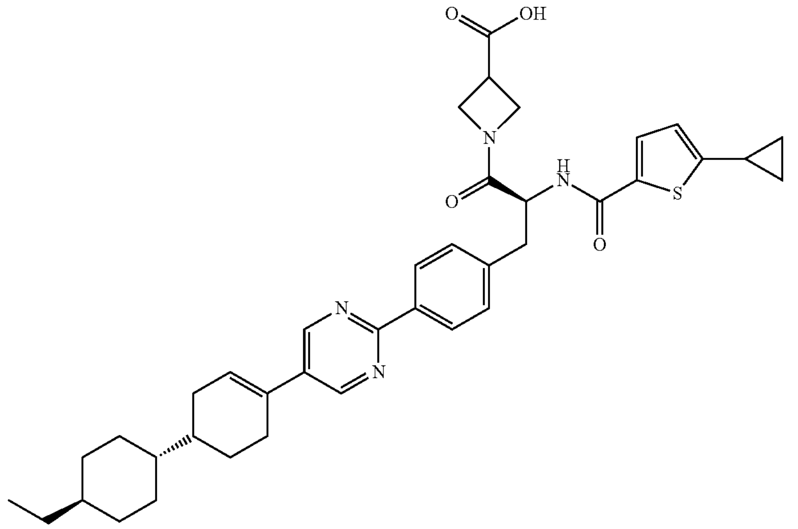
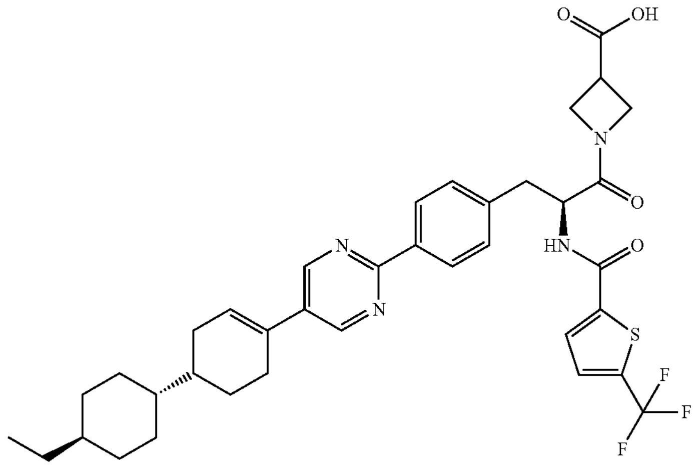

-continued
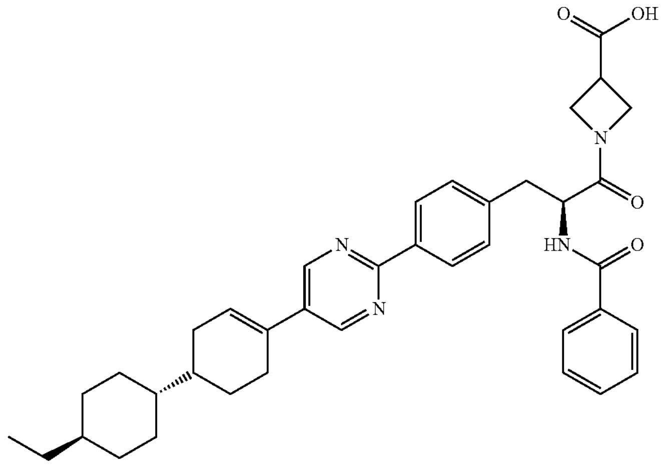
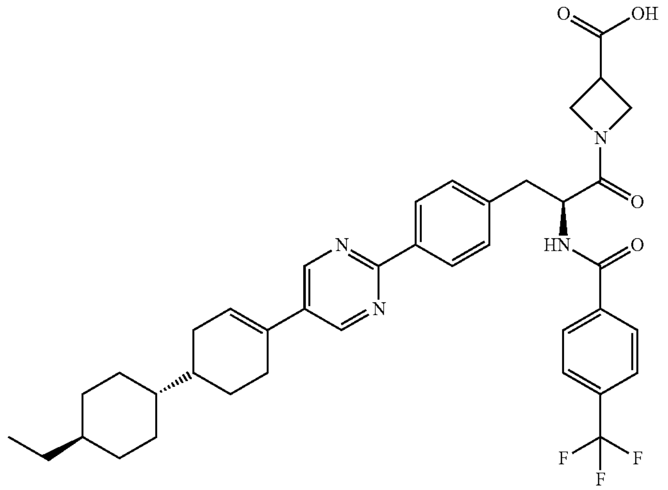
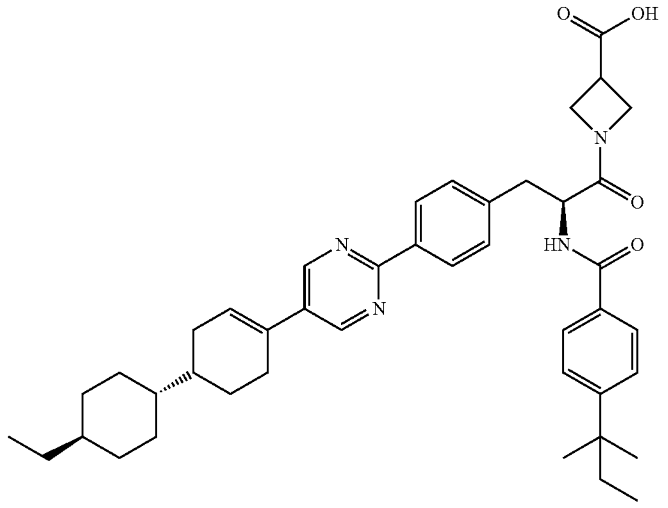

-continued
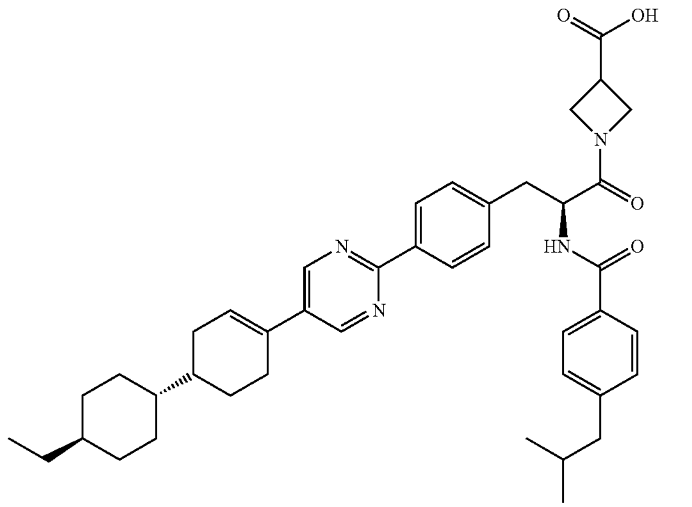
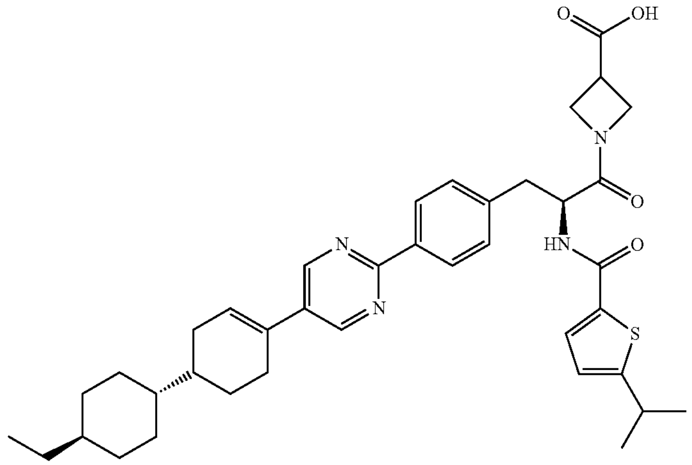
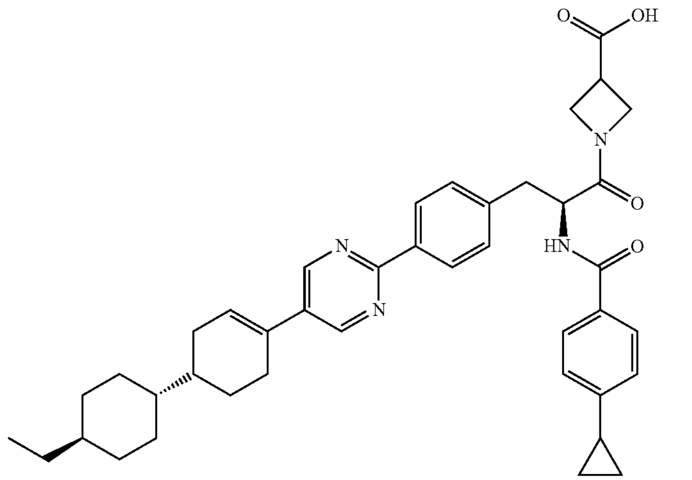

-continued
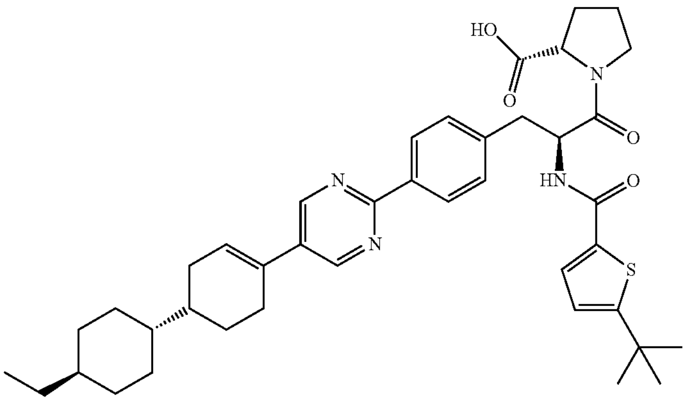
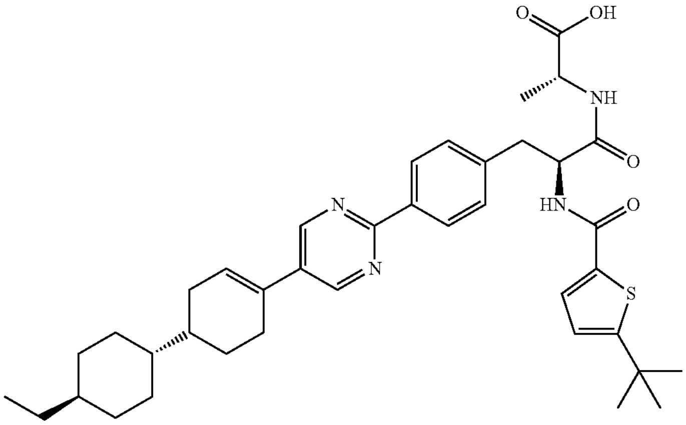
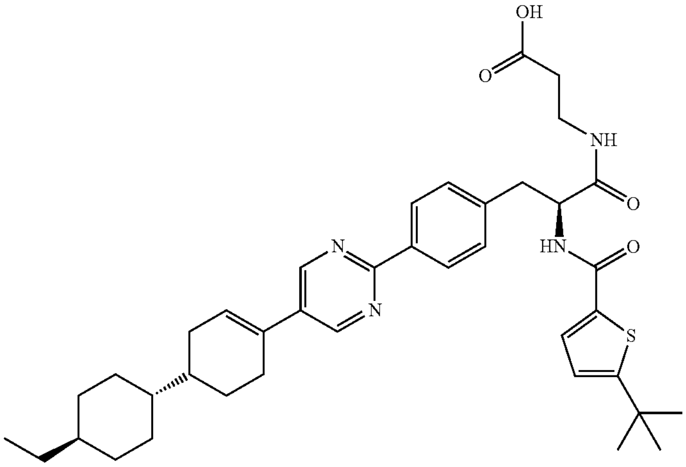

-continued
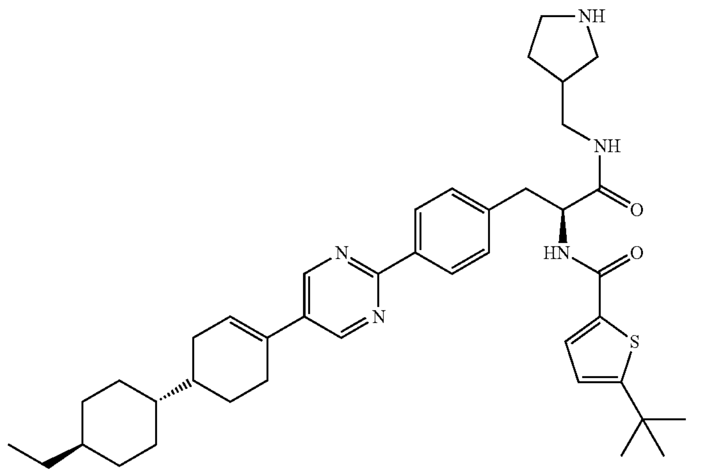
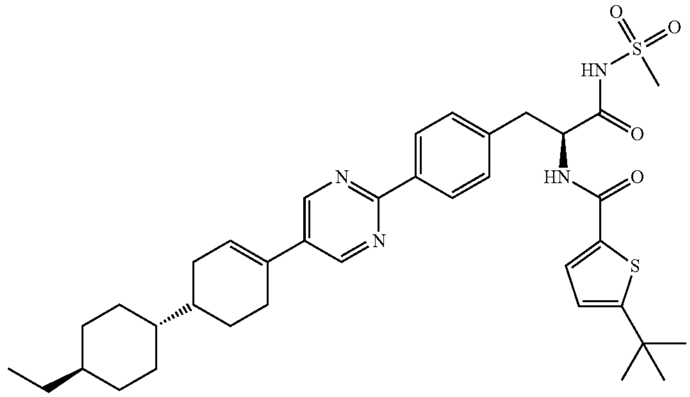 [SMILES: CC[C@H]1CC[C@H](C2CC=C(c3cnc(-c4ccc(C[C@H](NC(=O)c5ccc(C(C)(C)C)s5)C(=O)NS(C)(=O)=O)cc4)nc3)CC2)CC1]
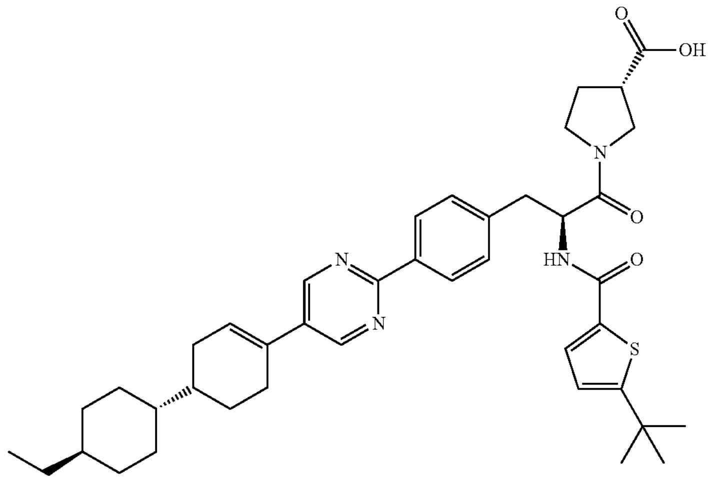 [SMILES: CC[C@H]1CC[C@H](C2CC=C(c3cnc(-c4ccc(C[C@H](NC(=O)c5ccc(C(C)(C)C)s5)C(=O)N5CC[C@H](C(=O)O)C5)cc4)nc3)CC2)CC1]

-continued
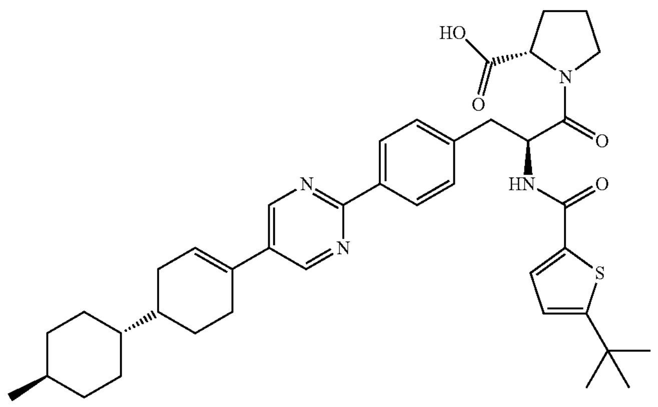
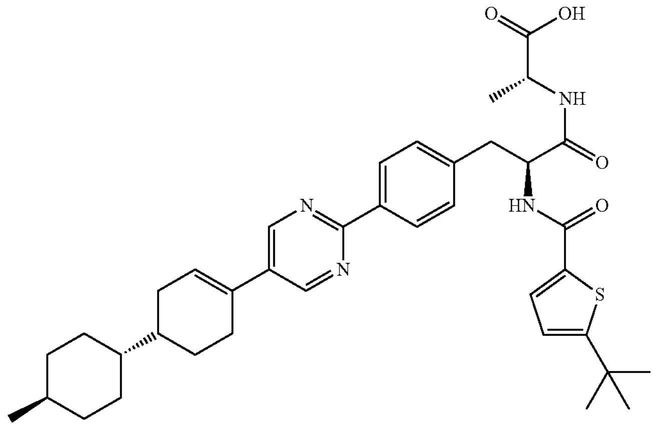
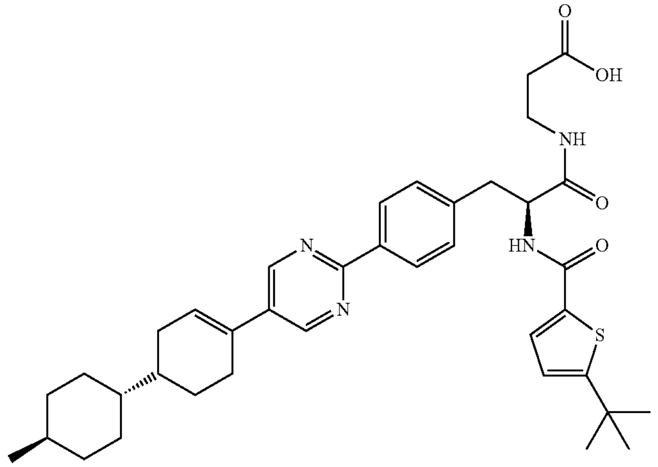

-continued
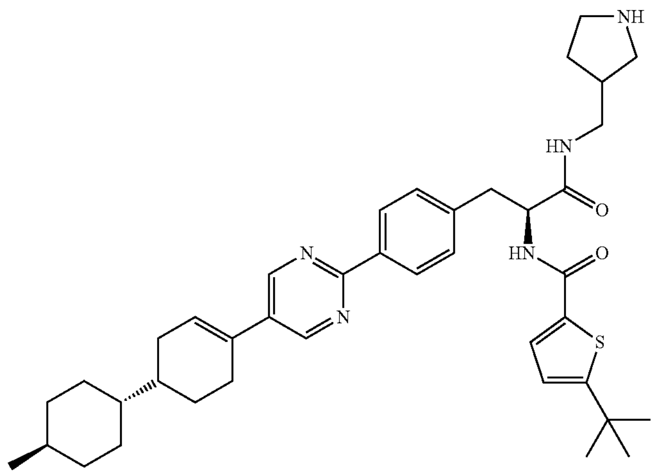
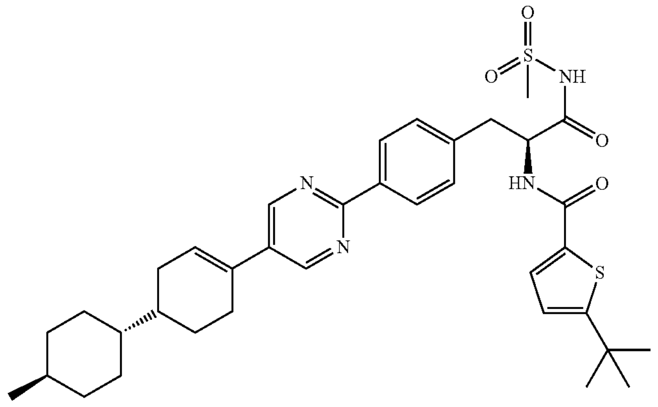
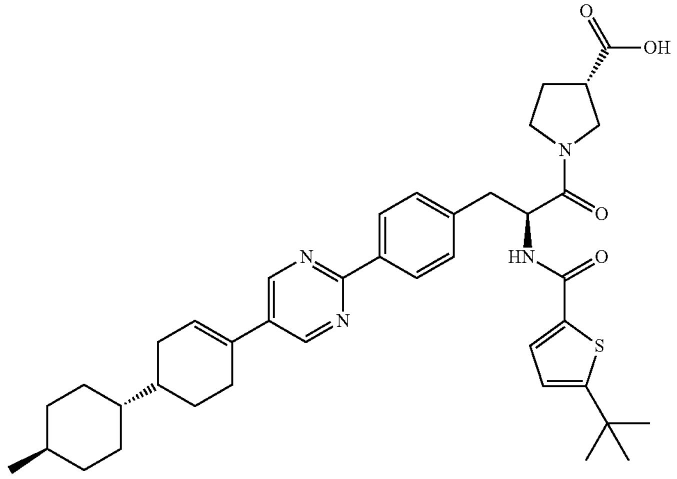

-continued
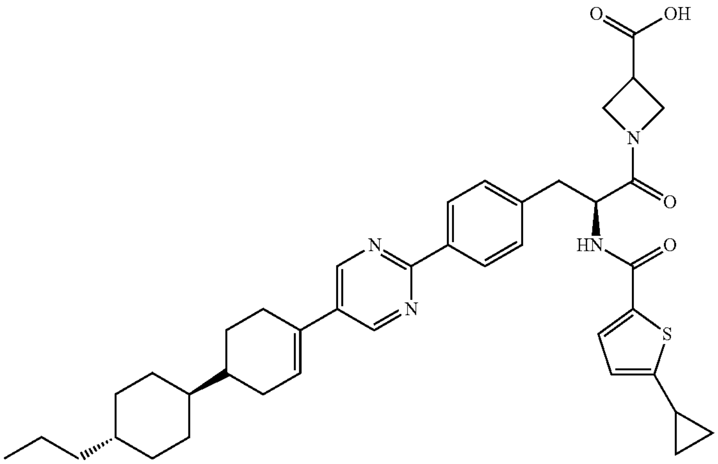
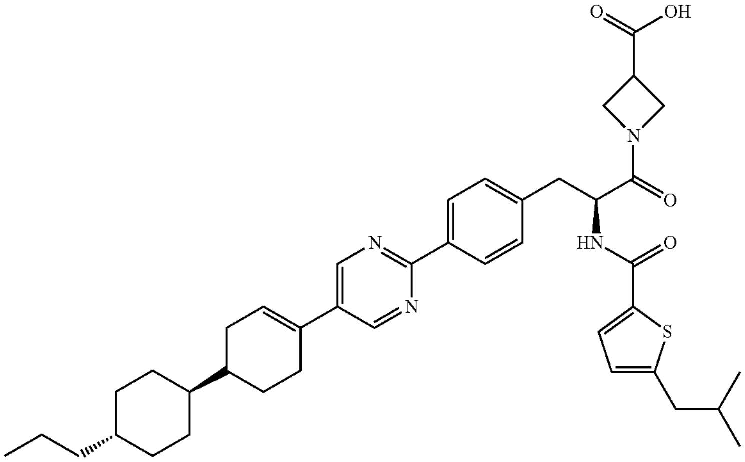
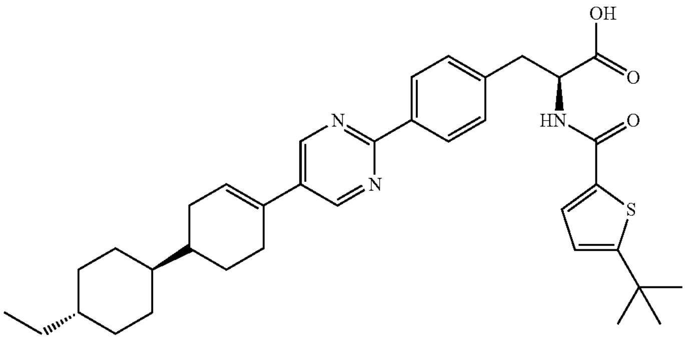
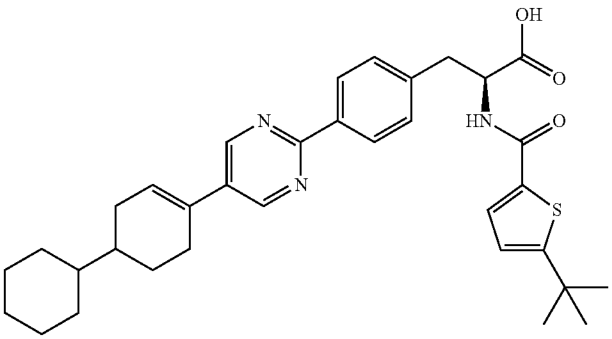

-continued
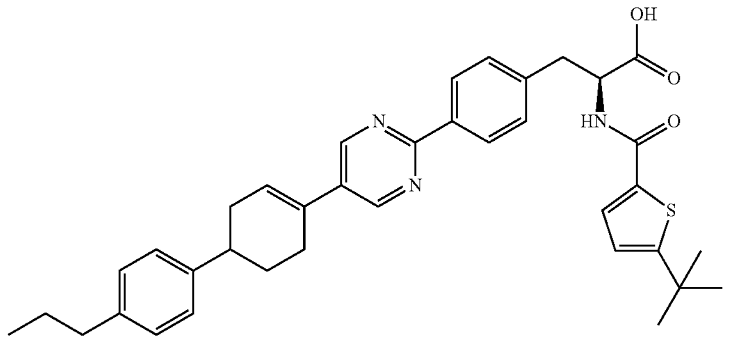
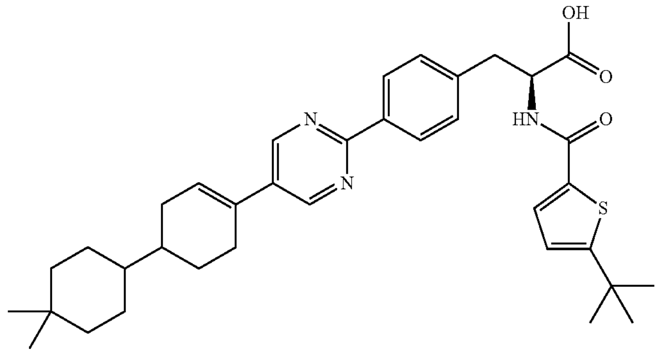
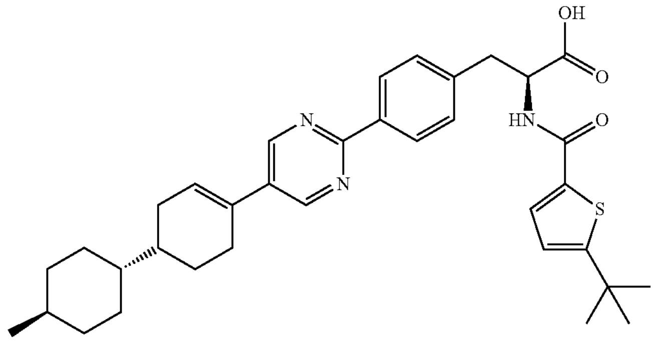 [SMILES: CC(C)(C)c1ccc(C(=O)N[C@@H](Cc2ccc(-c3ncc(C4=CCC([C@H]5CC[C@H](C)CC5)CC4)cn3)cc2)C(=O)O)s1]
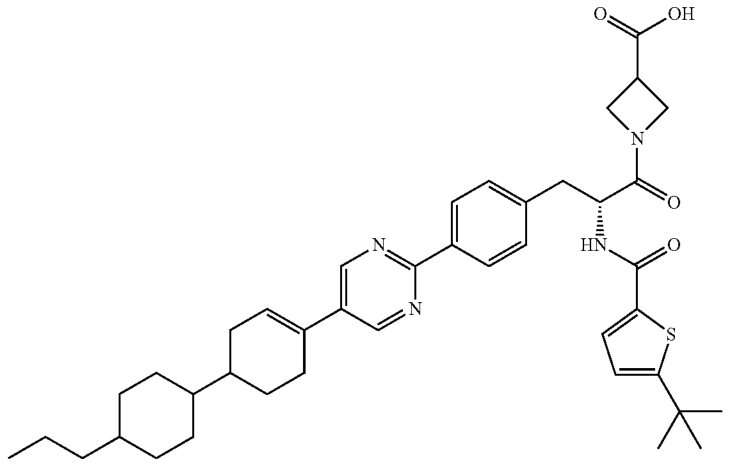

-continued

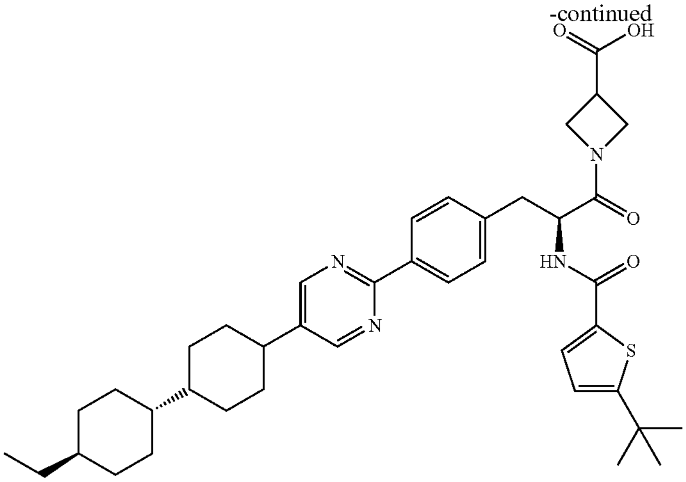

or a pharmaceutically acceptable enantiomer, diastereomer, racemate, salt, hydrate or solvate thereof.

66. A pharmaceutical composition comprising a compound of claim 1 together with at least one pharmaceutically acceptable carrier, diluent or excipient.

67. A pharmaceutical combination comprising the compound of claim 1 and a second medicament.

68. A method for treating type II diabetes comprising administering an effective amount of a compound of claim 1, or a pharmaceutically acceptable enantiomer, diastereomer, racemate, salt, hydrate or solvate thereof, to a patient at a frequency and for a duration of time sufficient to provide a beneficial effect to the patient.

69. The compound of claim 1, wherein the compound has the following structure:

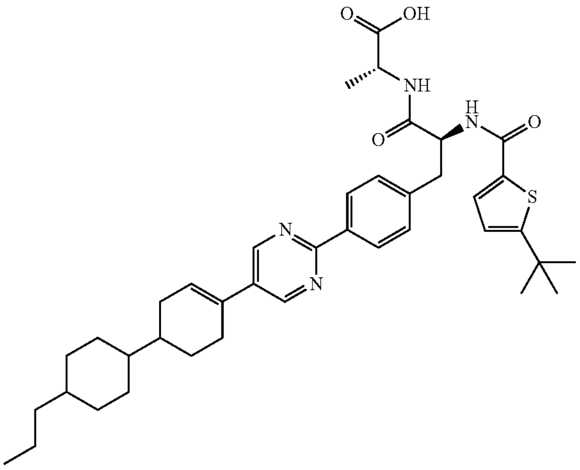

or a pharmaceutically acceptable enantiomer, diastereomer, racemate, salt, hydrate or solvate thereof.

70. The compound of claim 1, wherein the compound has the following structure:

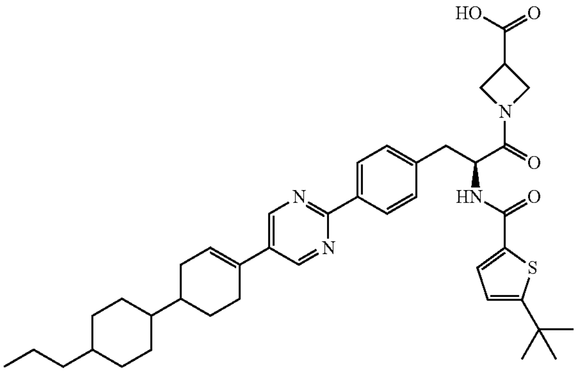

or a pharmaceutically acceptable enantiomer, diastereomer, racemate, salt, hydrate or solvate thereof.

71. The compound of claim 1, wherein the compound has the following structure:

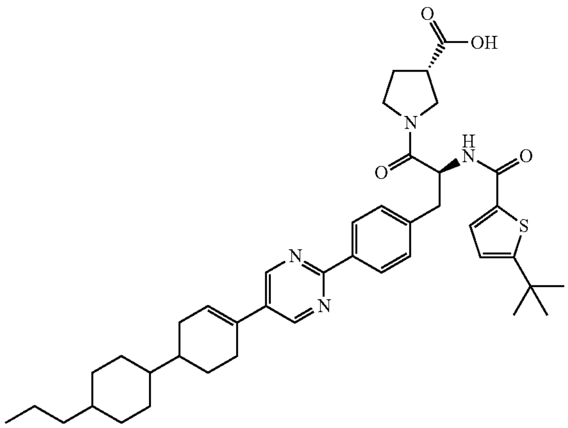

or a pharmaceutically acceptable enantiomer, diastereomer, racemate, salt, hydrate or solvate thereof.

72. The compound of claim 1, wherein the compound has the following structure:

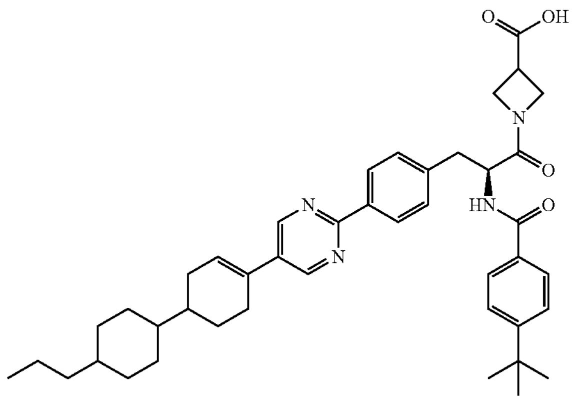

or a pharmaceutically acceptable enantiomer, diastereomer, racemate, salt, hydrate or solvate thereof.

73. The compound of claim 1, wherein the compound has the following structure:

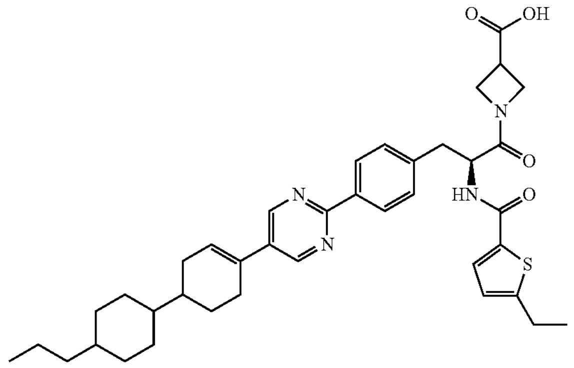

or a pharmaceutically acceptable enantiomer, diastereomer, racemate, salt, hydrate or solvate thereof.

74. The compound of claim 1, wherein the compound has the following structure:

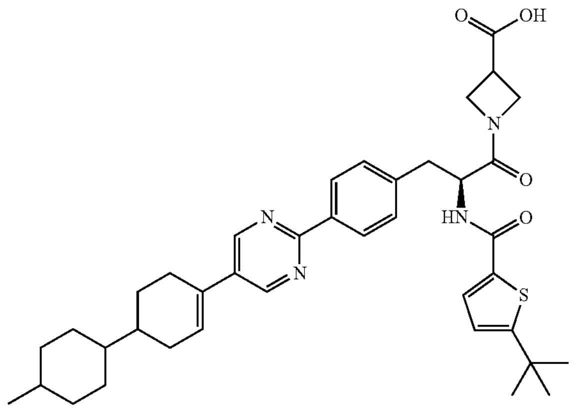

or a pharmaceutically acceptable enantiomer, diastereomer, racemate, salt, hydrate or solvate thereof.

75. The compound of claim 1, wherein the compound has the following structure:

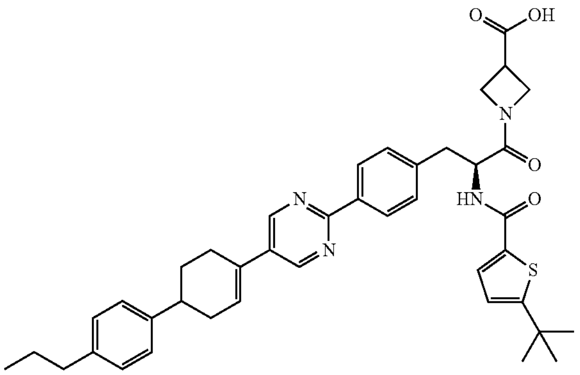

or a pharmaceutically acceptable enantiomer, diastereomer, racemate, salt, hydrate or solvate thereof.

76. The compound of claim 1, wherein the compound has the following structure:

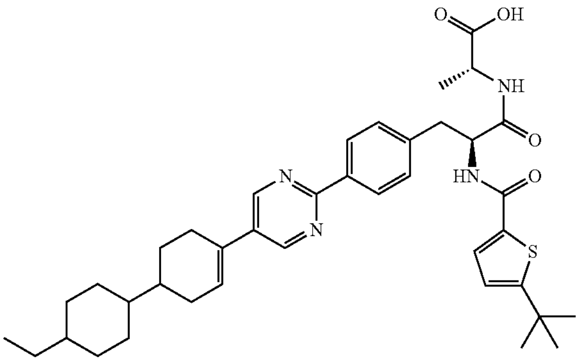

or a pharmaceutically acceptable enantiomer, diastereomer, racemate, salt, hydrate or solvate thereof.

77. The compound of claim 1, wherein the compound has the following structure:

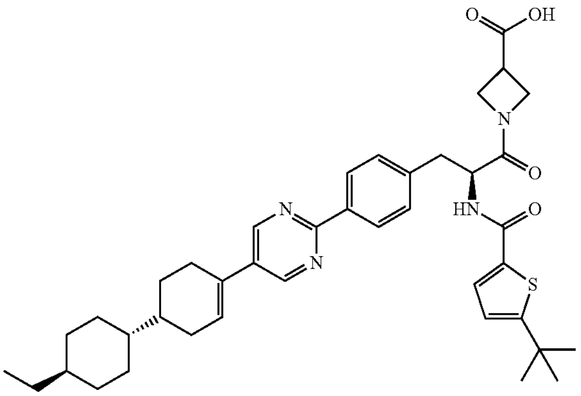

or a pharmaceutically acceptable enantiomer, diastereomer, racemate, salt, hydrate or solvate thereof.

78. The compound of claim 1, wherein the compound has the following structure:

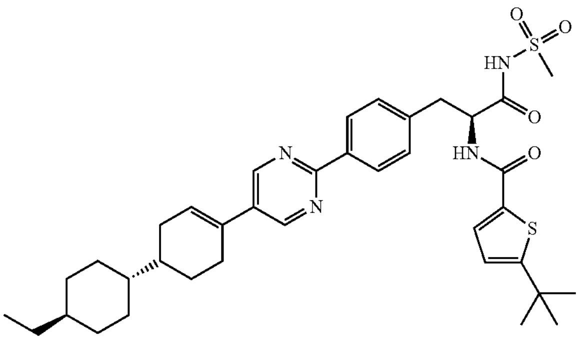

or a pharmaceutically acceptable enantiomer, diastereomer, racemate, salt, hydrate or solvate thereof.

79. The compound of claim 1, wherein the compound has the following structure:

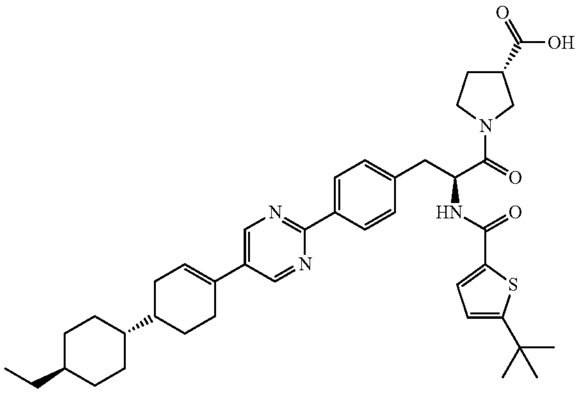

or a pharmaceutically acceptable enantiomer, diastereomer, racemate, salt, hydrate or solvate thereof.

80. The compound of claim 1, wherein the compound has the following structure:

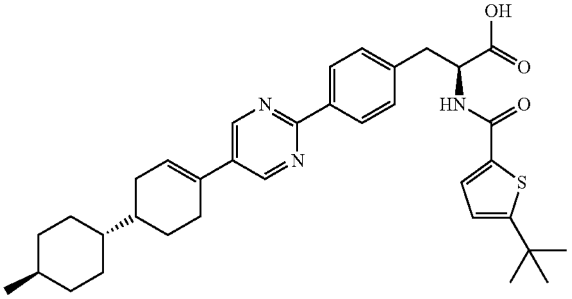

or a pharmaceutically acceptable enantiomer, diastereomer, racemate, salt, hydrate or solvate thereof.

* * * * *

UNITED STATES PATENT AND TRADEMARK OFFICE

CERTIFICATE OF CORRECTION

PATENT NO. : 9,474,755 B2
APPLICATION NO. : 14/809020
DATED : October 25, 2016
INVENTOR(S) : Marcus F. Boehm et al.

It is certified that error appears in the above-identified patent and that said Letters Patent is hereby corrected as shown below:

In the Claims

Column 229, Line 54:
"$N(R_1)-(CR_aR_b)_m-COOR_8$, $-N(R_1)-(CR_aR_b)_m-$" should read, -- $-N(R_1)-(CR_aR_b)_m-COOR_8$, $-N(R_1)-(CR_aR_b)_m-$ --.

Column 230, Line 53:
"$-(CR_aR_b)_mS(O)R_8$, $-(CR_aR_b)-S(O)_2R_8$," should read, -- $-(CR_aR_b)_mS(O)R_8$, $-(CR_aR_b)_mS(O)_2R_8$,--.

Column 239, Line 20:
"and $R_{42}$ is $-(CHR_{40})_nC(O)OR_{40}$, $-(CHR_{40})_n(O)R_{40}$," should read, --and $R_{42}$ is $-(CHR_{40})_nC(O)OR_{40}$, $-(CHR_{40})_nC(O)R_{40}$,--.

Column 240, Line 1:
"The compound of of claim 56 wherein $R_{41}$ and $R_{42}$" should read, --The compound of claim 56 wherein $R_{41}$ and $R_{42}$--.

Column 240, Line 6:
"is $N(R_1)(CR_aR_b)_mCON(R_1)(R_{40})$." should read, --is $-N(R_1)(CR_aR_b)_mCON(R_1)(R_{40})$.--.

Column 240, Line 17:
"is $-N(R_1)(CR_aR_b)_mN(ROC(O)OR_8$, $-N(R_1)(CR_aR_b)_mN$" should read,
--is $-N(R_1)(CR_aR_b)_mN(R_1)C(O)OR_8$, $-N(R_1)(CR_aR_b)_mN$--.

Signed and Sealed this
Thirtieth Day of May, 2017

Michelle K. Lee
*Director of the United States Patent and Trademark Office*

```
SEQUENCE LISTING


<160> NUMBER OF SEQ ID NOS: 3

<210> SEQ ID NO 1
<211> LENGTH: 31
<212> TYPE: PRT
<213> ORGANISM: Artificial Sequence
<220> FEATURE:
<223> OTHER INFORMATION: the GLP-1agonist is liraglutide(VICTOZA) (also
      called NN-2211

<400> SEQUENCE: 1

His Ala Glu Gly Thr Phe Thr Ser Asp Val Ser Ser Tyr Leu Glu Gly
 1              5                   10                  15

Gln Ala Ala Lys Glu Phe Ile Ala Trp Lys Val Arg Gly Arg Gly
            20                  25                  30


<210> SEQ ID NO 2
<211> LENGTH: 30
<212> TYPE: PRT
<213> ORGANISM: Artificial Sequence
<220> FEATURE:
<223> OTHER INFORMATION: GLP-1(7-36) sequence

<400> SEQUENCE: 2

His Ala Glu Gly Thr Phe Thr Ser Asp Val Ser Ser Tyr Leu Glu Gly
 1              5                   10                  15

Gln Ala Ala Lys Glu Phe Ile Ala Trp Leu Val Lys Gly Arg
            20                  25                  30
```

-continued

```
<210> SEQ ID NO 3
<211> LENGTH: 28
<212> TYPE: PRT
<213> ORGANISM: Artificial Sequence
<220> FEATURE:
<223> OTHER INFORMATION: GLP-1(9-36) sequence

<400> SEQUENCE: 3

Glu Gly Thr Phe Thr Ser Asp Val Ser Ser Tyr Leu Glu Gly Gln Ala
 1               5                  10                  15

Ala Lys Glu Phe Ile Ala Trp Leu Val Lys Gly Arg
                20                  25
```